(12) United States Patent
Power et al.

(10) Patent No.: US 7,541,026 B2
(45) Date of Patent: Jun. 2, 2009

(54) ALPHA-AMYLASE VARIANTS WITH ALTERED PROPERTIES

(75) Inventors: Scott D. Power, San Bruno, CA (US); Sandra W. Ramer, Sunnyvale, CA (US); Andrew Shaw, San Francisco, CA (US)

(73) Assignee: Danisco US Inc., Genencor Division, Palo Alto, CA (US)

( * ) Notice: Subject to any disclaimer, the term of this patent is extended or adjusted under 35 U.S.C. 154(b) by 0 days.

(21) Appl. No.: 12/263,631

(22) Filed: Nov. 3, 2008

(65) Prior Publication Data

US 2009/0117642 A1    May 7, 2009

Related U.S. Application Data

(60) Provisional application No. 60/985,619, filed on Nov. 5, 2007, provisional application No. 60/026,579, filed on Feb. 6, 2008, provisional application No. 61/041,075, filed on Mar. 31, 2008, provisional application No. 61/059,411, filed on Jun. 6, 2008.

(51) Int. Cl.
*A61K 38/46* (2006.01)
*C12N 9/28* (2006.01)

(52) U.S. Cl. ..................................... 424/94.6; 435/202
(58) Field of Classification Search ................ 424/94.6; 435/202

See application file for complete search history.

(56) References Cited

U.S. PATENT DOCUMENTS

| 6,867,031 B2 | 3/2005 | Bisgard-Frantzen |
| 2004/0096952 A1 | 5/2004 | Svendsen et al. |
| 2005/0250663 A1 | 11/2005 | Thisted et al. |

*Primary Examiner*—Tekchand Saidha

(57) ABSTRACT

Disclosed are compositions comprising variants of a parent *G. stearothermophilus* alpha-amylase that have alpha-amylase activity and which exhibit altered properties relative to a parent AmyS-like alpha-amylase from which they are derived. The compositions comprise an additional enzyme such as a phytase. Also disclosed are methods of using the compositions, and kits related thereto.

11 Claims, 36 Drawing Sheets

```
                      1                                                50
SEQID No  1   (1)  -AAPFNGTMMQYFEWYLPDDGTLWTKVANEANNLSSLGITALWLPPAYKG
SEQID No  2   (1)  -AAPFNGTMMQYFEWYLPDDGTLWTKVANEANNLSSLGITALWLPPAYKG
SEQID No  3   (1)  -AAPFNGTMMQYFEWYLPDDGTLWTKVANEANNLSSLGITALWLPPAYKG
SEQID No  4   (1)  -AAPFNGTMMQYFEWYLPDDGTLWTKVANEANNLSSLGITALWLPPAYKG
SEQID No  5   (1)  -AAPFNGTMMQYFEWYLPDDGTLWTKVANEANNLSSLGITALWLPPAYKG
SEQID No  6   (1)  HHNGTNGTMMQYFEWYLPNDGNHWNRLNSDASNLKSKGITAVWIPPAWKG
SEQID No  7   (1)  --ANLNGTLMQYFEWYMPNDGQHWKRLQNDSAYLAEHGITAVWIPPAYKG
SEQID No  8   (1)  --ANLNGTLMQYFEWYMPNDGQHWRRLQNDSAYLAEHGITAVWIPPAYKG
SEQID No  9   (1)  ----VNGTLMQYFEWYTPNDGQHWKRLQNDAEHLSDIGITAVWIPPAYKG
SEQID No 10   (1)  HHNGTNGTMMQYFEWYLPNDGNHWNRLRSDASNLKDKGISAVWIPPAWKG
SEQID No 11   (1)  HHNGTNGTMMQYFEWHLPNDGNHWNRLRDDASNLRNRGITAIWIPPAWKG
SEQID No 12   (1)  HHNGTNGTMMQYFEWHLPNDGNHWNRLRDDAANLKSKGITAVWIPPAWKG
SEQID No 13   (1)  --DGLNGTMMQYYEWHLENDGQHWNRLHDDAAALSDAGITAIWIPPAYKG
SEQID No 14   (1)  --DGLNGTMMQYYEWHLENDGQHWNRLHDDAEALSNAGITAIWIPPAYKG
SEQID No 15   (1)  -AAPFNGTMMQYFEWYLPDDGTLWTKVANEANNLSSLGITALWLPPAYKG
Consensus 1   (1)    A  NGTMMQYFEWYLPNDGQHW RL NDA NLSS GITALWIPPAYKG
                      51                                               100
SEQID No  1  (50)  TSRSDVGYGVYDLYDLGEFNQKGTVRTKYGTKAQYLQAIQAAHAAGMQVY
SEQID No  2  (50)  TSRSDVGYGVYDLYDLGEFNQKGTVRTKYGTKAQYLQAIQAAHAAGMQVY
SEQID No  3  (50)  TSRSDVGYGVYDLYDLGEFNQKGTVRTKYGTKAQYLQAIQAAHAAGMQVY
SEQID No  4  (50)  TSRSDVGYGVYDLYDLGEFNQKGTVRTKYGTKAQYLQAIQAAHAAGMQVY
SEQID No  5  (50)  TSRSDVGYGVYDLYDLGEFNQKGTVRTKYGTKAQYLQAIQAAHAAGMQVY
SEQID No  6  (51)  ASQNDVGYGAYDLYDLGEFNQKGTVRTKYGTRSQLQAAVTSLKNNGIQVY
SEQID No  7  (49)  TSQADVGYGAYDLYDLGEFHQKGTVRTKYGTKGELQSAIKSLHSRDINVY
SEQID No  8  (49)  TSQADVGYGAYDLYDLGEFHQKGTVRTKYGTKGELQSAIKSLHSRDINVY
SEQID No  9  (47)  LSQSDNGYGPYDLYDLGEFQQKGTVRTKYGTKSELQDAIGSLHSRNVQVY
SEQID No 10  (51)  ASQNDVGYGAYDLYDLGEFNQKGTIRTKYGTRNQLQAAVNALKSNGIQVY
SEQID No 11  (51)  TSQNDVGYGAYDLYDLGEFNQKGTVRTKYGTRSQLESAIHALKNNGVQVY
SEQID No 12  (51)  TSQNDVGYGAYDLYDLGEFNQKGTVRTKYGTRSQLQGAVTSLKNNGIQVY
SEQID No 13  (49)  NSQADVGYGAYDLYDLGEFNQKGTVRTKYGTKAQLERAIGSLKSNDINVY
SEQID No 14  (49)  NSQADVGYGAYDLYDLGEFNQKGTVRTKYGTKAQLERAIGSLKSNDINVY
SEQID No 15  (50)  TSRSDVGYGVYDLYDLGEFNQKGTVRTKYGTKAQYLQAIQAAHAAGMQVY
Consensus 1  (51)  TSQSDVGYGAYDLYDLGEFNQKGTVRTKYGTKAQL  AI ALHA GIQVY
                      101                                              150
SEQID No  1 (100)  ADVVFDHKGGADGTEWVDAVEVNPSDRNQEISGTYQIQAWTKFDFPGRGN
SEQID No  2 (100)  ADVVFDHKGGADGTEWVDAVEVNPSDRNQEISGTYQIQAWTKFDFPGRGN
SEQID No  3 (100)  ADVVFDHKGGADGTEWVDAVEVNPSDRNQEISGTYQIQAWTKFDFPGRGN
SEQID No  4 (100)  ADVVFDHKGGADGTEWVDAVEVNPSDRNQEISGTYQIQAWTKFDFPGRGN
SEQID No  5 (100)  ADVVFDHKGGADGTEWVDAVEVNPSDRNQEISGTYQIQAWTKFDFPGRGN
SEQID No  6 (101)  GDVVMNHKGGADATEMVRAVEVNPNNRNQEVTGEYTIEAWTRFDFPGRGN
SEQID No  7  (99)  GDVVINHKGGADATEDVTAVEVDPADRNRVISGEHLIKAWTHFHFPGRGS
SEQID No  8  (99)  GDVVINHKGGADATEDVTAVEVDPADRNRVISGEHLIKAWTHFHFPGRGS
SEQID No  9  (97)  GDVVLNHKAGADATEDVTAVEVNPANRNQETSEEYQIKAWTDFRFPGRGN
SEQID No 10 (101)  GDVVMNHKGGADATEMVRAVEVNPNNRNQEVSGEYTIEAWTKFDFPGRGN
SEQID No 11 (101)  GDVVMNHKGGADATENVLAVEVNPNNRNQEISGDYTIEAWTKFDFPGRGN
SEQID No 12 (101)  GDVVMNHKGGADGTEMVNAVEVNRSNRNQEISGEYTIEAWTKFDFPGRGN
SEQID No 13  (99)  GDVVMNHKMGADFTEAVQAVQVNPTNRWQDISGAYTIDAWTGFDFSGRNN
SEQID No 14  (99)  GDVVMNHKLGADFTEAVQAVQVNPSNRWQDISGVYTIDAWTGFDFPGRNN
SEQID No 15 (100)  ADVVFDHKGGADGTEWVDAVEVNPSDRNQEISGTYQIQAWTKFDFPGRGN
Consensus 1 (101)  GDVVMNHKGGADGTE V AVEVNPSDRNQEISG Y I AWTKFDFPGRGN
```

Figure 1 (1 of 4)

```
                        151                                                200
SEQID No 1      (150)   TYSSFKWRWYHFDGVDWDESRKLS-RIYKFRGIGKAWDWEVDTENGNYDY
SEQID No 2      (150)   TYSSFKWRWYHFDGVDWDESRKLS-RIYKFRGIGKAWDWEVDTENGNYDY
SEQID No 3      (150)   TYSSFKWRWYHFDGVDWDESRKLS-RIYKFRGIGKAWDWEVDTENGNYDY
SEQID No 4      (150)   TYSSFKWRWYHFDGVDWDESRKLS-RIYKFRGIGKAWDWEVDTENGNYDY
SEQID No 5      (150)   TYSSFKWRWYHFDGVDWDESRKLS-RIYKFRGIGKAWDWEVDTENGNYDY
SEQID No 6      (151)   THSSFKWRWYHFDGVDWDQSRRLNNRIYKFRGHGKAWDWEVDTENGNYDY
SEQID No 7      (149)   TYSDFKWHWYHFDGTDWDESRKLN-RIYKFQG--KAWDWEVSNENGNYDY
SEQID No 8      (149)   TYSDFKWHWYHFDGTDWDESRKLN-RIYKFQG--KAWDWEVSNENGNYDY
SEQID No 9      (147)   TYSDFKWHWYHFDGADWDESRKIS-RIFKFRGEGKAWDWEVSSENGNYDY
SEQID No 10     (151)   THSNFKWRWYHFDGVDWDQSRKLNNRIYKFRGDGKGWDWEVDTENGNYDY
SEQID No 11     (151)   TYSDFKWRWYHFDGVDWDQSRQFQNRIYKFRGDGKAWDWEVDSENGNYDY
SEQID No 12     (151)   THSNFKWRWYHFDGTDWDQSRQLQNKIYKFRGTGKAWDWEVDIENGNYDY
SEQID No 13     (149)   AYSDFKWRWFHFNGVDWDQRYQEN-HIFRFAN--TNWNWRVDEENGNYDY
SEQID No 14     (149)   AYSDFKWRWFHFNGVDWDQRYQEN-HLFRFAN--TNWNWRVDEENGNYDY
SEQID No 15     (150)   TYSSFKWRWYHFDGVDWDESRKLS-RIYKFRG--KAWDWEVDTEFGNYDY
Consensus 1     (151)   TYS FKWRWYHFDGVDWDESRKLN RIYKFRG GKAWDWEVDTENGNYDY
                        201                                                250
SEQID No 1      (199)   LMYADLDMDHPEVVTELKNWGKWYVNTTNIDGFRLDAVKHIKFSFFPDWL
SEQID No 2      (199)   LMYADLDMDHPEVVTELKNWGKWYVNTTNIDGFRLDAVKHIKFSFFPDWL
SEQID No 3      (199)   LMYADLDMDHPEVVTELKNWGKWYVNTTNIDGFRLDAVKHIKFAFFPDWL
SEQID No 4      (199)   LMYADLDMDHPEVVTELKNWGKWYVNTTNIDGFRLDAVKHIKFQFFPDWL
SEQID No 5      (199)   LMYADLDMDHPEVVTELKNWGKWYVNTTNIDGFRLDAVKHIKFEFFPDWL
SEQID No 6      (201)   LMYADIDMDHPEVVNELRNWGVWYTNTLGLDGFRIDAVKHIKYSFTRDWI
SEQID No 7      (196)   LMYADIDYDHPDVAAEIKRWGTWYANELQLDGFRLDAVKHIKFSFLRDWV
SEQID No 8      (196)   LMYADIDYDHPDVAAEIKRWGTWYANELQLDGFRLDAVKHIKFSFLRDWV
SEQID No 9      (196)   LMYADVDYDHPDVVAETKKWGIWYANELSLDGFRIDAAKHIKFSFLRDWV
SEQID No 10     (201)   LMYADIDMDHPEVVNELRNWGVWYTNTLGLDGFRIDAVKHIKYSFTRDWI
SEQID No 11     (201)   LMYADVDMDHPEVVNELRRWGEWYTNTLNLDGFRIDAVKHIKYSFTRDWL
SEQID No 12     (201)   LMYADIDMDHPEVINELRNWGVWYTNTLNLDGFRIDAVKHIKYSYTRDWL
SEQID No 13     (196)   LLGSNIDFSHPEVQDELKDWGSWFTDELDLDGYRLDAIKHIPFWYTSDWV
SEQID No 14     (196)   LLGSNIDFSHPEVQEELKDWGSWFTDELDLDGYRLDAIKHIPFWYTSDWV
SEQID No 15     (197)   LMYADLDMDHPEVVTELKNWGKWYVNTTNIDGFRLDAVKHIKFSFFPDWL
Consensus 1     (201)   LMYADIDMDHPEVV ELKNWG WY NTLNLDGFRLDAVKHIKFSF  DWL
                        251                                                300
SEQID No 1      (249)   SYVRSQTGKPLFTVGEYWSYDINKLHNYITKTNGTMSLFDAPLHNKFYTA
SEQID No 2      (249)   SYVRSQTGKPLFTVGEYWSYDINKLHNYITKTNGTMSLFDAPLHNKFYTA
SEQID No 3      (249)   SYVRSQTGKPLFTVGEYWSYDINKLHNYITKTNGTMSLFDAPLHNKFYTA
SEQID No 4      (249)   SYVRSQTGKPLFTVGEYWSYDINKLHNYITKTNGTMSLFDAPLHNKFYTA
SEQID No 5      (249)   SYVRSQTGKPLFTVGEYWSYDINKLHNYITKTNGTMSLFDAPLHNKFYTA
SEQID No 6      (251)   NHVRSATGKNMFAVAEFWKNDLGAIENYLQKTNWNHSVFDVPLHYNLYNA
SEQID No 7      (246)   NHVREKTGKEMFTVAEYWQNDLGALENYLNKTNFNHSVFDVPLHYQFHAA
SEQID No 8      (246)   NHVREKTGKEMFTVAEYWQNDLGALENYLNKTNFNHSVFDVPLHYQFHAA
SEQID No 9      (246)   QAVRQATGKEMFTVAEYWQNNAGKLENYLNKTSFNQSVFDVPLHFNLQAA
SEQID No 10     (251)   NHVRSATGKNMFAVAEFWKNDLGAIENYLNKTNWNHSVFDVPLHYNLYNA
SEQID No 11     (251)   THVRNATGKEMFAVAEFWKNDLGALENYLNKTNWNHSVFDVPLHYNLYNA
SEQID No 12     (251)   THVRNTTGKPMFAVAEFWKNDLAAIENYLNKTSWNHSVFDVPLHYNLYNA
SEQID No 13     (246)   RHQRNEADQDLFVVGEYWKDDVGALEFYLDEMNWEMSLFDVPLNYNFYRA
SEQID No 14     (246)   RHQRSEADQDLFVVGEYWKDDVGALEFYLDEMNWEMSLFDVPLNYNFYRA
SEQID No 15     (247)   SYVRSQTGKPLFTVGEYWSYDINKLHNYITKTNGTMSLFDAPLHNKFYTA
Consensus 1     (251)   SHVRS TGK LFTVGEYW  DIGALENYL KTNW MSLFDVPLHYNFY A
```

Figure 1 (2 of 4)

```
                        301                                               350
SEQID No  1   (299) SKSGGAFDMRTLMTNTLMKDQPTLAVTFVDNHDTEPGQALQSWVDPWFKP
SEQID No  2   (299) SKSGGAFDMRTLMTNTLMKDQPTLAVTFVDNHDTEPGQALQSWVDPWFKP
SEQID No  3   (299) SKSGGAFDMRTLMTNTLMKDQPTLAVTFVDNHDTEPGQALQSWVDPWFKP
SEQID No  4   (299) SKSGGAFDMRTLMTNTLMKDQPTLAVTFVDNHDTEPGQALQSWVDPWFKP
SEQID No  5   (299) SKSGGAFDMRTLMTNTLMKDQPTLAVTFVDNHDTEPGQALQSWVDPWFKP
SEQID No  6   (301) SKSGGNYDMRNIFNGTVVQRHPSHAVTFVDNHDSQPEEALESFVEEWFKP
SEQID No  7   (296) STQGGGYDMRKLLNGTVVSKHPLKSVTFVDNHDTQPGQSLESTVQTWFKP
SEQID No  8   (296) STQGGGYDMRKLLNGTVVSKHPLKSVTFVDNHDTQPGQSLESTVQTWFKP
SEQID No  9   (296) SSQGGGYDMRRLLDGTVVSRHPEKAVTFVENHDTQPGQSLESTVQTWFKP
SEQID No 10   (301) SKSGGNYDMRQIFNGTVVQRHPMHAVTFVDNHDSQPEEALESFVEEWFKP
SEQID No 11   (301) SNSGGNYDMAKLLNGTVVQKHPMHAVTFVDNHDSQPGESLESFVQEWFKP
SEQID No 12   (301) SNSGGYFDMRNILNGSVVQKHPIHAVTFVDNHDSQPGEALESFVQSWFKP
SEQID No 13   (296) SQQGGSYDMRNILRGSLVEAHPMHAVTFVDNHDTQPGESLESWVADWFKP
SEQID No 14   (296) SKQGGSYDMRNILRGSLVEAHPIHAVTFVDNHDTQPGESLESWVADWFKP
SEQID No 15   (297) SKSGGAFDMRTLMTNTLMKDQPTLAVTFVDNHDTEPGQALQSWVDPWFKP
Consensus 1   (301) SKSGGAYDMR LL GTLV  HP   AVTFVDNHDTQPGQALESWVD WFKP
                        351                                               400
SEQID No  1   (349) LAYAFILTRQEGYPCVFYGDYYGIPQYN---IPSLKSKIDPLLIARRDYA
SEQID No  2   (349) LAYAFILTRQEGYPCVFYGDYYGIPQYN---IPSLKSKIDPLLIARRDYA
SEQID No  3   (349) LAYAFILTRQEGYPCVFYGDYYGIPQYN---IPSLKSKIDPLLIARRDYA
SEQID No  4   (349) LAYAFILTRQEGYPCVFYGDYYGIPQYN---IPSLKSKIDPLLIARRDYA
SEQID No  5   (349) LAYAFILTRQEGYPCVFYGDYYGIPQYN---IPSLKSKIDPLLIARRDYA
SEQID No  6   (351) LAYALTLTREQGYPSVFYGDYYGIPTHG---VPAMRSKIDPILEARQKYA
SEQID No  7   (346) LAYAFILTRESGYPQVFYGDMYGTKGDSQREIPALKHKIEPILKARKQYA
SEQID No  8   (346) LAYAFILTRESGYPQVFYGDMYGTKGDSQREIPALKHKIEPILKARKQYA
SEQID No  9   (346) LAYAFILTRESGYPQVFYGDMYGTKGTSPKEIPSLKDNIEPILKARKEYA
SEQID No 10   (351) LAYALTLTREQGYPSVFYGDYYGIPTHG---VPAMKSKIDPILEARQKYA
SEQID No 11   (351) LAYALILTREQGYPSVFYGDYYGIPTHS---VPAMKAKIDPILEARQNFA
SEQID No 12   (351) LAYALILTREQGYPSVFYGDYYGIPTHG---VPSMKSKIDPLLQARQTYA
SEQID No 13   (346) LAYATILTREGGYPNVFYGDYYGIPNDN---ISAKKDMIDELLDARQNYA
SEQID No 14   (346) LAYATILTREGGYPNVFYGDYYGIPNDN---ISAKKDMIDELLDARQNYA
SEQID No 15   (347) LAYAFILTRQEGYPCVFYGDYYGIPQYN---IPSLKSKIDPLLIARRDYA
Consensus 1   (351) LAYAFILTRE GYP VFYGDYYGIPQYN   IPSLKSKIDPLL ARR YA
                        401                                               450
SEQID No  1   (396) YGTQHDYLDHSDIIGWTREGVTEKPGSGLAALITDGPGGSKWMYVGKQHA
SEQID No  2   (396) YGTQHDYLDHSDIIGWTREGVTEKPGSGLAALITDGPGGSKWMYVGKQHA
SEQID No  3   (396) YGTQHDYLDHSDIIGWTREGVTEKPGSGLAALITDGPGGSKWMYVGKQHA
SEQID No  4   (396) YGTQHDYLDHSDIIGWTREGVTEKPGSGLAALITDGPGGSKWMYVGKQHA
SEQID No  5   (396) YGTQHDYLDHSDIIGWTREGVTEKPGSGLAALITDGPGGSKWMYVGKQHA
SEQID No  6   (398) YGKQNDYLDHHNIIGWTREGNTAHPNSGLATIMSDGAGGSKWMFVGRNKA
SEQID No  7   (396) YGAQHDYFDHHDIVGWTREGDSSVANSGLAALITDGPGGAKRMYVGRQNA
SEQID No  8   (396) YGAQHDYFDHHDIVGWTREGDSSVANSGLAALITDGPGGAKRMYVGRQNA
SEQID No  9   (396) YGPQHDYIDHPDVIGWTREGDSSAAKSGLAALITDGPGGSKRMYAGLKNA
SEQID No 10   (398) YGRQNDYLDHHNIIGWTREGNTAHPNSGLATIMSDGAGGNKWMFVGRNKA
SEQID No 11   (398) YGTQHDYFDHHNIIGWTREGNTTHPNSGLATIMSDGPGGEKWMYVGQNKA
SEQID No 12   (398) YGTQHDYFDHHDIIGWTREGDSSHPNSGLATIMSDGPGGNKWMYVGKHKA
SEQID No 13   (393) YGTQHDYFDHWDVVGWTREGSSSRPNSGLATIMSNGPGGSKWMYVGRQNA
SEQID No 14   (393) YGTQHDYFDHWDIVGWTREGTSSRPNSGLATIMSNGPGGSKWMYVGQQHA
SEQID No 15   (394) YGTQHDYLDHSDIIGWTREGGTEKPGSGLAALITDGPGGSKWMYVGKQHA
Consensus 1   (401) YGTQHDYLDH DIIGWTREG TSKPNSGLAALITDGPGGSKWMYVGKQ A
```

Figure 1 (3 of 4)

```
                   451                                              500
SEQID No  1 (446)  GKVFYDLTGNRSDTVTINSDGWGEFKVNGGSVSVWVPRKTTVSTIARPIT
SEQID No  2 (446)  GKVFYDLTGNRSDTVTINSDGWGEFKVNGGSVSVWVPRKTT---------
SEQID No  3 (446)  GKVFYDLTGNRSDTVTINSDGWGEFKVNGGSVSVWVPRKTTVSTIARPIT
SEQID No  4 (446)  GKVFYDLTGNRSDTVTINSDGWGEFKVNGGSVSVWVPRKTTVSTIARPIT
SEQID No  5 (446)  GKVFYDLTGNRSDTVTINSDGWGEFKVNGGSVSVWVPRKTTVSTIARPIT
SEQID No  6 (448)  GQVWSDITGNRTGTVTINADGWGNFSVNGGSVSIWVNK------------
SEQID No  7 (446)  GETWHDITGNRSEPVVINSEGWGEFHVNGGSVSIYVQR------------
SEQID No  8 (446)  GETWHDITGNRSEPVVINSEGWGEFHVNGGSVSIYVQR------------
SEQID No  9 (446)  GETWYDITGNRSDTVKIGSDGWGEFHVNDGSVSIYVQK------------
SEQID No 10 (448)  GQVWTDITGNRAGTVTINADGWGNFSVNGGSVSIWVNK------------
SEQID No 11 (448)  GQVWHDITGNKPGTVTINADGWANFSVNGGSVSIWVKR------------
SEQID No 12 (448)  GQVWRDITGNRSGTVTINADGWGNFTVNGGAVSVWVKQ------------
SEQID No 13 (443)  GQTWDDLTGNNGASVTINGDGWGEFFTNGGSVSVYVNQ------------
SEQID No 14 (443)  GQTWTDLTGNHAASVTINGDGWGEFFTNGGSVSVYVNQ------------
SEQID No 15 (444)  GKVFYDLTGNRSDTVTINSDGWGEFKVNGGSVSVWVPRKTTVS-------
Consensus 1 (451)  G VWYDLTGNRSDTVTINSDGWGEF VNGGSVSVWV R
                   501        520
SEQID No  1 (496)  TRPWTGEFVRWTEPRLVAWP
SEQID No  2 (487)  --------------------
SEQID No  3 (496)  TRPWTGEFVRWTEPRLVAWP
SEQID No  4 (496)  TRPWTGEFVRWTEPRLVAWP
SEQID No  5 (496)  TRPWTGEFVRWTEPRLVAWP
SEQID No  6 (486)  --------------------
SEQID No  7 (484)  --------------------
SEQID No  8 (484)  --------------------
SEQID No  9 (484)  --------------------
SEQID No 10 (486)  --------------------
SEQID No 11 (486)  --------------------
SEQID No 12 (486)  --------------------
SEQID No 13 (481)  --------------------
SEQID No 14 (481)  --------------------
SEQID No 15 (487)  --------------------
Consensus 1 (501)
```

Figure 1 (4 of 4)

```
                        1                                                50
SEQID No 1    (1)   -AAPFNGTMMQYFEWYLPDDGTLWTKVANEANNLSSLGITALWLPPAYKG
SEQID No 6    (1)   HHNGTNGTMMQYFEWYLPNDGNHWNRLNSDASNLKSKGITAVWIPPAWKG
 Consensus 2  (1)         NGTMMQYFEWYLP DG  W KL  DA NL S GITALWIPPAWKG
                        51                                              100
SEQID No 1   (50)   TSRSDVGYGVYDLYDLGEFNQKGTVRTKYGTKAQYLQAIQAAHAAGMQVY
SEQID No 6   (51)   ASQNDVGYGAYDLYDLGEFNQKGTVRTKYGTRSQLQAAVTSLKNNGIQVY
 Consensus 2 (51)    S  DVGYG YDLYDLGEFNQKGTVRTKYGTKAQ    AI A    GIQVY
                       101                                              150
SEQID No 1  (100)   ADVVFDHKGGADGTEWVDAVEVNPSDRNQEISGTYQIQAWTKFDFPGRGN
SEQID No 6  (101)   GDVVMNHKGGADATEMVRAVEVNPNNRNQEVTGEYTIEAWTRFDFPGRGN
 Consensus 2 (101)  ADVV  HKGGADATE V AVEVNP  RNQEISG Y I AWTKFDFPGRGN
                       151                                              200
SEQID No 1  (150)   TYSSFKWRWYHFDGVDWDESRKLS-RIYKFRGIGKAWDWEVDTENGNYDY
SEQID No 6  (151)   THSSFKWRWYHFDGVDWDQSRRLNNRIYKFRGHGKAWDWEVDTENGNYDY
 Consensus 2 (151)  THSSFKWRWYHFDGVDWD SRKL  RIYKFRG GKAWDWEVDTENGNYDY
                       201                                              250
SEQID No 1  (199)   LMYADLDMDHPEVVTELKNWGKWYVNTTNIDGFRLDAVKHIKFSFFPDWL
SEQID No 6  (201)   LMYADIDMDHPEVVNELRNWGVWYTNTLGLDGFRIDAVKHIKYSFTRDWI
 Consensus 2 (201)  LMYADIDMDHPEVV ELKNWG WY NT   IDGFRIDAVKHIKFSF  DWI
                       251                                              300
SEQID No 1  (249)   SYVRSQTGKPLFTVGEYWSYDINKLHNYITKTNGTMSLFDAPLHNKFYTA
SEQID No 6  (251)   NHVRSATGKNMFAVAEFWKNDLGAIENYLQKTNWNHSVFDVPLHYNLYNA
 Consensus 2 (251)   HVRS TGK LF VAEFW  DI I NYI KTN   SLFD PLH  Y  A
                       301                                              350
SEQID No 1  (299)   SKSGGAFDMRTLMTNTLMKDQPTLAVTFVDNHDTEPGQALQSWVDPWFKP
SEQID No 6  (301)   SKSGGNYDMRNIFNGTVVQRHPSHAVTFVDNHDSQPEEALESFVEEWFKP
 Consensus 2 (301)  SKSGG FDMR I   TLM   PS AVTFVDNHDS P AL SFVD WFKP
                       351                                              400
SEQID No 1  (349)   LAYAFILTRQEGYPCVFYGDYYGIPQYNIPSLKSKIDPLLIARRDYAYGT
SEQID No 6  (351)   LAYALTLTREQGYPSVFYGDYYGIPTHGVPAMRSKIDPILEARQKYAYGK
 Consensus 2 (351)  LAYA  LTR GYP VFYGDYYGIP H IPALKSKIDPIL AR  YAYG
                       401                                              450
SEQID No 1  (399)   QHDYLDHSDIIGWTREGVTEKPGSGLAALITDGPGGSKWMYVGKQHAGKV
SEQID No 6  (401)   QNDYLDHHNIIGWTREGNTAHPNSGLATIMSDGAGGSKWMFVGRNKAGQV
 Consensus 2 (401)  Q DYLDH  IIGWTREG T  P SGLA IISDG GGSKWMFVGKN AG V
                       451                                              500
SEQID No 1  (449)   FYDLTGNRSDTVTINSDWGEFKVNGGSVSVWVPRKTTVSTIARPITTRP
SEQID No 6  (451)   WSDITGNRTGTVTINADGWGNFSVNGGSVSIWVNK---------------
 Consensus 2 (451)  F DITGNRS TVTINADGWG F VNGGSVSIWV K
                       501        517
SEQID No 1  (499)   WTGEFVRWTEPRLVAWP
SEQID No 6  (486)   -----------------
 Consensus 2 (501)
```

Figure 4A

|  |  | 1 | 50 |
|---|---|---|---|
| SEQID No 1 | (1) | AAPFNGTMMQYFEWYLPDDGTLWTKVANEANNLSSLGITALWLPPAYKGT | |
| SEQID No 8 | (1) | -ANLNGTLMQYFEWYMPNDGQHWRRLQNDSAYLAEHGITAVWIPPAYKGT | |
| Consensus 3 | (1) | A NGTLMQYFEWYLP DG W KL NDA LA GITALWIPPAYKGT | |
|  |  | 51 | 100 |
| SEQID No 1 | (51) | SRSDVGYGVYDLYDLGEFNQKGTVRTKYGTKAQYLQAIQAAHAAGMQVYA | |
| SEQID No 8 | (50) | SQADVGYGAYDLYDLGEFHQKGTVRTKYGTKGELQSAIKSLHSRDINVYG | |
| Consensus 3 | (51) | S ADVGYG YDLYDLGEF QKGTVRTKYGTKA AI A HA INVYA | |
|  |  | 101 | 150 |
| SEQID No 1 | (101) | DVVFDHKGGADGTEWVDAVEVNPSDRNQEISGTYQIQAWTKFDFPGRGNT | |
| SEQID No 8 | (100) | DVVINHKGGADATEDVTAVEVDPADRNRVISGEHLIKAWTHFHFPGRGST | |
| Consensus 3 | (101) | DVV HKGGADATE V AVEV PADRN ISG H I AWT F FPGRG T | |
|  |  | 151 | 200 |
| SEQID No 1 | (151) | YSSFKWRWYHFDGVDWDESRKLSRIYKFRGIGKAWDWEVDTENGNYDYLM | |
| SEQID No 8 | (150) | YSDFKWHWYHFDGTDWDESRKLNRIYKFQ--GKAWDWEVSNENGNYDYLM | |
| Consensus 3 | (151) | YS FKW WYHFDG DWDESRKL RIYKF GKAWDWEV ENGNYDYLM | |
|  |  | 201 | 250 |
| SEQID No 1 | (201) | YADLDMDHPEVVTELKNWGKWYVNTTNIDGFRLDAVKHIKFSFFPDWLSY | |
| SEQID No 8 | (198) | YADIDYDHPDVAAEIKRWGTWYANELQLDGFRLDAVKHIKFSFLRDWVNH | |
| Consensus 3 | (201) | YADID DHPDV EIK WG WY N NIDGFRLDAVKHIKFSF DWL H | |
|  |  | 251 | 300 |
| SEQID No 1 | (251) | VRSQTGKPLFTVGEYWSYDINKLHNYITKTNGTMSLFDAPLHNKFYTASK | |
| SEQID No 8 | (248) | VREKTGKEMFTVAEYWQNDLGALENYLNKTNFNHSVFDVPLHYQFHAAST | |
| Consensus 3 | (251) | VR TGK LFTVAEYW DI L NYI KTN SLFD PLH FH AS | |
|  |  | 301 | 350 |
| SEQID No 1 | (301) | SGGAFDMRTLMTNTLMKDQPTLAVTFVDNHDTEPGQALQSWVDPWFKPLA | |
| SEQID No 8 | (298) | QGGGYDMRKLLNGTVVSKHPLKSVTFVDNHDTQPGQSLESTVQTWFKPLA | |
| Consensus 3 | (301) | GGAFDMR LL TLM P AVTFVDNHDT PGQAL S V WFKPLA | |
|  |  | 351 | 400 |
| SEQID No 1 | (351) | YAFILTRQEGYPCVFYGDYYGIP---QYNIPSLKSKIDPLLIARRDYAYG | |
| SEQID No 8 | (348) | YAFILTRESGYPQVFYGDMYGTKGDSQREIPALKHKIEPILKARKQYAYG | |
| Consensus 3 | (351) | YAFILTR GYP VFYGD YG Q IPALK KIDPIL ARK YAYG | |
|  |  | 401 | 450 |
| SEQID No 1 | (398) | TQHDYLDHSDIIGWTREGVTEKPGSGLAALITDGPGGSKWMYVGKQHAGK | |
| SEQID No 8 | (398) | AQHDYFDHHDIVGWTREGDSSVANSGLAALITDGPGGAKRMYVGRQNAGE | |
| Consensus 3 | (401) | QHDY DH DIIGWTREG S SGLAALITDGPGGAK MYVGKQ AG | |
|  |  | 451 | 500 |
| SEQID No 1 | (448) | VFYDLTGNRSDTVTINSDGWGEFKVNGGSVSVWVPRKTTVSTIARPITTR | |
| SEQID No 8 | (448) | TWHDITGNRSEPVVINSEGWGEFHVNGGSVSIYVQR-------------- | |
| Consensus 3 | (451) | FHDITGNRSD V INSDGWGEF VNGGSVSIWV R | |
|  |  | 501 | 518 |
| SEQID No 1 | (498) | PWTGEFVRWTEPRLVAWP | |
| SEQID No 8 | (484) | ------------------ | |
| Consensus 3 | (501) | | |

Figure 4B

```
                           1                                               50
SEQID No 1      (1)   AAPFNGTMMQYFEWYLPDDGTLWTKVANEANNLSSLGITALWLPPAYKGT
SEQID No 9      (1)   ---VNGTLMQYFEWYTPNDGQHWKRLQNDAEHLSDIGITAVWIPPAYKGL
Consensus 4     (1)         NGTLMQYFEWY P DG  W KL NDA   LS IGITALWIPPAYKG
                           51                                             100
SEQID No 1     (51)   SRSDVGYGVYDLYDLGEFNQKGTVRTKYGTKAQYLQAIQAAHAAGMQVYA
SEQID No 9     (48)   SQSDNGYGPYDLYDLGEFQQKGTVRTKYGTKSELQDAIGSLHSRNVQVYG
Consensus 4    (51)   S SD GYG YDLYDLGEFNQKGTVRTKYGTKA    AI A HA  MQVYA
                          101                                             150
SEQID No 1    (101)   DVVFDHKGGADGTEWVDAVEVNPSDRNQEISGTYQIQAWTKFDFPGRGNT
SEQID No 9     (98)   DVVLNHKAGADATEDVTAVEVNPANRNQETSEEYQIKAWTDFRFPGRGNT
Consensus 4   (101)   DVV  HKAGADATE V AVEVNPA RNQE S  YQI AWT F FPGRGNT
                          151                                             200
SEQID No 1    (151)   YSSFKWRWYHFDGVDWDESRKLSRIYKFRGIGKAWDWEVDTENGNYDYLM
SEQID No 9    (148)   YSDFKWHWYHFDGADWDESRKISRIFKFRGEGKAWDWEVSSENGNYDYLM
Consensus 4   (151)   YS FKW WYHFDG DWDESRKISRIFKFRG GKAWDWEV SENGNYDYLM
                          201                                             250
SEQID No 1    (201)   YADLDMDHPEVVTELKNWGKWYVNTTNIDGFRLDAVKHIKFSFFPDWLSY
SEQID No 9    (198)   YADVDYDHPDVVAETKKWGIWYANELSLDGFRIDAAKHIKFSFLRDWVQA
Consensus 4   (201)   YADLD DHPDVV E K WG WY N   IDGFRIDA KHIKFSF  DWL
                          251                                             300
SEQID No 1    (251)   VRSQTGKPLFTVGEYWSYDINKLHNYITKTNGTMSLFDAPLHNKFYTASK
SEQID No 9    (248)   VRQATGKEMFTVAEYWQNNAGKLENYLNKTSFNQSVFDVPLHFNLQAASS
Consensus 4   (251)   VR  TGK  LFTVAEYW    KL NYI KT   SLFD PLH       AS
                          301                                             350
SEQID No 1    (301)   SGGAFDMRTLMTNTLMKDQPTLAVTFVDNHDTEPGQALQSWVDPWFKPLA
SEQID No 9    (298)   QGGGYDMRRLLDGTVVSRHPEKAVTFVENHDTQPGQSLESTVQTWFKPLA
Consensus 4   (301)    GGAFDMR LL  TLM   P  AVTFVDNHDT PGQAL S V  WFKPLA
                          351                                             400
SEQID No 1    (351)   YAFILTRQEGYPCVFYGDYYGIPQYN---IPSLKSKIDPLLIARRDYAYG
SEQID No 9    (348)   YAFILTRESGYPQVFYGDMYGTKGTSPKEIPSLKDNIEPILKARKEYAYG
Consensus 4   (351)   YAFILTR  GYP VFYGD YG        IPSLK  IDPIL ARKDYAYG
                          401                                             450
SEQID No 1    (398)   TQHDYLDHSDIIGWTREGVTEKPGSGLAALITDGPGGSKWMYVGKQHAGK
SEQID No 9    (398)   PQHDYIDHPDVIGWTREGDSSAAKSGLAALITDGPGGSKRMYAGLKNAGE
Consensus 4   (401)    QHDYIDH DIIGWTREG S    SGLAALITDGPGGSK MY G   AG
                          451                                             500
SEQID No 1    (448)   VFYDLTGNRSDTVTINSDGWGEFKVNGGSVSVWVPRKTTVSTIARPITTR
SEQID No 9    (448)   TWYDITGNRSDTVKIGSDGWGEFHVNDGSVSIYVQK--------------
Consensus 4   (451)     FYDITGNRSDTV I SDGWGEF VN GSVSIWV K
                          501            518
SEQID No 1    (498)   PWTGEFVRWTEPRLVAWP
SEQID No 9    (484)   ------------------
Consensus 4   (501)
```

Figure 4C

|                |       | 1                                                   50 |
|----------------|-------|---------------------------------------------------------|
| SEQID No 1     | (1)   | -AAPFNGTMMQYFEWYLPDDGTLWTKVANEANNLSSLGITALWLPPAYKG       |
| SEQID No 10    | (1)   | HHNGTNGTMMQYFEWYLPNDGNHWNRLRSDASNLKDKGISAVWIPPAWKG       |
| Consensus 5    | (1)   |     NGTMMQYFEWYLP DG  W KL  DA NL    GISALWIPPAWKG |
|                |       | 51                                                 100 |
| SEQID No 1     | (50)  | TSRSDVGYGVYDLYDLGEFNQKGTVRTKYGTKAQYLQAIQAAHAAGMQVY       |
| SEQID No 10    | (51)  | ASQNDVGYGAYDLYDLGEFNQKGTIRTKYGTRNQLQAAVNALKSNGIQVY       |
| Consensus 5    | (51)  | S  DVGYG YDLYDLGEFNQKGTIRTKYGTK Q   AINA  A GIQVY        |
|                |       | 101                                                150 |
| SEQID No 1     | (100) | ADVVFDHKGGADGTEWVDAVEVNPSDRNQEISGTYQIQAWTKFDFPGRGN       |
| SEQID No 10    | (101) | GDVVMNHKGGADATEMVRAVEVNPNNRNQEVSGEYTIEAWTKFDFPGRGN       |
| Consensus 5    | (101) | ADVV   HKGGADATE V AVEVNP  RNQEISG Y I AWTKFDFPGRGN      |
|                |       | 151                                                200 |
| SEQID No 1     | (150) | TYSSFKWRWYHFDGVDWDESRKLS-RIYKFRGIGKAWDWEVDTENGNYDY       |
| SEQID No 10    | (151) | THSNFKWRWYHFDGVDWDQSRKLNNRIYKFRGDGKGWDWEVDTENGNYDY       |
| Consensus 5    | (151) | THS FKWRWYHFDGVDWD SRKL  RIYKFRG GKAWDWEVDTENGNYDY       |
|                |       | 201                                                250 |
| SEQID No 1     | (199) | LMYADLDMDHPEVVTELKNWGKWYVNTTNIDGFRLDAVKHIKFSFFPDWL       |
| SEQID No 10    | (201) | LMYADIDMDHPEVVNELRNWGVWYTNTLGLDGFRIDAVKHIKYSFTRDWI       |
| Consensus 5    | (201) | LMYADIDMDHPEVV ELKNWG WY NT  IDGFRIDAVKHIKFSF   DWI      |
|                |       | 251                                                300 |
| SEQID No 1     | (249) | SYVRSQTGKPLFTVGEYWSYDINKLHNYITKTNGTMSLFDAPLHNKFYTA       |
| SEQID No 10    | (251) | NHVRSATGKNMFAVAEFWKNDLGAIENYLNKTNWNHSVFDVPLHYNLYNA       |
| Consensus 5    | (251) | HVRS TGK LF VAEFW  DI  I NYI KTN    SLFD PLH   Y A       |
|                |       | 301                                                350 |
| SEQID No 1     | (299) | SKSGGAFDMRTLMTNTLMKDQPTLAVTFVDNHDTEPGQALQSWVDPWFKP       |
| SEQID No 10    | (301) | SKSGGNYDMRQIFNGTVVQRHPMHAVTFVDNHDSQPEEALESFVEEWFKP       |
| Consensus 5    | (301) | SKSGG FDMR I    TLM  P  AVTFVDNHDS P  AL SFVD WFKP       |
|                |       | 351                                                400 |
| SEQID No 1     | (349) | LAYAFILTRQEGYPCVFYGDYYGIPQYNIPSLKSKIDPLLIARRDYAYGT       |
| SEQID No 10    | (351) | LAYALTLTREQGYPSVFYGDYYGIPTHGVPAMKSKIDPILEARQKYAYGR       |
| Consensus 5    | (351) | LAYA  LTR  GYP VFYGDYYGIP H IPALKSKIDPIL AR   YAYG       |
|                |       | 401                                                450 |
| SEQID No 1     | (399) | QHDYLDHSDIIGWTREGVTEKPGSGLAALITDGPGGSKWMYVGKQHAGKV       |
| SEQID No 10    | (401) | QNDYLDHHNIIGWTREGNTAHPNSGLATIMSDGAGGNKWMFVGRNKAGQV       |
| Consensus 5    | (401) | Q DYLDH   IIGWTREG T  P SGLA IISDG GG KWMFVGKN AG V      |
|                |       | 451                                                500 |
| SEQID No 1     | (449) | FYDLTGNRSDTVTINSDGWGEFKVNGGSVSWVPRKTTVSTIARPITTRP        |
| SEQID No 10    | (451) | WTDITGNRAGTVTINADGWGNFSVNGGSVSIWVNK--------------        |
| Consensus 5    | (451) | F DITGNRA TVTINADGWG F VNGGSVSIWV K                      |
|                |       | 501                         517                         |
| SEQID No 1     | (499) | WTGEFVRWTEPRLVAWP                                        |
| SEQID No 10    | (486) | -----------------                                       |
| Consensus 5    | (501) |                                                         |

Figure 4D

```
                            1                                                 50
SEQID No 1     (1)    -AAPFNGTMMQYFEWYLPDDGTLWTKVANEANNLSSLGITALWLPPAYKG
SEQID No 11    (1)    HHNGTNGTMMQYFEWHLPNDGNHWNRLRDDASNLRNRGITAIWIPPAWKG
 Consensus 6   (1)            NGTMMQYFEWHLP DG  W KL  DA NL  GITAIWIPPAWKG
                           51                                                100
SEQID No 1    (50)    TSRSDVGYGVYDLYDLGEFNQKGTVRTKYGTKAQYLQAIQAAHAAGMQVY
SEQID No 11   (51)    TSQNDVGYGAYDLYDLGEFNQKGTVRTKYGTRSQLESAIHALKNNGVQVY
 Consensus 6  (51)    TS  DVGYG YDLYDLGEFNQKGTVRTKYGTKAQ    AI A    GMQVY
                          101                                                150
SEQID No 1   (100)    ADVVFDHKGGADGTEWVDAVEVNPSDRNQEISGTYQIQAWTKFDFPGRGN
SEQID No 11  (101)    GDVVMNHKGGADATENVLAVEVNPNNRNQEISGDYTIEAWTKFDFPGRGN
 Consensus 6 (101)    ADVV  HKGGADATE V AVEVNP  RNQEISG Y I AWTKFDFPGRGN
                          151                                                200
SEQID No 1   (150)    TYSSFKWRWYHFDGVDWDESR-KLSRIYKFRGIGKAWDWEVDTENGNYDY
SEQID No 11  (151)    TYSDFKWRWYHFDGVDWDQSRQFQNRIYKFRGDGKAWDWEVDSENGNYDY
 Consensus 6 (151)    TYS FKWRWYHFDGVDWD SR     RIYKFRG GKAWDWEVDSENGNYDY
                          201                                                250
SEQID No 1   (199)    LMYADLDMDHPEVVTELKNWGKWYVNTTNIDGFRLDAVKHIKFSFFPDWL
SEQID No 11  (201)    LMYADVDMDHPEVVNELRRWGEWYTNTLNLDGFRIDAVKHIKYSFTRDWL
 Consensus 6 (201)    LMYADLDMDHPEVV ELK WG WY NT NIDGFRIDAVKHIKFSF  DWL
                          251                                                300
SEQID No 1   (249)    SYVRSQTGKPLFTVGEYWSYDINKLHNYITKTNGTMSLFDAPLHNKFYTA
SEQID No 11  (251)    THVRNATGKEMFAVAEFWKNDLGALENYLNKTNWNHSVFDVPLHYNLYNA
 Consensus 6 (251)    SHVR  TGK LF VAEFW  DI L NYI KTN   SLFD PLH  Y A
                          301                                                350
SEQID No 1   (299)    SKSGGAFDMRTLMTNTLMKDQPTLAVTFVDNHDTEPGQALQSWVDPWFKP
SEQID No 11  (301)    SNSGGNYDMAKLLNGTVVQKHPMHAVTFVDNHDSQPGESLESFVQEWFKP
 Consensus 6 (301)    S SGG  FDM   LL  TLM    P  AVTFVDNHDS PG AL SFV  WFKP
                          351                                                400
SEQID No 1   (349)    LAYAFILTRQEGYPCVFYGDYYGIPQYNIPSLKSKIDPLLIARRDYAYGT
SEQID No 11  (351)    LAYALILTREQGYPSVFYGDYYGIPTHSVPAMKAKIDPILEARQNFAYGT
 Consensus 6 (351)    LAYA ILTR  GYP VFYGDYYGIP H  IPALKAKIDPIL AR  FAYGT
                          401                                                450
SEQID No 1   (399)    QHDYLDHSDIIGWTREGVTEKPGSGLAALITDGPGGSKWMYVGKQHAGKV
SEQID No 11  (401)    QHDYFDHHNIIGWTREGNTTHPNSGLATIMSDGPGGEKWMYVGQNKAGQV
 Consensus 6 (401)    QHDY DH  IIGWTREG T  P SGLA IISDGPGG KWMYVG N AG V
                          451                                                500
SEQID No 1   (449)    FYDLTGNRSDTVTINSDGWGEFKVNGGSVSWVPRKTTVSTIARPITTRP
SEQID No 11  (451)    WHDITGNKPGTVTINADGWANFSVNGGSVSIWVKR---------------
 Consensus 6 (451)    FHDITGNK  TVTINADGWA F VNGGSVSIWV R
                          501           517
SEQID No 1   (499)    WTGEFVRWTEPRLVAWP
SEQID No 11  (486)    -----------------
 Consensus 6 (501)
```

Figure 4E

```
                             1                                               50
SEQID No 1      (1)  -AAPFNGTMMQYFEWYLPDDGTLWTKVANEANNLSSLGITALWLPPAYKG
SEQID No 12     (1)  HHNGTNGTMMQYFEWHLPNDGNHWNRLRDDAANLKSKGITAVWIPPAWKG
  Consensus 7   (1)       NGTMMQYFEWHLP DG  W KL  DA NL S GITALWIPPAWKG
                            51                                              100
SEQID No 1     (50)  TSRSDVGYGVYDLYDLGEFNQKGTVRTKYGTKAQYLQAIQAAHAAGMQVY
SEQID No 12    (51)  TSQNDVGYGAYDLYDLGEFNQKGTVRTKYGTRSQLQGAVTSLKNNGIQVY
  Consensus 7  (51)  TS DVGYG YDLYDLGEFNQKGTVRTKYGTKAQ    AI A    GIQVY
                           101                                              150
SEQID No 1    (100)  ADVVFDHKGGADGTEWVDAVEVNPSDRNQEISGTYQIQAWTKFDFPGRGN
SEQID No 12   (101)  GDVVMNHKGGADGTEMVNAVEVNRSNRNQEISGEYTIEAWTKFDFPGRGN
  Consensus 7 (101)  ADVV  HKGGADGTE V AVEVN S RNQEISG Y I AWTKFDFPGRGN
                           151                                              200
SEQID No 1    (150)  TYSSFKWRWYHFDGVDWDESR-KLSRIYKFRGIGKAWDWEVDTENGNYDY
SEQID No 12   (151)  THSNFKWRWYHFDGTDWDQSRQLQNKIYKFRGTGKAWDWEVDIENGNYDY
  Consensus 7 (151)  THS FKWRWYHFDG DWD SR    KIYKFRG GKAWDWEVD ENGNYDY
                           201                                              250
SEQID No 1    (199)  LMYADLDMDHPEVVTELKNWGKWYVNTTNIDGFRLDAVKHIKFSFFPDWL
SEQID No 12   (201)  LMYADIDMDHPEVINELRNWGVWYTNTLNLDGFRIDAVKHIKYSYTRDWL
  Consensus 7 (201)  LMYADIDMDHPEVI ELKNWG WY NT NIDGFRIDAVKHIKFSF  DWL
                           251                                              300
SEQID No 1    (249)  SYVRSQTGKPLFTVGEYWSYDINKLHNYITKTNGTMSLFDAPLHNKFYTA
SEQID No 12   (251)  THVRNTTGKPMFAVAEFWKNDLAAIENYLNKTSWNHSVFDVPLHYNLYNA
  Consensus 7 (251)  SHVR  TGKPLF VAEFW  DI  I NYI KT    SLFD PLH  Y A
                           301                                              350
SEQID No 1    (299)  SKSGGAFDMRTLMTNTLMKDQPTLAVTFVDNHDTEPGQALQSWVDPWFKP
SEQID No 12   (301)  SNSGGYFDMRNILNGSVVQKHPIHAVTFVDNHDSQPGEALESFVQSWFKP
  Consensus 7 (301)  S SGG FDMR IL  SLM   P  AVTFVDNHDS PG AL SFV  WFKP
                           351                                              400
SEQID No 1    (349)  LAYAFILTRQEGYPCVFYGDYYGIPQYNIPSLKSKIDPLLIARRDYAYGT
SEQID No 12   (351)  LAYALILTREQGYPSVFYGDYYGIPTHGVPSMKSKIDPLLQARQTYAYGT
  Consensus 7 (351)  LAYA ILTR  GYP VFYGDYYGIP H IPSLKSKIDPLL AR  YAYGT
                           401                                              450
SEQID No 1    (399)  QHDYLDHSDIIGWTREGVTEKPGSGLAALITDGPGGSKWMYVGKQHAGKV
SEQID No 12   (401)  QHDYFDHHDIIGWTREGDSSHPNSGLATIMSDGPGGNKWMYVGKHKAGQV
  Consensus 7 (401)  QHDY DH DIIGWTREG S  P SGLA IISDGPGG KWMYVGK  AG V
                           451                                              500
SEQID No 1    (449)  FYDLTGNRSDTVTINSDGWGEFKVNGGSVSVWVPRKTTVSTIARPITTRP
SEQID No 12   (451)  WRDITGNRSGTVTINADGWGNFTVNGGAVSVWVKQ---------------
  Consensus 7 (451)  F DITGNRS TVTINADGWG F VNGGAVSVWV
                           501              517
SEQID No 1    (499)  WTGEFVRWTEPRLVAWP
SEQID No 12   (486)  -----------------
  Consensus 7 (501)
```

Figure 4F

```
                    1                                                50
SEQID No 1     (1)  AAPFNGTMMQYFEWYLPDDGTLWTKVANEANNLSSLGITALWLPPAYKGT
SEQID No 13    (1)  -DGLNGTMMQYYEWHLENDGQHWNRLHDDAAALSDAGITAIWIPPAYKGN
 Consensus 8   (1)      NGTMMQYFEWHL  DG  W KL  DA  LS  GITAIWIPPAYKG
                    51                                              100
SEQID No 1    (51)  SRSDVGYGVYDLYDLGEFNQKGTVRTKYGTKAQYLQAIQAAHAAGMQVYA
SEQID No 13   (50)  SQADVGYGAYDLYDLGEFNQKGTVRTKYGTKAQLERAIGSLKSNDINVYG
 Consensus 8  (51)  S ADVGYG YDLYDLGEFNQKGTVRTKYGTKAQ    AI A  A INVYA
                    101                                             150
SEQID No 1   (101)  DVVFDHKGGADGTEWVDAVEVNPSDRNQEISGTYQIQAWTKFDFPGRGNT
SEQID No 13  (100)  DVVMNHKMGADFTEAVQAVQVNPTNRWQDISGAYTIDAWTGFDFSGRNNA
 Consensus 8 (101)  DVV  HK GAD TE V AV VNPS R QDISG Y I  AWT FDF GR N
                    151                                             200
SEQID No 1   (151)  YSSFKWRWYHFDGVDWDESRKLSRIYKFRGIGKAWDWEVDTENGNYDYLM
SEQID No 13  (150)  YSDFKWRWFHFNGVDWDQRYQENHIFRFANTN--WNWRVDEENGNYDYLL
 Consensus 8 (151)  YS FKWRWFHF GVDWD          IFKF       W W VD ENGNYDYLL
                    201                                             250
SEQID No 1   (201)  YADLDMDHPEVVTELKNWGKWYVNTTNIDGFRLDAVKHIKFSFFPDWLSY
SEQID No 13  (198)  GSNIDFSHPEVQDELKDWGSWFTDELDLDGYRLDAIKHIPFWYTSDWVRH
 Consensus 8 (201)   A ID  HPEV  ELK WG WF      IDGFRLDAIKHI F F  DWL H
                    251                                             300
SEQID No 1   (251)  VRSQTGKPLFTVGEYWSYDINKLHNYITKTNGTMSLFDAPLHNKFYTASK
SEQID No 13  (248)  QRNEADQDLFVVGEYWKDDVGALEFYLDEMNWEMSLFDVPLNYNFYRASQ
 Consensus 8 (251)   R         LF VGEYW   DI  L   YI  N   MSLFD PL   FY AS
                    301                                             350
SEQID No 1   (301)  SGGAFDMRTLMTNTLMKDQPTLAVTFVDNHDTEPGQALQSWVDPWFKPLA
SEQID No 13  (298)  QGGSYDMRNILRGSLVEAHPMHAVTFVDNHDTQPGESLESWVADWFKPLA
 Consensus 8 (301)   GGAFDMR IL  SLM    P  AVTFVDNHDT PG AL SWV  WFKPLA
                    351                                             400
SEQID No 1   (351)  YAFILTRQEGYPCVFYGDYYGIPQYNIPSLKSKIDPLLIARRDYAYGTQH
SEQID No 13  (348)  YATILTREGGYPNVFYGDYYGIPNDNISAKKDMIDELLDARQNYAYGTQH
 Consensus 8 (351)  YA ILTR  GYP VFYGDYYGIPN NI A K  ID LL AR  YAYGTQH
                    401                                             450
SEQID No 1   (401)  DYLDHSDIIGWTREGVTEKPGSGLAALITDGPGGSKWMYVGKQHAGKVFY
SEQID No 13  (398)  DYFDHWDVVGWTREGSSSRPNSGLATIMSNGPGGSKWMYVGRQNAGQWT
 Consensus 8 (401)  DY DH DIIGWTREG S KP SGLA IIS GPGGSKWMYVGKQ AG  F
                    451                                             500
SEQID No 1   (451)  DLTGNRSDTVTINSDGWGEFKVNGGSVSVWVPRKTTVSTIARPITTRPWT
SEQID No 13  (448)  DLTGNNGASVTINGDGWGEFFTNGGSVSVYVNQ-----------------
 Consensus 8 (451)  DLTGN   SVTIN DGWGEF  NGGSVSVWV
                    501          515
SEQID No 1   (501)  GEFVRWTEPRLVAWP
SEQID No 13  (481)  ---------------
 Consensus 8 (501)
```

Figure 4G

```
                        1                                                  50
SEQID No 1     (1)  AAPFNGTMMQYFEWYLPDDGTLWTKVANEANNLSSLGITALWLPPAYKGT
SEQID No 14    (1)  -DGLNGTMMQYYEWHLENDGQHWNRLHDDAEALSNAGITAIWIPPAYKGN
  Consensus 9  (1)       NGTMMQYFEWHL  DG  W KL  DA  LS  GITAIWIPPAYKG
                        51                                                100
SEQID No 1    (51)  SRSDVGYGVYDLYDLGEFNQKGTVRTKYGTKAQYLQAIQAAHAAGMQVYA
SEQID No 14   (50)  SQADVGYGAYDLYDLGEFNQKGTVRTKYGTKAQLERAIGSLKSNDINVYG
  Consensus 9 (51)  S ADVGYG YDLYDLGEFNQKGTVRTKYGTKAQ   AI A  A   INVYA
                        101                                               150
SEQID No 1   (101)  DVVFDHKGGADGTEWVDAVEVNPSDRNQEISGTYQIQAWTKFDFPGRGNT
SEQID No 14  (100)  DVVMNHKLGADFTEAVQAVQVNPSNRWQDISGVYTIDAWTGFDFPGRNNA
  Consensus 9(101)  DVV  HK GAD TE V AV VNPS R QDISG Y I AWT FDFPGR N
                        151                                               200
SEQID No 1   (151)  YSSFKWRWYHFDGVDWDESRKLSRIYKFRGIGKAWDWEVDTENGNYDYLM
SEQID No 14  (150)  YSDFKWRWFHFNGVDWDQRYQENHLFRFANTN--WNWRVDEENGNYDYLL
  Consensus 9(151)  YS FKWRWFHF GVDW        IFKF       W W VD ENGNYDYLL
                        201                                               250
SEQID No 1   (201)  YADLDMDHPEVVTELKNWGKWYVNTTNIDGFRLDAVKHIKFSFFPDWLSY
SEQID No 14  (198)  GSNIDFSHPEVQEELKDWGSWFTDELDLDGYRLDAIKHIPFWYTSDWVRH
  Consensus 9(201)   A ID  HPEV  ELK WG WF       IDGFRLDAIKHI F F DWL H
                        251                                               300
SEQID No 1   (251)  VRSQTGKPLFTVGEYWSYDINKLHNYITKTNGTMSLFDAPLHNKFYTASK
SEQID No 14  (248)  QRSEADQDLFVVGEYWKDDVGALEFYLDEMNWEMSLFDVPLNYNFYRASK
  Consensus 9(251)   RS    LF VGEYW  DI  L  YI   N  MSLFD PL    FY ASK
                        301                                               350
SEQID No 1   (301)  SGGAFDMRTLMTNTLMKDQPTLAVTFVDNHDTEPGQALQSWVDPWFKPLA
SEQID No 14  (298)  QGGSYDMRNILRGSLVEAHPIHAVTFVDNHDTQPGESLESWVADWFKPLA
  Consensus 9(301)    GGAFDMR IL  SLM   P  AVTFVDNHDT PG AL SWV  WFKPLA
                        351                                               400
SEQID No 1   (351)  YAFILTRQEGYPCVFYGDYYGIPQYNIPSLKSKIDPLLIARRDYAYGTQH
SEQID No 14  (348)  YATILTREGGYPNVFYGDYYGIPNDNISAKKDMIDELLDARQNYAYGTQH
  Consensus 9(351)  YA ILTR  GYP VFYGDYYGIPN NI A K  ID LL AR  YAYGTQH
                        401                                               450
SEQID No 1   (401)  DYLDHSDIIGWTREGVTEKPGSGLAALITDGPGGSKWMYVGKQHAGKVFY
SEQID No 14  (398)  DYFDHWDIVGWTREGTSSRPNSGLATIMSNGPGGSKWMYVGQQHAGQTWT
  Consensus 9(401)  DY DH DIIGWTREG S KP SGLA IIS NGPGGSKWMYVG QHAG   F
                        451                                               500
SEQID No 1   (451)  DLTGNRSDTVTINSDGWGEFKVNGGSVSVWVPRKTTVSTIARPITTRPWT
SEQID No 14  (448)  DLTGNHAASVTINGDGWGEFFTNGGSVSVYVNQ-----------------
  Consensus 9(451)  DLTGN A SVTIN DGWGEF  NGGSVSVWV
                        501        515
SEQID No 1   (501)  GEFVRWTEPRLVAWP
SEQID No 14  (481)  ---------------
  Consensus 9(501)
```

Figure 4H

|              |       | 1                                                  50 |
|---|---|---|
| SEQID No 1   | (1)   | AAPFNGTMMQYFEWYLPDDGTLWTKVANEANNLSSLGITALWLPPAYKGT |
| SEQID No 15  | (1)   | AAPFNGTMMQYFEWYLPDDGTLWTKVANEANNLSSLGITALWLPPAYKGT |
| Consensus 10 | (1)   | AAPFNGTMMQYFEWYLPDDGTLWTKVANEANNLSSLGITALWLPPAYKGT |
|              |       | 51                                                100 |
| SEQID No 1   | (51)  | SRSDVGYGVYDLYDLGEFNQKGTVRTKYGTKAQYLQAIQAAHAAGMQVYA |
| SEQID No 15  | (51)  | SRSDVGYGVYDLYDLGEFNQKGTVRTKYGTKAQYLQAIQAAHAAGMQVYA |
| Consensus 10 | (51)  | SRSDVGYGVYDLYDLGEFNQKGTVRTKYGTKAQYLQAIQAAHAAGMQVYA |
|              |       | 101                                               150 |
| SEQID No 1   | (101) | DVVFDHKGGADGTEWVDAVEVNPSDRNQEISGTYQIQAWTKFDFPGRGNT |
| SEQID No 15  | (101) | DVVFDHKGGADGTEWVDAVEVNPSDRNQEISGTYQIQAWTKFDFPGRGNT |
| Consensus 10 | (101) | DVVFDHKGGADGTEWVDAVEVNPSDRNQEISGTYQIQAWTKFDFPGRGNT |
|              |       | 151                                               200 |
| SEQID No 1   | (151) | YSSFKWRWYHFDGVDWDESRKLSRIYKFRGIGKAWDWEVDTENGNYDYLM |
| SEQID No 15  | (151) | YSSFKWRWYHFDGVDWDESRKLSRIYKFR--GKAWDWEVDTEFGNYDYLM |
| Consensus 10 | (151) | YSSFKWRWYHFDGVDWDESRKLSRIYKFR  GKAWDWEVDTE GNYDYLM |
|              |       | 201                                               250 |
| SEQID No 1   | (201) | YADLDMDHPEVVTELKNWGKWYVNTTNIDGFRLDAVKHIKFSFFPDWLSY |
| SEQID No 15  | (199) | YADLDMDHPEVVTELKNWGKWYVNTTNIDGFRLDAVKHIKFSFFPDWLSY |
| Consensus 10 | (201) | YADLDMDHPEVVTELKNWGKWYVNTTNIDGFRLDAVKHIKFSFFPDWLSY |
|              |       | 251                                               300 |
| SEQID No 1   | (251) | VRSQTGKPLFTVGEYWSYDINKLHNYITKTNGTMSLFDAPLHNKFYTASK |
| SEQID No 15  | (249) | VRSQTGKPLFTVGEYWSYDINKLHNYITKTNGTMSLFDAPLHNKFYTASK |
| Consensus 10 | (251) | VRSQTGKPLFTVGEYWSYDINKLHNYITKTNGTMSLFDAPLHNKFYTASK |
|              |       | 301                                               350 |
| SEQID No 1   | (301) | SGGAFDMRTLMTNTLMKDQPTLAVTFVDNHDTEPGQALQSWVDPWFKPLA |
| SEQID No 15  | (299) | SGGAFDMRTLMTNTLMKDQPTLAVTFVDNHDTEPGQALQSWVDPWFKPLA |
| Consensus 10 | (301) | SGGAFDMRTLMTNTLMKDQPTLAVTFVDNHDTEPGQALQSWVDPWFKPLA |
|              |       | 351                                               400 |
| SEQID No 1   | (351) | YAFILTRQEGYPCVFYGDYYGIPQYNIPSLKSKIDPLLIARRDYAYGTQH |
| SEQID No 15  | (349) | YAFILTRQEGYPCVFYGDYYGIPQYNIPSLKSKIDPLLIARRDYAYGTQH |
| Consensus 10 | (351) | YAFILTRQEGYPCVFYGDYYGIPQYNIPSLKSKIDPLLIARRDYAYGTQH |
|              |       | 401                                               450 |
| SEQID No 1   | (401) | DYLDHSDIIGWTREGVTEKPGSGLAALITDGPGGSKWMYVGKQHAGKVFY |
| SEQID No 15  | (399) | DYLDHSDIIGWTREGGTEKPGSGLAALITDGPGGSKWMYVGKQHAGKVFY |
| Consensus 10 | (401) | DYLDHSDIIGWTREG TEKPGSGLAALITDGPGGSKWMYVGKQHAGKVFY |
|              |       | 451                                               500 |
| SEQID No 1   | (451) | DLTGNRSDTVTINSDGWGEFKVNGGSVSVWVPRKTTVSTIARPITTRPWT |
| SEQID No 15  | (449) | DLTGNRSDTVTINSDGWGEFKVNGGSVSVWVPRKTTVS------------ |
| Consensus 10 | (451) | DLTGNRSDTVTINSDGWGEFKVNGGSVSVWVPRKTTVS |
|              |       | 501           515 |
| SEQID No 1   | (501) | GEFVRWTEPRLVAWP |
| SEQID No 15  | (487) | --------------- |
| Consensus 10 | (501) |  |

SEQUENCE LISTING

<160> NUMBER OF SEQ ID NOS: 31

<210> SEQ ID NO 1
<211> LENGTH: 515
<212> TYPE: PRT
<213> ORGANISM: Geobacillus stearothermophilus

<400> SEQUENCE: 1

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
```

```
                195                 200                 205
Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 2
<211> LENGTH: 486
<212> TYPE: PRT
<213> ORGANISM: Geobacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45
```

```
Gly Thr Ser Arg Ser Asp Val Gly Tyr Gly Val Tyr Asp Leu Tyr Asp
 50                  55                  60

Leu Gly Glu Phe Asn Gln Lys Gly Thr Val Arg Thr Lys Tyr Gly Thr
 65                  70                  75                  80

Lys Ala Gln Tyr Leu Gln Ala Ile Gln Ala Ala His Ala Ala Gly Met
                 85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
```

```
                    465                 470                 475                 480
Val Pro Arg Lys Thr Thr
                485

<210> SEQ ID NO 3
<211> LENGTH: 515
<212> TYPE: PRT
<213> ORGANISM: Geobacillus stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ala Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350
```

```
Phe Ile Leu Thr Arg Gln Glu Gly Tyr Pro Cys Val Phe Tyr Gly Asp
            355                 360                 365
Tyr Tyr Gly Ile Pro Gln Tyr Asn Ile Pro Ser Leu Lys Ser Lys Ile
370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
            405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
            435                 440                 445
Phe Tyr Asp Leu Thr Gly Asn Arg Ser Asp Thr Val Thr Ile Asn Ser
450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
            485                 490                 495
Arg Pro Trp Thr Gly Glu Phe Val Arg Trp Thr Glu Pro Arg Leu Val
            500                 505                 510
Ala Trp Pro
        515

<210> SEQ ID NO 4
<211> LENGTH: 515
<212> TYPE: PRT
<213> ORGANISM: Geobacillus stearothermophilus

<400> SEQUENCE: 4

Ala Ala Pro Phe Asn Gly Thr Met Met Gln Tyr Phe Glu Trp Tyr Leu
1               5                   10                  15
Pro Asp Asp Gly Thr Leu Trp Thr Lys Val Ala Asn Glu Ala Asn Asn
            20                  25                  30
Leu Ser Ser Leu Gly Ile Thr Ala Leu Trp Leu Pro Pro Ala Tyr Lys
        35                  40                  45
Gly Thr Ser Arg Ser Asp Val Gly Tyr Gly Val Tyr Asp Leu Tyr Asp
    50                  55                  60
Leu Gly Glu Phe Asn Gln Lys Gly Thr Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
Glu Ile Ser Gly Thr Tyr Gln Ile Gln Ala Trp Thr Lys Phe Asp Phe
    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
```

```
Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Gln Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515
```

<210> SEQ ID NO 5
<211> LENGTH: 515
<212> TYPE: PRT
<213> ORGANISM: Geobacillus stearothermophilus

<400> SEQUENCE: 5

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
```

-continued

```
                50                  55                  60
Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Glu Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480
```

Val Pro Arg Lys Thr Thr Val Ser Thr Ile Ala Arg Pro Ile Thr Thr
                485             490                 495

Arg Pro Trp Thr Gly Glu Phe Val Arg Trp Thr Glu Pro Arg Leu Val
            500             505                 510

Ala Trp Pro
        515

<210> SEQ ID NO 6
<211> LENGTH: 485
<212> TYPE: PRT
<213> ORGANISM: Bacillus sp. 707

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro

```
                       325                 330                 335
Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 7
<211> LENGTH: 483
<212> TYPE: PRT
<213> ORGANISM: Bacillus sp. 707

<400> SEQUENCE: 7

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205
```

-continued

```
Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 8
<211> LENGTH: 483
<212> TYPE: PRT
<213> ORGANISM: Bacillus licheniformis

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95
```

Val Tyr Gly Asp Val Val Ile Asn His Lys Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 483
<212> TYPE: PRT
<213> ORGANISM: Bacillus amyloliquefaciens

<400> SEQUENCE: 9

```
Val Asn Gly Thr Leu Met Gln Tyr Phe Glu Trp Tyr Thr Pro Asn Asp
1               5                   10                  15
Gly Gln His Trp Lys Arg Leu Gln Asn Asp Ala Glu His Leu Ser Asp
            20                  25                  30
Ile Gly Ile Thr Ala Val Trp Ile Pro Pro Ala Tyr Lys Gly Leu Ser
        35                  40                  45
Gln Ser Asp Asn Gly Tyr Gly Pro Tyr Asp Leu Tyr Asp Leu Gly Glu
    50                  55                  60
Phe Gln Gln Lys Gly Thr Val Arg Thr Lys Tyr Gly Thr Lys Ser Glu
65                  70                  75                  80
Leu Gln Asp Ala Ile Gly Ser Leu His Ser Arg Asn Val Gln Val Tyr
                85                  90                  95
Gly Asp Val Val Leu Asn His Lys Ala Gly Ala Asp Ala Thr Glu Asp
            100                 105                 110
Val Thr Ala Val Glu Val Asn Pro Ala Asn Arg Asn Gln Glu Thr Ser
        115                 120                 125
Glu Glu Tyr Gln Ile Lys Ala Trp Thr Asp Phe Arg Phe Pro Gly Arg
    130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
            180                 185                 190
Tyr Asp Tyr Leu Met Tyr Ala Asp Val Asp Tyr Asp His Pro Asp Val
        195                 200                 205
Val Ala Glu Thr Lys Lys Trp Gly Ile Trp Tyr Ala Asn Glu Leu Ser
    210                 215                 220
Leu Asp Gly Phe Arg Ile Asp Ala Ala Lys His Ile Lys Phe Ser Phe
225                 230                 235                 240
Leu Arg Asp Trp Val Gln Ala Val Arg Gln Ala Thr Gly Lys Glu Met
                245                 250                 255
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
        275                 280                 285
His Phe Asn Leu Gln Ala Ala Ser Ser Gln Gly Gly Gly Tyr Asp Met
    290                 295                 300
Arg Arg Leu Leu Asp Gly Thr Val Val Ser Arg His Pro Glu Lys Ala
305                 310                 315                 320
Val Thr Phe Val Glu Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Thr Ser Pro Lys Glu Ile Pro Ser Leu Lys Asp Asn Ile
    370                 375                 380
Glu Pro Ile Leu Lys Ala Arg Lys Glu Tyr Ala Tyr Gly Pro Gln His
385                 390                 395                 400
Asp Tyr Ile Asp His Pro Asp Val Ile Gly Trp Thr Arg Glu Gly Asp
```

```
                    405                 410                 415
Ser Ser Ala Ala Lys Ser Gly Leu Ala Ala Leu Ile Thr Asp Gly Pro
                420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
        450                 455                 460

Asp Gly Trp Gly Glu Phe His Val Asn Asp Gly Ser Val Ser Ile Tyr
465                 470                 475                 480

Val Gln Lys

<210> SEQ ID NO 10
<211> LENGTH: 485
<212> TYPE: PRT
<213> ORGANISM: Bacillus sp. 707

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
```

-continued

```
                  290                 295                 300
Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
                435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 11
<211> LENGTH: 485
<212> TYPE: PRT
<213> ORGANISM: Bacillus halmapalus

<400> SEQUENCE: 11

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
                35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
                115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175
```

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 12
<211> LENGTH: 485
<212> TYPE: PRT
<213> ORGANISM: Bacillus sp.

<400> SEQUENCE: 12

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
    50                  55                  60

-continued

```
Asp Leu Gly Glu Phe Asn Gln Lys Gly Thr Val Arg Thr Lys Tyr Gly
 65                  70                  75                  80

Thr Arg Ser Gln Leu Gln Gly Ala Val Thr Ser Leu Lys Asn Asn Gly
             85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Gly Val Pro Ser Met Lys Ser
    370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
            420                 425                 430

Gly Pro Gly Gly Asn Lys Trp Met Tyr Val Gly Lys His Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Thr Val Asn Gly Gly Ala Val Ser
465                 470                 475                 480
```

```
Val Trp Val Lys Gln
            485

<210> SEQ ID NO 13
<211> LENGTH: 480
<212> TYPE: PRT
<213> ORGANISM: Bacillus sp.

<400> SEQUENCE: 13

Asp Gly Leu Asn Gly Thr Met Met Gln Tyr Tyr Glu Trp His Leu Glu
1               5                  10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Ser Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365
```

-continued

```
Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
                420                 425                 430

Lys Trp Met Tyr Val Gly Arg Gln Asn Ala Gly Gln Thr Trp Thr Asp
                435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480
```

<210> SEQ ID NO 14
<211> LENGTH: 480
<212> TYPE: PRT
<213> ORGANISM: Bacillus sp.

<400> SEQUENCE: 14

```
Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Glu Ala Leu
                20                  25                  30

Ser Asn Ala Gly Ile Thr Ala Ile Trp Ile Pro Pro Ala Tyr Lys Gly
            35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Leu Gly Ala Asp Phe Thr
            100                 105                 110

Glu Ala Val Gln Ala Val Gln Val Asn Pro Ser Asn Arg Trp Gln Asp
        115                 120                 125

Ile Ser Gly Val Tyr Thr Ile Asp Ala Trp Thr Gly Phe Asp Phe Pro
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Leu Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Glu Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Ser Glu Ala Asp Gln Asp Leu
                245                 250                 255

Phe Val Val Gly Glu Tyr Trp Lys Asp Asp Val Gly Ala Leu Glu Phe
```

```
                   260                 265                 270
Tyr Leu Asp Glu Met Asn Trp Glu Met Ser Leu Phe Asp Val Pro Leu
                275                 280                 285

Asn Tyr Asn Phe Tyr Arg Ala Ser Lys Gln Gly Gly Ser Tyr Asp Met
            290                 295                 300

Arg Asn Ile Leu Arg Gly Ser Leu Val Glu Ala His Pro Ile His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
                340                 345                 350

Thr Arg Glu Gly Gly Tyr Pro Asn Val Phe Tyr Gly Asp Tyr Tyr Gly
                355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Ile Val Gly Trp Thr Arg Glu Gly Thr Ser Ser Arg
                405                 410                 415

Pro Asn Ser Gly Leu Ala Thr Ile Met Ser Asn Gly Pro Gly Gly Ser
                420                 425                 430

Lys Trp Met Tyr Val Gly Gln Gln His Ala Gly Gln Thr Trp Thr Asp
                435                 440                 445

Leu Thr Gly Asn His Ala Ala Ser Val Thr Ile Asn Gly Asp Gly Trp
                450                 455                 460

Gly Glu Phe Phe Thr Asn Gly Gly Ser Val Ser Val Tyr Val Asn Gln
465                 470                 475                 480

<210> SEQ ID NO 15
<211> LENGTH: 486
<212> TYPE: PRT
<213> ORGANISM: Geobacillus stearothermophilus

<400> SEQUENCE: 15

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160
```

```
Phe Asp Gly Val Asp Trp Asp Glu Ser Arg Lys Leu Ser Arg Ile Tyr
            165                 170                 175
Lys Phe Arg Gly Lys Ala Trp Asp Trp Glu Val Asp Thr Glu Phe Gly
        180                 185                 190
Asn Tyr Asp Tyr Leu Met Tyr Ala Asp Leu Asp Met Asp His Pro Glu
            195                 200                 205
Val Val Thr Glu Leu Lys Asn Trp Gly Lys Trp Tyr Val Asn Thr Thr
        210                 215                 220
Asn Ile Asp Gly Phe Arg Leu Asp Ala Val Lys His Ile Lys Phe Ser
225                 230                 235                 240
Phe Phe Pro Asp Trp Leu Ser Tyr Val Arg Ser Gln Thr Gly Lys Pro
                245                 250                 255
Leu Phe Thr Val Gly Glu Tyr Trp Ser Tyr Asp Ile Asn Lys Leu His
            260                 265                 270
Asn Tyr Ile Thr Lys Thr Asn Gly Thr Met Ser Leu Phe Asp Ala Pro
            275                 280                 285
Leu His Asn Lys Phe Tyr Thr Ala Ser Lys Ser Gly Gly Ala Phe Asp
        290                 295                 300
Met Arg Thr Leu Met Thr Asn Thr Leu Met Lys Asp Gln Pro Thr Leu
305                 310                 315                 320
Ala Val Thr Phe Val Asp Asn His Asp Thr Glu Pro Gly Gln Ala Leu
                325                 330                 335
Gln Ser Trp Val Asp Pro Trp Phe Lys Pro Leu Ala Tyr Ala Phe Ile
            340                 345                 350
Leu Thr Arg Gln Glu Gly Tyr Pro Cys Val Phe Tyr Gly Asp Tyr Tyr
        355                 360                 365
Gly Ile Pro Gln Tyr Asn Ile Pro Ser Leu Lys Ser Lys Ile Asp Pro
            370                 375                 380
Leu Leu Ile Ala Arg Arg Asp Tyr Ala Tyr Gly Thr Gln His Asp Tyr
385                 390                 395                 400
Leu Asp His Ser Asp Ile Ile Gly Trp Thr Arg Glu Gly Gly Thr Glu
                405                 410                 415
Lys Pro Gly Ser Gly Leu Ala Ala Leu Ile Thr Asp Gly Pro Gly Gly
            420                 425                 430
Ser Lys Trp Met Tyr Val Gly Lys Gln His Ala Gly Lys Val Phe Tyr
        435                 440                 445
Asp Leu Thr Gly Asn Arg Ser Asp Thr Val Thr Ile Asn Ser Asp Gly
    450                 455                 460
Trp Gly Glu Phe Lys Val Asn Gly Gly Ser Val Ser Val Trp Val Pro
465                 470                 475                 480
Arg Lys Thr Thr Val Ser
                485

<210> SEQ ID NO 16
<211> LENGTH: 520
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His or not present
<220> FEATURE:
<221> NAME/KEY: MOD_RES
<222> LOCATION: (2)..(2)
<223> OTHER INFORMATION: Ala, His or not present
```

```
<220> FEATURE:
<221> NAME/KEY: MOD_RES
<222> LOCATION: (4)..(4)
<223> OTHER INFORMATION: Pro, Gly, Asn or not present
<220> FEATURE:
<221> NAME/KEY: MOD_RES
<222> LOCATION: (5)..(5)
<223> OTHER INFORMATION: Phe, Thr, Leu or Val
<220> FEATURE:
<221> NAME/KEY: MOD_RES
<222> LOCATION: (25)..(25)
<223> OTHER INFORMATION: Thr, Asn, Lys or Arg
<220> FEATURE:
<221> NAME/KEY: MOD_RES
<222> LOCATION: (28)..(28)
<223> OTHER INFORMATION: Ala, Asn, Gln, Arg or His
<220> FEATURE:
<221> NAME/KEY: MOD_RES
<222> LOCATION: (32)..(32)
<223> OTHER INFORMATION: Asn, Ser, Ala or Glu
<220> FEATURE:
<221> NAME/KEY: MOD_RES
<222> LOCATION: (37)..(37)
<223> OTHER INFORMATION: Leu, Lys, His, Ile, Arg or Ala
<220> FEATURE:
<221> NAME/KEY: MOD_RES
<222> LOCATION: (86)..(86)
<223> OTHER INFORMATION: Leu, Gln or Glu
<220> FEATURE:
<221> NAME/KEY: MOD_RES
<222> LOCATION: (87)..(87)
<223> OTHER INFORMATION: Gln, Ala, Ser, Asp, Gly or Arg
<220> FEATURE:
<221> NAME/KEY: MOD_RES
<222> LOCATION: (90)..(90)
<223> OTHER INFORMATION: Gln, Thr, Lys, Gly, Asn or His
<220> FEATURE:
<221> NAME/KEY: MOD_RES
<222> LOCATION: (95)..(95)
<223> OTHER INFORMATION: Ala, Asn or Arg
<220> FEATURE:
<221> NAME/KEY: MOD_RES
<222> LOCATION: (116)..(116)
<223> OTHER INFORMATION: Trp, Met, Asp, Asn or Ala
<220> FEATURE:
<221> NAME/KEY: MOD_RES
<222> LOCATION: (118)..(118)
<223> OTHER INFORMATION: Asp, Arg, Thr, Leu, Asn or Gln
<220> FEATURE:
<221> NAME/KEY: MOD_RES
<222> LOCATION: (134)..(134)
<223> OTHER INFORMATION: Thr, Glu, Asp, Ala or Val
<220> FEATURE:
<221> NAME/KEY: MOD_RES
<222> LOCATION: (136)..(136)
<223> OTHER INFORMATION: Gln, Thr or Leu
<220> FEATURE:
<221> NAME/KEY: MOD_RES
<222> LOCATION: (138)..(138)
<223> OTHER INFORMATION: Gln, Glu, Lys or Asp
<220> FEATURE:
<221> NAME/KEY: MOD_RES
<222> LOCATION: (154)..(154)
<223> OTHER INFORMATION: Ser, Asp or Asn
<220> FEATURE:
<221> NAME/KEY: MOD_RES
<222> LOCATION: (175)..(175)
<223> OTHER INFORMATION: Asn or not present
<220> FEATURE:
<221> NAME/KEY: MOD_RES
<222> LOCATION: (183)..(183)
<223> OTHER INFORMATION: Ile, His, Glu, Asp, Thr or not present
<220> FEATURE:
<221> NAME/KEY: MOD_RES
<222> LOCATION: (215)..(215)
<223> OTHER INFORMATION: Thr, Asn, Ala, Asp or Glu
<220> FEATURE:
<221> NAME/KEY: MOD_RES
<222> LOCATION: (222)..(222)
```

```
<223> OTHER INFORMATION: Lys, Val, Thr, Ile, Glu or Ser
<220> FEATURE:
<221> NAME/KEY: MOD_RES
<222> LOCATION: (225)..(225)
<223> OTHER INFORMATION: Val, Thr or Ala
<220> FEATURE:
<221> NAME/KEY: MOD_RES
<222> LOCATION: (246)..(246)
<223> OTHER INFORMATION: Phe, Thr or Leu
<220> FEATURE:
<221> NAME/KEY: MOD_RES
<222> LOCATION: (247)..(247)
<223> OTHER INFORMATION: Pro, Arg or Ser
<220> FEATURE:
<221> NAME/KEY: MOD_RES
<222> LOCATION: (256)..(256)
<223> OTHER INFORMATION: Gln, Ala, Lys, Thr or Glu
<220> FEATURE:
<221> NAME/KEY: MOD_RES
<222> LOCATION: (260)..(260)
<223> OTHER INFORMATION: Pro, Asn, Glu or Asp
<220> FEATURE:
<221> NAME/KEY: MOD_RES
<222> LOCATION: (269)..(269)
<223> OTHER INFORMATION: Ser, Lys or Gln
<220> FEATURE:
<221> NAME/KEY: MOD_RES
<222> LOCATION: (270)..(270)
<223> OTHER INFORMATION: Tyr, Asn or Asp
<220> FEATURE:
<221> NAME/KEY: MOD_RES
<222> LOCATION: (280)..(280)
<223> OTHER INFORMATION: Thr, Gln, Asn or Asp
<220> FEATURE:
<221> NAME/KEY: MOD_RES
<222> LOCATION: (285)..(285)
<223> OTHER INFORMATION: Thr, Asn or Glu
<220> FEATURE:
<221> NAME/KEY: MOD_RES
<222> LOCATION: (299)..(299)
<223> OTHER INFORMATION: Thr, Asn, Ala or Arg
<220> FEATURE:
<221> NAME/KEY: MOD_RES
<222> LOCATION: (311)..(311)
<223> OTHER INFORMATION: Thr, Asn, Lys, Arg or Gln
<220> FEATURE:
<221> NAME/KEY: MOD_RES
<222> LOCATION: (314)..(314)
<223> OTHER INFORMATION: Thr, Asn, Asp or Arg
<220> FEATURE:
<221> NAME/KEY: MOD_RES
<222> LOCATION: (319)..(319)
<223> OTHER INFORMATION: Lys, Gln, Ser or Glu
<220> FEATURE:
<221> NAME/KEY: MOD_RES
<222> LOCATION: (320)..(320)
<223> OTHER INFORMATION: Asp, Arg, Lys or Ala
<220> FEATURE:
<221> NAME/KEY: MOD_RES
<222> LOCATION: (323)..(323)
<223> OTHER INFORMATION: Thr, Ser, Leu, Glu, Met or Ile
<220> FEATURE:
<221> NAME/KEY: MOD_RES
<222> LOCATION: (324)..(324)
<223> OTHER INFORMATION: Leu, His or Lys
<220> FEATURE:
<221> NAME/KEY: MOD_RES
<222> LOCATION: (346)..(346)
<223> OTHER INFORMATION: Pro, Glu, Thr, Ser or Asp
<220> FEATURE:
<221> NAME/KEY: MOD_RES
<222> LOCATION: (361)..(361)
<223> OTHER INFORMATION: Glu, Gln or Ser
<220> FEATURE:
<221> NAME/KEY: MOD_RES
<222> LOCATION: (365)..(365)
<223> OTHER INFORMATION: Cys, Ser, Gln or Asn
<220> FEATURE:
<221> NAME/KEY: MOD_RES
```

```
<222> LOCATION: (379)..(379)
<223> OTHER INFORMATION: Gln, Pro or not present
<220> FEATURE:
<221> NAME/KEY: MOD_RES
<222> LOCATION: (380)..(380)
<223> OTHER INFORMATION: Arg, Lys or not present
<220> FEATURE:
<221> NAME/KEY: MOD_RES
<222> LOCATION: (381)..(381)
<223> OTHER INFORMATION: Glu or not present
<220> FEATURE:
<221> NAME/KEY: MOD_RES
<222> LOCATION: (394)..(394)
<223> OTHER INFORMATION: Ile, Glu, Lys, Gln or Asp
<220> FEATURE:
<221> NAME/KEY: MOD_RES
<222> LOCATION: (398)..(398)
<223> OTHER INFORMATION: Asp, Lys, Gln, Glu, Asn or Thr
<220> FEATURE:
<221> NAME/KEY: MOD_RES
<222> LOCATION: (411)..(411)
<223> OTHER INFORMATION: Ser, His, Pro or Trp
<220> FEATURE:
<221> NAME/KEY: MOD_RES
<222> LOCATION: (421)..(421)
<223> OTHER INFORMATION: Val, Asn, Asp, Ser, Thr or Gly
<220> FEATURE:
<221> NAME/KEY: MOD_RES
<222> LOCATION: (449)..(449)
<223> OTHER INFORMATION: His, Lys or Asn
<220> FEATURE:
<221> NAME/KEY: MOD_RES
<222> LOCATION: (452)..(452)
<223> OTHER INFORMATION: Lys, Gln or Glu
<220> FEATURE:
<221> NAME/KEY: MOD_RES
<222> LOCATION: (476)..(476)
<223> OTHER INFORMATION: Lys, Ser, His, Thr or Phe
<220> FEATURE:
<221> NAME/KEY: MOD_RES
<222> LOCATION: (487)..(487)
<223> OTHER INFORMATION: Pro, Asn, Gln or Lys
<220> FEATURE:
<221> NAME/KEY: MOD_RES
<222> LOCATION: (489)..(489)
<223> OTHER INFORMATION: Lys or not present
<220> FEATURE:
<221> NAME/KEY: MOD_RES
<222> LOCATION: (490)..(491)
<223> OTHER INFORMATION: Thr or not present
<220> FEATURE:
<221> NAME/KEY: MOD_RES
<222> LOCATION: (492)..(492)
<223> OTHER INFORMATION: Val or not present
<220> FEATURE:
<221> NAME/KEY: MOD_RES
<222> LOCATION: (493)..(493)
<223> OTHER INFORMATION: Ser or not present
<220> FEATURE:
<221> NAME/KEY: MOD_RES
<222> LOCATION: (494)..(494)
<223> OTHER INFORMATION: Thr or not present
<220> FEATURE:
<221> NAME/KEY: MOD_RES
<222> LOCATION: (495)..(495)
<223> OTHER INFORMATION: Ile or not present
<220> FEATURE:
<221> NAME/KEY: MOD_RES
<222> LOCATION: (496)..(496)
<223> OTHER INFORMATION: Ala or not present
<220> FEATURE:
<221> NAME/KEY: MOD_RES
<222> LOCATION: (497)..(497)
<223> OTHER INFORMATION: Arg or not present
<220> FEATURE:
<221> NAME/KEY: MOD_RES
<222> LOCATION: (498)..(498)
<223> OTHER INFORMATION: Pro or not present
<220> FEATURE:
```

```
<221> NAME/KEY: MOD_RES
<222> LOCATION: (499)..(499)
<223> OTHER INFORMATION: Ile or not present
<220> FEATURE:
<221> NAME/KEY: MOD_RES
<222> LOCATION: (500)..(501)
<223> OTHER INFORMATION: Thr or not present
<220> FEATURE:
<221> NAME/KEY: MOD_RES
<222> LOCATION: (502)..(502)
<223> OTHER INFORMATION: Arg or not present
<220> FEATURE:
<221> NAME/KEY: MOD_RES
<222> LOCATION: (503)..(503)
<223> OTHER INFORMATION: Pro or not present
<220> FEATURE:
<221> NAME/KEY: MOD_RES
<222> LOCATION: (504)..(504)
<223> OTHER INFORMATION: Trp or not present
<220> FEATURE:
<221> NAME/KEY: MOD_RES
<222> LOCATION: (505)..(505)
<223> OTHER INFORMATION: Thr or not present
<220> FEATURE:
<221> NAME/KEY: MOD_RES
<222> LOCATION: (506)..(506)
<223> OTHER INFORMATION: Gly or not present
<220> FEATURE:
<221> NAME/KEY: MOD_RES
<222> LOCATION: (507)..(507)
<223> OTHER INFORMATION: Glu or not present
<220> FEATURE:
<221> NAME/KEY: MOD_RES
<222> LOCATION: (508)..(508)
<223> OTHER INFORMATION: Phe or not present
<220> FEATURE:
<221> NAME/KEY: MOD_RES
<222> LOCATION: (509)..(509)
<223> OTHER INFORMATION: Val or not present
<220> FEATURE:
<221> NAME/KEY: MOD_RES
<222> LOCATION: (510)..(510)
<223> OTHER INFORMATION: Arg or not present
<220> FEATURE:
<221> NAME/KEY: MOD_RES
<222> LOCATION: (511)..(511)
<223> OTHER INFORMATION: Trp or not present
<220> FEATURE:
<221> NAME/KEY: MOD_RES
<222> LOCATION: (512)..(512)
<223> OTHER INFORMATION: Thr or not present
<220> FEATURE:
<221> NAME/KEY: MOD_RES
<222> LOCATION: (513)..(513)
<223> OTHER INFORMATION: Glu or not present
<220> FEATURE:
<221> NAME/KEY: MOD_RES
<222> LOCATION: (514)..(514)
<223> OTHER INFORMATION: Pro or not present
<220> FEATURE:
<221> NAME/KEY: MOD_RES
<222> LOCATION: (515)..(515)
<223> OTHER INFORMATION: Arg or not present
<220> FEATURE:
<221> NAME/KEY: MOD_RES
<222> LOCATION: (516)..(516)
<223> OTHER INFORMATION: Leu or not present
<220> FEATURE:
<221> NAME/KEY: MOD_RES
<222> LOCATION: (517)..(517)
<223> OTHER INFORMATION: Val or not present
<220> FEATURE:
<221> NAME/KEY: MOD_RES
<222> LOCATION: (518)..(518)
<223> OTHER INFORMATION: Ala or not present
<220> FEATURE:
<221> NAME/KEY: MOD_RES
<222> LOCATION: (519)..(519)
<223> OTHER INFORMATION: Trp or not present
```

-continued

```
<220> FEATURE:
<221> NAME/KEY: MOD_RES
<222> LOCATION: (520)..(520)
<223> OTHER INFORMATION: Pro or not present

<400> SEQUENCE: 16

Xaa Xaa Ala Xaa Xaa Asn Gly Thr Met Met Gln Tyr Phe Glu Trp Tyr
1               5                   10                  15

Leu Pro Asn Asp Gly Gln His Trp Xaa Arg Leu Xaa Asn Asp Ala Xaa
            20                  25                  30

Asn Leu Ser Ser Xaa Gly Ile Thr Ala Leu Trp Ile Pro Pro Ala Tyr
        35                  40                  45

Lys Gly Thr Ser Gln Ser Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Gln Leu Xaa Xaa Ala Ile Xaa Ala Leu His Ala Xaa Gly
                85                  90                  95

Ile Gln Val Tyr Gly Asp Val Val Met Asn His Lys Gly Gly Ala Asp
            100                 105                 110

Gly Thr Glu Xaa Val Xaa Ala Val Glu Val Asn Pro Ser Asp Arg Asn
            115                 120                 125

Gln Glu Ile Ser Gly Xaa Tyr Xaa Ile Xaa Ala Trp Thr Lys Phe Asp
    130                 135                 140

Phe Pro Gly Arg Gly Asn Thr Tyr Ser Xaa Phe Lys Trp Arg Trp Tyr
145                 150                 155                 160

His Phe Asp Gly Val Asp Trp Asp Glu Ser Arg Lys Leu Asn Xaa Arg
            165                 170                 175

Ile Tyr Lys Phe Arg Gly Xaa Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Xaa Glu Leu Lys Asn Trp Gly Xaa Trp Tyr
    210                 215                 220

Xaa Asn Thr Leu Asn Leu Asp Gly Phe Arg Leu Asp Ala Val Lys His
225                 230                 235                 240

Ile Lys Phe Ser Phe Xaa Xaa Asp Trp Leu Ser His Val Arg Ser Xaa
            245                 250                 255

Thr Gly Lys Xaa Leu Phe Thr Val Gly Glu Tyr Trp Xaa Xaa Asp Ile
            260                 265                 270

Gly Ala Leu Glu Asn Tyr Leu Xaa Lys Thr Asn Trp Xaa Met Ser Leu
        275                 280                 285

Phe Asp Val Pro Leu His Tyr Asn Phe Tyr Xaa Ala Ser Lys Ser Gly
    290                 295                 300

Gly Ala Tyr Asp Met Arg Xaa Leu Leu Xaa Gly Thr Leu Val Xaa Xaa
305                 310                 315                 320

His Pro Xaa Xaa Ala Val Thr Phe Val Asp Asn His Asp Thr Gln Pro
            325                 330                 335

Gly Gln Ala Leu Glu Ser Trp Val Asp Xaa Trp Phe Lys Pro Leu Ala
        340                 345                 350

Tyr Ala Phe Ile Leu Thr Arg Glu Xaa Gly Tyr Pro Xaa Val Phe Tyr
    355                 360                 365

Gly Asp Tyr Tyr Gly Ile Pro Gln Tyr Asn Xaa Xaa Xaa Ile Pro Ser
370                 375                 380
```

```
Leu Lys Ser Lys Ile Asp Pro Leu Leu Xaa Ala Arg Arg Xaa Tyr Ala
385                 390                 395                 400

Tyr Gly Thr Gln His Asp Tyr Leu Asp His Xaa Asp Ile Ile Gly Trp
            405                 410                 415

Thr Arg Glu Gly Xaa Thr Ser Lys Pro Asn Ser Gly Leu Ala Ala Leu
            420                 425                 430

Ile Thr Asp Gly Pro Gly Gly Ser Lys Trp Met Tyr Val Gly Lys Gln
            435                 440                 445

Xaa Ala Gly Xaa Val Trp Tyr Asp Leu Thr Gly Asn Arg Ser Asp Thr
    450                 455                 460

Val Thr Ile Asn Ser Asp Gly Trp Gly Glu Phe Xaa Val Asn Gly Gly
465                 470                 475                 480

Ser Val Ser Val Trp Val Xaa Arg Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa
            515                 520

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, t, g, unknown or other

<400> SEQUENCE: 17
gtcaagcata ttaagttcnn sttttttcct gattggttg                            39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, t, g, unknown or other

<400> SEQUENCE: 18
caaccaatca ggaaaaaasn ngaacttaat atgcttgac                            39

<210> SEQ ID NO 19
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atgaaacaac aaaaacggct ttacgcccga ttgctgacgc tgttatttgc gctcatcttc     60
ttgctgcctc attctgcagc ttcagca                                        87

<210> SEQ ID NO 20
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 21
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Gln Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285
```

```
Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
                485

<210> SEQ ID NO 22
<211> LENGTH: 413
<212> TYPE: PRT
<213> ORGANISM: Buttiauxella sp.

<400> SEQUENCE: 22

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175
```

```
Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
            195                 200                 205

Ala Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
            290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 23
<211> LENGTH: 517
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His or not present
<220> FEATURE:
<221> NAME/KEY: MOD_RES
<222> LOCATION: (2)..(2)
<223> OTHER INFORMATION: Ala or His
<220> FEATURE:
<221> NAME/KEY: MOD_RES
<222> LOCATION: (3)..(3)
<223> OTHER INFORMATION: Ala or Asn
<220> FEATURE:
<221> NAME/KEY: MOD_RES
<222> LOCATION: (4)..(4)
<223> OTHER INFORMATION: Pro or Gly
<220> FEATURE:
<221> NAME/KEY: MOD_RES
<222> LOCATION: (5)..(5)
<223> OTHER INFORMATION: Phe or Thr
<220> FEATURE:
<221> NAME/KEY: MOD_RES
<222> LOCATION: (19)..(19)
<223> OTHER INFORMATION: Asp or Asn
<220> FEATURE:
```

```
<221> NAME/KEY: MOD_RES
<222> LOCATION: (22)..(22)
<223> OTHER INFORMATION: Thr or Asn
<220> FEATURE:
<221> NAME/KEY: MOD_RES
<222> LOCATION: (23)..(23)
<223> OTHER INFORMATION: Leu or His
<220> FEATURE:
<221> NAME/KEY: MOD_RES
<222> LOCATION: (25)..(25)
<223> OTHER INFORMATION: Thr or Asn
<220> FEATURE:
<221> NAME/KEY: MOD_RES
<222> LOCATION: (28)..(28)
<223> OTHER INFORMATION: Ala or Asn
<220> FEATURE:
<221> NAME/KEY: MOD_RES
<222> LOCATION: (29)..(29)
<223> OTHER INFORMATION: Asn or Ser
<220> FEATURE:
<221> NAME/KEY: MOD_RES
<222> LOCATION: (32)..(32)
<223> OTHER INFORMATION: Asn or Ser
<220> FEATURE:
<221> NAME/KEY: MOD_RES
<222> LOCATION: (35)..(35)
<223> OTHER INFORMATION: Ser or Lys
<220> FEATURE:
<221> NAME/KEY: MOD_RES
<222> LOCATION: (37)..(37)
<223> OTHER INFORMATION: Leu or Lys
<220> FEATURE:
<221> NAME/KEY: MOD_RES
<222> LOCATION: (51)..(51)
<223> OTHER INFORMATION: Thr or Ala
<220> FEATURE:
<221> NAME/KEY: MOD_RES
<222> LOCATION: (53)..(53)
<223> OTHER INFORMATION: Arg or Gln
<220> FEATURE:
<221> NAME/KEY: MOD_RES
<222> LOCATION: (54)..(54)
<223> OTHER INFORMATION: Ser or Asn
<220> FEATURE:
<221> NAME/KEY: MOD_RES
<222> LOCATION: (60)..(60)
<223> OTHER INFORMATION: Val or Ala
<220> FEATURE:
<221> NAME/KEY: MOD_RES
<222> LOCATION: (85)..(85)
<223> OTHER INFORMATION: Tyr or Leu
<220> FEATURE:
<221> NAME/KEY: MOD_RES
<222> LOCATION: (86)..(86)
<223> OTHER INFORMATION: Leu or Gln
<220> FEATURE:
<221> NAME/KEY: MOD_RES
<222> LOCATION: (87)..(87)
<223> OTHER INFORMATION: Gln or Ala
<220> FEATURE:
<221> NAME/KEY: MOD_RES
<222> LOCATION: (90)..(90)
<223> OTHER INFORMATION: Gln or Thr
<220> FEATURE:
<221> NAME/KEY: MOD_RES
<222> LOCATION: (92)..(92)
<223> OTHER INFORMATION: Ala or Leu
<220> FEATURE:
<221> NAME/KEY: MOD_RES
<222> LOCATION: (93)..(93)
<223> OTHER INFORMATION: His or Lys
<220> FEATURE:
<221> NAME/KEY: MOD_RES
<222> LOCATION: (94)..(95)
<223> OTHER INFORMATION: Ala or Asn
<220> FEATURE:
<221> NAME/KEY: MOD_RES
<222> LOCATION: (105)..(105)
<223> OTHER INFORMATION: Phe or Met
```

```
<220> FEATURE:
<221> NAME/KEY: MOD_RES
<222> LOCATION: (106)..(106)
<223> OTHER INFORMATION: Asp or Asn
<220> FEATURE:
<221> NAME/KEY: MOD_RES
<222> LOCATION: (116)..(116)
<223> OTHER INFORMATION: Trp or Met
<220> FEATURE:
<221> NAME/KEY: MOD_RES
<222> LOCATION: (118)..(118)
<223> OTHER INFORMATION: Asp or Arg
<220> FEATURE:
<221> NAME/KEY: MOD_RES
<222> LOCATION: (125)..(125)
<223> OTHER INFORMATION: Ser or Asn
<220> FEATURE:
<221> NAME/KEY: MOD_RES
<222> LOCATION: (126)..(126)
<223> OTHER INFORMATION: Asp or Asn
<220> FEATURE:
<221> NAME/KEY: MOD_RES
<222> LOCATION: (134)..(134)
<223> OTHER INFORMATION: Thr or Glu
<220> FEATURE:
<221> NAME/KEY: MOD_RES
<222> LOCATION: (136)..(136)
<223> OTHER INFORMATION: Gln or Thr
<220> FEATURE:
<221> NAME/KEY: MOD_RES
<222> LOCATION: (138)..(138)
<223> OTHER INFORMATION: Gln or Glu
<220> FEATURE:
<221> NAME/KEY: MOD_RES
<222> LOCATION: (169)..(169)
<223> OTHER INFORMATION: Glu or Gln
<220> FEATURE:
<221> NAME/KEY: MOD_RES
<222> LOCATION: (174)..(174)
<223> OTHER INFORMATION: Ser or Asn
<220> FEATURE:
<221> NAME/KEY: MOD_RES
<222> LOCATION: (175)..(175)
<223> OTHER INFORMATION: Asn or not present
<220> FEATURE:
<221> NAME/KEY: MOD_RES
<222> LOCATION: (183)..(183)
<223> OTHER INFORMATION: Ile or His
<220> FEATURE:
<221> NAME/KEY: MOD_RES
<222> LOCATION: (215)..(215)
<223> OTHER INFORMATION: Thr or Asn
<220> FEATURE:
<221> NAME/KEY: MOD_RES
<222> LOCATION: (222)..(222)
<223> OTHER INFORMATION: Lys or Val
<220> FEATURE:
<221> NAME/KEY: MOD_RES
<222> LOCATION: (225)..(225)
<223> OTHER INFORMATION: Val or Thr
<220> FEATURE:
<221> NAME/KEY: MOD_RES
<222> LOCATION: (228)..(228)
<223> OTHER INFORMATION: Thr or Leu
<220> FEATURE:
<221> NAME/KEY: MOD_RES
<222> LOCATION: (229)..(229)
<223> OTHER INFORMATION: Asn or Gly
<220> FEATURE:
<221> NAME/KEY: MOD_RES
<222> LOCATION: (246)..(246)
<223> OTHER INFORMATION: Phe or Thr
<220> FEATURE:
<221> NAME/KEY: MOD_RES
<222> LOCATION: (247)..(247)
<223> OTHER INFORMATION: Pro or Arg
<220> FEATURE:
<221> NAME/KEY: MOD_RES
<222> LOCATION: (251)..(251)
```

-continued

```
<223> OTHER INFORMATION: Ser or Asn
<220> FEATURE:
<221> NAME/KEY: MOD_RES
<222> LOCATION: (256)..(256)
<223> OTHER INFORMATION: Gln or Ala
<220> FEATURE:
<221> NAME/KEY: MOD_RES
<222> LOCATION: (260)..(260)
<223> OTHER INFORMATION: Pro or Asn
<220> FEATURE:
<221> NAME/KEY: MOD_RES
<222> LOCATION: (263)..(263)
<223> OTHER INFORMATION: Thr or Ala
<220> FEATURE:
<221> NAME/KEY: MOD_RES
<222> LOCATION: (269)..(269)
<223> OTHER INFORMATION: Ser or Lys
<220> FEATURE:
<221> NAME/KEY: MOD_RES
<222> LOCATION: (270)..(270)
<223> OTHER INFORMATION: Tyr or Asn
<220> FEATURE:
<221> NAME/KEY: MOD_RES
<222> LOCATION: (273)..(273)
<223> OTHER INFORMATION: Asn or Gly
<220> FEATURE:
<221> NAME/KEY: MOD_RES
<222> LOCATION: (274)..(274)
<223> OTHER INFORMATION: Lys or Ala
<220> FEATURE:
<221> NAME/KEY: MOD_RES
<222> LOCATION: (276)..(276)
<223> OTHER INFORMATION: His or Glu
<220> FEATURE:
<221> NAME/KEY: MOD_RES
<222> LOCATION: (280)..(280)
<223> OTHER INFORMATION: Thr or Gln
<220> FEATURE:
<221> NAME/KEY: MOD_RES
<222> LOCATION: (284)..(284)
<223> OTHER INFORMATION: Gly or Trp
<220> FEATURE:
<221> NAME/KEY: MOD_RES
<222> LOCATION: (285)..(285)
<223> OTHER INFORMATION: Thr or Asn
<220> FEATURE:
<221> NAME/KEY: MOD_RES
<222> LOCATION: (286)..(286)
<223> OTHER INFORMATION: Met or His
<220> FEATURE:
<221> NAME/KEY: MOD_RES
<222> LOCATION: (291)..(291)
<223> OTHER INFORMATION: Ala or Val
<220> FEATURE:
<221> NAME/KEY: MOD_RES
<222> LOCATION: (295)..(295)
<223> OTHER INFORMATION: Asn or Tyr
<220> FEATURE:
<221> NAME/KEY: MOD_RES
<222> LOCATION: (296)..(296)
<223> OTHER INFORMATION: Lys or Asn
<220> FEATURE:
<221> NAME/KEY: MOD_RES
<222> LOCATION: (297)..(297)
<223> OTHER INFORMATION: Phe or Leu
<220> FEATURE:
<221> NAME/KEY: MOD_RES
<222> LOCATION: (299)..(299)
<223> OTHER INFORMATION: Thr or Asn
<220> FEATURE:
<221> NAME/KEY: MOD_RES
<222> LOCATION: (306)..(306)
<223> OTHER INFORMATION: Ala or Asn
<220> FEATURE:
<221> NAME/KEY: MOD_RES
<222> LOCATION: (311)..(311)
<223> OTHER INFORMATION: Thr or Asn
<220> FEATURE:
<221> NAME/KEY: MOD_RES
```

```
<222> LOCATION: (313)..(313)
<223> OTHER INFORMATION: Met or Phe
<220> FEATURE:
<221> NAME/KEY: MOD_RES
<222> LOCATION: (314)..(314)
<223> OTHER INFORMATION: Thr or Asn
<220> FEATURE:
<221> NAME/KEY: MOD_RES
<222> LOCATION: (315)..(315)
<223> OTHER INFORMATION: Asn or Gly
<220> FEATURE:
<221> NAME/KEY: MOD_RES
<222> LOCATION: (319)..(319)
<223> OTHER INFORMATION: Lys or Gln
<220> FEATURE:
<221> NAME/KEY: MOD_RES
<222> LOCATION: (320)..(320)
<223> OTHER INFORMATION: Asp or Arg
<220> FEATURE:
<221> NAME/KEY: MOD_RES
<222> LOCATION: (321)..(321)
<223> OTHER INFORMATION: Gln or His
<220> FEATURE:
<221> NAME/KEY: MOD_RES
<222> LOCATION: (324)..(324)
<223> OTHER INFORMATION: Leu or His
<220> FEATURE:
<221> NAME/KEY: MOD_RES
<222> LOCATION: (335)..(335)
<223> OTHER INFORMATION: Glu or Gln
<220> FEATURE:
<221> NAME/KEY: MOD_RES
<222> LOCATION: (337)..(337)
<223> OTHER INFORMATION: Gly or Glu
<220> FEATURE:
<221> NAME/KEY: MOD_RES
<222> LOCATION: (338)..(338)
<223> OTHER INFORMATION: Gln or Glu
<220> FEATURE:
<221> NAME/KEY: MOD_RES
<222> LOCATION: (341)..(341)
<223> OTHER INFORMATION: Gln or Glu
<220> FEATURE:
<221> NAME/KEY: MOD_RES
<222> LOCATION: (346)..(346)
<223> OTHER INFORMATION: Pro or Glu
<220> FEATURE:
<221> NAME/KEY: MOD_RES
<222> LOCATION: (355)..(355)
<223> OTHER INFORMATION: Phe or Leu
<220> FEATURE:
<221> NAME/KEY: MOD_RES
<222> LOCATION: (356)..(356)
<223> OTHER INFORMATION: Ile or Thr
<220> FEATURE:
<221> NAME/KEY: MOD_RES
<222> LOCATION: (360)..(360)
<223> OTHER INFORMATION: Gln or Glu
<220> FEATURE:
<221> NAME/KEY: MOD_RES
<222> LOCATION: (361)..(361)
<223> OTHER INFORMATION: Glu or Gln
<220> FEATURE:
<221> NAME/KEY: MOD_RES
<222> LOCATION: (365)..(365)
<223> OTHER INFORMATION: Cys or Ser
<220> FEATURE:
<221> NAME/KEY: MOD_RES
<222> LOCATION: (376)..(376)
<223> OTHER INFORMATION: Gln or Thr
<220> FEATURE:
<221> NAME/KEY: MOD_RES
<222> LOCATION: (378)..(378)
<223> OTHER INFORMATION: Asn or Gly
<220> FEATURE:
<221> NAME/KEY: MOD_RES
<222> LOCATION: (391)..(391)
<223> OTHER INFORMATION: Ile or Glu
<220> FEATURE:
```

-continued

```
<221> NAME/KEY: MOD_RES
<222> LOCATION: (394)..(394)
<223> OTHER INFORMATION: Arg or Gln
<220> FEATURE:
<221> NAME/KEY: MOD_RES
<222> LOCATION: (395)..(395)
<223> OTHER INFORMATION: Asp or Lys
<220> FEATURE:
<221> NAME/KEY: MOD_RES
<222> LOCATION: (400)..(400)
<223> OTHER INFORMATION: Thr or Lys
<220> FEATURE:
<221> NAME/KEY: MOD_RES
<222> LOCATION: (402)..(402)
<223> OTHER INFORMATION: His or Asn
<220> FEATURE:
<221> NAME/KEY: MOD_RES
<222> LOCATION: (408)..(408)
<223> OTHER INFORMATION: Ser or His
<220> FEATURE:
<221> NAME/KEY: MOD_RES
<222> LOCATION: (409)..(409)
<223> OTHER INFORMATION: Asp or Asn
<220> FEATURE:
<221> NAME/KEY: MOD_RES
<222> LOCATION: (418)..(418)
<223> OTHER INFORMATION: Val or Asn
<220> FEATURE:
<221> NAME/KEY: MOD_RES
<222> LOCATION: (420)..(420)
<223> OTHER INFORMATION: Glu or Ala
<220> FEATURE:
<221> NAME/KEY: MOD_RES
<222> LOCATION: (421)..(421)
<223> OTHER INFORMATION: Lys or His
<220> FEATURE:
<221> NAME/KEY: MOD_RES
<222> LOCATION: (423)..(423)
<223> OTHER INFORMATION: Gly or Asn
<220> FEATURE:
<221> NAME/KEY: MOD_RES
<222> LOCATION: (428)..(428)
<223> OTHER INFORMATION: Ala or Thr
<220> FEATURE:
<221> NAME/KEY: MOD_RES
<222> LOCATION: (434)..(434)
<223> OTHER INFORMATION: Pro or Ala
<220> FEATURE:
<221> NAME/KEY: MOD_RES
<222> LOCATION: (446)..(446)
<223> OTHER INFORMATION: His or Lys
<220> FEATURE:
<221> NAME/KEY: MOD_RES
<222> LOCATION: (449)..(449)
<223> OTHER INFORMATION: Lys or Gln
<220> FEATURE:
<221> NAME/KEY: MOD_RES
<222> LOCATION: (452)..(452)
<223> OTHER INFORMATION: Tyr or Ser
<220> FEATURE:
<221> NAME/KEY: MOD_RES
<222> LOCATION: (460)..(460)
<223> OTHER INFORMATION: Asp or Gly
<220> FEATURE:
<221> NAME/KEY: MOD_RES
<222> LOCATION: (471)..(471)
<223> OTHER INFORMATION: Glu or Asn
<220> FEATURE:
<221> NAME/KEY: MOD_RES
<222> LOCATION: (473)..(473)
<223> OTHER INFORMATION: Lys or Ser
<220> FEATURE:
<221> NAME/KEY: MOD_RES
<222> LOCATION: (484)..(484)
<223> OTHER INFORMATION: Pro or Asn
<220> FEATURE:
<221> NAME/KEY: MOD_RES
<222> LOCATION: (486)..(486)
<223> OTHER INFORMATION: Lys or not present
```

-continued

```
<220> FEATURE:
<221> NAME/KEY: MOD_RES
<222> LOCATION: (487)..(488)
<223> OTHER INFORMATION: Thr or not present
<220> FEATURE:
<221> NAME/KEY: MOD_RES
<222> LOCATION: (489)..(489)
<223> OTHER INFORMATION: Val or not present
<220> FEATURE:
<221> NAME/KEY: MOD_RES
<222> LOCATION: (490)..(490)
<223> OTHER INFORMATION: Ser or not present
<220> FEATURE:
<221> NAME/KEY: MOD_RES
<222> LOCATION: (491)..(491)
<223> OTHER INFORMATION: Thr or not present
<220> FEATURE:
<221> NAME/KEY: MOD_RES
<222> LOCATION: (492)..(492)
<223> OTHER INFORMATION: Ile or not present
<220> FEATURE:
<221> NAME/KEY: MOD_RES
<222> LOCATION: (493)..(493)
<223> OTHER INFORMATION: Ala or not present
<220> FEATURE:
<221> NAME/KEY: MOD_RES
<222> LOCATION: (494)..(494)
<223> OTHER INFORMATION: Arg or not present
<220> FEATURE:
<221> NAME/KEY: MOD_RES
<222> LOCATION: (495)..(495)
<223> OTHER INFORMATION: Pro or not present
<220> FEATURE:
<221> NAME/KEY: MOD_RES
<222> LOCATION: (496)..(496)
<223> OTHER INFORMATION: Ile or note present
<220> FEATURE:
<221> NAME/KEY: MOD_RES
<222> LOCATION: (497)..(498)
<223> OTHER INFORMATION: Thr or not present
<220> FEATURE:
<221> NAME/KEY: MOD_RES
<222> LOCATION: (499)..(499)
<223> OTHER INFORMATION: Arg or not present
<220> FEATURE:
<221> NAME/KEY: MOD_RES
<222> LOCATION: (500)..(500)
<223> OTHER INFORMATION: Pro or not present
<220> FEATURE:
<221> NAME/KEY: MOD_RES
<222> LOCATION: (501)..(501)
<223> OTHER INFORMATION: Trp or not present
<220> FEATURE:
<221> NAME/KEY: MOD_RES
<222> LOCATION: (502)..(502)
<223> OTHER INFORMATION: Thr or not present
<220> FEATURE:
<221> NAME/KEY: MOD_RES
<222> LOCATION: (503)..(503)
<223> OTHER INFORMATION: Gly or not present
<220> FEATURE:
<221> NAME/KEY: MOD_RES
<222> LOCATION: (504)..(504)
<223> OTHER INFORMATION: Glu or not present
<220> FEATURE:
<221> NAME/KEY: MOD_RES
<222> LOCATION: (505)..(505)
<223> OTHER INFORMATION: Phe or not present
<220> FEATURE:
<221> NAME/KEY: MOD_RES
<222> LOCATION: (506)..(506)
<223> OTHER INFORMATION: Val or not present
<220> FEATURE:
<221> NAME/KEY: MOD_RES
<222> LOCATION: (507)..(507)
<223> OTHER INFORMATION: Arg or not present
<220> FEATURE:
<221> NAME/KEY: MOD_RES
<222> LOCATION: (508)..(508)
```

```
<223> OTHER INFORMATION: Trp or not present
<220> FEATURE:
<221> NAME/KEY: MOD_RES
<222> LOCATION: (509)..(509)
<223> OTHER INFORMATION: Thr or not present
<220> FEATURE:
<221> NAME/KEY: MOD_RES
<222> LOCATION: (510)..(510)
<223> OTHER INFORMATION: Glu or not present
<220> FEATURE:
<221> NAME/KEY: MOD_RES
<222> LOCATION: (511)..(511)
<223> OTHER INFORMATION: Pro or not present
<220> FEATURE:
<221> NAME/KEY: MOD_RES
<222> LOCATION: (512)..(512)
<223> OTHER INFORMATION: Arg or not present
<220> FEATURE:
<221> NAME/KEY: MOD_RES
<222> LOCATION: (513)..(513)
<223> OTHER INFORMATION: Leu or not present
<220> FEATURE:
<221> NAME/KEY: MOD_RES
<222> LOCATION: (514)..(514)
<223> OTHER INFORMATION: Val or not present
<220> FEATURE:
<221> NAME/KEY: MOD_RES
<222> LOCATION: (515)..(515)
<223> OTHER INFORMATION: Ala or not present
<220> FEATURE:
<221> NAME/KEY: MOD_RES
<222> LOCATION: (516)..(516)
<223> OTHER INFORMATION: Trp or not present
<220> FEATURE:
<221> NAME/KEY: MOD_RES
<222> LOCATION: (517)..(517)
<223> OTHER INFORMATION: Pro or not present

<400> SEQUENCE: 23

Xaa Xaa Xaa Xaa Xaa Asn Gly Thr Met Met Gln Tyr Phe Glu Trp Tyr
 1               5                  10                  15

Leu Pro Xaa Asp Gly Xaa Xaa Trp Xaa Lys Leu Xaa Xaa Asp Ala Xaa
             20                  25                  30

Asn Leu Xaa Ser Xaa Gly Ile Thr Ala Leu Trp Ile Pro Pro Ala Trp
         35                  40                  45

Lys Gly Xaa Ser Xaa Xaa Asp Val Gly Tyr Gly Xaa Tyr Asp Leu Tyr
 50                  55                  60

Asp Leu Gly Glu Phe Asn Gln Lys Gly Thr Val Arg Thr Lys Tyr Gly
 65                  70                  75                  80

Thr Lys Ala Gln Xaa Xaa Xaa Ala Ile Xaa Ala Xaa Xaa Xaa Xaa Gly
                 85                  90                  95

Ile Gln Val Tyr Ala Asp Val Val Xaa Xaa His Lys Gly Gly Ala Asp
            100                 105                 110

Ala Thr Glu Xaa Val Xaa Ala Val Glu Val Asn Pro Xaa Xaa Arg Asn
            115                 120                 125

Gln Glu Ile Ser Gly Xaa Tyr Xaa Ile Xaa Ala Trp Thr Lys Phe Asp
            130                 135                 140

Phe Pro Gly Arg Gly Asn Thr His Ser Ser Phe Lys Trp Arg Trp Tyr
145                 150                 155                 160

His Phe Asp Gly Val Asp Trp Asp Xaa Ser Arg Lys Leu Xaa Xaa Arg
                165                 170                 175

Ile Tyr Lys Phe Arg Gly Xaa Gly Lys Ala Trp Asp Trp Glu Val Asp
            180                 185                 190

Thr Glu Asn Gly Asn Tyr Asp Tyr Leu Met Tyr Ala Asp Ile Asp Met
            195                 200                 205
```

```
Asp His Pro Glu Val Val Xaa Glu Leu Lys Asn Trp Gly Xaa Trp Tyr
210                 215                 220

Xaa Asn Thr Xaa Xaa Ile Asp Gly Phe Arg Ile Asp Ala Val Lys His
225                 230                 235                 240

Ile Lys Phe Ser Phe Xaa Xaa Asp Trp Ile Xaa His Val Arg Ser Xaa
                245                 250                 255

Thr Gly Lys Xaa Leu Phe Xaa Val Ala Glu Phe Trp Xaa Xaa Asp Ile
            260                 265                 270

Xaa Xaa Ile Xaa Asn Tyr Ile Xaa Lys Thr Asn Xaa Xaa Xaa Ser Leu
        275                 280                 285

Phe Asp Xaa Pro Leu His Xaa Xaa Xaa Tyr Xaa Ala Ser Lys Ser Gly
290                 295                 300

Gly Xaa Phe Asp Met Arg Xaa Ile Xaa Xaa Xaa Thr Leu Met Xaa Xaa
305                 310                 315                 320

Xaa Pro Ser Xaa Ala Val Thr Phe Val Asp Asn His Asp Ser Xaa Pro
                325                 330                 335

Xaa Xaa Ala Leu Xaa Ser Phe Val Asp Xaa Trp Phe Lys Pro Leu Ala
            340                 345                 350

Tyr Ala Xaa Xaa Leu Thr Arg Xaa Xaa Gly Tyr Pro Xaa Val Phe Tyr
            355                 360                 365

Gly Asp Tyr Tyr Gly Ile Pro Xaa His Xaa Ile Pro Ala Leu Lys Ser
370                 375                 380

Lys Ile Asp Pro Ile Leu Xaa Ala Arg Xaa Xaa Tyr Ala Tyr Gly Xaa
385                 390                 395                 400

Gln Xaa Asp Tyr Leu Asp His Xaa Xaa Ile Ile Gly Trp Thr Arg Glu
        405                 410                 415

Gly Xaa Thr Xaa Xaa Pro Xaa Ser Gly Leu Ala Xaa Ile Ile Ser Asp
            420                 425                 430

Gly Xaa Gly Gly Ser Lys Trp Met Phe Val Gly Lys Asn Xaa Ala Gly
            435                 440                 445

Xaa Val Phe Xaa Asp Ile Thr Gly Asn Arg Ser Xaa Thr Val Thr Ile
450                 455                 460

Asn Ala Asp Gly Trp Gly Xaa Phe Xaa Val Asn Gly Gly Ser Val Ser
465                 470                 475                 480

Ile Trp Val Xaa Lys Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
                500                 505                 510

Xaa Xaa Xaa Xaa Xaa
            515

<210> SEQ ID NO 24
<211> LENGTH: 518
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ala or not present
<220> FEATURE:
<221> NAME/KEY: MOD_RES
<222> LOCATION: (3)..(3)
<223> OTHER INFORMATION: Pro or Asn
<220> FEATURE:
<221> NAME/KEY: MOD_RES
<222> LOCATION: (4)..(4)
```

```
<223> OTHER INFORMATION: Phe or Leu
<220> FEATURE:
<221> NAME/KEY: MOD_RES
<222> LOCATION: (18)..(18)
<223> OTHER INFORMATION: Asp or Asn
<220> FEATURE:
<221> NAME/KEY: MOD_RES
<222> LOCATION: (21)..(21)
<223> OTHER INFORMATION: Thr or Gln
<220> FEATURE:
<221> NAME/KEY: MOD_RES
<222> LOCATION: (22)..(22)
<223> OTHER INFORMATION: Leu or His
<220> FEATURE:
<221> NAME/KEY: MOD_RES
<222> LOCATION: (24)..(24)
<223> OTHER INFORMATION: Thr or Arg
<220> FEATURE:
<221> NAME/KEY: MOD_RES
<222> LOCATION: (27)..(27)
<223> OTHER INFORMATION: Ala or Gln
<220> FEATURE:
<221> NAME/KEY: MOD_RES
<222> LOCATION: (31)..(31)
<223> OTHER INFORMATION: Asn or Ala
<220> FEATURE:
<221> NAME/KEY: MOD_RES
<222> LOCATION: (32)..(32)
<223> OTHER INFORMATION: Asn or Tyr
<220> FEATURE:
<221> NAME/KEY: MOD_RES
<222> LOCATION: (35)..(35)
<223> OTHER INFORMATION: Ser or Glu
<220> FEATURE:
<221> NAME/KEY: MOD_RES
<222> LOCATION: (36)..(36)
<223> OTHER INFORMATION: Leu or His
<220> FEATURE:
<221> NAME/KEY: MOD_RES
<222> LOCATION: (52)..(52)
<223> OTHER INFORMATION: Arg or Gln
<220> FEATURE:
<221> NAME/KEY: MOD_RES
<222> LOCATION: (59)..(59)
<223> OTHER INFORMATION: Val or Ala
<220> FEATURE:
<221> NAME/KEY: MOD_RES
<222> LOCATION: (69)..(69)
<223> OTHER INFORMATION: Asn or His
<220> FEATURE:
<221> NAME/KEY: MOD_RES
<222> LOCATION: (83)..(83)
<223> OTHER INFORMATION: Gln or Glu
<220> FEATURE:
<221> NAME/KEY: MOD_RES
<222> LOCATION: (84)..(84)
<223> OTHER INFORMATION: Tyr or Leu
<220> FEATURE:
<221> NAME/KEY: MOD_RES
<222> LOCATION: (85)..(85)
<223> OTHER INFORMATION: Leu or Gln
<220> FEATURE:
<221> NAME/KEY: MOD_RES
<222> LOCATION: (86)..(86)
<223> OTHER INFORMATION: Gln or Ser
<220> FEATURE:
<221> NAME/KEY: MOD_RES
<222> LOCATION: (89)..(89)
<223> OTHER INFORMATION: Gln or Lys
<220> FEATURE:
<221> NAME/KEY: MOD_RES
<222> LOCATION: (91)..(91)
<223> OTHER INFORMATION: Ala or Leu
<220> FEATURE:
<221> NAME/KEY: MOD_RES
<222> LOCATION: (94)..(94)
<223> OTHER INFORMATION: Ala or Arg
<220> FEATURE:
<221> NAME/KEY: MOD_RES
```

```
<222> LOCATION: (95)..(95)
<223> OTHER INFORMATION: Gly or Asp
<220> FEATURE:
<221> NAME/KEY: MOD_RES
<222> LOCATION: (104)..(104)
<223> OTHER INFORMATION: Phe or Ile
<220> FEATURE:
<221> NAME/KEY: MOD_RES
<222> LOCATION: (105)..(105)
<223> OTHER INFORMATION: Asp or Asn
<220> FEATURE:
<221> NAME/KEY: MOD_RES
<222> LOCATION: (115)..(115)
<223> OTHER INFORMATION: Trp or Asp
<220> FEATURE:
<221> NAME/KEY: MOD_RES
<222> LOCATION: (117)..(117)
<223> OTHER INFORMATION: Asp or Thr
<220> FEATURE:
<221> NAME/KEY: MOD_RES
<222> LOCATION: (122)..(122)
<223> OTHER INFORMATION: Asn or Asp
<220> FEATURE:
<221> NAME/KEY: MOD_RES
<222> LOCATION: (128)..(128)
<223> OTHER INFORMATION: Gln or Arg
<220> FEATURE:
<221> NAME/KEY: MOD_RES
<222> LOCATION: (129)..(129)
<223> OTHER INFORMATION: Glu or Val
<220> FEATURE:
<221> NAME/KEY: MOD_RES
<222> LOCATION: (133)..(133)
<223> OTHER INFORMATION: Thr or Glu
<220> FEATURE:
<221> NAME/KEY: MOD_RES
<222> LOCATION: (135)..(135)
<223> OTHER INFORMATION: Gln or Leu
<220> FEATURE:
<221> NAME/KEY: MOD_RES
<222> LOCATION: (137)..(137)
<223> OTHER INFORMATION: Gln or Lys
<220> FEATURE:
<221> NAME/KEY: MOD_RES
<222> LOCATION: (141)..(141)
<223> OTHER INFORMATION: Lys or His
<220> FEATURE:
<221> NAME/KEY: MOD_RES
<222> LOCATION: (143)..(143)
<223> OTHER INFORMATION: Asp or His
<220> FEATURE:
<221> NAME/KEY: MOD_RES
<222> LOCATION: (149)..(149)
<223> OTHER INFORMATION: Asn or Ser
<220> FEATURE:
<221> NAME/KEY: MOD_RES
<222> LOCATION: (153)..(153)
<223> OTHER INFORMATION: Ser or Asp
<220> FEATURE:
<221> NAME/KEY: MOD_RES
<222> LOCATION: (157)..(157)
<223> OTHER INFORMATION: Arg or His
<220> FEATURE:
<221> NAME/KEY: MOD_RES
<222> LOCATION: (164)..(164)
<223> OTHER INFORMATION: Val or Thr
<220> FEATURE:
<221> NAME/KEY: MOD_RES
<222> LOCATION: (173)..(173)
<223> OTHER INFORMATION: Ser or Asn
<220> FEATURE:
<221> NAME/KEY: MOD_RES
<222> LOCATION: (179)..(179)
<223> OTHER INFORMATION: Arg or Gln
<220> FEATURE:
<221> NAME/KEY: MOD_RES
<222> LOCATION: (180)..(180)
<223> OTHER INFORMATION: Gly or not present
<220> FEATURE:
```

```
<221> NAME/KEY: MOD_RES
<222> LOCATION: (181)..(181)
<223> OTHER INFORMATION: Ile or not present
<220> FEATURE:
<221> NAME/KEY: MOD_RES
<222> LOCATION: (190)..(190)
<223> OTHER INFORMATION: Asp or Ser
<220> FEATURE:
<221> NAME/KEY: MOD_RES
<222> LOCATION: (191)..(191)
<223> OTHER INFORMATION: Thr or Asn
<220> FEATURE:
<221> NAME/KEY: MOD_RES
<222> LOCATION: (206)..(206)
<223> OTHER INFORMATION: Met or Tyr
<220> FEATURE:
<221> NAME/KEY: MOD_RES
<222> LOCATION: (212)..(212)
<223> OTHER INFORMATION: Val or Ala
<220> FEATURE:
<221> NAME/KEY: MOD_RES
<222> LOCATION: (213)..(213)
<223> OTHER INFORMATION: Thr or Ala
<220> FEATURE:
<221> NAME/KEY: MOD_RES
<222> LOCATION: (217)..(217)
<223> OTHER INFORMATION: Asn or Arg
<220> FEATURE:
<221> NAME/KEY: MOD_RES
<222> LOCATION: (220)..(220)
<223> OTHER INFORMATION: Lys or Thr
<220> FEATURE:
<221> NAME/KEY: MOD_RES
<222> LOCATION: (223)..(223)
<223> OTHER INFORMATION: Val or Ala
<220> FEATURE:
<221> NAME/KEY: MOD_RES
<222> LOCATION: (225)..(225)
<223> OTHER INFORMATION: Thr or Glu
<220> FEATURE:
<221> NAME/KEY: MOD_RES
<222> LOCATION: (226)..(226)
<223> OTHER INFORMATION: Thr or Leu
<220> FEATURE:
<221> NAME/KEY: MOD_RES
<222> LOCATION: (244)..(244)
<223> OTHER INFORMATION: Phe or Leu
<220> FEATURE:
<221> NAME/KEY: MOD_RES
<222> LOCATION: (245)..(245)
<223> OTHER INFORMATION: Pro or Arg
<220> FEATURE:
<221> NAME/KEY: MOD_RES
<222> LOCATION: (249)..(249)
<223> OTHER INFORMATION: Ser or Asn
<220> FEATURE:
<221> NAME/KEY: MOD_RES
<222> LOCATION: (253)..(253)
<223> OTHER INFORMATION: Ser or Glu
<220> FEATURE:
<221> NAME/KEY: MOD_RES
<222> LOCATION: (254)..(254)
<223> OTHER INFORMATION: Gln or Lys
<220> FEATURE:
<221> NAME/KEY: MOD_RES
<222> LOCATION: (258)..(258)
<223> OTHER INFORMATION: Pro or Glu
<220> FEATURE:
<221> NAME/KEY: MOD_RES
<222> LOCATION: (267)..(267)
<223> OTHER INFORMATION: Ser or Gln
<220> FEATURE:
<221> NAME/KEY: MOD_RES
<222> LOCATION: (268)..(268)
<223> OTHER INFORMATION: Tyr or Asn
<220> FEATURE:
<221> NAME/KEY: MOD_RES
<222> LOCATION: (271)..(271)
<223> OTHER INFORMATION: Asn or Gly
```

```
<220> FEATURE:
<221> NAME/KEY: MOD_RES
<222> LOCATION: (272)..(272)
<223> OTHER INFORMATION: Lys or Ala
<220> FEATURE:
<221> NAME/KEY: MOD_RES
<222> LOCATION: (274)..(274)
<223> OTHER INFORMATION: His or Glu
<220> FEATURE:
<221> NAME/KEY: MOD_RES
<222> LOCATION: (278)..(278)
<223> OTHER INFORMATION: Thr or Asn
<220> FEATURE:
<221> NAME/KEY: MOD_RES
<222> LOCATION: (282)..(282)
<223> OTHER INFORMATION: Gly or Phe
<220> FEATURE:
<221> NAME/KEY: MOD_RES
<222> LOCATION: (283)..(283)
<223> OTHER INFORMATION: Thr or Asn
<220> FEATURE:
<221> NAME/KEY: MOD_RES
<222> LOCATION: (284)..(284)
<223> OTHER INFORMATION: Met or His
<220> FEATURE:
<221> NAME/KEY: MOD_RES
<222> LOCATION: (289)..(289)
<223> OTHER INFORMATION: Ala or Val
<220> FEATURE:
<221> NAME/KEY: MOD_RES
<222> LOCATION: (293)..(293)
<223> OTHER INFORMATION: Asn or Tyr
<220> FEATURE:
<221> NAME/KEY: MOD_RES
<222> LOCATION: (294)..(294)
<223> OTHER INFORMATION: Lys or Gln
<220> FEATURE:
<221> NAME/KEY: MOD_RES
<222> LOCATION: (297)..(297)
<223> OTHER INFORMATION: Thr or Ala
<220> FEATURE:
<221> NAME/KEY: MOD_RES
<222> LOCATION: (300)..(300)
<223> OTHER INFORMATION: Lys or Thr
<220> FEATURE:
<221> NAME/KEY: MOD_RES
<222> LOCATION: (301)..(301)
<223> OTHER INFORMATION: Ser or Gln
<220> FEATURE:
<221> NAME/KEY: MOD_RES
<222> LOCATION: (309)..(309)
<223> OTHER INFORMATION: Thr or Lys
<220> FEATURE:
<221> NAME/KEY: MOD_RES
<222> LOCATION: (312)..(312)
<223> OTHER INFORMATION: Thr or Asn
<220> FEATURE:
<221> NAME/KEY: MOD_RES
<222> LOCATION: (313)..(313)
<223> OTHER INFORMATION: Asn or Gly
<220> FEATURE:
<221> NAME/KEY: MOD_RES
<222> LOCATION: (317)..(317)
<223> OTHER INFORMATION: Lys or Ser
<220> FEATURE:
<221> NAME/KEY: MOD_RES
<222> LOCATION: (318)..(318)
<223> OTHER INFORMATION: Asp or Lys
<220> FEATURE:
<221> NAME/KEY: MOD_RES
<222> LOCATION: (319)..(319)
<223> OTHER INFORMATION: Gln or His
<220> FEATURE:
<221> NAME/KEY: MOD_RES
<222> LOCATION: (321)..(321)
<223> OTHER INFORMATION: Thr or Leu
<220> FEATURE:
<221> NAME/KEY: MOD_RES
<222> LOCATION: (322)..(322)
```

-continued

```
<223> OTHER INFORMATION: Leu or Lys
<220> FEATURE:
<221> NAME/KEY: MOD_RES
<222> LOCATION: (333)..(333)
<223> OTHER INFORMATION: Glu or Gln
<220> FEATURE:
<221> NAME/KEY: MOD_RES
<222> LOCATION: (339)..(339)
<223> OTHER INFORMATION: Gln or Glu
<220> FEATURE:
<221> NAME/KEY: MOD_RES
<222> LOCATION: (341)..(341)
<223> OTHER INFORMATION: Trp or Thr
<220> FEATURE:
<221> NAME/KEY: MOD_RES
<222> LOCATION: (343)..(343)
<223> OTHER INFORMATION: Asp or Gln
<220> FEATURE:
<221> NAME/KEY: MOD_RES
<222> LOCATION: (344)..(344)
<223> OTHER INFORMATION: Pro or Thr
<220> FEATURE:
<221> NAME/KEY: MOD_RES
<222> LOCATION: (358)..(358)
<223> OTHER INFORMATION: Gln or Glu
<220> FEATURE:
<221> NAME/KEY: MOD_RES
<222> LOCATION: (359)..(359)
<223> OTHER INFORMATION: Glu or Ser
<220> FEATURE:
<221> NAME/KEY: MOD_RES
<222> LOCATION: (363)..(363)
<223> OTHER INFORMATION: Cys or Gln
<220> FEATURE:
<221> NAME/KEY: MOD_RES
<222> LOCATION: (369)..(369)
<223> OTHER INFORMATION: Tyr or Met
<220> FEATURE:
<221> NAME/KEY: MOD_RES
<222> LOCATION: (372)..(372)
<223> OTHER INFORMATION: Ile or Thr
<220> FEATURE:
<221> NAME/KEY: MOD_RES
<222> LOCATION: (373)..(373)
<223> OTHER INFORMATION: Pro or Lys
<220> FEATURE:
<221> NAME/KEY: MOD_RES
<222> LOCATION: (374)..(374)
<223> OTHER INFORMATION: Gly or not present
<220> FEATURE:
<221> NAME/KEY: MOD_RES
<222> LOCATION: (375)..(375)
<223> OTHER INFORMATION: Asp or not present
<220> FEATURE:
<221> NAME/KEY: MOD_RES
<222> LOCATION: (376)..(376)
<223> OTHER INFORMATION: Ser or not present
<220> FEATURE:
<221> NAME/KEY: MOD_RES
<222> LOCATION: (378)..(378)
<223> OTHER INFORMATION: Tyr or Arg
<220> FEATURE:
<221> NAME/KEY: MOD_RES
<222> LOCATION: (379)..(379)
<223> OTHER INFORMATION: Asn or Glu
<220> FEATURE:
<221> NAME/KEY: MOD_RES
<222> LOCATION: (385)..(385)
<223> OTHER INFORMATION: Ser or His
<220> FEATURE:
<221> NAME/KEY: MOD_RES
<222> LOCATION: (392)..(392)
<223> OTHER INFORMATION: Ile or Lys
<220> FEATURE:
<221> NAME/KEY: MOD_RES
<222> LOCATION: (396)..(396)
<223> OTHER INFORMATION: Asp or Gln
<220> FEATURE:
<221> NAME/KEY: MOD_RES
```

```
<222> LOCATION: (401)..(401)
<223> OTHER INFORMATION: Thr or Ala
<220> FEATURE:
<221> NAME/KEY: MOD_RES
<222> LOCATION: (406)..(406)
<223> OTHER INFORMATION: Leu or Phe
<220> FEATURE:
<221> NAME/KEY: MOD_RES
<222> LOCATION: (409)..(409)
<223> OTHER INFORMATION: Ser or His
<220> FEATURE:
<221> NAME/KEY: MOD_RES
<222> LOCATION: (419)..(419)
<223> OTHER INFORMATION: Val or Asp
<220> FEATURE:
<221> NAME/KEY: MOD_RES
<222> LOCATION: (421)..(421)
<223> OTHER INFORMATION: Glu or Ser
<220> FEATURE:
<221> NAME/KEY: MOD_RES
<222> LOCATION: (422)..(422)
<223> OTHER INFORMATION: Lys or Val
<220> FEATURE:
<221> NAME/KEY: MOD_RES
<222> LOCATION: (423)..(423)
<223> OTHER INFORMATION: Pro or Ala
<220> FEATURE:
<221> NAME/KEY: MOD_RES
<222> LOCATION: (424)..(424)
<223> OTHER INFORMATION: Gly or Asn
<220> FEATURE:
<221> NAME/KEY: MOD_RES
<222> LOCATION: (440)..(440)
<223> OTHER INFORMATION: Trp or Arg
<220> FEATURE:
<221> NAME/KEY: MOD_RES
<222> LOCATION: (447)..(447)
<223> OTHER INFORMATION: His or Asn
<220> FEATURE:
<221> NAME/KEY: MOD_RES
<222> LOCATION: (450)..(450)
<223> OTHER INFORMATION: Lys or Glu
<220> FEATURE:
<221> NAME/KEY: MOD_RES
<222> LOCATION: (451)..(451)
<223> OTHER INFORMATION: Val or Thr
<220> FEATURE:
<221> NAME/KEY: MOD_RES
<222> LOCATION: (462)..(462)
<223> OTHER INFORMATION: Thr or Pro
<220> FEATURE:
<221> NAME/KEY: MOD_RES
<222> LOCATION: (464)..(464)
<223> OTHER INFORMATION: Thr or Val
<220> FEATURE:
<221> NAME/KEY: MOD_RES
<222> LOCATION: (474)..(474)
<223> OTHER INFORMATION: Lys or His
<220> FEATURE:
<221> NAME/KEY: MOD_RES
<222> LOCATION: (485)..(485)
<223> OTHER INFORMATION: Pro or Gln
<220> FEATURE:
<221> NAME/KEY: MOD_RES
<222> LOCATION: (487)..(487)
<223> OTHER INFORMATION: Lys or not present
<220> FEATURE:
<221> NAME/KEY: MOD_RES
<222> LOCATION: (488)..(489)
<223> OTHER INFORMATION: Thr or not present
<220> FEATURE:
<221> NAME/KEY: MOD_RES
<222> LOCATION: (490)..(490)
<223> OTHER INFORMATION: Val or not present
<220> FEATURE:
<221> NAME/KEY: MOD_RES
<222> LOCATION: (491)..(491)
<223> OTHER INFORMATION: Ser or not present
<220> FEATURE:
```

```
<221> NAME/KEY: MOD_RES
<222> LOCATION: (492)..(492)
<223> OTHER INFORMATION: Thr or not present
<220> FEATURE:
<221> NAME/KEY: MOD_RES
<222> LOCATION: (493)..(493)
<223> OTHER INFORMATION: Ile or not present
<220> FEATURE:
<221> NAME/KEY: MOD_RES
<222> LOCATION: (494)..(494)
<223> OTHER INFORMATION: Ala or not present
<220> FEATURE:
<221> NAME/KEY: MOD_RES
<222> LOCATION: (495)..(495)
<223> OTHER INFORMATION: Arg or not present
<220> FEATURE:
<221> NAME/KEY: MOD_RES
<222> LOCATION: (496)..(496)
<223> OTHER INFORMATION: Pro or not present
<220> FEATURE:
<221> NAME/KEY: MOD_RES
<222> LOCATION: (497)..(497)
<223> OTHER INFORMATION: Ile or note present
<220> FEATURE:
<221> NAME/KEY: MOD_RES
<222> LOCATION: (498)..(499)
<223> OTHER INFORMATION: Thr or not present
<220> FEATURE:
<221> NAME/KEY: MOD_RES
<222> LOCATION: (500)..(500)
<223> OTHER INFORMATION: Arg or not present
<220> FEATURE:
<221> NAME/KEY: MOD_RES
<222> LOCATION: (501)..(501)
<223> OTHER INFORMATION: Pro or not present
<220> FEATURE:
<221> NAME/KEY: MOD_RES
<222> LOCATION: (502)..(502)
<223> OTHER INFORMATION: Trp or not present
<220> FEATURE:
<221> NAME/KEY: MOD_RES
<222> LOCATION: (503)..(503)
<223> OTHER INFORMATION: Thr or not present
<220> FEATURE:
<221> NAME/KEY: MOD_RES
<222> LOCATION: (504)..(504)
<223> OTHER INFORMATION: Gly or not present
<220> FEATURE:
<221> NAME/KEY: MOD_RES
<222> LOCATION: (505)..(505)
<223> OTHER INFORMATION: Glu or not present
<220> FEATURE:
<221> NAME/KEY: MOD_RES
<222> LOCATION: (506)..(506)
<223> OTHER INFORMATION: Phe or not present
<220> FEATURE:
<221> NAME/KEY: MOD_RES
<222> LOCATION: (507)..(507)
<223> OTHER INFORMATION: Val or not present
<220> FEATURE:
<221> NAME/KEY: MOD_RES
<222> LOCATION: (508)..(508)
<223> OTHER INFORMATION: Arg or not present
<220> FEATURE:
<221> NAME/KEY: MOD_RES
<222> LOCATION: (509)..(509)
<223> OTHER INFORMATION: Trp or not present
<220> FEATURE:
<221> NAME/KEY: MOD_RES
<222> LOCATION: (510)..(510)
<223> OTHER INFORMATION: Thr or not present
<220> FEATURE:
<221> NAME/KEY: MOD_RES
<222> LOCATION: (511)..(511)
<223> OTHER INFORMATION: Glu or not present
<220> FEATURE:
<221> NAME/KEY: MOD_RES
<222> LOCATION: (512)..(512)
<223> OTHER INFORMATION: Pro or not present
```

<220> FEATURE:
<221> NAME/KEY: MOD_RES
<222> LOCATION: (513)..(513)
<223> OTHER INFORMATION: Arg or not present
<220> FEATURE:
<221> NAME/KEY: MOD_RES
<222> LOCATION: (514)..(514)
<223> OTHER INFORMATION: Leu or not present
<220> FEATURE:
<221> NAME/KEY: MOD_RES
<222> LOCATION: (515)..(515)
<223> OTHER INFORMATION: Val or not present
<220> FEATURE:
<221> NAME/KEY: MOD_RES
<222> LOCATION: (516)..(516)
<223> OTHER INFORMATION: Ala or not present
<220> FEATURE:
<221> NAME/KEY: MOD_RES
<222> LOCATION: (517)..(517)
<223> OTHER INFORMATION: Trp or not present
<220> FEATURE:
<221> NAME/KEY: MOD_RES
<222> LOCATION: (518)..(518)
<223> OTHER INFORMATION: Pro or not present

<400> SEQUENCE: 24

Xaa Ala Xaa Xaa Asn Gly Thr Leu Met Gln Tyr Phe Glu Trp Tyr Leu
1               5                   10                  15

Pro Xaa Asp Gly Xaa Xaa Trp Xaa Lys Leu Xaa Asn Asp Ala Xaa Xaa
            20                  25                  30

Leu Ala Xaa Xaa Gly Ile Thr Ala Leu Trp Ile Pro Pro Ala Tyr Lys
        35                  40                  45

Gly Thr Ser Xaa Ala Asp Val Gly Tyr Gly Xaa Tyr Asp Leu Tyr Asp
50                  55                  60

Leu Gly Glu Phe Xaa Gln Lys Gly Thr Val Arg Thr Lys Tyr Gly Thr
65                  70                  75                  80

Lys Ala Xaa Xaa Xaa Xaa Ala Ile Xaa Ala Xaa His Ala Xaa Xaa Ile
                85                  90                  95

Asn Val Tyr Ala Asp Val Val Xaa Xaa His Lys Gly Gly Ala Asp Ala
            100                 105                 110

Thr Glu Xaa Val Xaa Ala Val Glu Val Xaa Pro Ala Asp Arg Asn Xaa
        115                 120                 125

Xaa Ile Ser Gly Xaa His Xaa Ile Xaa Ala Trp Thr Xaa Phe Xaa Phe
130                 135                 140

Pro Gly Arg Gly Xaa Thr Tyr Ser Xaa Phe Lys Trp Xaa Trp Tyr His
145                 150                 155                 160

Phe Asp Gly Xaa Asp Trp Asp Glu Ser Arg Lys Leu Xaa Arg Ile Tyr
            165                 170                 175

Lys Phe Xaa Xaa Xaa Gly Lys Ala Trp Asp Trp Glu Val Xaa Xaa Glu
        180                 185                 190

Asn Gly Asn Tyr Asp Tyr Leu Met Tyr Ala Asp Ile Asp Xaa Asp His
            195                 200                 205

Pro Asp Val Xaa Xaa Glu Ile Lys Xaa Trp Gly Xaa Trp Tyr Xaa Asn
        210                 215                 220

Xaa Xaa Asn Ile Asp Gly Phe Arg Leu Asp Ala Val Lys His Ile Lys
225                 230                 235                 240

Phe Ser Phe Xaa Xaa Asp Trp Leu Xaa His Val Arg Xaa Xaa Thr Gly
            245                 250                 255

Lys Xaa Leu Phe Thr Val Ala Glu Tyr Trp Xaa Xaa Asp Ile Xaa Xaa
        260                 265                 270

Leu Xaa Asn Tyr Ile Xaa Lys Thr Asn Xaa Xaa Xaa Ser Leu Phe Asp

```
                   275                 280                 285
Xaa Pro Leu His Xaa Xaa Phe His Xaa Ala Ser Xaa Xaa Gly Gly Ala
                290                 295                 300

Phe Asp Met Arg Xaa Leu Leu Xaa Xaa Thr Leu Met Xaa Xaa Xaa Pro
305                 310                 315                 320

Xaa Xaa Ala Val Thr Phe Val Asp Asn His Asp Thr Xaa Pro Gly Gln
                325                 330                 335

Ala Leu Xaa Ser Xaa Val Xaa Xaa Trp Phe Lys Pro Leu Ala Tyr Ala
                340                 345                 350

Phe Ile Leu Thr Arg Xaa Xaa Gly Tyr Pro Xaa Val Phe Tyr Gly Asp
                355                 360                 365

Xaa Tyr Gly Xaa Xaa Xaa Xaa Xaa Gln Xaa Xaa Ile Pro Ala Leu Lys
                370                 375                 380

Xaa Lys Ile Asp Pro Ile Leu Xaa Ala Arg Lys Xaa Tyr Ala Tyr Gly
385                 390                 395                 400

Xaa Gln His Asp Tyr Xaa Asp His Xaa Asp Ile Ile Gly Trp Thr Arg
                405                 410                 415

Glu Gly Xaa Ser Xaa Xaa Xaa Xaa Ser Gly Leu Ala Ala Leu Ile Thr
                420                 425                 430

Asp Gly Pro Gly Gly Ala Lys Xaa Met Tyr Val Gly Lys Gln Xaa Ala
                435                 440                 445

Gly Xaa Xaa Phe His Asp Ile Thr Gly Asn Arg Ser Asp Xaa Val Xaa
                450                 455                 460

Ile Asn Ser Asp Gly Trp Gly Glu Phe Xaa Val Asn Gly Gly Ser Val
465                 470                 475                 480

Ser Ile Trp Val Xaa Arg Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
                500                 505                 510

Xaa Xaa Xaa Xaa Xaa Xaa
                515

<210> SEQ ID NO 25
<211> LENGTH: 518
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(2)
<223> OTHER INFORMATION: Ala or not present
<220> FEATURE:
<221> NAME/KEY: MOD_RES
<222> LOCATION: (3)..(3)
<223> OTHER INFORMATION: Pro or not present
<220> FEATURE:
<221> NAME/KEY: MOD_RES
<222> LOCATION: (4)..(4)
<223> OTHER INFORMATION: Phe or Val
<220> FEATURE:
<221> NAME/KEY: MOD_RES
<222> LOCATION: (16)..(16)
<223> OTHER INFORMATION: Leu or Thr
<220> FEATURE:
<221> NAME/KEY: MOD_RES
<222> LOCATION: (18)..(18)
<223> OTHER INFORMATION: Asp or Asn
<220> FEATURE:
<221> NAME/KEY: MOD_RES
<222> LOCATION: (21)..(21)
<223> OTHER INFORMATION: Thr or Gln
```

-continued

```
<220> FEATURE:
<221> NAME/KEY: MOD_RES
<222> LOCATION: (22)..(22)
<223> OTHER INFORMATION: Leu or His
<220> FEATURE:
<221> NAME/KEY: MOD_RES
<222> LOCATION: (24)..(24)
<223> OTHER INFORMATION: Thr or Lys
<220> FEATURE:
<221> NAME/KEY: MOD_RES
<222> LOCATION: (27)..(27)
<223> OTHER INFORMATION: Ala or Gln
<220> FEATURE:
<221> NAME/KEY: MOD_RES
<222> LOCATION: (31)..(31)
<223> OTHER INFORMATION: Asn or Glu
<220> FEATURE:
<221> NAME/KEY: MOD_RES
<222> LOCATION: (32)..(32)
<223> OTHER INFORMATION: Asn or His
<220> FEATURE:
<221> NAME/KEY: MOD_RES
<222> LOCATION: (35)..(35)
<223> OTHER INFORMATION: Ser or Asp
<220> FEATURE:
<221> NAME/KEY: MOD_RES
<222> LOCATION: (50)..(50)
<223> OTHER INFORMATION: Thr or Leu
<220> FEATURE:
<221> NAME/KEY: MOD_RES
<222> LOCATION: (52)..(52)
<223> OTHER INFORMATION: Arg or Gln
<220> FEATURE:
<221> NAME/KEY: MOD_RES
<222> LOCATION: (55)..(55)
<223> OTHER INFORMATION: Val or Asn
<220> FEATURE:
<221> NAME/KEY: MOD_RES
<222> LOCATION: (59)..(59)
<223> OTHER INFORMATION: Val or Pro
<220> FEATURE:
<221> NAME/KEY: MOD_RES
<222> LOCATION: (83)..(83)
<223> OTHER INFORMATION: Gln or Glu
<220> FEATURE:
<221> NAME/KEY: MOD_RES
<222> LOCATION: (84)..(84)
<223> OTHER INFORMATION: Tyr or Leu
<220> FEATURE:
<221> NAME/KEY: MOD_RES
<222> LOCATION: (85)..(85)
<223> OTHER INFORMATION: Leu or Gln
<220> FEATURE:
<221> NAME/KEY: MOD_RES
<222> LOCATION: (86)..(86)
<223> OTHER INFORMATION: Gln or Asp
<220> FEATURE:
<221> NAME/KEY: MOD_RES
<222> LOCATION: (89)..(89)
<223> OTHER INFORMATION: Gln or Gly
<220> FEATURE:
<221> NAME/KEY: MOD_RES
<222> LOCATION: (91)..(91)
<223> OTHER INFORMATION: Ala or Leu
<220> FEATURE:
<221> NAME/KEY: MOD_RES
<222> LOCATION: (94)..(94)
<223> OTHER INFORMATION: Ala or Arg
<220> FEATURE:
<221> NAME/KEY: MOD_RES
<222> LOCATION: (95)..(95)
<223> OTHER INFORMATION: Gly or Asn
<220> FEATURE:
<221> NAME/KEY: MOD_RES
<222> LOCATION: (104)..(104)
<223> OTHER INFORMATION: Phe or Leu
<220> FEATURE:
<221> NAME/KEY: MOD_RES
<222> LOCATION: (105)..(105)
```

```
<223> OTHER INFORMATION: Asp or Asn
<220> FEATURE:
<221> NAME/KEY: MOD_RES
<222> LOCATION: (115)..(115)
<223> OTHER INFORMATION: Trp or Asp
<220> FEATURE:
<221> NAME/KEY: MOD_RES
<222> LOCATION: (117)..(117)
<223> OTHER INFORMATION: Asp or Thr
<220> FEATURE:
<221> NAME/KEY: MOD_RES
<222> LOCATION: (125)..(125)
<223> OTHER INFORMATION: Asp or Asn
<220> FEATURE:
<221> NAME/KEY: MOD_RES
<222> LOCATION: (130)..(130)
<223> OTHER INFORMATION: Ile or Thr
<220> FEATURE:
<221> NAME/KEY: MOD_RES
<222> LOCATION: (132)..(132)
<223> OTHER INFORMATION: Gly or Glu
<220> FEATURE:
<221> NAME/KEY: MOD_RES
<222> LOCATION: (133)..(133)
<223> OTHER INFORMATION: Thr or Glu
<220> FEATURE:
<221> NAME/KEY: MOD_RES
<222> LOCATION: (137)..(137)
<223> OTHER INFORMATION: Gln or Lys
<220> FEATURE:
<221> NAME/KEY: MOD_RES
<222> LOCATION: (141)..(141)
<223> OTHER INFORMATION: Lys or Asp
<220> FEATURE:
<221> NAME/KEY: MOD_RES
<222> LOCATION: (143)..(143)
<223> OTHER INFORMATION: Asp or Arg
<220> FEATURE:
<221> NAME/KEY: MOD_RES
<222> LOCATION: (153)..(153)
<223> OTHER INFORMATION: Ser or Asp
<220> FEATURE:
<221> NAME/KEY: MOD_RES
<222> LOCATION: (157)..(157)
<223> OTHER INFORMATION: Arg or His
<220> FEATURE:
<221> NAME/KEY: MOD_RES
<222> LOCATION: (164)..(164)
<223> OTHER INFORMATION: Val or Ala
<220> FEATURE:
<221> NAME/KEY: MOD_RES
<222> LOCATION: (181)..(181)
<223> OTHER INFORMATION: Ile or Glu
<220> FEATURE:
<221> NAME/KEY: MOD_RES
<222> LOCATION: (190)..(190)
<223> OTHER INFORMATION: Asp or Ser
<220> FEATURE:
<221> NAME/KEY: MOD_RES
<222> LOCATION: (206)..(206)
<223> OTHER INFORMATION: Met or Tyr
<220> FEATURE:
<221> NAME/KEY: MOD_RES
<222> LOCATION: (213)..(213)
<223> OTHER INFORMATION: Thr or Ala
<220> FEATURE:
<221> NAME/KEY: MOD_RES
<222> LOCATION: (215)..(215)
<223> OTHER INFORMATION: Leu or Thr
<220> FEATURE:
<221> NAME/KEY: MOD_RES
<222> LOCATION: (217)..(217)
<223> OTHER INFORMATION: Asn or Lys
<220> FEATURE:
<221> NAME/KEY: MOD_RES
<222> LOCATION: (220)..(220)
<223> OTHER INFORMATION: Lys or Ile
<220> FEATURE:
<221> NAME/KEY: MOD_RES
```

```
<222> LOCATION: (223)..(223)
<223> OTHER INFORMATION: Val or Ala
<220> FEATURE:
<221> NAME/KEY: MOD_RES
<222> LOCATION: (225)..(225)
<223> OTHER INFORMATION: Thr or Glu
<220> FEATURE:
<221> NAME/KEY: MOD_RES
<222> LOCATION: (226)..(226)
<223> OTHER INFORMATION: Thr or Leu
<220> FEATURE:
<221> NAME/KEY: MOD_RES
<222> LOCATION: (227)..(227)
<223> OTHER INFORMATION: Asn or Ser
<220> FEATURE:
<221> NAME/KEY: MOD_RES
<222> LOCATION: (236)..(236)
<223> OTHER INFORMATION: Val or Ala
<220> FEATURE:
<221> NAME/KEY: MOD_RES
<222> LOCATION: (244)..(244)
<223> OTHER INFORMATION: Phe or Leu
<220> FEATURE:
<221> NAME/KEY: MOD_RES
<222> LOCATION: (245)..(245)
<223> OTHER INFORMATION: Pro or Arg
<220> FEATURE:
<221> NAME/KEY: MOD_RES
<222> LOCATION: (249)..(249)
<223> OTHER INFORMATION: Ser or Gln
<220> FEATURE:
<221> NAME/KEY: MOD_RES
<222> LOCATION: (250)..(250)
<223> OTHER INFORMATION: Tyr or Ala
<220> FEATURE:
<221> NAME/KEY: MOD_RES
<222> LOCATION: (253)..(253)
<223> OTHER INFORMATION: Ser or Gln
<220> FEATURE:
<221> NAME/KEY: MOD_RES
<222> LOCATION: (254)..(254)
<223> OTHER INFORMATION: Gln or Ala
<220> FEATURE:
<221> NAME/KEY: MOD_RES
<222> LOCATION: (258)..(258)
<223> OTHER INFORMATION: Pro or Glu
<220> FEATURE:
<221> NAME/KEY: MOD_RES
<222> LOCATION: (267)..(267)
<223> OTHER INFORMATION: Ser or Gln
<220> FEATURE:
<221> NAME/KEY: MOD_RES
<222> LOCATION: (268)..(268)
<223> OTHER INFORMATION: Tyr or Asn
<220> FEATURE:
<221> NAME/KEY: MOD_RES
<222> LOCATION: (269)..(269)
<223> OTHER INFORMATION: Asp or Asn
<220> FEATURE:
<221> NAME/KEY: MOD_RES
<222> LOCATION: (270)..(270)
<223> OTHER INFORMATION: Ile or Ala
<220> FEATURE:
<221> NAME/KEY: MOD_RES
<222> LOCATION: (271)..(271)
<223> OTHER INFORMATION: Asn or Gly
<220> FEATURE:
<221> NAME/KEY: MOD_RES
<222> LOCATION: (274)..(274)
<223> OTHER INFORMATION: His or Glu
<220> FEATURE:
<221> NAME/KEY: MOD_RES
<222> LOCATION: (278)..(278)
<223> OTHER INFORMATION: Thr or Asn
<220> FEATURE:
<221> NAME/KEY: MOD_RES
<222> LOCATION: (281)..(281)
<223> OTHER INFORMATION: Asn or Ser
<220> FEATURE:
```

```
<221> NAME/KEY: MOD_RES
<222> LOCATION: (282)..(282)
<223> OTHER INFORMATION: Gly or Phe
<220> FEATURE:
<221> NAME/KEY: MOD_RES
<222> LOCATION: (283)..(283)
<223> OTHER INFORMATION: Thr or Asn
<220> FEATURE:
<221> NAME/KEY: MOD_RES
<222> LOCATION: (284)..(284)
<223> OTHER INFORMATION: Met or Gln
<220> FEATURE:
<221> NAME/KEY: MOD_RES
<222> LOCATION: (289)..(289)
<223> OTHER INFORMATION: Ala or Val
<220> FEATURE:
<221> NAME/KEY: MOD_RES
<222> LOCATION: (293)..(293)
<223> OTHER INFORMATION: Asn or Phe
<220> FEATURE:
<221> NAME/KEY: MOD_RES
<222> LOCATION: (294)..(294)
<223> OTHER INFORMATION: Lys or Asn
<220> FEATURE:
<221> NAME/KEY: MOD_RES
<222> LOCATION: (295)..(295)
<223> OTHER INFORMATION: Phe or Leu
<220> FEATURE:
<221> NAME/KEY: MOD_RES
<222> LOCATION: (296)..(296)
<223> OTHER INFORMATION: Tyr or Gln
<220> FEATURE:
<221> NAME/KEY: MOD_RES
<222> LOCATION: (297)..(297)
<223> OTHER INFORMATION: Thr or Ala
<220> FEATURE:
<221> NAME/KEY: MOD_RES
<222> LOCATION: (300)..(300)
<223> OTHER INFORMATION: Lys or Ser
<220> FEATURE:
<221> NAME/KEY: MOD_RES
<222> LOCATION: (301)..(301)
<223> OTHER INFORMATION: Ser or Gln
<220> FEATURE:
<221> NAME/KEY: MOD_RES
<222> LOCATION: (309)..(309)
<223> OTHER INFORMATION: Thr or Arg
<220> FEATURE:
<221> NAME/KEY: MOD_RES
<222> LOCATION: (312)..(312)
<223> OTHER INFORMATION: Thr or Asp
<220> FEATURE:
<221> NAME/KEY: MOD_RES
<222> LOCATION: (313)..(313)
<223> OTHER INFORMATION: Asn or Gly
<220> FEATURE:
<221> NAME/KEY: MOD_RES
<222> LOCATION: (317)..(317)
<223> OTHER INFORMATION: Lys or Ser
<220> FEATURE:
<221> NAME/KEY: MOD_RES
<222> LOCATION: (318)..(318)
<223> OTHER INFORMATION: Asp or Arg
<220> FEATURE:
<221> NAME/KEY: MOD_RES
<222> LOCATION: (319)..(319)
<223> OTHER INFORMATION: Gln or His
<220> FEATURE:
<221> NAME/KEY: MOD_RES
<222> LOCATION: (321)..(321)
<223> OTHER INFORMATION: Thr or Glu
<220> FEATURE:
<221> NAME/KEY: MOD_RES
<222> LOCATION: (322)..(322)
<223> OTHER INFORMATION: Leu or Lys
<220> FEATURE:
<221> NAME/KEY: MOD_RES
<222> LOCATION: (333)..(333)
<223> OTHER INFORMATION: Glu or Gln
```

```
<220> FEATURE:
<221> NAME/KEY: MOD_RES
<222> LOCATION: (339)..(339)
<223> OTHER INFORMATION: Gln or Glu
<220> FEATURE:
<221> NAME/KEY: MOD_RES
<222> LOCATION: (341)..(341)
<223> OTHER INFORMATION: Trp or Thr
<220> FEATURE:
<221> NAME/KEY: MOD_RES
<222> LOCATION: (343)..(343)
<223> OTHER INFORMATION: Asp or Gln
<220> FEATURE:
<221> NAME/KEY: MOD_RES
<222> LOCATION: (344)..(344)
<223> OTHER INFORMATION: Pro or Thr
<220> FEATURE:
<221> NAME/KEY: MOD_RES
<222> LOCATION: (358)..(358)
<223> OTHER INFORMATION: Gln or Glu
<220> FEATURE:
<221> NAME/KEY: MOD_RES
<222> LOCATION: (359)..(359)
<223> OTHER INFORMATION: Glu or Ser
<220> FEATURE:
<221> NAME/KEY: MOD_RES
<222> LOCATION: (363)..(363)
<223> OTHER INFORMATION: Cys or Gln
<220> FEATURE:
<221> NAME/KEY: MOD_RES
<222> LOCATION: (369)..(369)
<223> OTHER INFORMATION: Tyr or Met
<220> FEATURE:
<221> NAME/KEY: MOD_RES
<222> LOCATION: (372)..(372)
<223> OTHER INFORMATION: Ile or Thr
<220> FEATURE:
<221> NAME/KEY: MOD_RES
<222> LOCATION: (373)..(373)
<223> OTHER INFORMATION: Pro or Lys
<220> FEATURE:
<221> NAME/KEY: MOD_RES
<222> LOCATION: (374)..(374)
<223> OTHER INFORMATION: Gln or Gly
<220> FEATURE:
<221> NAME/KEY: MOD_RES
<222> LOCATION: (375)..(375)
<223> OTHER INFORMATION: Tyr or Thr
<220> FEATURE:
<221> NAME/KEY: MOD_RES
<222> LOCATION: (376)..(376)
<223> OTHER INFORMATION: Asn or Ser
<220> FEATURE:
<221> NAME/KEY: MOD_RES
<222> LOCATION: (377)..(377)
<223> OTHER INFORMATION: Pro or not present
<220> FEATURE:
<221> NAME/KEY: MOD_RES
<222> LOCATION: (378)..(378)
<223> OTHER INFORMATION: Lys or not present
<220> FEATURE:
<221> NAME/KEY: MOD_RES
<222> LOCATION: (379)..(379)
<223> OTHER INFORMATION: Glu or not present
<220> FEATURE:
<221> NAME/KEY: MOD_RES
<222> LOCATION: (385)..(385)
<223> OTHER INFORMATION: Ser or Asp
<220> FEATURE:
<221> NAME/KEY: MOD_RES
<222> LOCATION: (386)..(386)
<223> OTHER INFORMATION: Lys or Asn
<220> FEATURE:
<221> NAME/KEY: MOD_RES
<222> LOCATION: (392)..(392)
<223> OTHER INFORMATION: Ile or Lys
<220> FEATURE:
<221> NAME/KEY: MOD_RES
<222> LOCATION: (401)..(401)
```

-continued

```
<223> OTHER INFORMATION: Thr or Pro
<220> FEATURE:
<221> NAME/KEY: MOD_RES
<222> LOCATION: (409)..(409)
<223> OTHER INFORMATION: Ser or Pro
<220> FEATURE:
<221> NAME/KEY: MOD_RES
<222> LOCATION: (419)..(419)
<223> OTHER INFORMATION: Val or Asp
<220> FEATURE:
<221> NAME/KEY: MOD_RES
<222> LOCATION: (421)..(421)
<223> OTHER INFORMATION: Glu or Ser
<220> FEATURE:
<221> NAME/KEY: MOD_RES
<222> LOCATION: (422)..(422)
<223> OTHER INFORMATION: Lys or Ala
<220> FEATURE:
<221> NAME/KEY: MOD_RES
<222> LOCATION: (423)..(423)
<223> OTHER INFORMATION: Pro or Ala
<220> FEATURE:
<221> NAME/KEY: MOD_RES
<222> LOCATION: (424)..(424)
<223> OTHER INFORMATION: Gly or Lys
<220> FEATURE:
<221> NAME/KEY: MOD_RES
<222> LOCATION: (440)..(440)
<223> OTHER INFORMATION: Trp or Arg
<220> FEATURE:
<221> NAME/KEY: MOD_RES
<222> LOCATION: (443)..(443)
<223> OTHER INFORMATION: Val or Ala
<220> FEATURE:
<221> NAME/KEY: MOD_RES
<222> LOCATION: (445)..(445)
<223> OTHER INFORMATION: Lys or Leu
<220> FEATURE:
<221> NAME/KEY: MOD_RES
<222> LOCATION: (446)..(446)
<223> OTHER INFORMATION: Gln or Lys
<220> FEATURE:
<221> NAME/KEY: MOD_RES
<222> LOCATION: (447)..(447)
<223> OTHER INFORMATION: His or Asn
<220> FEATURE:
<221> NAME/KEY: MOD_RES
<222> LOCATION: (450)..(450)
<223> OTHER INFORMATION: Lys or Glu
<220> FEATURE:
<221> NAME/KEY: MOD_RES
<222> LOCATION: (451)..(451)
<223> OTHER INFORMATION: Val or Thr
<220> FEATURE:
<221> NAME/KEY: MOD_RES
<222> LOCATION: (464)..(464)
<223> OTHER INFORMATION: Thr or Lys
<220> FEATURE:
<221> NAME/KEY: MOD_RES
<222> LOCATION: (466)..(466)
<223> OTHER INFORMATION: Asn or Gly
<220> FEATURE:
<221> NAME/KEY: MOD_RES
<222> LOCATION: (474)..(474)
<223> OTHER INFORMATION: Lys or His
<220> FEATURE:
<221> NAME/KEY: MOD_RES
<222> LOCATION: (477)..(477)
<223> OTHER INFORMATION: Gly or Asp
<220> FEATURE:
<221> NAME/KEY: MOD_RES
<222> LOCATION: (485)..(485)
<223> OTHER INFORMATION: Pro or Gln
<220> FEATURE:
<221> NAME/KEY: MOD_RES
<222> LOCATION: (487)..(487)
<223> OTHER INFORMATION: Lys or not present
<220> FEATURE:
<221> NAME/KEY: MOD_RES
```

```
<222> LOCATION: (488)..(489)
<223> OTHER INFORMATION: Thr or not present
<220> FEATURE:
<221> NAME/KEY: MOD_RES
<222> LOCATION: (490)..(490)
<223> OTHER INFORMATION: Val or not present
<220> FEATURE:
<221> NAME/KEY: MOD_RES
<222> LOCATION: (491)..(491)
<223> OTHER INFORMATION: Ser or not present
<220> FEATURE:
<221> NAME/KEY: MOD_RES
<222> LOCATION: (492)..(492)
<223> OTHER INFORMATION: Thr or not present
<220> FEATURE:
<221> NAME/KEY: MOD_RES
<222> LOCATION: (493)..(493)
<223> OTHER INFORMATION: Ile or not present
<220> FEATURE:
<221> NAME/KEY: MOD_RES
<222> LOCATION: (494)..(494)
<223> OTHER INFORMATION: Ala or not present
<220> FEATURE:
<221> NAME/KEY: MOD_RES
<222> LOCATION: (495)..(495)
<223> OTHER INFORMATION: Arg or not present
<220> FEATURE:
<221> NAME/KEY: MOD_RES
<222> LOCATION: (496)..(496)
<223> OTHER INFORMATION: Pro or not present
<220> FEATURE:
<221> NAME/KEY: MOD_RES
<222> LOCATION: (497)..(497)
<223> OTHER INFORMATION: Ile or not present
<220> FEATURE:
<221> NAME/KEY: MOD_RES
<222> LOCATION: (498)..(499)
<223> OTHER INFORMATION: Thr or not present
<220> FEATURE:
<221> NAME/KEY: MOD_RES
<222> LOCATION: (500)..(500)
<223> OTHER INFORMATION: Arg or not present
<220> FEATURE:
<221> NAME/KEY: MOD_RES
<222> LOCATION: (501)..(501)
<223> OTHER INFORMATION: Pro or not present
<220> FEATURE:
<221> NAME/KEY: MOD_RES
<222> LOCATION: (502)..(502)
<223> OTHER INFORMATION: Trp or not present
<220> FEATURE:
<221> NAME/KEY: MOD_RES
<222> LOCATION: (503)..(503)
<223> OTHER INFORMATION: Thr or not present
<220> FEATURE:
<221> NAME/KEY: MOD_RES
<222> LOCATION: (504)..(504)
<223> OTHER INFORMATION: Gly or not present
<220> FEATURE:
<221> NAME/KEY: MOD_RES
<222> LOCATION: (505)..(505)
<223> OTHER INFORMATION: Glu or not present
<220> FEATURE:
<221> NAME/KEY: MOD_RES
<222> LOCATION: (506)..(506)
<223> OTHER INFORMATION: Phe or not present
<220> FEATURE:
<221> NAME/KEY: MOD_RES
<222> LOCATION: (507)..(507)
<223> OTHER INFORMATION: Val or not present
<220> FEATURE:
<221> NAME/KEY: MOD_RES
<222> LOCATION: (508)..(508)
<223> OTHER INFORMATION: Arg or not present
<220> FEATURE:
<221> NAME/KEY: MOD_RES
<222> LOCATION: (509)..(509)
<223> OTHER INFORMATION: Trp or not present
<220> FEATURE:
```

```
<221> NAME/KEY: MOD_RES
<222> LOCATION: (510)..(510)
<223> OTHER INFORMATION: Thr or not present
<220> FEATURE:
<221> NAME/KEY: MOD_RES
<222> LOCATION: (511)..(511)
<223> OTHER INFORMATION: Glu or not present
<220> FEATURE:
<221> NAME/KEY: MOD_RES
<222> LOCATION: (512)..(512)
<223> OTHER INFORMATION: Pro or not present
<220> FEATURE:
<221> NAME/KEY: MOD_RES
<222> LOCATION: (513)..(513)
<223> OTHER INFORMATION: Arg or not present
<220> FEATURE:
<221> NAME/KEY: MOD_RES
<222> LOCATION: (514)..(514)
<223> OTHER INFORMATION: Leu or not present
<220> FEATURE:
<221> NAME/KEY: MOD_RES
<222> LOCATION: (515)..(515)
<223> OTHER INFORMATION: Val or not present
<220> FEATURE:
<221> NAME/KEY: MOD_RES
<222> LOCATION: (516)..(516)
<223> OTHER INFORMATION: Ala or not present
<220> FEATURE:
<221> NAME/KEY: MOD_RES
<222> LOCATION: (517)..(517)
<223> OTHER INFORMATION: Trp or not present
<220> FEATURE:
<221> NAME/KEY: MOD_RES
<222> LOCATION: (518)..(518)
<223> OTHER INFORMATION: Pro or not present

<400> SEQUENCE: 25

Xaa Xaa Xaa Xaa Asn Gly Thr Leu Met Gln Tyr Phe Glu Trp Tyr Xaa
 1               5                  10                  15

Pro Xaa Asp Gly Xaa Xaa Trp Xaa Lys Leu Xaa Asn Asp Ala Xaa Xaa
            20                  25                  30

Leu Ser Xaa Ile Gly Ile Thr Ala Leu Trp Ile Pro Pro Ala Tyr Lys
        35                  40                  45

Gly Xaa Ser Xaa Ser Asp Xaa Gly Tyr Gly Xaa Tyr Asp Leu Tyr Asp
50                  55                  60

Leu Gly Glu Phe Asn Gln Lys Gly Thr Val Arg Thr Lys Tyr Gly Thr
65                  70                  75                  80

Lys Ala Xaa Xaa Xaa Xaa Ala Ile Xaa Ala Xaa His Ala Xaa Xaa Met
                85                  90                  95

Gln Val Tyr Ala Asp Val Val Xaa Xaa His Lys Ala Gly Ala Asp Ala
            100                 105                 110

Thr Glu Xaa Val Xaa Ala Val Glu Val Asn Pro Ala Xaa Arg Asn Gln
        115                 120                 125

Glu Xaa Ser Xaa Xaa Tyr Gln Ile Xaa Ala Trp Thr Xaa Phe Xaa Phe
130                 135                 140

Pro Gly Arg Gly Asn Thr Tyr Ser Xaa Phe Lys Trp Xaa Trp Tyr His
145                 150                 155                 160

Phe Asp Gly Xaa Asp Trp Asp Glu Ser Arg Lys Ile Ser Arg Ile Phe
                165                 170                 175

Lys Phe Arg Gly Xaa Gly Lys Ala Trp Asp Trp Glu Val Xaa Ser Glu
            180                 185                 190

Asn Gly Asn Tyr Asp Tyr Leu Met Tyr Ala Asp Leu Asp Xaa Asp His
        195                 200                 205

Pro Asp Val Val Xaa Glu Xaa Lys Xaa Trp Gly Xaa Trp Tyr Xaa Asn
210                 215                 220
```

```
Xaa Xaa Xaa Ile Asp Gly Phe Arg Ile Asp Ala Xaa Lys His Ile Lys
225                 230                 235                 240

Phe Ser Phe Xaa Xaa Asp Trp Leu Xaa Xaa Val Arg Xaa Xaa Thr Gly
            245                 250                 255

Lys Xaa Leu Phe Thr Val Ala Glu Tyr Trp Xaa Xaa Xaa Xaa Xaa Lys
        260                 265                 270

Leu Xaa Asn Tyr Ile Xaa Lys Thr Xaa Xaa Xaa Xaa Ser Leu Phe Asp
        275                 280                 285

Xaa Pro Leu His Xaa Xaa Xaa Xaa Xaa Ala Ser Xaa Xaa Gly Gly Ala
        290                 295                 300

Phe Asp Met Arg Xaa Leu Leu Xaa Xaa Thr Leu Met Xaa Xaa Xaa Pro
305                 310                 315                 320

Xaa Xaa Ala Val Thr Phe Val Asp Asn His Asp Thr Xaa Pro Gly Gln
            325                 330                 335

Ala Leu Xaa Ser Xaa Val Xaa Xaa Trp Phe Lys Pro Leu Ala Tyr Ala
        340                 345                 350

Phe Ile Leu Thr Arg Xaa Xaa Gly Tyr Pro Xaa Val Phe Tyr Gly Asp
            355                 360                 365

Xaa Tyr Gly Xaa Xaa Xaa Xaa Xaa Xaa Xaa Ile Pro Ser Leu Lys
370                 375                 380

Xaa Xaa Ile Asp Pro Ile Leu Xaa Ala Arg Lys Asp Tyr Ala Tyr Gly
385                 390                 395                 400

Xaa Gln His Asp Tyr Ile Asp His Xaa Asp Ile Ile Gly Trp Thr Arg
            405                 410                 415

Glu Gly Xaa Ser Xaa Xaa Xaa Xaa Ser Gly Leu Ala Ala Leu Ile Thr
            420                 425                 430

Asp Gly Pro Gly Gly Ser Lys Xaa Met Tyr Xaa Gly Xaa Xaa Xaa Ala
            435                 440                 445

Gly Xaa Xaa Phe Tyr Asp Ile Thr Gly Asn Arg Ser Asp Thr Val Xaa
450                 455                 460

Ile Xaa Ser Asp Gly Trp Gly Glu Phe Xaa Val Asn Xaa Gly Ser Val
465                 470                 475                 480

Ser Ile Trp Val Xaa Lys Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa
        515

<210> SEQ ID NO 26
<211> LENGTH: 517
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His or not present
<220> FEATURE:
<221> NAME/KEY: MOD_RES
<222> LOCATION: (2)..(2)
<223> OTHER INFORMATION: Ala or His
<220> FEATURE:
<221> NAME/KEY: MOD_RES
<222> LOCATION: (3)..(3)
<223> OTHER INFORMATION: Ala or Asn
<220> FEATURE:
```

```
<221> NAME/KEY: MOD_RES
<222> LOCATION: (4)..(4)
<223> OTHER INFORMATION: Pro or Gly
<220> FEATURE:
<221> NAME/KEY: MOD_RES
<222> LOCATION: (5)..(5)
<223> OTHER INFORMATION: Phe or Thr
<220> FEATURE:
<221> NAME/KEY: MOD_RES
<222> LOCATION: (19)..(19)
<223> OTHER INFORMATION: Asp or Asn
<220> FEATURE:
<221> NAME/KEY: MOD_RES
<222> LOCATION: (22)..(22)
<223> OTHER INFORMATION: Thr or Asn
<220> FEATURE:
<221> NAME/KEY: MOD_RES
<222> LOCATION: (23)..(23)
<223> OTHER INFORMATION: Leu or His
<220> FEATURE:
<221> NAME/KEY: MOD_RES
<222> LOCATION: (25)..(25)
<223> OTHER INFORMATION: Thr or Asn
<220> FEATURE:
<221> NAME/KEY: MOD_RES
<222> LOCATION: (28)..(28)
<223> OTHER INFORMATION: Ala or Arg
<220> FEATURE:
<221> NAME/KEY: MOD_RES
<222> LOCATION: (29)..(29)
<223> OTHER INFORMATION: Asn or Ser
<220> FEATURE:
<221> NAME/KEY: MOD_RES
<222> LOCATION: (32)..(32)
<223> OTHER INFORMATION: Asn or Ser
<220> FEATURE:
<221> NAME/KEY: MOD_RES
<222> LOCATION: (35)..(35)
<223> OTHER INFORMATION: Ser or Lys
<220> FEATURE:
<221> NAME/KEY: MOD_RES
<222> LOCATION: (36)..(36)
<223> OTHER INFORMATION: Ser or Asp
<220> FEATURE:
<221> NAME/KEY: MOD_RES
<222> LOCATION: (37)..(37)
<223> OTHER INFORMATION: Leu or Lys
<220> FEATURE:
<221> NAME/KEY: MOD_RES
<222> LOCATION: (51)..(51)
<223> OTHER INFORMATION: Thr or Ala
<220> FEATURE:
<221> NAME/KEY: MOD_RES
<222> LOCATION: (53)..(53)
<223> OTHER INFORMATION: Arg or Gln
<220> FEATURE:
<221> NAME/KEY: MOD_RES
<222> LOCATION: (54)..(54)
<223> OTHER INFORMATION: Ser or Asn
<220> FEATURE:
<221> NAME/KEY: MOD_RES
<222> LOCATION: (60)..(60)
<223> OTHER INFORMATION: Val or Ala
<220> FEATURE:
<221> NAME/KEY: MOD_RES
<222> LOCATION: (83)..(83)
<223> OTHER INFORMATION: Ala or Asn
<220> FEATURE:
<221> NAME/KEY: MOD_RES
<222> LOCATION: (85)..(85)
<223> OTHER INFORMATION: Tyr or Leu
<220> FEATURE:
<221> NAME/KEY: MOD_RES
<222> LOCATION: (86)..(86)
<223> OTHER INFORMATION: Leu or Gln
<220> FEATURE:
<221> NAME/KEY: MOD_RES
<222> LOCATION: (87)..(87)
<223> OTHER INFORMATION: Gln or Ala
```

```
<220> FEATURE:
<221> NAME/KEY: MOD_RES
<222> LOCATION: (92)..(92)
<223> OTHER INFORMATION: Ala or Leu
<220> FEATURE:
<221> NAME/KEY: MOD_RES
<222> LOCATION: (93)..(93)
<223> OTHER INFORMATION: His or Lys
<220> FEATURE:
<221> NAME/KEY: MOD_RES
<222> LOCATION: (95)..(95)
<223> OTHER INFORMATION: Ala or Asn
<220> FEATURE:
<221> NAME/KEY: MOD_RES
<222> LOCATION: (105)..(105)
<223> OTHER INFORMATION: Phe or Met
<220> FEATURE:
<221> NAME/KEY: MOD_RES
<222> LOCATION: (106)..(106)
<223> OTHER INFORMATION: Asp or Asn
<220> FEATURE:
<221> NAME/KEY: MOD_RES
<222> LOCATION: (116)..(116)
<223> OTHER INFORMATION: Trp or Met
<220> FEATURE:
<221> NAME/KEY: MOD_RES
<222> LOCATION: (118)..(118)
<223> OTHER INFORMATION: Asp or Arg
<220> FEATURE:
<221> NAME/KEY: MOD_RES
<222> LOCATION: (125)..(125)
<223> OTHER INFORMATION: Ser or Asn
<220> FEATURE:
<221> NAME/KEY: MOD_RES
<222> LOCATION: (126)..(126)
<223> OTHER INFORMATION: Asp or Asn
<220> FEATURE:
<221> NAME/KEY: MOD_RES
<222> LOCATION: (134)..(134)
<223> OTHER INFORMATION: Thr or Glu
<220> FEATURE:
<221> NAME/KEY: MOD_RES
<222> LOCATION: (136)..(136)
<223> OTHER INFORMATION: Gln or Thr
<220> FEATURE:
<221> NAME/KEY: MOD_RES
<222> LOCATION: (138)..(138)
<223> OTHER INFORMATION: Gln or Glu
<220> FEATURE:
<221> NAME/KEY: MOD_RES
<222> LOCATION: (154)..(154)
<223> OTHER INFORMATION: Ser or Asn
<220> FEATURE:
<221> NAME/KEY: MOD_RES
<222> LOCATION: (169)..(169)
<223> OTHER INFORMATION: Glu or Gln
<220> FEATURE:
<221> NAME/KEY: MOD_RES
<222> LOCATION: (174)..(174)
<223> OTHER INFORMATION: Ser or Asn
<220> FEATURE:
<221> NAME/KEY: MOD_RES
<222> LOCATION: (175)..(175)
<223> OTHER INFORMATION: Asn or not present
<220> FEATURE:
<221> NAME/KEY: MOD_RES
<222> LOCATION: (183)..(183)
<223> OTHER INFORMATION: Ile or Asp
<220> FEATURE:
<221> NAME/KEY: MOD_RES
<222> LOCATION: (215)..(215)
<223> OTHER INFORMATION: Thr or Asn
<220> FEATURE:
<221> NAME/KEY: MOD_RES
<222> LOCATION: (222)..(222)
<223> OTHER INFORMATION: Lys or Val
<220> FEATURE:
<221> NAME/KEY: MOD_RES
<222> LOCATION: (225)..(225)
```

```
<223> OTHER INFORMATION: Val or Thr
<220> FEATURE:
<221> NAME/KEY: MOD_RES
<222> LOCATION: (228)..(228)
<223> OTHER INFORMATION: Thr or Leu
<220> FEATURE:
<221> NAME/KEY: MOD_RES
<222> LOCATION: (229)..(229)
<223> OTHER INFORMATION: Asn or Gly
<220> FEATURE:
<221> NAME/KEY: MOD_RES
<222> LOCATION: (246)..(246)
<223> OTHER INFORMATION: Phe or Thr
<220> FEATURE:
<221> NAME/KEY: MOD_RES
<222> LOCATION: (247)..(247)
<223> OTHER INFORMATION: Pro or Arg
<220> FEATURE:
<221> NAME/KEY: MOD_RES
<222> LOCATION: (251)..(251)
<223> OTHER INFORMATION: Ser or Asn
<220> FEATURE:
<221> NAME/KEY: MOD_RES
<222> LOCATION: (256)..(256)
<223> OTHER INFORMATION: Gln or Ala
<220> FEATURE:
<221> NAME/KEY: MOD_RES
<222> LOCATION: (260)..(260)
<223> OTHER INFORMATION: Pro or Asn
<220> FEATURE:
<221> NAME/KEY: MOD_RES
<222> LOCATION: (263)..(263)
<223> OTHER INFORMATION: Thr or Ala
<220> FEATURE:
<221> NAME/KEY: MOD_RES
<222> LOCATION: (269)..(269)
<223> OTHER INFORMATION: Ser or Lys
<220> FEATURE:
<221> NAME/KEY: MOD_RES
<222> LOCATION: (270)..(270)
<223> OTHER INFORMATION: Tyr or Asn
<220> FEATURE:
<221> NAME/KEY: MOD_RES
<222> LOCATION: (273)..(273)
<223> OTHER INFORMATION: Asn or Gly
<220> FEATURE:
<221> NAME/KEY: MOD_RES
<222> LOCATION: (274)..(274)
<223> OTHER INFORMATION: Lys or Ala
<220> FEATURE:
<221> NAME/KEY: MOD_RES
<222> LOCATION: (276)..(276)
<223> OTHER INFORMATION: His or Glu
<220> FEATURE:
<221> NAME/KEY: MOD_RES
<222> LOCATION: (280)..(280)
<223> OTHER INFORMATION: Thr or Asn
<220> FEATURE:
<221> NAME/KEY: MOD_RES
<222> LOCATION: (284)..(284)
<223> OTHER INFORMATION: Gly or Trp
<220> FEATURE:
<221> NAME/KEY: MOD_RES
<222> LOCATION: (285)..(285)
<223> OTHER INFORMATION: Thr or Asn
<220> FEATURE:
<221> NAME/KEY: MOD_RES
<222> LOCATION: (286)..(286)
<223> OTHER INFORMATION: Met or His
<220> FEATURE:
<221> NAME/KEY: MOD_RES
<222> LOCATION: (291)..(291)
<223> OTHER INFORMATION: Ala or Val
<220> FEATURE:
<221> NAME/KEY: MOD_RES
<222> LOCATION: (295)..(295)
<223> OTHER INFORMATION: Asn or Tyr
<220> FEATURE:
<221> NAME/KEY: MOD_RES
```

```
<222> LOCATION: (296)..(296)
<223> OTHER INFORMATION: Lys or Asn
<220> FEATURE:
<221> NAME/KEY: MOD_RES
<222> LOCATION: (297)..(297)
<223> OTHER INFORMATION: Phe or Leu
<220> FEATURE:
<221> NAME/KEY: MOD_RES
<222> LOCATION: (299)..(299)
<223> OTHER INFORMATION: Thr or Asn
<220> FEATURE:
<221> NAME/KEY: MOD_RES
<222> LOCATION: (306)..(306)
<223> OTHER INFORMATION: Ala or Asn
<220> FEATURE:
<221> NAME/KEY: MOD_RES
<222> LOCATION: (311)..(311)
<223> OTHER INFORMATION: Thr or Gln
<220> FEATURE:
<221> NAME/KEY: MOD_RES
<222> LOCATION: (313)..(313)
<223> OTHER INFORMATION: Met or Phe
<220> FEATURE:
<221> NAME/KEY: MOD_RES
<222> LOCATION: (314)..(314)
<223> OTHER INFORMATION: Thr or Asn
<220> FEATURE:
<221> NAME/KEY: MOD_RES
<222> LOCATION: (315)..(315)
<223> OTHER INFORMATION: Asn or Gly
<220> FEATURE:
<221> NAME/KEY: MOD_RES
<222> LOCATION: (319)..(319)
<223> OTHER INFORMATION: Lys or Gln
<220> FEATURE:
<221> NAME/KEY: MOD_RES
<222> LOCATION: (320)..(320)
<223> OTHER INFORMATION: Asp or Arg
<220> FEATURE:
<221> NAME/KEY: MOD_RES
<222> LOCATION: (321)..(321)
<223> OTHER INFORMATION: Gln or His
<220> FEATURE:
<221> NAME/KEY: MOD_RES
<222> LOCATION: (323)..(323)
<223> OTHER INFORMATION: Thr or Met
<220> FEATURE:
<221> NAME/KEY: MOD_RES
<222> LOCATION: (324)..(324)
<223> OTHER INFORMATION: Leu or His
<220> FEATURE:
<221> NAME/KEY: MOD_RES
<222> LOCATION: (335)..(335)
<223> OTHER INFORMATION: Glu or Gln
<220> FEATURE:
<221> NAME/KEY: MOD_RES
<222> LOCATION: (337)..(337)
<223> OTHER INFORMATION: Gly or Glu
<220> FEATURE:
<221> NAME/KEY: MOD_RES
<222> LOCATION: (338)..(338)
<223> OTHER INFORMATION: Gln or Glu
<220> FEATURE:
<221> NAME/KEY: MOD_RES
<222> LOCATION: (341)..(341)
<223> OTHER INFORMATION: Gln or Glu
<220> FEATURE:
<221> NAME/KEY: MOD_RES
<222> LOCATION: (346)..(346)
<223> OTHER INFORMATION: Pro or Glu
<220> FEATURE:
<221> NAME/KEY: MOD_RES
<222> LOCATION: (355)..(355)
<223> OTHER INFORMATION: Phe or Leu
<220> FEATURE:
<221> NAME/KEY: MOD_RES
<222> LOCATION: (356)..(356)
<223> OTHER INFORMATION: Ile or Thr
<220> FEATURE:
```

-continued

```
<221> NAME/KEY: MOD_RES
<222> LOCATION: (360)..(360)
<223> OTHER INFORMATION: Gln or Glu
<220> FEATURE:
<221> NAME/KEY: MOD_RES
<222> LOCATION: (361)..(361)
<223> OTHER INFORMATION: Glu or Gln
<220> FEATURE:
<221> NAME/KEY: MOD_RES
<222> LOCATION: (365)..(365)
<223> OTHER INFORMATION: Cys or Ser
<220> FEATURE:
<221> NAME/KEY: MOD_RES
<222> LOCATION: (376)..(376)
<223> OTHER INFORMATION: Gln or Thr
<220> FEATURE:
<221> NAME/KEY: MOD_RES
<222> LOCATION: (378)..(378)
<223> OTHER INFORMATION: Asn or Gly
<220> FEATURE:
<221> NAME/KEY: MOD_RES
<222> LOCATION: (391)..(391)
<223> OTHER INFORMATION: Ile or Glu
<220> FEATURE:
<221> NAME/KEY: MOD_RES
<222> LOCATION: (394)..(394)
<223> OTHER INFORMATION: Arg or Gln
<220> FEATURE:
<221> NAME/KEY: MOD_RES
<222> LOCATION: (395)..(395)
<223> OTHER INFORMATION: Asp or Lys
<220> FEATURE:
<221> NAME/KEY: MOD_RES
<222> LOCATION: (400)..(400)
<223> OTHER INFORMATION: Thr or Arg
<220> FEATURE:
<221> NAME/KEY: MOD_RES
<222> LOCATION: (402)..(402)
<223> OTHER INFORMATION: His or Asn
<220> FEATURE:
<221> NAME/KEY: MOD_RES
<222> LOCATION: (408)..(408)
<223> OTHER INFORMATION: Ser or His
<220> FEATURE:
<221> NAME/KEY: MOD_RES
<222> LOCATION: (409)..(409)
<223> OTHER INFORMATION: Asp or Asn
<220> FEATURE:
<221> NAME/KEY: MOD_RES
<222> LOCATION: (418)..(418)
<223> OTHER INFORMATION: Val or Asn
<220> FEATURE:
<221> NAME/KEY: MOD_RES
<222> LOCATION: (420)..(420)
<223> OTHER INFORMATION: Glu or Ala
<220> FEATURE:
<221> NAME/KEY: MOD_RES
<222> LOCATION: (421)..(421)
<223> OTHER INFORMATION: Lys or His
<220> FEATURE:
<221> NAME/KEY: MOD_RES
<222> LOCATION: (423)..(423)
<223> OTHER INFORMATION: Gly or Asn
<220> FEATURE:
<221> NAME/KEY: MOD_RES
<222> LOCATION: (428)..(428)
<223> OTHER INFORMATION: Ala or Thr
<220> FEATURE:
<221> NAME/KEY: MOD_RES
<222> LOCATION: (434)..(434)
<223> OTHER INFORMATION: Pro or Ala
<220> FEATURE:
<221> NAME/KEY: MOD_RES
<222> LOCATION: (437)..(437)
<223> OTHER INFORMATION: Ser or Asn
<220> FEATURE:
<221> NAME/KEY: MOD_RES
<222> LOCATION: (446)..(446)
<223> OTHER INFORMATION: His or Lys
```

```
<220> FEATURE:
<221> NAME/KEY: MOD_RES
<222> LOCATION: (449)..(449)
<223> OTHER INFORMATION: Lys or Gln
<220> FEATURE:
<221> NAME/KEY: MOD_RES
<222> LOCATION: (452)..(452)
<223> OTHER INFORMATION: Tyr or Thr
<220> FEATURE:
<221> NAME/KEY: MOD_RES
<222> LOCATION: (460)..(460)
<223> OTHER INFORMATION: Asp or Gly
<220> FEATURE:
<221> NAME/KEY: MOD_RES
<222> LOCATION: (471)..(471)
<223> OTHER INFORMATION: Glu or Asn
<220> FEATURE:
<221> NAME/KEY: MOD_RES
<222> LOCATION: (473)..(473)
<223> OTHER INFORMATION: Lys or Ser
<220> FEATURE:
<221> NAME/KEY: MOD_RES
<222> LOCATION: (484)..(484)
<223> OTHER INFORMATION: Pro or Asn
<220> FEATURE:
<221> NAME/KEY: MOD_RES
<222> LOCATION: (486)..(486)
<223> OTHER INFORMATION: Lys or not present
<220> FEATURE:
<221> NAME/KEY: MOD_RES
<222> LOCATION: (487)..(488)
<223> OTHER INFORMATION: Thr or not present
<220> FEATURE:
<221> NAME/KEY: MOD_RES
<222> LOCATION: (489)..(489)
<223> OTHER INFORMATION: Val or not present
<220> FEATURE:
<221> NAME/KEY: MOD_RES
<222> LOCATION: (490)..(490)
<223> OTHER INFORMATION: Ser or not present
<220> FEATURE:
<221> NAME/KEY: MOD_RES
<222> LOCATION: (491)..(491)
<223> OTHER INFORMATION: Thr or not present
<220> FEATURE:
<221> NAME/KEY: MOD_RES
<222> LOCATION: (492)..(492)
<223> OTHER INFORMATION: Ile or not present
<220> FEATURE:
<221> NAME/KEY: MOD_RES
<222> LOCATION: (493)..(493)
<223> OTHER INFORMATION: Ala or not present
<220> FEATURE:
<221> NAME/KEY: MOD_RES
<222> LOCATION: (494)..(494)
<223> OTHER INFORMATION: Arg or not present
<220> FEATURE:
<221> NAME/KEY: MOD_RES
<222> LOCATION: (495)..(495)
<223> OTHER INFORMATION: Pro or not present
<220> FEATURE:
<221> NAME/KEY: MOD_RES
<222> LOCATION: (496)..(496)
<223> OTHER INFORMATION: Ile or not present
<220> FEATURE:
<221> NAME/KEY: MOD_RES
<222> LOCATION: (497)..(498)
<223> OTHER INFORMATION: Thr or not present
<220> FEATURE:
<221> NAME/KEY: MOD_RES
<222> LOCATION: (499)..(499)
<223> OTHER INFORMATION: Arg or not present
<220> FEATURE:
<221> NAME/KEY: MOD_RES
<222> LOCATION: (500)..(500)
<223> OTHER INFORMATION: Pro or not present
<220> FEATURE:
<221> NAME/KEY: MOD_RES
<222> LOCATION: (501)..(501)
```

-continued

```
<223> OTHER INFORMATION: Trp or not present
<220> FEATURE:
<221> NAME/KEY: MOD_RES
<222> LOCATION: (502)..(502)
<223> OTHER INFORMATION: Thr or not present
<220> FEATURE:
<221> NAME/KEY: MOD_RES
<222> LOCATION: (503)..(503)
<223> OTHER INFORMATION: Gly or not present
<220> FEATURE:
<221> NAME/KEY: MOD_RES
<222> LOCATION: (504)..(504)
<223> OTHER INFORMATION: Glu or not present
<220> FEATURE:
<221> NAME/KEY: MOD_RES
<222> LOCATION: (505)..(505)
<223> OTHER INFORMATION: Phe or not present
<220> FEATURE:
<221> NAME/KEY: MOD_RES
<222> LOCATION: (506)..(506)
<223> OTHER INFORMATION: Val or not present
<220> FEATURE:
<221> NAME/KEY: MOD_RES
<222> LOCATION: (507)..(507)
<223> OTHER INFORMATION: Arg or not present
<220> FEATURE:
<221> NAME/KEY: MOD_RES
<222> LOCATION: (508)..(508)
<223> OTHER INFORMATION: Trp or not present
<220> FEATURE:
<221> NAME/KEY: MOD_RES
<222> LOCATION: (509)..(509)
<223> OTHER INFORMATION: Thr or not present
<220> FEATURE:
<221> NAME/KEY: MOD_RES
<222> LOCATION: (510)..(510)
<223> OTHER INFORMATION: Glu or not present
<220> FEATURE:
<221> NAME/KEY: MOD_RES
<222> LOCATION: (511)..(511)
<223> OTHER INFORMATION: Pro or not present
<220> FEATURE:
<221> NAME/KEY: MOD_RES
<222> LOCATION: (512)..(512)
<223> OTHER INFORMATION: Arg or not present
<220> FEATURE:
<221> NAME/KEY: MOD_RES
<222> LOCATION: (513)..(513)
<223> OTHER INFORMATION: Leu or not present
<220> FEATURE:
<221> NAME/KEY: MOD_RES
<222> LOCATION: (514)..(514)
<223> OTHER INFORMATION: Val or not present
<220> FEATURE:
<221> NAME/KEY: MOD_RES
<222> LOCATION: (515)..(515)
<223> OTHER INFORMATION: Ala or not present
<220> FEATURE:
<221> NAME/KEY: MOD_RES
<222> LOCATION: (516)..(516)
<223> OTHER INFORMATION: Trp or not present
<220> FEATURE:
<221> NAME/KEY: MOD_RES
<222> LOCATION: (517)..(517)
<223> OTHER INFORMATION: Pro or not present

<400> SEQUENCE: 26

Xaa Xaa Xaa Xaa Xaa Asn Gly Thr Met Met Gln Tyr Phe Glu Trp Tyr
1               5                   10                  15

Leu Pro Xaa Asp Gly Xaa Xaa Trp Xaa Lys Leu Xaa Xaa Asp Ala Xaa
            20                  25                  30

Asn Leu Xaa Xaa Xaa Gly Ile Ser Ala Leu Trp Ile Pro Pro Ala Trp
        35                  40                  45

Lys Gly Xaa Ser Xaa Xaa Asp Val Gly Tyr Gly Xaa Tyr Asp Leu Tyr
50                  55                  60
```

```
Asp Leu Gly Glu Phe Asn Gln Lys Gly Thr Ile Arg Thr Lys Tyr Gly
 65                  70                  75                  80

Thr Lys Xaa Gln Xaa Xaa Xaa Ala Ile Asn Ala Xaa Xaa Ala Xaa Gly
                 85                  90                  95

Ile Gln Val Tyr Ala Asp Val Val Xaa Xaa His Lys Gly Gly Ala Asp
            100                 105                 110

Ala Thr Glu Xaa Val Xaa Ala Val Glu Val Asn Pro Xaa Xaa Arg Asn
            115                 120                 125

Gln Glu Ile Ser Gly Xaa Tyr Xaa Ile Xaa Ala Trp Thr Lys Phe Asp
            130                 135                 140

Phe Pro Gly Arg Gly Asn Thr His Ser Xaa Phe Lys Trp Arg Trp Tyr
145                 150                 155                 160

His Phe Asp Gly Val Asp Trp Asp Xaa Ser Arg Lys Leu Xaa Xaa Arg
                165                 170                 175

Ile Tyr Lys Phe Arg Gly Xaa Gly Lys Ala Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Xaa Glu Leu Lys Asn Trp Gly Xaa Trp Tyr
            210                 215                 220

Xaa Asn Thr Xaa Xaa Ile Asp Gly Phe Arg Ile Asp Ala Val Lys His
225                 230                 235                 240

Ile Lys Phe Ser Phe Xaa Xaa Asp Trp Ile Xaa His Val Arg Ser Xaa
                245                 250                 255

Thr Gly Lys Xaa Leu Phe Xaa Val Ala Glu Phe Trp Xaa Xaa Asp Ile
            260                 265                 270

Xaa Xaa Ile Xaa Asn Tyr Ile Xaa Lys Thr Asn Xaa Xaa Xaa Ser Leu
            275                 280                 285

Phe Asp Xaa Pro Leu His Xaa Xaa Xaa Tyr Xaa Ala Ser Lys Ser Gly
290                 295                 300

Gly Xaa Phe Asp Met Arg Xaa Ile Xaa Xaa Xaa Thr Leu Met Xaa Xaa
305                 310                 315                 320

Xaa Pro Xaa Xaa Ala Val Thr Phe Val Asp Asn His Asp Ser Xaa Pro
            325                 330                 335

Xaa Xaa Ala Leu Xaa Ser Phe Val Asp Xaa Trp Phe Lys Pro Leu Ala
            340                 345                 350

Tyr Ala Xaa Xaa Leu Thr Arg Xaa Xaa Gly Tyr Pro Xaa Val Phe Tyr
            355                 360                 365

Gly Asp Tyr Tyr Gly Ile Pro Xaa His Xaa Ile Pro Ala Leu Lys Ser
370                 375                 380

Lys Ile Asp Pro Ile Leu Xaa Ala Arg Xaa Xaa Tyr Ala Tyr Gly Xaa
385                 390                 395                 400

Gln Xaa Asp Tyr Leu Asp His Xaa Xaa Ile Ile Gly Trp Thr Arg Glu
            405                 410                 415

Gly Xaa Thr Xaa Xaa Pro Xaa Ser Gly Leu Ala Xaa Ile Ile Ser Asp
            420                 425                 430

Gly Xaa Gly Gly Xaa Lys Trp Met Phe Val Gly Lys Asn Xaa Ala Gly
            435                 440                 445

Xaa Val Phe Xaa Asp Ile Thr Gly Asn Arg Ala Xaa Thr Val Thr Ile
            450                 455                 460

Asn Ala Asp Gly Trp Gly Xaa Phe Xaa Val Asn Gly Gly Ser Val Ser
465                 470                 475                 480
```

```
Ile Trp Val Xaa Lys Xaa Xaa Xaa Xaa Xaa Xaa Xaa Xaa Xaa
            485             490             495

Xaa Xaa Xaa Xaa Xaa Xaa Xaa Xaa Xaa Xaa Xaa Xaa Xaa
        500             505             510

Xaa Xaa Xaa Xaa Xaa
        515

<210> SEQ ID NO 27
<211> LENGTH: 517
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His or not present
<220> FEATURE:
<221> NAME/KEY: MOD_RES
<222> LOCATION: (2)..(2)
<223> OTHER INFORMATION: Ala or His
<220> FEATURE:
<221> NAME/KEY: MOD_RES
<222> LOCATION: (3)..(3)
<223> OTHER INFORMATION: Ala or Asn
<220> FEATURE:
<221> NAME/KEY: MOD_RES
<222> LOCATION: (4)..(4)
<223> OTHER INFORMATION: Pro or Gly
<220> FEATURE:
<221> NAME/KEY: MOD_RES
<222> LOCATION: (5)..(5)
<223> OTHER INFORMATION: Phe or Thr
<220> FEATURE:
<221> NAME/KEY: MOD_RES
<222> LOCATION: (19)..(19)
<223> OTHER INFORMATION: Asp or Asn
<220> FEATURE:
<221> NAME/KEY: MOD_RES
<222> LOCATION: (22)..(22)
<223> OTHER INFORMATION: Thr or Asn
<220> FEATURE:
<221> NAME/KEY: MOD_RES
<222> LOCATION: (23)..(23)
<223> OTHER INFORMATION: Leu or His
<220> FEATURE:
<221> NAME/KEY: MOD_RES
<222> LOCATION: (25)..(25)
<223> OTHER INFORMATION: Thr or Asn
<220> FEATURE:
<221> NAME/KEY: MOD_RES
<222> LOCATION: (28)..(28)
<223> OTHER INFORMATION: Ala or Arg
<220> FEATURE:
<221> NAME/KEY: MOD_RES
<222> LOCATION: (29)..(29)
<223> OTHER INFORMATION: Asn or Asp
<220> FEATURE:
<221> NAME/KEY: MOD_RES
<222> LOCATION: (32)..(32)
<223> OTHER INFORMATION: Asn or Ser
<220> FEATURE:
<221> NAME/KEY: MOD_RES
<222> LOCATION: (35)..(35)
<223> OTHER INFORMATION: Ser or Arg
<220> FEATURE:
<221> NAME/KEY: MOD_RES
<222> LOCATION: (36)..(36)
<223> OTHER INFORMATION: Ser or Asn
<220> FEATURE:
<221> NAME/KEY: MOD_RES
<222> LOCATION: (37)..(37)
<223> OTHER INFORMATION: Leu or Arg
<220> FEATURE:
<221> NAME/KEY: MOD_RES
```

```
<222> LOCATION: (53)..(53)
<223> OTHER INFORMATION: Arg or Gln
<220> FEATURE:
<221> NAME/KEY: MOD_RES
<222> LOCATION: (54)..(54)
<223> OTHER INFORMATION: Ser or Asn
<220> FEATURE:
<221> NAME/KEY: MOD_RES
<222> LOCATION: (60)..(60)
<223> OTHER INFORMATION: Val or Ala
<220> FEATURE:
<221> NAME/KEY: MOD_RES
<222> LOCATION: (85)..(85)
<223> OTHER INFORMATION: Tyr or Leu
<220> FEATURE:
<221> NAME/KEY: MOD_RES
<222> LOCATION: (86)..(86)
<223> OTHER INFORMATION: Leu or Glu
<220> FEATURE:
<221> NAME/KEY: MOD_RES
<222> LOCATION: (87)..(87)
<223> OTHER INFORMATION: Gln or Ser
<220> FEATURE:
<221> NAME/KEY: MOD_RES
<222> LOCATION: (90)..(90)
<223> OTHER INFORMATION: Gln or His
<220> FEATURE:
<221> NAME/KEY: MOD_RES
<222> LOCATION: (92)..(92)
<223> OTHER INFORMATION: Ala or Leu
<220> FEATURE:
<221> NAME/KEY: MOD_RES
<222> LOCATION: (93)..(93)
<223> OTHER INFORMATION: His or Lys
<220> FEATURE:
<221> NAME/KEY: MOD_RES
<222> LOCATION: (94)..(95)
<223> OTHER INFORMATION: Ala or Asn
<220> FEATURE:
<221> NAME/KEY: MOD_RES
<222> LOCATION: (105)..(105)
<223> OTHER INFORMATION: Phe or Met
<220> FEATURE:
<221> NAME/KEY: MOD_RES
<222> LOCATION: (106)..(106)
<223> OTHER INFORMATION: Asp or Asn
<220> FEATURE:
<221> NAME/KEY: MOD_RES
<222> LOCATION: (116)..(116)
<223> OTHER INFORMATION: Trp or Asn
<220> FEATURE:
<221> NAME/KEY: MOD_RES
<222> LOCATION: (118)..(118)
<223> OTHER INFORMATION: Asp or Leu
<220> FEATURE:
<221> NAME/KEY: MOD_RES
<222> LOCATION: (125)..(125)
<223> OTHER INFORMATION: Ser or Asn
<220> FEATURE:
<221> NAME/KEY: MOD_RES
<222> LOCATION: (126)..(126)
<223> OTHER INFORMATION: Asp or Asn
<220> FEATURE:
<221> NAME/KEY: MOD_RES
<222> LOCATION: (134)..(134)
<223> OTHER INFORMATION: Thr or Asp
<220> FEATURE:
<221> NAME/KEY: MOD_RES
<222> LOCATION: (136)..(136)
<223> OTHER INFORMATION: Gln or Thr
<220> FEATURE:
<221> NAME/KEY: MOD_RES
<222> LOCATION: (138)..(138)
<223> OTHER INFORMATION: Gln or Glu
<220> FEATURE:
<221> NAME/KEY: MOD_RES
<222> LOCATION: (154)..(154)
<223> OTHER INFORMATION: Ser or Asp
<220> FEATURE:
```

```
<221> NAME/KEY: MOD_RES
<222> LOCATION: (169)..(169)
<223> OTHER INFORMATION: Glu or Gln
<220> FEATURE:
<221> NAME/KEY: MOD_RES
<222> LOCATION: (172)..(172)
<223> OTHER INFORMATION: Gln or not present
<220> FEATURE:
<221> NAME/KEY: MOD_RES
<222> LOCATION: (173)..(173)
<223> OTHER INFORMATION: Lys or Phe
<220> FEATURE:
<221> NAME/KEY: MOD_RES
<222> LOCATION: (174)..(174)
<223> OTHER INFORMATION: Leu or Gln
<220> FEATURE:
<221> NAME/KEY: MOD_RES
<222> LOCATION: (175)..(175)
<223> OTHER INFORMATION: Ser or Asn
<220> FEATURE:
<221> NAME/KEY: MOD_RES
<222> LOCATION: (183)..(183)
<223> OTHER INFORMATION: Ile or Asp
<220> FEATURE:
<221> NAME/KEY: MOD_RES
<222> LOCATION: (215)..(215)
<223> OTHER INFORMATION: Thr or Asn
<220> FEATURE:
<221> NAME/KEY: MOD_RES
<222> LOCATION: (219)..(219)
<223> OTHER INFORMATION: Asn or Arg
<220> FEATURE:
<221> NAME/KEY: MOD_RES
<222> LOCATION: (222)..(222)
<223> OTHER INFORMATION: Lys or Glu
<220> FEATURE:
<221> NAME/KEY: MOD_RES
<222> LOCATION: (225)..(225)
<223> OTHER INFORMATION: Val or Thr
<220> FEATURE:
<221> NAME/KEY: MOD_RES
<222> LOCATION: (228)..(228)
<223> OTHER INFORMATION: Thr or Leu
<220> FEATURE:
<221> NAME/KEY: MOD_RES
<222> LOCATION: (246)..(246)
<223> OTHER INFORMATION: Phe or Thr
<220> FEATURE:
<221> NAME/KEY: MOD_RES
<222> LOCATION: (247)..(247)
<223> OTHER INFORMATION: Pro or Arg
<220> FEATURE:
<221> NAME/KEY: MOD_RES
<222> LOCATION: (255)..(255)
<223> OTHER INFORMATION: Ser or Asn
<220> FEATURE:
<221> NAME/KEY: MOD_RES
<222> LOCATION: (256)..(256)
<223> OTHER INFORMATION: Gln or Ala
<220> FEATURE:
<221> NAME/KEY: MOD_RES
<222> LOCATION: (260)..(260)
<223> OTHER INFORMATION: Pro or Glu
<220> FEATURE:
<221> NAME/KEY: MOD_RES
<222> LOCATION: (263)..(263)
<223> OTHER INFORMATION: Thr or Ala
<220> FEATURE:
<221> NAME/KEY: MOD_RES
<222> LOCATION: (269)..(269)
<223> OTHER INFORMATION: Ser or Lys
<220> FEATURE:
<221> NAME/KEY: MOD_RES
<222> LOCATION: (270)..(270)
<223> OTHER INFORMATION: Tyr or Asn
<220> FEATURE:
<221> NAME/KEY: MOD_RES
<222> LOCATION: (273)..(273)
<223> OTHER INFORMATION: Asn or Gly
```

```
<220> FEATURE:
<221> NAME/KEY: MOD_RES
<222> LOCATION: (274)..(274)
<223> OTHER INFORMATION: Lys or Ala
<220> FEATURE:
<221> NAME/KEY: MOD_RES
<222> LOCATION: (276)..(276)
<223> OTHER INFORMATION: His or Glu
<220> FEATURE:
<221> NAME/KEY: MOD_RES
<222> LOCATION: (280)..(280)
<223> OTHER INFORMATION: Thr or Asn
<220> FEATURE:
<221> NAME/KEY: MOD_RES
<222> LOCATION: (284)..(284)
<223> OTHER INFORMATION: Gly or Trp
<220> FEATURE:
<221> NAME/KEY: MOD_RES
<222> LOCATION: (285)..(285)
<223> OTHER INFORMATION: Thr or Asn
<220> FEATURE:
<221> NAME/KEY: MOD_RES
<222> LOCATION: (286)..(286)
<223> OTHER INFORMATION: Met or His
<220> FEATURE:
<221> NAME/KEY: MOD_RES
<222> LOCATION: (291)..(291)
<223> OTHER INFORMATION: Ala or Val
<220> FEATURE:
<221> NAME/KEY: MOD_RES
<222> LOCATION: (295)..(295)
<223> OTHER INFORMATION: Asn or Tyr
<220> FEATURE:
<221> NAME/KEY: MOD_RES
<222> LOCATION: (296)..(296)
<223> OTHER INFORMATION: Lys or Asn
<220> FEATURE:
<221> NAME/KEY: MOD_RES
<222> LOCATION: (297)..(297)
<223> OTHER INFORMATION: Phe or Leu
<220> FEATURE:
<221> NAME/KEY: MOD_RES
<222> LOCATION: (299)..(299)
<223> OTHER INFORMATION: Thr or Asn
<220> FEATURE:
<221> NAME/KEY: MOD_RES
<222> LOCATION: (302)..(302)
<223> OTHER INFORMATION: Lys or Asn
<220> FEATURE:
<221> NAME/KEY: MOD_RES
<222> LOCATION: (306)..(306)
<223> OTHER INFORMATION: Ala or Asn
<220> FEATURE:
<221> NAME/KEY: MOD_RES
<222> LOCATION: (310)..(310)
<223> OTHER INFORMATION: Arg or Ala
<220> FEATURE:
<221> NAME/KEY: MOD_RES
<222> LOCATION: (311)..(311)
<223> OTHER INFORMATION: Thr or Lys
<220> FEATURE:
<221> NAME/KEY: MOD_RES
<222> LOCATION: (314)..(314)
<223> OTHER INFORMATION: Thr or Asn
<220> FEATURE:
<221> NAME/KEY: MOD_RES
<222> LOCATION: (315)..(315)
<223> OTHER INFORMATION: Asn or Gly
<220> FEATURE:
<221> NAME/KEY: MOD_RES
<222> LOCATION: (319)..(319)
<223> OTHER INFORMATION: Lys or Gln
<220> FEATURE:
<221> NAME/KEY: MOD_RES
<222> LOCATION: (320)..(320)
<223> OTHER INFORMATION: Asp or Lys
<220> FEATURE:
<221> NAME/KEY: MOD_RES
<222> LOCATION: (321)..(321)
```

```
<223> OTHER INFORMATION: Gln or His
<220> FEATURE:
<221> NAME/KEY: MOD_RES
<222> LOCATION: (323)..(323)
<223> OTHER INFORMATION: Thr or Met
<220> FEATURE:
<221> NAME/KEY: MOD_RES
<222> LOCATION: (324)..(324)
<223> OTHER INFORMATION: Leu or His
<220> FEATURE:
<221> NAME/KEY: MOD_RES
<222> LOCATION: (335)..(335)
<223> OTHER INFORMATION: Glu or Gln
<220> FEATURE:
<221> NAME/KEY: MOD_RES
<222> LOCATION: (338)..(338)
<223> OTHER INFORMATION: Gln or Glu
<220> FEATURE:
<221> NAME/KEY: MOD_RES
<222> LOCATION: (341)..(341)
<223> OTHER INFORMATION: Gln or Glu
<220> FEATURE:
<221> NAME/KEY: MOD_RES
<222> LOCATION: (345)..(345)
<223> OTHER INFORMATION: Asp or Gln
<220> FEATURE:
<221> NAME/KEY: MOD_RES
<222> LOCATION: (346)..(346)
<223> OTHER INFORMATION: Pro or Glu
<220> FEATURE:
<221> NAME/KEY: MOD_RES
<222> LOCATION: (355)..(355)
<223> OTHER INFORMATION: Phe or Leu
<220> FEATURE:
<221> NAME/KEY: MOD_RES
<222> LOCATION: (360)..(360)
<223> OTHER INFORMATION: Gln or Glu
<220> FEATURE:
<221> NAME/KEY: MOD_RES
<222> LOCATION: (361)..(361)
<223> OTHER INFORMATION: Glu or Gln
<220> FEATURE:
<221> NAME/KEY: MOD_RES
<222> LOCATION: (365)..(365)
<223> OTHER INFORMATION: Cys or Ser
<220> FEATURE:
<221> NAME/KEY: MOD_RES
<222> LOCATION: (376)..(376)
<223> OTHER INFORMATION: Gln or Thr
<220> FEATURE:
<221> NAME/KEY: MOD_RES
<222> LOCATION: (378)..(378)
<223> OTHER INFORMATION: Asn or Ser
<220> FEATURE:
<221> NAME/KEY: MOD_RES
<222> LOCATION: (391)..(391)
<223> OTHER INFORMATION: Ile or Glu
<220> FEATURE:
<221> NAME/KEY: MOD_RES
<222> LOCATION: (394)..(394)
<223> OTHER INFORMATION: Arg or Gln
<220> FEATURE:
<221> NAME/KEY: MOD_RES
<222> LOCATION: (395)..(395)
<223> OTHER INFORMATION: Asp or Asn
<220> FEATURE:
<221> NAME/KEY: MOD_RES
<222> LOCATION: (405)..(405)
<223> OTHER INFORMATION: Leu or Phe
<220> FEATURE:
<221> NAME/KEY: MOD_RES
<222> LOCATION: (408)..(408)
<223> OTHER INFORMATION: Ser or His
<220> FEATURE:
<221> NAME/KEY: MOD_RES
<222> LOCATION: (409)..(409)
<223> OTHER INFORMATION: Asp or Asn
<220> FEATURE:
<221> NAME/KEY: MOD_RES
```

```
<222> LOCATION: (418)..(418)
<223> OTHER INFORMATION: Val or Asn
<220> FEATURE:
<221> NAME/KEY: MOD_RES
<222> LOCATION: (420)..(420)
<223> OTHER INFORMATION: Glu or Thr
<220> FEATURE:
<221> NAME/KEY: MOD_RES
<222> LOCATION: (421)..(421)
<223> OTHER INFORMATION: Lys or His
<220> FEATURE:
<221> NAME/KEY: MOD_RES
<222> LOCATION: (423)..(423)
<223> OTHER INFORMATION: Gly or Asn
<220> FEATURE:
<221> NAME/KEY: MOD_RES
<222> LOCATION: (428)..(428)
<223> OTHER INFORMATION: Ala or Thr
<220> FEATURE:
<221> NAME/KEY: MOD_RES
<222> LOCATION: (437)..(437)
<223> OTHER INFORMATION: Ser or Glu
<220> FEATURE:
<221> NAME/KEY: MOD_RES
<222> LOCATION: (444)..(444)
<223> OTHER INFORMATION: Lys or Gln
<220> FEATURE:
<221> NAME/KEY: MOD_RES
<222> LOCATION: (446)..(446)
<223> OTHER INFORMATION: His or Lys
<220> FEATURE:
<221> NAME/KEY: MOD_RES
<222> LOCATION: (449)..(449)
<223> OTHER INFORMATION: Lys or Gln
<220> FEATURE:
<221> NAME/KEY: MOD_RES
<222> LOCATION: (459)..(459)
<223> OTHER INFORMATION: Ser or Pro
<220> FEATURE:
<221> NAME/KEY: MOD_RES
<222> LOCATION: (460)..(460)
<223> OTHER INFORMATION: Asp or Gly
<220> FEATURE:
<221> NAME/KEY: MOD_RES
<222> LOCATION: (471)..(471)
<223> OTHER INFORMATION: Glu or Asn
<220> FEATURE:
<221> NAME/KEY: MOD_RES
<222> LOCATION: (473)..(473)
<223> OTHER INFORMATION: Lys or Ser
<220> FEATURE:
<221> NAME/KEY: MOD_RES
<222> LOCATION: (484)..(484)
<223> OTHER INFORMATION: Pro or Lys
<220> FEATURE:
<221> NAME/KEY: MOD_RES
<222> LOCATION: (486)..(486)
<223> OTHER INFORMATION: Lys or not present
<220> FEATURE:
<221> NAME/KEY: MOD_RES
<222> LOCATION: (487)..(488)
<223> OTHER INFORMATION: Thr or not present
<220> FEATURE:
<221> NAME/KEY: MOD_RES
<222> LOCATION: (489)..(489)
<223> OTHER INFORMATION: Val or not present
<220> FEATURE:
<221> NAME/KEY: MOD_RES
<222> LOCATION: (490)..(490)
<223> OTHER INFORMATION: Ser or not present
<220> FEATURE:
<221> NAME/KEY: MOD_RES
<222> LOCATION: (491)..(491)
<223> OTHER INFORMATION: Thr or not present
<220> FEATURE:
<221> NAME/KEY: MOD_RES
<222> LOCATION: (492)..(492)
<223> OTHER INFORMATION: Ile or not present
<220> FEATURE:
```

```
<221> NAME/KEY: MOD_RES
<222> LOCATION: (493)..(493)
<223> OTHER INFORMATION: Ala or not present
<220> FEATURE:
<221> NAME/KEY: MOD_RES
<222> LOCATION: (494)..(494)
<223> OTHER INFORMATION: Arg or not present
<220> FEATURE:
<221> NAME/KEY: MOD_RES
<222> LOCATION: (495)..(495)
<223> OTHER INFORMATION: Pro or not present
<220> FEATURE:
<221> NAME/KEY: MOD_RES
<222> LOCATION: (496)..(496)
<223> OTHER INFORMATION: Ile or not present
<220> FEATURE:
<221> NAME/KEY: MOD_RES
<222> LOCATION: (497)..(498)
<223> OTHER INFORMATION: Thr or not present
<220> FEATURE:
<221> NAME/KEY: MOD_RES
<222> LOCATION: (499)..(499)
<223> OTHER INFORMATION: Arg or not present
<220> FEATURE:
<221> NAME/KEY: MOD_RES
<222> LOCATION: (500)..(500)
<223> OTHER INFORMATION: Pro or not present
<220> FEATURE:
<221> NAME/KEY: MOD_RES
<222> LOCATION: (501)..(501)
<223> OTHER INFORMATION: Trp or not present
<220> FEATURE:
<221> NAME/KEY: MOD_RES
<222> LOCATION: (502)..(502)
<223> OTHER INFORMATION: Thr or not present
<220> FEATURE:
<221> NAME/KEY: MOD_RES
<222> LOCATION: (503)..(503)
<223> OTHER INFORMATION: Gly or not present
<220> FEATURE:
<221> NAME/KEY: MOD_RES
<222> LOCATION: (504)..(504)
<223> OTHER INFORMATION: Glu or not present
<220> FEATURE:
<221> NAME/KEY: MOD_RES
<222> LOCATION: (505)..(505)
<223> OTHER INFORMATION: Phe or not present
<220> FEATURE:
<221> NAME/KEY: MOD_RES
<222> LOCATION: (506)..(506)
<223> OTHER INFORMATION: Val or not present
<220> FEATURE:
<221> NAME/KEY: MOD_RES
<222> LOCATION: (507)..(507)
<223> OTHER INFORMATION: Arg or not present
<220> FEATURE:
<221> NAME/KEY: MOD_RES
<222> LOCATION: (508)..(508)
<223> OTHER INFORMATION: Trp or not present
<220> FEATURE:
<221> NAME/KEY: MOD_RES
<222> LOCATION: (509)..(509)
<223> OTHER INFORMATION: Thr or not present
<220> FEATURE:
<221> NAME/KEY: MOD_RES
<222> LOCATION: (510)..(510)
<223> OTHER INFORMATION: Glu or not present
<220> FEATURE:
<221> NAME/KEY: MOD_RES
<222> LOCATION: (511)..(511)
<223> OTHER INFORMATION: Pro or not present
<220> FEATURE:
<221> NAME/KEY: MOD_RES
<222> LOCATION: (512)..(512)
<223> OTHER INFORMATION: Arg or not present
<220> FEATURE:
<221> NAME/KEY: MOD_RES
<222> LOCATION: (513)..(513)
<223> OTHER INFORMATION: Leu or not present
```

```
<220> FEATURE:
<221> NAME/KEY: MOD_RES
<222> LOCATION: (514)..(514)
<223> OTHER INFORMATION: Val or not present
<220> FEATURE:
<221> NAME/KEY: MOD_RES
<222> LOCATION: (515)..(515)
<223> OTHER INFORMATION: Ala or not present
<220> FEATURE:
<221> NAME/KEY: MOD_RES
<222> LOCATION: (516)..(516)
<223> OTHER INFORMATION: Trp or not present
<220> FEATURE:
<221> NAME/KEY: MOD_RES
<222> LOCATION: (517)..(517)
<223> OTHER INFORMATION: Pro or not present

<400> SEQUENCE: 27

Xaa Xaa Xaa Xaa Xaa Asn Gly Thr Met Met Gln Tyr Phe Glu Trp His
1               5                   10                  15

Leu Pro Xaa Asp Gly Xaa Xaa Trp Xaa Lys Leu Xaa Xaa Asp Ala Xaa
            20                  25                  30

Asn Leu Xaa Xaa Xaa Gly Ile Thr Ala Ile Trp Ile Pro Pro Ala Trp
        35                  40                  45

Lys Gly Thr Ser Xaa Xaa Asp Val Gly Tyr Gly Xaa Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Ala Gln Xaa Xaa Xaa Ala Ile Xaa Ala Xaa Xaa Xaa Xaa Gly
                85                  90                  95

Met Gln Val Tyr Ala Asp Val Val Xaa Xaa His Lys Gly Gly Ala Asp
            100                 105                 110

Ala Thr Glu Xaa Val Xaa Ala Val Glu Val Asn Pro Xaa Xaa Arg Asn
        115                 120                 125

Gln Glu Ile Ser Gly Xaa Tyr Xaa Ile Xaa Ala Trp Thr Lys Phe Asp
130                 135                 140

Phe Pro Gly Arg Gly Asn Thr Tyr Ser Xaa Phe Lys Trp Arg Trp Tyr
145                 150                 155                 160

His Phe Asp Gly Val Asp Trp Asp Xaa Ser Arg Xaa Xaa Xaa Xaa Arg
                165                 170                 175

Ile Tyr Lys Phe Arg Gly Xaa Gly Lys Ala Trp Asp Trp Glu Val Asp
            180                 185                 190

Ser Glu Asn Gly Asn Tyr Asp Tyr Leu Met Tyr Ala Asp Leu Asp Met
        195                 200                 205

Asp His Pro Glu Val Val Xaa Glu Leu Lys Xaa Trp Gly Xaa Trp Tyr
210                 215                 220

Xaa Asn Thr Xaa Asn Ile Asp Gly Phe Arg Ile Asp Ala Val Lys His
225                 230                 235                 240

Ile Lys Phe Ser Phe Xaa Xaa Asp Trp Leu Ser His Val Arg Xaa Xaa
                245                 250                 255

Thr Gly Lys Xaa Leu Phe Xaa Val Ala Glu Phe Trp Xaa Xaa Asp Ile
            260                 265                 270

Xaa Xaa Leu Xaa Asn Tyr Ile Xaa Lys Thr Asn Xaa Xaa Xaa Ser Leu
        275                 280                 285

Phe Asp Xaa Pro Leu His Xaa Xaa Xaa Tyr Xaa Ala Ser Xaa Ser Gly
290                 295                 300

Gly Xaa Phe Asp Met Xaa Xaa Leu Leu Xaa Xaa Thr Leu Met Xaa Xaa
305                 310                 315                 320
```

-continued

```
Xaa Pro Xaa Xaa Ala Val Thr Phe Val Asp Asn His Asp Ser Xaa Pro
            325                 330                 335

Gly Xaa Ala Leu Xaa Ser Phe Val Xaa Xaa Trp Phe Lys Pro Leu Ala
            340                 345                 350

Tyr Ala Xaa Ile Leu Thr Arg Xaa Xaa Gly Tyr Pro Xaa Val Phe Tyr
            355                 360                 365

Gly Asp Tyr Tyr Gly Ile Pro Xaa His Xaa Ile Pro Ala Leu Lys Ala
370                 375                 380

Lys Ile Asp Pro Ile Leu Xaa Ala Arg Xaa Xaa Phe Ala Tyr Gly Thr
385                 390                 395                 400

Gln His Asp Tyr Xaa Asp His Xaa Xaa Ile Gly Trp Thr Arg Glu
                    405                 410                 415

Gly Xaa Thr Xaa Xaa Pro Xaa Ser Gly Leu Ala Xaa Ile Ile Ser Asp
            420                 425                 430

Gly Pro Gly Gly Xaa Lys Trp Met Tyr Val Gly Xaa Asn Xaa Ala Gly
            435                 440                 445

Xaa Val Phe His Asp Ile Thr Gly Asn Lys Xaa Xaa Thr Val Thr Ile
    450                 455                 460

Asn Ala Asp Gly Trp Ala Xaa Phe Xaa Val Asn Gly Gly Ser Val Ser
465                 470                 475                 480

Ile Trp Val Xaa Arg Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa
        515

<210> SEQ ID NO 28
<211> LENGTH: 517
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His or not present
<220> FEATURE:
<221> NAME/KEY: MOD_RES
<222> LOCATION: (2)..(2)
<223> OTHER INFORMATION: Ala or His
<220> FEATURE:
<221> NAME/KEY: MOD_RES
<222> LOCATION: (3)..(3)
<223> OTHER INFORMATION: Ala or Asn
<220> FEATURE:
<221> NAME/KEY: MOD_RES
<222> LOCATION: (4)..(4)
<223> OTHER INFORMATION: Pro or Gly
<220> FEATURE:
<221> NAME/KEY: MOD_RES
<222> LOCATION: (5)..(5)
<223> OTHER INFORMATION: Phe or Thr
<220> FEATURE:
<221> NAME/KEY: MOD_RES
<222> LOCATION: (19)..(19)
<223> OTHER INFORMATION: Asp or Asn
<220> FEATURE:
<221> NAME/KEY: MOD_RES
<222> LOCATION: (22)..(22)
<223> OTHER INFORMATION: Thr or Asn
<220> FEATURE:
<221> NAME/KEY: MOD_RES
<222> LOCATION: (23)..(23)
<223> OTHER INFORMATION: Leu or His
```

```
<220> FEATURE:
<221> NAME/KEY: MOD_RES
<222> LOCATION: (25)..(25)
<223> OTHER INFORMATION: Thr or Asn
<220> FEATURE:
<221> NAME/KEY: MOD_RES
<222> LOCATION: (28)..(28)
<223> OTHER INFORMATION: Ala or Arg
<220> FEATURE:
<221> NAME/KEY: MOD_RES
<222> LOCATION: (29)..(29)
<223> OTHER INFORMATION: Asn or Asp
<220> FEATURE:
<221> NAME/KEY: MOD_RES
<222> LOCATION: (32)..(32)
<223> OTHER INFORMATION: Asn or Ala
<220> FEATURE:
<221> NAME/KEY: MOD_RES
<222> LOCATION: (35)..(35)
<223> OTHER INFORMATION: Ser or Lys
<220> FEATURE:
<221> NAME/KEY: MOD_RES
<222> LOCATION: (37)..(37)
<223> OTHER INFORMATION: Leu or Lys
<220> FEATURE:
<221> NAME/KEY: MOD_RES
<222> LOCATION: (53)..(53)
<223> OTHER INFORMATION: Arg or Gln
<220> FEATURE:
<221> NAME/KEY: MOD_RES
<222> LOCATION: (54)..(54)
<223> OTHER INFORMATION: Ser or Asn
<220> FEATURE:
<221> NAME/KEY: MOD_RES
<222> LOCATION: (60)..(60)
<223> OTHER INFORMATION: Val or Ala
<220> FEATURE:
<221> NAME/KEY: MOD_RES
<222> LOCATION: (85)..(85)
<223> OTHER INFORMATION: Tyr or Leu
<220> FEATURE:
<221> NAME/KEY: MOD_RES
<222> LOCATION: (86)..(86)
<223> OTHER INFORMATION: Leu or Gln
<220> FEATURE:
<221> NAME/KEY: MOD_RES
<222> LOCATION: (87)..(87)
<223> OTHER INFORMATION: Gln or Gly
<220> FEATURE:
<221> NAME/KEY: MOD_RES
<222> LOCATION: (90)..(90)
<223> OTHER INFORMATION: Gln or Thr
<220> FEATURE:
<221> NAME/KEY: MOD_RES
<222> LOCATION: (92)..(92)
<223> OTHER INFORMATION: Ala or Leu
<220> FEATURE:
<221> NAME/KEY: MOD_RES
<222> LOCATION: (93)..(93)
<223> OTHER INFORMATION: His or Lys
<220> FEATURE:
<221> NAME/KEY: MOD_RES
<222> LOCATION: (94)..(95)
<223> OTHER INFORMATION: Ala or Asn
<220> FEATURE:
<221> NAME/KEY: MOD_RES
<222> LOCATION: (105)..(105)
<223> OTHER INFORMATION: Phe or Met
<220> FEATURE:
<221> NAME/KEY: MOD_RES
<222> LOCATION: (106)..(106)
<223> OTHER INFORMATION: Asp or Asn
<220> FEATURE:
<221> NAME/KEY: MOD_RES
<222> LOCATION: (116)..(116)
<223> OTHER INFORMATION: Trp or Met
<220> FEATURE:
<221> NAME/KEY: MOD_RES
<222> LOCATION: (118)..(118)
```

```
<223> OTHER INFORMATION: Asp or Asn
<220> FEATURE:
<221> NAME/KEY: MOD_RES
<222> LOCATION: (124)..(124)
<223> OTHER INFORMATION: Pro or Arg
<220> FEATURE:
<221> NAME/KEY: MOD_RES
<222> LOCATION: (126)..(126)
<223> OTHER INFORMATION: Asp or Asn
<220> FEATURE:
<221> NAME/KEY: MOD_RES
<222> LOCATION: (134)..(134)
<223> OTHER INFORMATION: Thr or Glu
<220> FEATURE:
<221> NAME/KEY: MOD_RES
<222> LOCATION: (136)..(136)
<223> OTHER INFORMATION: Gln or Thr
<220> FEATURE:
<221> NAME/KEY: MOD_RES
<222> LOCATION: (138)..(138)
<223> OTHER INFORMATION: Gln or Glu
<220> FEATURE:
<221> NAME/KEY: MOD_RES
<222> LOCATION: (154)..(154)
<223> OTHER INFORMATION: Ser or Asn
<220> FEATURE:
<221> NAME/KEY: MOD_RES
<222> LOCATION: (165)..(165)
<223> OTHER INFORMATION: Val or Thr
<220> FEATURE:
<221> NAME/KEY: MOD_RES
<222> LOCATION: (169)..(169)
<223> OTHER INFORMATION: Glu or Gln
<220> FEATURE:
<221> NAME/KEY: MOD_RES
<222> LOCATION: (172)..(172)
<223> OTHER INFORMATION: Gln or not present
<220> FEATURE:
<221> NAME/KEY: MOD_RES
<222> LOCATION: (173)..(173)
<223> OTHER INFORMATION: Lys or Leu
<220> FEATURE:
<221> NAME/KEY: MOD_RES
<222> LOCATION: (174)..(174)
<223> OTHER INFORMATION: Leu or Gln
<220> FEATURE:
<221> NAME/KEY: MOD_RES
<222> LOCATION: (175)..(175)
<223> OTHER INFORMATION: Ser or Asn
<220> FEATURE:
<221> NAME/KEY: MOD_RES
<222> LOCATION: (183)..(183)
<223> OTHER INFORMATION: Ile or Thr
<220> FEATURE:
<221> NAME/KEY: MOD_RES
<222> LOCATION: (193)..(193)
<223> OTHER INFORMATION: Thr or Ile
<220> FEATURE:
<221> NAME/KEY: MOD_RES
<222> LOCATION: (215)..(215)
<223> OTHER INFORMATION: Thr or Asn
<220> FEATURE:
<221> NAME/KEY: MOD_RES
<222> LOCATION: (222)..(222)
<223> OTHER INFORMATION: Lys or Val
<220> FEATURE:
<221> NAME/KEY: MOD_RES
<222> LOCATION: (225)..(225)
<223> OTHER INFORMATION: Val or Thr
<220> FEATURE:
<221> NAME/KEY: MOD_RES
<222> LOCATION: (228)..(228)
<223> OTHER INFORMATION: Thr or Leu
<220> FEATURE:
<221> NAME/KEY: MOD_RES
<222> LOCATION: (246)..(246)
<223> OTHER INFORMATION: Phe or Thr
<220> FEATURE:
<221> NAME/KEY: MOD_RES
```

```
<222> LOCATION: (247)..(247)
<223> OTHER INFORMATION: Pro or Arg
<220> FEATURE:
<221> NAME/KEY: MOD_RES
<222> LOCATION: (255)..(255)
<223> OTHER INFORMATION: Ser or Asn
<220> FEATURE:
<221> NAME/KEY: MOD_RES
<222> LOCATION: (256)..(256)
<223> OTHER INFORMATION: Gln or Thr
<220> FEATURE:
<221> NAME/KEY: MOD_RES
<222> LOCATION: (263)..(263)
<223> OTHER INFORMATION: Thr or Ala
<220> FEATURE:
<221> NAME/KEY: MOD_RES
<222> LOCATION: (269)..(269)
<223> OTHER INFORMATION: Ser or Lys
<220> FEATURE:
<221> NAME/KEY: MOD_RES
<222> LOCATION: (270)..(270)
<223> OTHER INFORMATION: Tyr or Asn
<220> FEATURE:
<221> NAME/KEY: MOD_RES
<222> LOCATION: (273)..(273)
<223> OTHER INFORMATION: Asn or Ala
<220> FEATURE:
<221> NAME/KEY: MOD_RES
<222> LOCATION: (274)..(274)
<223> OTHER INFORMATION: Lys or Ala
<220> FEATURE:
<221> NAME/KEY: MOD_RES
<222> LOCATION: (276)..(276)
<223> OTHER INFORMATION: His or Glu
<220> FEATURE:
<221> NAME/KEY: MOD_RES
<222> LOCATION: (280)..(280)
<223> OTHER INFORMATION: Thr or Asn
<220> FEATURE:
<221> NAME/KEY: MOD_RES
<222> LOCATION: (283)..(283)
<223> OTHER INFORMATION: Asn or Ser
<220> FEATURE:
<221> NAME/KEY: MOD_RES
<222> LOCATION: (284)..(284)
<223> OTHER INFORMATION: Gly or Trp
<220> FEATURE:
<221> NAME/KEY: MOD_RES
<222> LOCATION: (285)..(285)
<223> OTHER INFORMATION: Thr or Asn
<220> FEATURE:
<221> NAME/KEY: MOD_RES
<222> LOCATION: (286)..(286)
<223> OTHER INFORMATION: Met or His
<220> FEATURE:
<221> NAME/KEY: MOD_RES
<222> LOCATION: (291)..(291)
<223> OTHER INFORMATION: Ala or Val
<220> FEATURE:
<221> NAME/KEY: MOD_RES
<222> LOCATION: (295)..(295)
<223> OTHER INFORMATION: Asn or Tyr
<220> FEATURE:
<221> NAME/KEY: MOD_RES
<222> LOCATION: (296)..(296)
<223> OTHER INFORMATION: Lys or Asn
<220> FEATURE:
<221> NAME/KEY: MOD_RES
<222> LOCATION: (297)..(297)
<223> OTHER INFORMATION: Phe or Leu
<220> FEATURE:
<221> NAME/KEY: MOD_RES
<222> LOCATION: (299)..(299)
<223> OTHER INFORMATION: Thr or Asn
<220> FEATURE:
<221> NAME/KEY: MOD_RES
<222> LOCATION: (302)..(302)
<223> OTHER INFORMATION: Lys or Asn
<220> FEATURE:
```

```
<221> NAME/KEY: MOD_RES
<222> LOCATION: (306)..(306)
<223> OTHER INFORMATION: Ala or Tyr
<220> FEATURE:
<221> NAME/KEY: MOD_RES
<222> LOCATION: (311)..(311)
<223> OTHER INFORMATION: Thr or Asn
<220> FEATURE:
<221> NAME/KEY: MOD_RES
<222> LOCATION: (314)..(314)
<223> OTHER INFORMATION: Thr or Asn
<220> FEATURE:
<221> NAME/KEY: MOD_RES
<222> LOCATION: (315)..(315)
<223> OTHER INFORMATION: Asn or Gly
<220> FEATURE:
<221> NAME/KEY: MOD_RES
<222> LOCATION: (319)..(319)
<223> OTHER INFORMATION: Lys or Gln
<220> FEATURE:
<221> NAME/KEY: MOD_RES
<222> LOCATION: (320)..(320)
<223> OTHER INFORMATION: Asp or Lys
<220> FEATURE:
<221> NAME/KEY: MOD_RES
<222> LOCATION: (321)..(321)
<223> OTHER INFORMATION: Gln or His
<220> FEATURE:
<221> NAME/KEY: MOD_RES
<222> LOCATION: (323)..(323)
<223> OTHER INFORMATION: Thr or Ile
<220> FEATURE:
<221> NAME/KEY: MOD_RES
<222> LOCATION: (324)..(324)
<223> OTHER INFORMATION: Leu or His
<220> FEATURE:
<221> NAME/KEY: MOD_RES
<222> LOCATION: (335)..(335)
<223> OTHER INFORMATION: Glu or Gln
<220> FEATURE:
<221> NAME/KEY: MOD_RES
<222> LOCATION: (338)..(338)
<223> OTHER INFORMATION: Gln or Glu
<220> FEATURE:
<221> NAME/KEY: MOD_RES
<222> LOCATION: (341)..(341)
<223> OTHER INFORMATION: Gln or Glu
<220> FEATURE:
<221> NAME/KEY: MOD_RES
<222> LOCATION: (345)..(345)
<223> OTHER INFORMATION: Asp or Gln
<220> FEATURE:
<221> NAME/KEY: MOD_RES
<222> LOCATION: (346)..(346)
<223> OTHER INFORMATION: Pro or Ser
<220> FEATURE:
<221> NAME/KEY: MOD_RES
<222> LOCATION: (355)..(355)
<223> OTHER INFORMATION: Phe or Leu
<220> FEATURE:
<221> NAME/KEY: MOD_RES
<222> LOCATION: (360)..(360)
<223> OTHER INFORMATION: Gln or Glu
<220> FEATURE:
<221> NAME/KEY: MOD_RES
<222> LOCATION: (361)..(361)
<223> OTHER INFORMATION: Glu or Gln
<220> FEATURE:
<221> NAME/KEY: MOD_RES
<222> LOCATION: (365)..(365)
<223> OTHER INFORMATION: Cys or Ser
<220> FEATURE:
<221> NAME/KEY: MOD_RES
<222> LOCATION: (376)..(376)
<223> OTHER INFORMATION: Gln or Thr
<220> FEATURE:
<221> NAME/KEY: MOD_RES
<222> LOCATION: (378)..(378)
<223> OTHER INFORMATION: Asn or Gly
```

```
<220> FEATURE:
<221> NAME/KEY: MOD_RES
<222> LOCATION: (391)..(391)
<223> OTHER INFORMATION: Ile or Gln
<220> FEATURE:
<221> NAME/KEY: MOD_RES
<222> LOCATION: (394)..(394)
<223> OTHER INFORMATION: Arg or Gln
<220> FEATURE:
<221> NAME/KEY: MOD_RES
<222> LOCATION: (395)..(395)
<223> OTHER INFORMATION: Asp or Thr
<220> FEATURE:
<221> NAME/KEY: MOD_RES
<222> LOCATION: (405)..(405)
<223> OTHER INFORMATION: Leu or Phe
<220> FEATURE:
<221> NAME/KEY: MOD_RES
<222> LOCATION: (408)..(408)
<223> OTHER INFORMATION: Ser or His
<220> FEATURE:
<221> NAME/KEY: MOD_RES
<222> LOCATION: (418)..(418)
<223> OTHER INFORMATION: Val or Asp
<220> FEATURE:
<221> NAME/KEY: MOD_RES
<222> LOCATION: (420)..(420)
<223> OTHER INFORMATION: Glu or Ser
<220> FEATURE:
<221> NAME/KEY: MOD_RES
<222> LOCATION: (421)..(421)
<223> OTHER INFORMATION: Lys or His
<220> FEATURE:
<221> NAME/KEY: MOD_RES
<222> LOCATION: (423)..(423)
<223> OTHER INFORMATION: Gly or Asn
<220> FEATURE:
<221> NAME/KEY: MOD_RES
<222> LOCATION: (428)..(428)
<223> OTHER INFORMATION: Ala or Thr
<220> FEATURE:
<221> NAME/KEY: MOD_RES
<222> LOCATION: (437)..(437)
<223> OTHER INFORMATION: Ser or Asn
<220> FEATURE:
<221> NAME/KEY: MOD_RES
<222> LOCATION: (445)..(445)
<223> OTHER INFORMATION: Gln or His
<220> FEATURE:
<221> NAME/KEY: MOD_RES
<222> LOCATION: (446)..(446)
<223> OTHER INFORMATION: His or Lys
<220> FEATURE:
<221> NAME/KEY: MOD_RES
<222> LOCATION: (449)..(449)
<223> OTHER INFORMATION: Lys or Gln
<220> FEATURE:
<221> NAME/KEY: MOD_RES
<222> LOCATION: (452)..(452)
<223> OTHER INFORMATION: Tyr or Arg
<220> FEATURE:
<221> NAME/KEY: MOD_RES
<222> LOCATION: (460)..(460)
<223> OTHER INFORMATION: Asp or Gly
<220> FEATURE:
<221> NAME/KEY: MOD_RES
<222> LOCATION: (471)..(471)
<223> OTHER INFORMATION: Glu or Asn
<220> FEATURE:
<221> NAME/KEY: MOD_RES
<222> LOCATION: (473)..(473)
<223> OTHER INFORMATION: Lys or Thr
<220> FEATURE:
<221> NAME/KEY: MOD_RES
<222> LOCATION: (484)..(484)
<223> OTHER INFORMATION: Pro or Lys
<220> FEATURE:
<221> NAME/KEY: MOD_RES
<222> LOCATION: (485)..(485)
```

```
<223> OTHER INFORMATION: Arg or Gln
<220> FEATURE:
<221> NAME/KEY: MOD_RES
<222> LOCATION: (486)..(486)
<223> OTHER INFORMATION: Lys or not present
<220> FEATURE:
<221> NAME/KEY: MOD_RES
<222> LOCATION: (487)..(488)
<223> OTHER INFORMATION: Thr or not present
<220> FEATURE:
<221> NAME/KEY: MOD_RES
<222> LOCATION: (489)..(489)
<223> OTHER INFORMATION: Val or not present
<220> FEATURE:
<221> NAME/KEY: MOD_RES
<222> LOCATION: (490)..(490)
<223> OTHER INFORMATION: Ser or not present
<220> FEATURE:
<221> NAME/KEY: MOD_RES
<222> LOCATION: (491)..(491)
<223> OTHER INFORMATION: Thr or not present
<220> FEATURE:
<221> NAME/KEY: MOD_RES
<222> LOCATION: (492)..(492)
<223> OTHER INFORMATION: Ile or not present
<220> FEATURE:
<221> NAME/KEY: MOD_RES
<222> LOCATION: (493)..(493)
<223> OTHER INFORMATION: Ala or not present
<220> FEATURE:
<221> NAME/KEY: MOD_RES
<222> LOCATION: (494)..(494)
<223> OTHER INFORMATION: Arg or not present
<220> FEATURE:
<221> NAME/KEY: MOD_RES
<222> LOCATION: (495)..(495)
<223> OTHER INFORMATION: Pro or not present
<220> FEATURE:
<221> NAME/KEY: MOD_RES
<222> LOCATION: (496)..(496)
<223> OTHER INFORMATION: Ile or not present
<220> FEATURE:
<221> NAME/KEY: MOD_RES
<222> LOCATION: (497)..(498)
<223> OTHER INFORMATION: Thr or not present
<220> FEATURE:
<221> NAME/KEY: MOD_RES
<222> LOCATION: (499)..(499)
<223> OTHER INFORMATION: Arg or not present
<220> FEATURE:
<221> NAME/KEY: MOD_RES
<222> LOCATION: (500)..(500)
<223> OTHER INFORMATION: Pro or not present
<220> FEATURE:
<221> NAME/KEY: MOD_RES
<222> LOCATION: (501)..(501)
<223> OTHER INFORMATION: Trp or not present
<220> FEATURE:
<221> NAME/KEY: MOD_RES
<222> LOCATION: (502)..(502)
<223> OTHER INFORMATION: Thr or not present
<220> FEATURE:
<221> NAME/KEY: MOD_RES
<222> LOCATION: (503)..(503)
<223> OTHER INFORMATION: Gly or not present
<220> FEATURE:
<221> NAME/KEY: MOD_RES
<222> LOCATION: (504)..(504)
<223> OTHER INFORMATION: Glu or not present
<220> FEATURE:
<221> NAME/KEY: MOD_RES
<222> LOCATION: (505)..(505)
<223> OTHER INFORMATION: Phe or not present
<220> FEATURE:
<221> NAME/KEY: MOD_RES
<222> LOCATION: (506)..(506)
<223> OTHER INFORMATION: Val or not present
<220> FEATURE:
<221> NAME/KEY: MOD_RES
```

-continued

```
<222> LOCATION: (507)..(507)
<223> OTHER INFORMATION: Arg or not present
<220> FEATURE:
<221> NAME/KEY: MOD_RES
<222> LOCATION: (508)..(508)
<223> OTHER INFORMATION: Trp or not present
<220> FEATURE:
<221> NAME/KEY: MOD_RES
<222> LOCATION: (509)..(509)
<223> OTHER INFORMATION: Thr or not present
<220> FEATURE:
<221> NAME/KEY: MOD_RES
<222> LOCATION: (510)..(510)
<223> OTHER INFORMATION: Glu or not present
<220> FEATURE:
<221> NAME/KEY: MOD_RES
<222> LOCATION: (511)..(511)
<223> OTHER INFORMATION: Pro or not present
<220> FEATURE:
<221> NAME/KEY: MOD_RES
<222> LOCATION: (512)..(512)
<223> OTHER INFORMATION: Arg or not present
<220> FEATURE:
<221> NAME/KEY: MOD_RES
<222> LOCATION: (513)..(513)
<223> OTHER INFORMATION: Leu or not present
<220> FEATURE:
<221> NAME/KEY: MOD_RES
<222> LOCATION: (514)..(514)
<223> OTHER INFORMATION: Val or not present
<220> FEATURE:
<221> NAME/KEY: MOD_RES
<222> LOCATION: (515)..(515)
<223> OTHER INFORMATION: Ala or not present
<220> FEATURE:
<221> NAME/KEY: MOD_RES
<222> LOCATION: (516)..(516)
<223> OTHER INFORMATION: Trp or not present
<220> FEATURE:
<221> NAME/KEY: MOD_RES
<222> LOCATION: (517)..(517)
<223> OTHER INFORMATION: Pro or not present

<400> SEQUENCE: 28

Xaa Xaa Xaa Xaa Xaa Asn Gly Thr Met Met Gln Tyr Phe Glu Trp His
 1               5                  10                  15

Leu Pro Xaa Asp Gly Xaa Xaa Trp Xaa Lys Leu Xaa Xaa Asp Ala Xaa
                20                  25                  30

Asn Leu Xaa Ser Xaa Gly Ile Thr Ala Leu Trp Ile Pro Pro Ala Trp
            35                  40                  45

Lys Gly Thr Ser Xaa Xaa Asp Val Gly Tyr Gly Xaa Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Ala Gln Xaa Xaa Xaa Ala Ile Xaa Ala Xaa Xaa Xaa Xaa Gly
                85                  90                  95

Ile Gln Val Tyr Ala Asp Val Val Xaa Xaa His Lys Gly Gly Ala Asp
            100                 105                 110

Gly Thr Glu Xaa Val Xaa Ala Val Glu Val Asn Xaa Ser Xaa Arg Asn
        115                 120                 125

Gln Glu Ile Ser Gly Xaa Tyr Xaa Ile Xaa Ala Trp Thr Lys Phe Asp
    130                 135                 140

Phe Pro Gly Arg Gly Asn Thr His Ser Xaa Phe Lys Trp Arg Trp Tyr
145                 150                 155                 160

His Phe Asp Gly Xaa Asp Trp Asp Xaa Ser Arg Xaa Xaa Xaa Xaa Lys
                165                 170                 175

Ile Tyr Lys Phe Arg Gly Xaa Gly Lys Ala Trp Asp Trp Glu Val Asp
```

```
            180                 185                 190
Xaa Glu Asn Gly Asn Tyr Asp Tyr Leu Met Tyr Ala Asp Ile Asp Met
    195                 200                 205

Asp His Pro Glu Val Ile Xaa Glu Leu Lys Asn Trp Gly Xaa Trp Tyr
210                 215                 220

Xaa Asn Thr Xaa Asn Ile Asp Gly Phe Arg Ile Asp Ala Val Lys His
225                 230                 235                 240

Ile Lys Phe Ser Phe Xaa Xaa Asp Trp Leu Ser His Val Arg Xaa Xaa
                245                 250                 255

Thr Gly Lys Pro Leu Phe Xaa Val Ala Glu Phe Trp Xaa Xaa Asp Ile
            260                 265                 270

Xaa Xaa Ile Xaa Asn Tyr Ile Xaa Lys Thr Xaa Xaa Xaa Xaa Ser Leu
        275                 280                 285

Phe Asp Xaa Pro Leu His Xaa Xaa Xaa Tyr Xaa Ala Ser Xaa Ser Gly
    290                 295                 300

Gly Xaa Phe Asp Met Arg Xaa Ile Leu Xaa Xaa Ser Leu Met Xaa Xaa
305                 310                 315                 320

Xaa Pro Xaa Xaa Ala Val Thr Phe Val Asp Asn His Asp Ser Xaa Pro
                325                 330                 335

Gly Xaa Ala Leu Xaa Ser Phe Val Xaa Xaa Trp Phe Lys Pro Leu Ala
            340                 345                 350

Tyr Ala Xaa Ile Leu Thr Arg Xaa Xaa Gly Tyr Pro Xaa Val Phe Tyr
        355                 360                 365

Gly Asp Tyr Tyr Gly Ile Pro Xaa His Xaa Ile Pro Ser Leu Lys Ser
    370                 375                 380

Lys Ile Asp Pro Leu Leu Xaa Ala Arg Xaa Xaa Tyr Ala Tyr Gly Thr
385                 390                 395                 400

Gln His Asp Tyr Xaa Asp His Xaa Asp Ile Ile Gly Trp Thr Arg Glu
                405                 410                 415

Gly Xaa Ser Xaa Xaa Pro Xaa Ser Gly Leu Ala Xaa Ile Ile Ser Asp
            420                 425                 430

Gly Pro Gly Gly Xaa Lys Trp Met Tyr Val Gly Lys Xaa Xaa Ala Gly
        435                 440                 445

Xaa Val Phe Xaa Asp Ile Thr Gly Asn Arg Ser Xaa Thr Val Thr Ile
    450                 455                 460

Asn Ala Asp Gly Trp Gly Xaa Phe Xaa Val Asn Gly Gly Ala Val Ser
465                 470                 475                 480

Val Trp Val Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa
        515

<210> SEQ ID NO 29
<211> LENGTH: 515
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ala or not present
<220> FEATURE:
<221> NAME/KEY: MOD_RES
```

```
<222> LOCATION: (2)..(2)
<223> OTHER INFORMATION: Ala or Asp
<220> FEATURE:
<221> NAME/KEY: MOD_RES
<222> LOCATION: (3)..(3)
<223> OTHER INFORMATION: Pro or Gly
<220> FEATURE:
<221> NAME/KEY: MOD_RES
<222> LOCATION: (4)..(4)
<223> OTHER INFORMATION: Phe or Leu
<220> FEATURE:
<221> NAME/KEY: MOD_RES
<222> LOCATION: (17)..(17)
<223> OTHER INFORMATION: Pro or Glu
<220> FEATURE:
<221> NAME/KEY: MOD_RES
<222> LOCATION: (18)..(18)
<223> OTHER INFORMATION: Asp or Asn
<220> FEATURE:
<221> NAME/KEY: MOD_RES
<222> LOCATION: (21)..(21)
<223> OTHER INFORMATION: Thr or Gln
<220> FEATURE:
<221> NAME/KEY: MOD_RES
<222> LOCATION: (22)..(22)
<223> OTHER INFORMATION: Leu or His
<220> FEATURE:
<221> NAME/KEY: MOD_RES
<222> LOCATION: (24)..(24)
<223> OTHER INFORMATION: Thr or Asn
<220> FEATURE:
<221> NAME/KEY: MOD_RES
<222> LOCATION: (27)..(27)
<223> OTHER INFORMATION: Ala or His
<220> FEATURE:
<221> NAME/KEY: MOD_RES
<222> LOCATION: (28)..(28)
<223> OTHER INFORMATION: Asn or Asp
<220> FEATURE:
<221> NAME/KEY: MOD_RES
<222> LOCATION: (31)..(32)
<223> OTHER INFORMATION: Asn or Ala
<220> FEATURE:
<221> NAME/KEY: MOD_RES
<222> LOCATION: (35)..(35)
<223> OTHER INFORMATION: Ser or Asp
<220> FEATURE:
<221> NAME/KEY: MOD_RES
<222> LOCATION: (36)..(36)
<223> OTHER INFORMATION: Leu or Ala
<220> FEATURE:
<221> NAME/KEY: MOD_RES
<222> LOCATION: (50)..(50)
<223> OTHER INFORMATION: Thr or Asn
<220> FEATURE:
<221> NAME/KEY: MOD_RES
<222> LOCATION: (52)..(52)
<223> OTHER INFORMATION: Arg or Gln
<220> FEATURE:
<221> NAME/KEY: MOD_RES
<222> LOCATION: (59)..(59)
<223> OTHER INFORMATION: Val or Ala
<220> FEATURE:
<221> NAME/KEY: MOD_RES
<222> LOCATION: (84)..(84)
<223> OTHER INFORMATION: Tyr or Leu
<220> FEATURE:
<221> NAME/KEY: MOD_RES
<222> LOCATION: (85)..(85)
<223> OTHER INFORMATION: Leu or Glu
<220> FEATURE:
<221> NAME/KEY: MOD_RES
<222> LOCATION: (86)..(86)
<223> OTHER INFORMATION: Gln or Arg
<220> FEATURE:
<221> NAME/KEY: MOD_RES
<222> LOCATION: (89)..(89)
<223> OTHER INFORMATION: Gln or Gly
<220> FEATURE:
```

```
<221> NAME/KEY: MOD_RES
<222> LOCATION: (91)..(91)
<223> OTHER INFORMATION: Ala or Leu
<220> FEATURE:
<221> NAME/KEY: MOD_RES
<222> LOCATION: (92)..(92)
<223> OTHER INFORMATION: His or Lys
<220> FEATURE:
<221> NAME/KEY: MOD_RES
<222> LOCATION: (94)..(94)
<223> OTHER INFORMATION: Ala or Asn
<220> FEATURE:
<221> NAME/KEY: MOD_RES
<222> LOCATION: (95)..(95)
<223> OTHER INFORMATION: Gly or Asp
<220> FEATURE:
<221> NAME/KEY: MOD_RES
<222> LOCATION: (104)..(104)
<223> OTHER INFORMATION: Phe or Met
<220> FEATURE:
<221> NAME/KEY: MOD_RES
<222> LOCATION: (105)..(105)
<223> OTHER INFORMATION: Asp or Asn
<220> FEATURE:
<221> NAME/KEY: MOD_RES
<222> LOCATION: (108)..(108)
<223> OTHER INFORMATION: Gly or Met
<220> FEATURE:
<221> NAME/KEY: MOD_RES
<222> LOCATION: (112)..(112)
<223> OTHER INFORMATION: Gly or Phe
<220> FEATURE:
<221> NAME/KEY: MOD_RES
<222> LOCATION: (115)..(115)
<223> OTHER INFORMATION: Trp or Ala
<220> FEATURE:
<221> NAME/KEY: MOD_RES
<222> LOCATION: (117)..(117)
<223> OTHER INFORMATION: Asp or Gln
<220> FEATURE:
<221> NAME/KEY: MOD_RES
<222> LOCATION: (120)..(120)
<223> OTHER INFORMATION: Glu or Gln
<220> FEATURE:
<221> NAME/KEY: MOD_RES
<222> LOCATION: (125)..(125)
<223> OTHER INFORMATION: Asp or Asn
<220> FEATURE:
<221> NAME/KEY: MOD_RES
<222> LOCATION: (127)..(127)
<223> OTHER INFORMATION: Asn or Trp
<220> FEATURE:
<221> NAME/KEY: MOD_RES
<222> LOCATION: (133)..(133)
<223> OTHER INFORMATION: Thr or Ala
<220> FEATURE:
<221> NAME/KEY: MOD_RES
<222> LOCATION: (135)..(135)
<223> OTHER INFORMATION: Gln or Thr
<220> FEATURE:
<221> NAME/KEY: MOD_RES
<222> LOCATION: (137)..(137)
<223> OTHER INFORMATION: Gln or Asp
<220> FEATURE:
<221> NAME/KEY: MOD_RES
<222> LOCATION: (141)..(141)
<223> OTHER INFORMATION: Lys or Gly
<220> FEATURE:
<221> NAME/KEY: MOD_RES
<222> LOCATION: (145)..(145)
<223> OTHER INFORMATION: Pro or Ser
<220> FEATURE:
<221> NAME/KEY: MOD_RES
<222> LOCATION: (148)..(148)
<223> OTHER INFORMATION: Gly or Asn
<220> FEATURE:
<221> NAME/KEY: MOD_RES
<222> LOCATION: (150)..(150)
<223> OTHER INFORMATION: Thr or Ala
```

```
<220> FEATURE:
<221> NAME/KEY: MOD_RES
<222> LOCATION: (153)..(153)
<223> OTHER INFORMATION: Ser or Asp
<220> FEATURE:
<221> NAME/KEY: MOD_RES
<222> LOCATION: (162)..(162)
<223> OTHER INFORMATION: Asp or Asn
<220> FEATURE:
<221> NAME/KEY: MOD_RES
<222> LOCATION: (168)..(168)
<223> OTHER INFORMATION: Glu or Gln
<220> FEATURE:
<221> NAME/KEY: MOD_RES
<222> LOCATION: (169)..(169)
<223> OTHER INFORMATION: Ser or Arg
<220> FEATURE:
<221> NAME/KEY: MOD_RES
<222> LOCATION: (170)..(170)
<223> OTHER INFORMATION: Arg or Tyr
<220> FEATURE:
<221> NAME/KEY: MOD_RES
<222> LOCATION: (171)..(171)
<223> OTHER INFORMATION: Lys or Gln
<220> FEATURE:
<221> NAME/KEY: MOD_RES
<222> LOCATION: (172)..(172)
<223> OTHER INFORMATION: Leu or Glu
<220> FEATURE:
<221> NAME/KEY: MOD_RES
<222> LOCATION: (173)..(173)
<223> OTHER INFORMATION: Ser or Asn
<220> FEATURE:
<221> NAME/KEY: MOD_RES
<222> LOCATION: (174)..(174)
<223> OTHER INFORMATION: Arg or His
<220> FEATURE:
<221> NAME/KEY: MOD_RES
<222> LOCATION: (179)..(179)
<223> OTHER INFORMATION: Arg or Ala
<220> FEATURE:
<221> NAME/KEY: MOD_RES
<222> LOCATION: (180)..(180)
<223> OTHER INFORMATION: Gly or Asn
<220> FEATURE:
<221> NAME/KEY: MOD_RES
<222> LOCATION: (181)..(181)
<223> OTHER INFORMATION: Ile or Thr
<220> FEATURE:
<221> NAME/KEY: MOD_RES
<222> LOCATION: (182)..(182)
<223> OTHER INFORMATION: Gly or Asn
<220> FEATURE:
<221> NAME/KEY: MOD_RES
<222> LOCATION: (183)..(183)
<223> OTHER INFORMATION: Lys or not present
<220> FEATURE:
<221> NAME/KEY: MOD_RES
<222> LOCATION: (184)..(184)
<223> OTHER INFORMATION: Ala or not present
<220> FEATURE:
<221> NAME/KEY: MOD_RES
<222> LOCATION: (186)..(186)
<223> OTHER INFORMATION: Asp or Asn
<220> FEATURE:
<221> NAME/KEY: MOD_RES
<222> LOCATION: (188)..(188)
<223> OTHER INFORMATION: Glu or Arg
<220> FEATURE:
<221> NAME/KEY: MOD_RES
<222> LOCATION: (191)..(191)
<223> OTHER INFORMATION: Thr or Glu
<220> FEATURE:
<221> NAME/KEY: MOD_RES
<222> LOCATION: (201)..(201)
<223> OTHER INFORMATION: Tyr or Gly
<220> FEATURE:
<221> NAME/KEY: MOD_RES
<222> LOCATION: (203)..(203)
```

```
<223> OTHER INFORMATION: Asp or Asn
<220> FEATURE:
<221> NAME/KEY: MOD_RES
<222> LOCATION: (206)..(206)
<223> OTHER INFORMATION: Met or Phe
<220> FEATURE:
<221> NAME/KEY: MOD_RES
<222> LOCATION: (207)..(207)
<223> OTHER INFORMATION: Asp or Ser
<220> FEATURE:
<221> NAME/KEY: MOD_RES
<222> LOCATION: (212)..(212)
<223> OTHER INFORMATION: Val or Gln
<220> FEATURE:
<221> NAME/KEY: MOD_RES
<222> LOCATION: (213)..(213)
<223> OTHER INFORMATION: Thr or Asp
<220> FEATURE:
<221> NAME/KEY: MOD_RES
<222> LOCATION: (217)..(217)
<223> OTHER INFORMATION: Asn or Asp
<220> FEATURE:
<221> NAME/KEY: MOD_RES
<222> LOCATION: (220)..(220)
<223> OTHER INFORMATION: Lys or Ser
<220> FEATURE:
<221> NAME/KEY: MOD_RES
<222> LOCATION: (223)..(223)
<223> OTHER INFORMATION: Val or Thr
<220> FEATURE:
<221> NAME/KEY: MOD_RES
<222> LOCATION: (224)..(224)
<223> OTHER INFORMATION: Asn or Asp
<220> FEATURE:
<221> NAME/KEY: MOD_RES
<222> LOCATION: (225)..(225)
<223> OTHER INFORMATION: Thr or Glu
<220> FEATURE:
<221> NAME/KEY: MOD_RES
<222> LOCATION: (226)..(226)
<223> OTHER INFORMATION: Thr or Leu
<220> FEATURE:
<221> NAME/KEY: MOD_RES
<222> LOCATION: (227)..(227)
<223> OTHER INFORMATION: Asn or Asp
<220> FEATURE:
<221> NAME/KEY: MOD_RES
<222> LOCATION: (240)..(240)
<223> OTHER INFORMATION: Lys or Pro
<220> FEATURE:
<221> NAME/KEY: MOD_RES
<222> LOCATION: (242)..(242)
<223> OTHER INFORMATION: Ser or Trp
<220> FEATURE:
<221> NAME/KEY: MOD_RES
<222> LOCATION: (244)..(244)
<223> OTHER INFORMATION: Phe or Thr
<220> FEATURE:
<221> NAME/KEY: MOD_RES
<222> LOCATION: (245)..(245)
<223> OTHER INFORMATION: Pro or Ser
<220> FEATURE:
<221> NAME/KEY: MOD_RES
<222> LOCATION: (249)..(249)
<223> OTHER INFORMATION: Ser or Arg
<220> FEATURE:
<221> NAME/KEY: MOD_RES
<222> LOCATION: (251)..(251)
<223> OTHER INFORMATION: Val or Gln
<220> FEATURE:
<221> NAME/KEY: MOD_RES
<222> LOCATION: (253)..(253)
<223> OTHER INFORMATION: Ser or Asn
<220> FEATURE:
<221> NAME/KEY: MOD_RES
<222> LOCATION: (254)..(254)
<223> OTHER INFORMATION: Gln or Glu
<220> FEATURE:
<221> NAME/KEY: MOD_RES
```

```
<222> LOCATION: (255)..(255)
<223> OTHER INFORMATION: Thr or Ala
<220> FEATURE:
<221> NAME/KEY: MOD_RES
<222> LOCATION: (256)..(256)
<223> OTHER INFORMATION: Gly or Asp
<220> FEATURE:
<221> NAME/KEY: MOD_RES
<222> LOCATION: (257)..(257)
<223> OTHER INFORMATION: Lys or Gln
<220> FEATURE:
<221> NAME/KEY: MOD_RES
<222> LOCATION: (258)..(258)
<223> OTHER INFORMATION: Pro or Asp
<220> FEATURE:
<221> NAME/KEY: MOD_RES
<222> LOCATION: (261)..(261)
<223> OTHER INFORMATION: Thr or Val
<220> FEATURE:
<221> NAME/KEY: MOD_RES
<222> LOCATION: (267)..(267)
<223> OTHER INFORMATION: Ser or Lys
<220> FEATURE:
<221> NAME/KEY: MOD_RES
<222> LOCATION: (268)..(268)
<223> OTHER INFORMATION: Tyr or Asp
<220> FEATURE:
<221> NAME/KEY: MOD_RES
<222> LOCATION: (271)..(271)
<223> OTHER INFORMATION: Asn or Gly
<220> FEATURE:
<221> NAME/KEY: MOD_RES
<222> LOCATION: (272)..(272)
<223> OTHER INFORMATION: Lys or Ala
<220> FEATURE:
<221> NAME/KEY: MOD_RES
<222> LOCATION: (274)..(274)
<223> OTHER INFORMATION: His or Glu
<220> FEATURE:
<221> NAME/KEY: MOD_RES
<222> LOCATION: (275)..(275)
<223> OTHER INFORMATION: Asn or Phe
<220> FEATURE:
<221> NAME/KEY: MOD_RES
<222> LOCATION: (278)..(278)
<223> OTHER INFORMATION: Thr or Asp
<220> FEATURE:
<221> NAME/KEY: MOD_RES
<222> LOCATION: (279)..(279)
<223> OTHER INFORMATION: Lys or Glu
<220> FEATURE:
<221> NAME/KEY: MOD_RES
<222> LOCATION: (280)..(280)
<223> OTHER INFORMATION: Thr or Met
<220> FEATURE:
<221> NAME/KEY: MOD_RES
<222> LOCATION: (282)..(282)
<223> OTHER INFORMATION: Gly or Trp
<220> FEATURE:
<221> NAME/KEY: MOD_RES
<222> LOCATION: (283)..(283)
<223> OTHER INFORMATION: Thr or Glu
<220> FEATURE:
<221> NAME/KEY: MOD_RES
<222> LOCATION: (289)..(289)
<223> OTHER INFORMATION: Ala or Val
<220> FEATURE:
<221> NAME/KEY: MOD_RES
<222> LOCATION: (292)..(292)
<223> OTHER INFORMATION: His or Asn
<220> FEATURE:
<221> NAME/KEY: MOD_RES
<222> LOCATION: (293)..(293)
<223> OTHER INFORMATION: Asn or Tyr
<220> FEATURE:
<221> NAME/KEY: MOD_RES
<222> LOCATION: (294)..(294)
<223> OTHER INFORMATION: Lys or Asn
<220> FEATURE:
```

```
<221> NAME/KEY: MOD_RES
<222> LOCATION: (297)..(297)
<223> OTHER INFORMATION: Thr or Arg
<220> FEATURE:
<221> NAME/KEY: MOD_RES
<222> LOCATION: (300)..(300)
<223> OTHER INFORMATION: Lys or Gln
<220> FEATURE:
<221> NAME/KEY: MOD_RES
<222> LOCATION: (301)..(301)
<223> OTHER INFORMATION: Ser or Gln
<220> FEATURE:
<221> NAME/KEY: MOD_RES
<222> LOCATION: (309)..(309)
<223> OTHER INFORMATION: Thr or Asn
<220> FEATURE:
<221> NAME/KEY: MOD_RES
<222> LOCATION: (312)..(312)
<223> OTHER INFORMATION: Thr or Arg
<220> FEATURE:
<221> NAME/KEY: MOD_RES
<222> LOCATION: (313)..(313)
<223> OTHER INFORMATION: Asn or Gly
<220> FEATURE:
<221> NAME/KEY: MOD_RES
<222> LOCATION: (317)..(317)
<223> OTHER INFORMATION: Lys or Glu
<220> FEATURE:
<221> NAME/KEY: MOD_RES
<222> LOCATION: (318)..(318)
<223> OTHER INFORMATION: Asp or Ala
<220> FEATURE:
<221> NAME/KEY: MOD_RES
<222> LOCATION: (319)..(319)
<223> OTHER INFORMATION: Gln or His
<220> FEATURE:
<221> NAME/KEY: MOD_RES
<222> LOCATION: (321)..(321)
<223> OTHER INFORMATION: Thr or Met
<220> FEATURE:
<221> NAME/KEY: MOD_RES
<222> LOCATION: (322)..(322)
<223> OTHER INFORMATION: Leu or His
<220> FEATURE:
<221> NAME/KEY: MOD_RES
<222> LOCATION: (333)..(333)
<223> OTHER INFORMATION: Glu or Gln
<220> FEATURE:
<221> NAME/KEY: MOD_RES
<222> LOCATION: (336)..(336)
<223> OTHER INFORMATION: Gln or Glu
<220> FEATURE:
<221> NAME/KEY: MOD_RES
<222> LOCATION: (339)..(339)
<223> OTHER INFORMATION: Gln or Glu
<220> FEATURE:
<221> NAME/KEY: MOD_RES
<222> LOCATION: (343)..(343)
<223> OTHER INFORMATION: Asp or Ala
<220> FEATURE:
<221> NAME/KEY: MOD_RES
<222> LOCATION: (344)..(344)
<223> OTHER INFORMATION: Pro or Asp
<220> FEATURE:
<221> NAME/KEY: MOD_RES
<222> LOCATION: (353)..(353)
<223> OTHER INFORMATION: Phe or Thr
<220> FEATURE:
<221> NAME/KEY: MOD_RES
<222> LOCATION: (358)..(358)
<223> OTHER INFORMATION: Gln or Glu
<220> FEATURE:
<221> NAME/KEY: MOD_RES
<222> LOCATION: (359)..(359)
<223> OTHER INFORMATION: Glu or Gly
<220> FEATURE:
<221> NAME/KEY: MOD_RES
<222> LOCATION: (363)..(363)
<223> OTHER INFORMATION: Cys or Asn
```

```
<220> FEATURE:
<221> NAME/KEY: MOD_RES
<222> LOCATION: (375)..(375)
<223> OTHER INFORMATION: Tyr or Asp
<220> FEATURE:
<221> NAME/KEY: MOD_RES
<222> LOCATION: (378)..(378)
<223> OTHER INFORMATION: Pro or Ser
<220> FEATURE:
<221> NAME/KEY: MOD_RES
<222> LOCATION: (380)..(380)
<223> OTHER INFORMATION: Leu or Lys
<220> FEATURE:
<221> NAME/KEY: MOD_RES
<222> LOCATION: (382)..(382)
<223> OTHER INFORMATION: Ser or Asp
<220> FEATURE:
<221> NAME/KEY: MOD_RES
<222> LOCATION: (383)..(383)
<223> OTHER INFORMATION: Lys or Met
<220> FEATURE:
<221> NAME/KEY: MOD_RES
<222> LOCATION: (386)..(386)
<223> OTHER INFORMATION: Pro or Glu
<220> FEATURE:
<221> NAME/KEY: MOD_RES
<222> LOCATION: (389)..(389)
<223> OTHER INFORMATION: Ile or Asp
<220> FEATURE:
<221> NAME/KEY: MOD_RES
<222> LOCATION: (392)..(392)
<223> OTHER INFORMATION: Arg or Gln
<220> FEATURE:
<221> NAME/KEY: MOD_RES
<222> LOCATION: (393)..(393)
<223> OTHER INFORMATION: Asp or Asn
<220> FEATURE:
<221> NAME/KEY: MOD_RES
<222> LOCATION: (403)..(403)
<223> OTHER INFORMATION: Leu or Phe
<220> FEATURE:
<221> NAME/KEY: MOD_RES
<222> LOCATION: (406)..(406)
<223> OTHER INFORMATION: Ser or Trp
<220> FEATURE:
<221> NAME/KEY: MOD_RES
<222> LOCATION: (416)..(416)
<223> OTHER INFORMATION: Val or Ser
<220> FEATURE:
<221> NAME/KEY: MOD_RES
<222> LOCATION: (418)..(418)
<223> OTHER INFORMATION: Glu or Ser
<220> FEATURE:
<221> NAME/KEY: MOD_RES
<222> LOCATION: (421)..(421)
<223> OTHER INFORMATION: Gly or Asn
<220> FEATURE:
<221> NAME/KEY: MOD_RES
<222> LOCATION: (426)..(426)
<223> OTHER INFORMATION: Ala or Thr
<220> FEATURE:
<221> NAME/KEY: MOD_RES
<222> LOCATION: (430)..(430)
<223> OTHER INFORMATION: Asp or Asn
<220> FEATURE:
<221> NAME/KEY: MOD_RES
<222> LOCATION: (444)..(444)
<223> OTHER INFORMATION: His or Asn
<220> FEATURE:
<221> NAME/KEY: MOD_RES
<222> LOCATION: (447)..(447)
<223> OTHER INFORMATION: Lys or Gln
<220> FEATURE:
<221> NAME/KEY: MOD_RES
<222> LOCATION: (448)..(448)
<223> OTHER INFORMATION: Val or Thr
<220> FEATURE:
<221> NAME/KEY: MOD_RES
<222> LOCATION: (450)..(450)
```

```
<223> OTHER INFORMATION: Tyr or Thr
<220> FEATURE:
<221> NAME/KEY: MOD_RES
<222> LOCATION: (456)..(456)
<223> OTHER INFORMATION: Arg or Asn
<220> FEATURE:
<221> NAME/KEY: MOD_RES
<222> LOCATION: (457)..(457)
<223> OTHER INFORMATION: Ser or Gly
<220> FEATURE:
<221> NAME/KEY: MOD_RES
<222> LOCATION: (458)..(458)
<223> OTHER INFORMATION: Asp or Ala
<220> FEATURE:
<221> NAME/KEY: MOD_RES
<222> LOCATION: (464)..(464)
<223> OTHER INFORMATION: Ser or Gly
<220> FEATURE:
<221> NAME/KEY: MOD_RES
<222> LOCATION: (471)..(471)
<223> OTHER INFORMATION: Lys or Phe
<220> FEATURE:
<221> NAME/KEY: MOD_RES
<222> LOCATION: (472)..(472)
<223> OTHER INFORMATION: Val or Thr
<220> FEATURE:
<221> NAME/KEY: MOD_RES
<222> LOCATION: (482)..(482)
<223> OTHER INFORMATION: Pro or Asn
<220> FEATURE:
<221> NAME/KEY: MOD_RES
<222> LOCATION: (483)..(483)
<223> OTHER INFORMATION: Arg or Gln
<220> FEATURE:
<221> NAME/KEY: MOD_RES
<222> LOCATION: (484)..(484)
<223> OTHER INFORMATION: Lys or not present
<220> FEATURE:
<221> NAME/KEY: MOD_RES
<222> LOCATION: (485)..(486)
<223> OTHER INFORMATION: Thr or not present
<220> FEATURE:
<221> NAME/KEY: MOD_RES
<222> LOCATION: (487)..(487)
<223> OTHER INFORMATION: Val or not present
<220> FEATURE:
<221> NAME/KEY: MOD_RES
<222> LOCATION: (488)..(488)
<223> OTHER INFORMATION: Ser or not present
<220> FEATURE:
<221> NAME/KEY: MOD_RES
<222> LOCATION: (489)..(489)
<223> OTHER INFORMATION: Thr or not present
<220> FEATURE:
<221> NAME/KEY: MOD_RES
<222> LOCATION: (490)..(490)
<223> OTHER INFORMATION: Ile or not present
<220> FEATURE:
<221> NAME/KEY: MOD_RES
<222> LOCATION: (491)..(491)
<223> OTHER INFORMATION: Ala or not present
<220> FEATURE:
<221> NAME/KEY: MOD_RES
<222> LOCATION: (492)..(492)
<223> OTHER INFORMATION: Arg or not present
<220> FEATURE:
<221> NAME/KEY: MOD_RES
<222> LOCATION: (493)..(493)
<223> OTHER INFORMATION: Pro or not present
<220> FEATURE:
<221> NAME/KEY: MOD_RES
<222> LOCATION: (494)..(494)
<223> OTHER INFORMATION: Ile or not present
<220> FEATURE:
<221> NAME/KEY: MOD_RES
<222> LOCATION: (495)..(496)
<223> OTHER INFORMATION: Thr or not present
<220> FEATURE:
<221> NAME/KEY: MOD_RES
```

```
<222> LOCATION: (497)..(497)
<223> OTHER INFORMATION: Arg or not present
<220> FEATURE:
<221> NAME/KEY: MOD_RES
<222> LOCATION: (498)..(498)
<223> OTHER INFORMATION: Pro or not present
<220> FEATURE:
<221> NAME/KEY: MOD_RES
<222> LOCATION: (499)..(499)
<223> OTHER INFORMATION: Trp or not present
<220> FEATURE:
<221> NAME/KEY: MOD_RES
<222> LOCATION: (500)..(500)
<223> OTHER INFORMATION: Thr or not present
<220> FEATURE:
<221> NAME/KEY: MOD_RES
<222> LOCATION: (501)..(501)
<223> OTHER INFORMATION: Gly or not present
<220> FEATURE:
<221> NAME/KEY: MOD_RES
<222> LOCATION: (502)..(502)
<223> OTHER INFORMATION: Glu or not present
<220> FEATURE:
<221> NAME/KEY: MOD_RES
<222> LOCATION: (503)..(503)
<223> OTHER INFORMATION: Phe or not present
<220> FEATURE:
<221> NAME/KEY: MOD_RES
<222> LOCATION: (504)..(504)
<223> OTHER INFORMATION: Val or not present
<220> FEATURE:
<221> NAME/KEY: MOD_RES
<222> LOCATION: (505)..(505)
<223> OTHER INFORMATION: Arg or not present
<220> FEATURE:
<221> NAME/KEY: MOD_RES
<222> LOCATION: (506)..(506)
<223> OTHER INFORMATION: Trp or not present
<220> FEATURE:
<221> NAME/KEY: MOD_RES
<222> LOCATION: (507)..(507)
<223> OTHER INFORMATION: Thr or not present
<220> FEATURE:
<221> NAME/KEY: MOD_RES
<222> LOCATION: (508)..(508)
<223> OTHER INFORMATION: Glu or not present
<220> FEATURE:
<221> NAME/KEY: MOD_RES
<222> LOCATION: (509)..(509)
<223> OTHER INFORMATION: Pro or not present
<220> FEATURE:
<221> NAME/KEY: MOD_RES
<222> LOCATION: (510)..(510)
<223> OTHER INFORMATION: Arg or not present
<220> FEATURE:
<221> NAME/KEY: MOD_RES
<222> LOCATION: (511)..(511)
<223> OTHER INFORMATION: Leu or not present
<220> FEATURE:
<221> NAME/KEY: MOD_RES
<222> LOCATION: (512)..(512)
<223> OTHER INFORMATION: Val or not present
<220> FEATURE:
<221> NAME/KEY: MOD_RES
<222> LOCATION: (513)..(513)
<223> OTHER INFORMATION: Ala or not present
<220> FEATURE:
<221> NAME/KEY: MOD_RES
<222> LOCATION: (514)..(514)
<223> OTHER INFORMATION: Trp or not present
<220> FEATURE:
<221> NAME/KEY: MOD_RES
<222> LOCATION: (515)..(515)
<223> OTHER INFORMATION: Pro or not present

<400> SEQUENCE: 29

Xaa Xaa Xaa Xaa Asn Gly Thr Met Met Gln Tyr Phe Glu Trp His Leu
1               5                   10                  15
```

-continued

```
Xaa Xaa Asp Gly Xaa Xaa Trp Xaa Lys Leu Xaa Xaa Asp Ala Xaa Xaa
            20                  25                  30

Leu Ser Xaa Xaa Gly Ile Thr Ala Ile Trp Ile Pro Pro Ala Tyr Lys
        35                  40                  45

Gly Xaa Ser Xaa Ala Asp Val Gly Tyr Gly Xaa Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Xaa Xaa Xaa Ala Ile Xaa Ala Xaa Xaa Ala Xaa Xaa Ile
                85                  90                  95

Asn Val Tyr Ala Asp Val Val Xaa Xaa His Lys Xaa Gly Ala Asp Xaa
            100                 105                 110

Thr Glu Xaa Val Xaa Ala Val Xaa Val Asn Pro Ser Xaa Arg Xaa Gln
        115                 120                 125

Asp Ile Ser Gly Xaa Tyr Xaa Ile Xaa Ala Trp Thr Xaa Phe Asp Phe
    130                 135                 140

Xaa Gly Arg Xaa Asn Xaa Tyr Ser Xaa Phe Lys Trp Arg Trp Phe His
145                 150                 155                 160

Phe Xaa Gly Val Asp Trp Asp Xaa Xaa Xaa Xaa Xaa Xaa Xaa Ile Phe
                165                 170                 175

Lys Phe Xaa Xaa Xaa Xaa Xaa Xaa Trp Xaa Trp Xaa Val Asp Xaa Glu
            180                 185                 190

Asn Gly Asn Tyr Asp Tyr Leu Leu Xaa Ala Xaa Ile Asp Xaa Xaa His
        195                 200                 205

Pro Glu Val Xaa Xaa Glu Leu Lys Xaa Trp Gly Xaa Trp Phe Xaa Xaa
    210                 215                 220

Xaa Xaa Xaa Ile Asp Gly Phe Arg Leu Asp Ala Ile Lys His Ile Xaa
225                 230                 235                 240

Phe Xaa Phe Xaa Xaa Asp Trp Leu Xaa His Xaa Arg Xaa Xaa Xaa Xaa
                245                 250                 255

Xaa Xaa Leu Phe Xaa Val Gly Glu Tyr Trp Xaa Xaa Asp Ile Xaa Xaa
            260                 265                 270

Leu Xaa Xaa Tyr Ile Xaa Xaa Xaa Asn Xaa Xaa Met Ser Leu Phe Asp
        275                 280                 285

Xaa Pro Leu Xaa Xaa Xaa Phe Tyr Xaa Ala Ser Xaa Xaa Gly Gly Ala
    290                 295                 300

Phe Asp Met Arg Xaa Ile Leu Xaa Xaa Ser Leu Met Xaa Xaa Xaa Pro
305                 310                 315                 320

Xaa Xaa Ala Val Thr Phe Val Asp Asn His Asp Thr Xaa Pro Gly Xaa
                325                 330                 335

Ala Leu Xaa Ser Trp Val Xaa Xaa Trp Phe Lys Pro Leu Ala Tyr Ala
            340                 345                 350

Xaa Ile Leu Thr Arg Xaa Xaa Gly Tyr Pro Xaa Val Phe Tyr Gly Asp
        355                 360                 365

Tyr Tyr Gly Ile Pro Asn Xaa Asn Ile Xaa Ala Xaa Lys Xaa Xaa Ile
    370                 375                 380

Asp Xaa Leu Leu Xaa Ala Arg Xaa Xaa Tyr Ala Tyr Gly Thr Gln His
385                 390                 395                 400

Asp Tyr Xaa Asp His Xaa Asp Ile Ile Gly Trp Thr Arg Glu Gly Xaa
                405                 410                 415

Ser Xaa Lys Pro Xaa Ser Gly Leu Ala Xaa Ile Ile Ser Xaa Gly Pro
            420                 425                 430
```

```
Gly Gly Ser Lys Trp Met Tyr Val Gly Lys Gln Xaa Ala Gly Xaa Xaa
        435                 440                 445

Phe Xaa Asp Leu Thr Gly Asn Xaa Xaa Xaa Ser Val Thr Ile Asn Xaa
    450                 455                 460

Asp Gly Trp Gly Glu Phe Xaa Xaa Asn Gly Gly Ser Val Ser Val Trp
465                 470                 475                 480

Val Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa
    515

<210> SEQ ID NO 30
<211> LENGTH: 515
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ala or not present
<220> FEATURE:
<221> NAME/KEY: MOD_RES
<222> LOCATION: (2)..(2)
<223> OTHER INFORMATION: Ala or Asp
<220> FEATURE:
<221> NAME/KEY: MOD_RES
<222> LOCATION: (3)..(3)
<223> OTHER INFORMATION: Pro or Gly
<220> FEATURE:
<221> NAME/KEY: MOD_RES
<222> LOCATION: (4)..(4)
<223> OTHER INFORMATION: Phe or Leu
<220> FEATURE:
<221> NAME/KEY: MOD_RES
<222> LOCATION: (17)..(17)
<223> OTHER INFORMATION: Pro or Glu
<220> FEATURE:
<221> NAME/KEY: MOD_RES
<222> LOCATION: (18)..(18)
<223> OTHER INFORMATION: Asp or Asn
<220> FEATURE:
<221> NAME/KEY: MOD_RES
<222> LOCATION: (21)..(21)
<223> OTHER INFORMATION: Thr or Gln
<220> FEATURE:
<221> NAME/KEY: MOD_RES
<222> LOCATION: (22)..(22)
<223> OTHER INFORMATION: Leu or His
<220> FEATURE:
<221> NAME/KEY: MOD_RES
<222> LOCATION: (24)..(24)
<223> OTHER INFORMATION: Thr or Asn
<220> FEATURE:
<221> NAME/KEY: MOD_RES
<222> LOCATION: (27)..(27)
<223> OTHER INFORMATION: Ala or His
<220> FEATURE:
<221> NAME/KEY: MOD_RES
<222> LOCATION: (28)..(28)
<223> OTHER INFORMATION: Asn or Asp
<220> FEATURE:
<221> NAME/KEY: MOD_RES
<222> LOCATION: (31)..(31)
<223> OTHER INFORMATION: Asn or Glu
<220> FEATURE:
<221> NAME/KEY: MOD_RES
<222> LOCATION: (32)..(32)
<223> OTHER INFORMATION: Asn or Ala
<220> FEATURE:
```

```
<221> NAME/KEY: MOD_RES
<222> LOCATION: (35)..(35)
<223> OTHER INFORMATION: Ser or Asn
<220> FEATURE:
<221> NAME/KEY: MOD_RES
<222> LOCATION: (36)..(36)
<223> OTHER INFORMATION: Leu or Ala
<220> FEATURE:
<221> NAME/KEY: MOD_RES
<222> LOCATION: (50)..(50)
<223> OTHER INFORMATION: Thr or Asn
<220> FEATURE:
<221> NAME/KEY: MOD_RES
<222> LOCATION: (52)..(52)
<223> OTHER INFORMATION: Arg or Gln
<220> FEATURE:
<221> NAME/KEY: MOD_RES
<222> LOCATION: (59)..(59)
<223> OTHER INFORMATION: Val or Ala
<220> FEATURE:
<221> NAME/KEY: MOD_RES
<222> LOCATION: (84)..(84)
<223> OTHER INFORMATION: Tyr or Leu
<220> FEATURE:
<221> NAME/KEY: MOD_RES
<222> LOCATION: (85)..(85)
<223> OTHER INFORMATION: Leu or Glu
<220> FEATURE:
<221> NAME/KEY: MOD_RES
<222> LOCATION: (86)..(86)
<223> OTHER INFORMATION: Gln or Arg
<220> FEATURE:
<221> NAME/KEY: MOD_RES
<222> LOCATION: (89)..(89)
<223> OTHER INFORMATION: Gln or Gly
<220> FEATURE:
<221> NAME/KEY: MOD_RES
<222> LOCATION: (91)..(91)
<223> OTHER INFORMATION: Ala or Leu
<220> FEATURE:
<221> NAME/KEY: MOD_RES
<222> LOCATION: (92)..(92)
<223> OTHER INFORMATION: His or Lys
<220> FEATURE:
<221> NAME/KEY: MOD_RES
<222> LOCATION: (94)..(94)
<223> OTHER INFORMATION: Ala or Asn
<220> FEATURE:
<221> NAME/KEY: MOD_RES
<222> LOCATION: (95)..(95)
<223> OTHER INFORMATION: Gly or Asp
<220> FEATURE:
<221> NAME/KEY: MOD_RES
<222> LOCATION: (104)..(104)
<223> OTHER INFORMATION: Phe or Met
<220> FEATURE:
<221> NAME/KEY: MOD_RES
<222> LOCATION: (105)..(105)
<223> OTHER INFORMATION: Asp or Asn
<220> FEATURE:
<221> NAME/KEY: MOD_RES
<222> LOCATION: (108)..(108)
<223> OTHER INFORMATION: Gly or Leu
<220> FEATURE:
<221> NAME/KEY: MOD_RES
<222> LOCATION: (112)..(112)
<223> OTHER INFORMATION: Gly or Phe
<220> FEATURE:
<221> NAME/KEY: MOD_RES
<222> LOCATION: (115)..(115)
<223> OTHER INFORMATION: Trp or Ala
<220> FEATURE:
<221> NAME/KEY: MOD_RES
<222> LOCATION: (117)..(117)
<223> OTHER INFORMATION: Asp or Gln
<220> FEATURE:
<221> NAME/KEY: MOD_RES
<222> LOCATION: (120)..(120)
<223> OTHER INFORMATION: Glu or Gln
```

```
<220> FEATURE:
<221> NAME/KEY: MOD_RES
<222> LOCATION: (125)..(125)
<223> OTHER INFORMATION: Asp or Asn
<220> FEATURE:
<221> NAME/KEY: MOD_RES
<222> LOCATION: (127)..(127)
<223> OTHER INFORMATION: Asn or Trp
<220> FEATURE:
<221> NAME/KEY: MOD_RES
<222> LOCATION: (133)..(133)
<223> OTHER INFORMATION: Thr or Val
<220> FEATURE:
<221> NAME/KEY: MOD_RES
<222> LOCATION: (135)..(135)
<223> OTHER INFORMATION: Gln or Thr
<220> FEATURE:
<221> NAME/KEY: MOD_RES
<222> LOCATION: (137)..(137)
<223> OTHER INFORMATION: Gln or Asp
<220> FEATURE:
<221> NAME/KEY: MOD_RES
<222> LOCATION: (141)..(141)
<223> OTHER INFORMATION: Lys or Gly
<220> FEATURE:
<221> NAME/KEY: MOD_RES
<222> LOCATION: (148)..(148)
<223> OTHER INFORMATION: Gly or Asn
<220> FEATURE:
<221> NAME/KEY: MOD_RES
<222> LOCATION: (150)..(150)
<223> OTHER INFORMATION: Thr or Ala
<220> FEATURE:
<221> NAME/KEY: MOD_RES
<222> LOCATION: (153)..(153)
<223> OTHER INFORMATION: Ser or Asp
<220> FEATURE:
<221> NAME/KEY: MOD_RES
<222> LOCATION: (162)..(162)
<223> OTHER INFORMATION: Asp or Asn
<220> FEATURE:
<221> NAME/KEY: MOD_RES
<222> LOCATION: (168)..(168)
<223> OTHER INFORMATION: Glu or Gln
<220> FEATURE:
<221> NAME/KEY: MOD_RES
<222> LOCATION: (169)..(169)
<223> OTHER INFORMATION: Ser or Arg
<220> FEATURE:
<221> NAME/KEY: MOD_RES
<222> LOCATION: (170)..(170)
<223> OTHER INFORMATION: Arg or Tyr
<220> FEATURE:
<221> NAME/KEY: MOD_RES
<222> LOCATION: (171)..(171)
<223> OTHER INFORMATION: Lys or Gln
<220> FEATURE:
<221> NAME/KEY: MOD_RES
<222> LOCATION: (172)..(172)
<223> OTHER INFORMATION: Leu or Glu
<220> FEATURE:
<221> NAME/KEY: MOD_RES
<222> LOCATION: (173)..(173)
<223> OTHER INFORMATION: Ser or Asn
<220> FEATURE:
<221> NAME/KEY: MOD_RES
<222> LOCATION: (174)..(174)
<223> OTHER INFORMATION: Arg or His
<220> FEATURE:
<221> NAME/KEY: MOD_RES
<222> LOCATION: (179)..(179)
<223> OTHER INFORMATION: Arg or Ala
<220> FEATURE:
<221> NAME/KEY: MOD_RES
<222> LOCATION: (180)..(180)
<223> OTHER INFORMATION: Gly or Asn
<220> FEATURE:
<221> NAME/KEY: MOD_RES
<222> LOCATION: (181)..(181)
```

```
<223> OTHER INFORMATION: Ile or Thr
<220> FEATURE:
<221> NAME/KEY: MOD_RES
<222> LOCATION: (182)..(182)
<223> OTHER INFORMATION: Gly or Asn
<220> FEATURE:
<221> NAME/KEY: MOD_RES
<222> LOCATION: (183)..(183)
<223> OTHER INFORMATION: Lys or not present
<220> FEATURE:
<221> NAME/KEY: MOD_RES
<222> LOCATION: (184)..(184)
<223> OTHER INFORMATION: Ala or not present
<220> FEATURE:
<221> NAME/KEY: MOD_RES
<222> LOCATION: (186)..(186)
<223> OTHER INFORMATION: Asp or Asn
<220> FEATURE:
<221> NAME/KEY: MOD_RES
<222> LOCATION: (188)..(188)
<223> OTHER INFORMATION: Glu or Arg
<220> FEATURE:
<221> NAME/KEY: MOD_RES
<222> LOCATION: (191)..(191)
<223> OTHER INFORMATION: Thr or Glu
<220> FEATURE:
<221> NAME/KEY: MOD_RES
<222> LOCATION: (201)..(201)
<223> OTHER INFORMATION: Tyr or Gly
<220> FEATURE:
<221> NAME/KEY: MOD_RES
<222> LOCATION: (203)..(203)
<223> OTHER INFORMATION: Asp or Asn
<220> FEATURE:
<221> NAME/KEY: MOD_RES
<222> LOCATION: (206)..(206)
<223> OTHER INFORMATION: Met or Phe
<220> FEATURE:
<221> NAME/KEY: MOD_RES
<222> LOCATION: (207)..(207)
<223> OTHER INFORMATION: Asp or Ser
<220> FEATURE:
<221> NAME/KEY: MOD_RES
<222> LOCATION: (212)..(212)
<223> OTHER INFORMATION: Val or Gln
<220> FEATURE:
<221> NAME/KEY: MOD_RES
<222> LOCATION: (213)..(213)
<223> OTHER INFORMATION: Thr or Glu
<220> FEATURE:
<221> NAME/KEY: MOD_RES
<222> LOCATION: (217)..(217)
<223> OTHER INFORMATION: Asn or Asp
<220> FEATURE:
<221> NAME/KEY: MOD_RES
<222> LOCATION: (220)..(220)
<223> OTHER INFORMATION: Lys or Ser
<220> FEATURE:
<221> NAME/KEY: MOD_RES
<222> LOCATION: (223)..(223)
<223> OTHER INFORMATION: Val or Thr
<220> FEATURE:
<221> NAME/KEY: MOD_RES
<222> LOCATION: (224)..(224)
<223> OTHER INFORMATION: Asn or Asp
<220> FEATURE:
<221> NAME/KEY: MOD_RES
<222> LOCATION: (225)..(225)
<223> OTHER INFORMATION: Thr or Glu
<220> FEATURE:
<221> NAME/KEY: MOD_RES
<222> LOCATION: (226)..(226)
<223> OTHER INFORMATION: Thr or Leu
<220> FEATURE:
<221> NAME/KEY: MOD_RES
<222> LOCATION: (227)..(227)
<223> OTHER INFORMATION: Asn or Asp
<220> FEATURE:
<221> NAME/KEY: MOD_RES
```

```
<222> LOCATION: (240)..(240)
<223> OTHER INFORMATION: Lys or Pro
<220> FEATURE:
<221> NAME/KEY: MOD_RES
<222> LOCATION: (242)..(242)
<223> OTHER INFORMATION: Ser or Trp
<220> FEATURE:
<221> NAME/KEY: MOD_RES
<222> LOCATION: (244)..(244)
<223> OTHER INFORMATION: Phe or Thr
<220> FEATURE:
<221> NAME/KEY: MOD_RES
<222> LOCATION: (245)..(245)
<223> OTHER INFORMATION: Pro or Ser
<220> FEATURE:
<221> NAME/KEY: MOD_RES
<222> LOCATION: (249)..(249)
<223> OTHER INFORMATION: Ser or Arg
<220> FEATURE:
<221> NAME/KEY: MOD_RES
<222> LOCATION: (251)..(251)
<223> OTHER INFORMATION: Val or Gln
<220> FEATURE:
<221> NAME/KEY: MOD_RES
<222> LOCATION: (254)..(254)
<223> OTHER INFORMATION: Gln or Glu
<220> FEATURE:
<221> NAME/KEY: MOD_RES
<222> LOCATION: (255)..(255)
<223> OTHER INFORMATION: Thr or Ala
<220> FEATURE:
<221> NAME/KEY: MOD_RES
<222> LOCATION: (256)..(256)
<223> OTHER INFORMATION: Gly or Asp
<220> FEATURE:
<221> NAME/KEY: MOD_RES
<222> LOCATION: (257)..(257)
<223> OTHER INFORMATION: Lys or Gln
<220> FEATURE:
<221> NAME/KEY: MOD_RES
<222> LOCATION: (258)..(258)
<223> OTHER INFORMATION: Pro or Asp
<220> FEATURE:
<221> NAME/KEY: MOD_RES
<222> LOCATION: (261)..(261)
<223> OTHER INFORMATION: Thr or Val
<220> FEATURE:
<221> NAME/KEY: MOD_RES
<222> LOCATION: (267)..(267)
<223> OTHER INFORMATION: Ser or Lys
<220> FEATURE:
<221> NAME/KEY: MOD_RES
<222> LOCATION: (268)..(268)
<223> OTHER INFORMATION: Tyr or Asp
<220> FEATURE:
<221> NAME/KEY: MOD_RES
<222> LOCATION: (271)..(271)
<223> OTHER INFORMATION: Asn or Gly
<220> FEATURE:
<221> NAME/KEY: MOD_RES
<222> LOCATION: (272)..(272)
<223> OTHER INFORMATION: Lys or Ala
<220> FEATURE:
<221> NAME/KEY: MOD_RES
<222> LOCATION: (274)..(274)
<223> OTHER INFORMATION: His or Glu
<220> FEATURE:
<221> NAME/KEY: MOD_RES
<222> LOCATION: (275)..(275)
<223> OTHER INFORMATION: Asn or Phe
<220> FEATURE:
<221> NAME/KEY: MOD_RES
<222> LOCATION: (278)..(278)
<223> OTHER INFORMATION: Thr or Asp
<220> FEATURE:
<221> NAME/KEY: MOD_RES
<222> LOCATION: (279)..(279)
<223> OTHER INFORMATION: Lys or Glu
<220> FEATURE:
```

```
<221> NAME/KEY: MOD_RES
<222> LOCATION: (280)..(280)
<223> OTHER INFORMATION: Thr or Met
<220> FEATURE:
<221> NAME/KEY: MOD_RES
<222> LOCATION: (282)..(282)
<223> OTHER INFORMATION: Gly or Trp
<220> FEATURE:
<221> NAME/KEY: MOD_RES
<222> LOCATION: (283)..(283)
<223> OTHER INFORMATION: Thr or Glu
<220> FEATURE:
<221> NAME/KEY: MOD_RES
<222> LOCATION: (289)..(289)
<223> OTHER INFORMATION: Ala or Val
<220> FEATURE:
<221> NAME/KEY: MOD_RES
<222> LOCATION: (292)..(292)
<223> OTHER INFORMATION: His or Asn
<220> FEATURE:
<221> NAME/KEY: MOD_RES
<222> LOCATION: (293)..(293)
<223> OTHER INFORMATION: Asn or Tyr
<220> FEATURE:
<221> NAME/KEY: MOD_RES
<222> LOCATION: (294)..(294)
<223> OTHER INFORMATION: Lys or Asn
<220> FEATURE:
<221> NAME/KEY: MOD_RES
<222> LOCATION: (297)..(297)
<223> OTHER INFORMATION: Thr or Arg
<220> FEATURE:
<221> NAME/KEY: MOD_RES
<222> LOCATION: (301)..(301)
<223> OTHER INFORMATION: Ser or Gln
<220> FEATURE:
<221> NAME/KEY: MOD_RES
<222> LOCATION: (309)..(309)
<223> OTHER INFORMATION: Thr or Asn
<220> FEATURE:
<221> NAME/KEY: MOD_RES
<222> LOCATION: (312)..(312)
<223> OTHER INFORMATION: Thr or Arg
<220> FEATURE:
<221> NAME/KEY: MOD_RES
<222> LOCATION: (313)..(313)
<223> OTHER INFORMATION: Asn or Gly
<220> FEATURE:
<221> NAME/KEY: MOD_RES
<222> LOCATION: (317)..(317)
<223> OTHER INFORMATION: Lys or Glu
<220> FEATURE:
<221> NAME/KEY: MOD_RES
<222> LOCATION: (318)..(318)
<223> OTHER INFORMATION: Asp or Ala
<220> FEATURE:
<221> NAME/KEY: MOD_RES
<222> LOCATION: (319)..(319)
<223> OTHER INFORMATION: Gln or His
<220> FEATURE:
<221> NAME/KEY: MOD_RES
<222> LOCATION: (321)..(321)
<223> OTHER INFORMATION: Thr or Ile
<220> FEATURE:
<221> NAME/KEY: MOD_RES
<222> LOCATION: (322)..(322)
<223> OTHER INFORMATION: Leu or His
<220> FEATURE:
<221> NAME/KEY: MOD_RES
<222> LOCATION: (333)..(333)
<223> OTHER INFORMATION: Glu or Gln
<220> FEATURE:
<221> NAME/KEY: MOD_RES
<222> LOCATION: (336)..(336)
<223> OTHER INFORMATION: Gln or Glu
<220> FEATURE:
<221> NAME/KEY: MOD_RES
<222> LOCATION: (339)..(339)
<223> OTHER INFORMATION: Gln or Glu
```

```
<220> FEATURE:
<221> NAME/KEY: MOD_RES
<222> LOCATION: (343)..(343)
<223> OTHER INFORMATION: Asp or Ala
<220> FEATURE:
<221> NAME/KEY: MOD_RES
<222> LOCATION: (344)..(344)
<223> OTHER INFORMATION: Pro or Asp
<220> FEATURE:
<221> NAME/KEY: MOD_RES
<222> LOCATION: (353)..(353)
<223> OTHER INFORMATION: Phe or Thr
<220> FEATURE:
<221> NAME/KEY: MOD_RES
<222> LOCATION: (358)..(358)
<223> OTHER INFORMATION: Gln or Glu
<220> FEATURE:
<221> NAME/KEY: MOD_RES
<222> LOCATION: (359)..(359)
<223> OTHER INFORMATION: Glu or Gly
<220> FEATURE:
<221> NAME/KEY: MOD_RES
<222> LOCATION: (363)..(363)
<223> OTHER INFORMATION: Cys or Asn
<220> FEATURE:
<221> NAME/KEY: MOD_RES
<222> LOCATION: (375)..(375)
<223> OTHER INFORMATION: Tyr or Asp
<220> FEATURE:
<221> NAME/KEY: MOD_RES
<222> LOCATION: (378)..(378)
<223> OTHER INFORMATION: Pro or Ser
<220> FEATURE:
<221> NAME/KEY: MOD_RES
<222> LOCATION: (380)..(380)
<223> OTHER INFORMATION: Leu or Lys
<220> FEATURE:
<221> NAME/KEY: MOD_RES
<222> LOCATION: (382)..(382)
<223> OTHER INFORMATION: Ser or Asp
<220> FEATURE:
<221> NAME/KEY: MOD_RES
<222> LOCATION: (383)..(383)
<223> OTHER INFORMATION: Lys or Met
<220> FEATURE:
<221> NAME/KEY: MOD_RES
<222> LOCATION: (386)..(386)
<223> OTHER INFORMATION: Pro or Glu
<220> FEATURE:
<221> NAME/KEY: MOD_RES
<222> LOCATION: (389)..(389)
<223> OTHER INFORMATION: Ile or Asp
<220> FEATURE:
<221> NAME/KEY: MOD_RES
<222> LOCATION: (392)..(392)
<223> OTHER INFORMATION: Arg or Gln
<220> FEATURE:
<221> NAME/KEY: MOD_RES
<222> LOCATION: (393)..(393)
<223> OTHER INFORMATION: Asp or Asn
<220> FEATURE:
<221> NAME/KEY: MOD_RES
<222> LOCATION: (403)..(403)
<223> OTHER INFORMATION: Leu or Phe
<220> FEATURE:
<221> NAME/KEY: MOD_RES
<222> LOCATION: (406)..(406)
<223> OTHER INFORMATION: Ser or Trp
<220> FEATURE:
<221> NAME/KEY: MOD_RES
<222> LOCATION: (416)..(416)
<223> OTHER INFORMATION: Val or Thr
<220> FEATURE:
<221> NAME/KEY: MOD_RES
<222> LOCATION: (418)..(418)
<223> OTHER INFORMATION: Glu or Ser
<220> FEATURE:
<221> NAME/KEY: MOD_RES
<222> LOCATION: (421)..(421)
```

```
<223> OTHER INFORMATION: Gly or Asn
<220> FEATURE:
<221> NAME/KEY: MOD_RES
<222> LOCATION: (426)..(426)
<223> OTHER INFORMATION: Ala or Thr
<220> FEATURE:
<221> NAME/KEY: MOD_RES
<222> LOCATION: (430)..(430)
<223> OTHER INFORMATION: Asp or Asn
<220> FEATURE:
<221> NAME/KEY: MOD_RES
<222> LOCATION: (442)..(442)
<223> OTHER INFORMATION: Lys or Gln
<220> FEATURE:
<221> NAME/KEY: MOD_RES
<222> LOCATION: (447)..(447)
<223> OTHER INFORMATION: Lys or Gln
<220> FEATURE:
<221> NAME/KEY: MOD_RES
<222> LOCATION: (448)..(448)
<223> OTHER INFORMATION: Val or Thr
<220> FEATURE:
<221> NAME/KEY: MOD_RES
<222> LOCATION: (450)..(450)
<223> OTHER INFORMATION: Tyr or Thr
<220> FEATURE:
<221> NAME/KEY: MOD_RES
<222> LOCATION: (456)..(456)
<223> OTHER INFORMATION: Arg or His
<220> FEATURE:
<221> NAME/KEY: MOD_RES
<222> LOCATION: (458)..(458)
<223> OTHER INFORMATION: Asp or Ala
<220> FEATURE:
<221> NAME/KEY: MOD_RES
<222> LOCATION: (464)..(464)
<223> OTHER INFORMATION: Ser or Gly
<220> FEATURE:
<221> NAME/KEY: MOD_RES
<222> LOCATION: (471)..(471)
<223> OTHER INFORMATION: Lys or Phe
<220> FEATURE:
<221> NAME/KEY: MOD_RES
<222> LOCATION: (472)..(472)
<223> OTHER INFORMATION: Val or Thr
<220> FEATURE:
<221> NAME/KEY: MOD_RES
<222> LOCATION: (482)..(482)
<223> OTHER INFORMATION: Pro or Asn
<220> FEATURE:
<221> NAME/KEY: MOD_RES
<222> LOCATION: (483)..(483)
<223> OTHER INFORMATION: Arg or Gln
<220> FEATURE:
<221> NAME/KEY: MOD_RES
<222> LOCATION: (484)..(484)
<223> OTHER INFORMATION: Lys or not present
<220> FEATURE:
<221> NAME/KEY: MOD_RES
<222> LOCATION: (485)..(486)
<223> OTHER INFORMATION: Thr or not present
<220> FEATURE:
<221> NAME/KEY: MOD_RES
<222> LOCATION: (487)..(487)
<223> OTHER INFORMATION: Val or not present
<220> FEATURE:
<221> NAME/KEY: MOD_RES
<222> LOCATION: (488)..(488)
<223> OTHER INFORMATION: Ser or not present
<220> FEATURE:
<221> NAME/KEY: MOD_RES
<222> LOCATION: (489)..(489)
<223> OTHER INFORMATION: Thr or not present
<220> FEATURE:
<221> NAME/KEY: MOD_RES
<222> LOCATION: (490)..(490)
<223> OTHER INFORMATION: Ile or not present
<220> FEATURE:
<221> NAME/KEY: MOD_RES
```

```
<222> LOCATION: (491)..(491)
<223> OTHER INFORMATION: Ala or not present
<220> FEATURE:
<221> NAME/KEY: MOD_RES
<222> LOCATION: (492)..(492)
<223> OTHER INFORMATION: Arg or not present
<220> FEATURE:
<221> NAME/KEY: MOD_RES
<222> LOCATION: (493)..(493)
<223> OTHER INFORMATION: Pro or not present
<220> FEATURE:
<221> NAME/KEY: MOD_RES
<222> LOCATION: (494)..(494)
<223> OTHER INFORMATION: Ile or not present
<220> FEATURE:
<221> NAME/KEY: MOD_RES
<222> LOCATION: (495)..(496)
<223> OTHER INFORMATION: Thr or not present
<220> FEATURE:
<221> NAME/KEY: MOD_RES
<222> LOCATION: (497)..(497)
<223> OTHER INFORMATION: Arg or not present
<220> FEATURE:
<221> NAME/KEY: MOD_RES
<222> LOCATION: (498)..(498)
<223> OTHER INFORMATION: Pro or not present
<220> FEATURE:
<221> NAME/KEY: MOD_RES
<222> LOCATION: (499)..(499)
<223> OTHER INFORMATION: Trp or not present
<220> FEATURE:
<221> NAME/KEY: MOD_RES
<222> LOCATION: (500)..(500)
<223> OTHER INFORMATION: Thr or not present
<220> FEATURE:
<221> NAME/KEY: MOD_RES
<222> LOCATION: (501)..(501)
<223> OTHER INFORMATION: Gly or not present
<220> FEATURE:
<221> NAME/KEY: MOD_RES
<222> LOCATION: (502)..(502)
<223> OTHER INFORMATION: Glu or not present
<220> FEATURE:
<221> NAME/KEY: MOD_RES
<222> LOCATION: (503)..(503)
<223> OTHER INFORMATION: Phe or not present
<220> FEATURE:
<221> NAME/KEY: MOD_RES
<222> LOCATION: (504)..(504)
<223> OTHER INFORMATION: Val or not present
<220> FEATURE:
<221> NAME/KEY: MOD_RES
<222> LOCATION: (505)..(505)
<223> OTHER INFORMATION: Arg or not present
<220> FEATURE:
<221> NAME/KEY: MOD_RES
<222> LOCATION: (506)..(506)
<223> OTHER INFORMATION: Trp or not present
<220> FEATURE:
<221> NAME/KEY: MOD_RES
<222> LOCATION: (507)..(507)
<223> OTHER INFORMATION: Thr or not present
<220> FEATURE:
<221> NAME/KEY: MOD_RES
<222> LOCATION: (508)..(508)
<223> OTHER INFORMATION: Glu or not present
<220> FEATURE:
<221> NAME/KEY: MOD_RES
<222> LOCATION: (509)..(509)
<223> OTHER INFORMATION: Pro or not present
<220> FEATURE:
<221> NAME/KEY: MOD_RES
<222> LOCATION: (510)..(510)
<223> OTHER INFORMATION: Arg or not present
<220> FEATURE:
<221> NAME/KEY: MOD_RES
<222> LOCATION: (511)..(511)
<223> OTHER INFORMATION: Leu or not present
<220> FEATURE:
```

-continued

```
<221> NAME/KEY: MOD_RES
<222> LOCATION: (512)..(512)
<223> OTHER INFORMATION: Val or not present
<220> FEATURE:
<221> NAME/KEY: MOD_RES
<222> LOCATION: (513)..(513)
<223> OTHER INFORMATION: Ala or not present
<220> FEATURE:
<221> NAME/KEY: MOD_RES
<222> LOCATION: (514)..(514)
<223> OTHER INFORMATION: Trp or not present
<220> FEATURE:
<221> NAME/KEY: MOD_RES
<222> LOCATION: (515)..(515)
<223> OTHER INFORMATION: Pro or not present

<400> SEQUENCE: 30

Xaa Xaa Xaa Xaa Asn Gly Thr Met Met Gln Tyr Phe Glu Trp His Leu
1               5                   10                  15

Xaa Xaa Asp Gly Xaa Xaa Trp Xaa Lys Leu Xaa Xaa Asp Ala Xaa Xaa
            20                  25                  30

Leu Ser Xaa Xaa Gly Ile Thr Ala Ile Trp Ile Pro Pro Ala Tyr Lys
        35                  40                  45

Gly Xaa Ser Xaa Ala Asp Val Gly Tyr Gly Xaa Tyr Asp Leu Tyr Asp
50                  55                  60

Leu Gly Glu Phe Asn Gln Lys Gly Thr Val Arg Thr Lys Tyr Gly Thr
65                  70                  75                  80

Lys Ala Gln Xaa Xaa Xaa Ala Ile Xaa Ala Xaa Xaa Ala Xaa Xaa Ile
                85                  90                  95

Asn Val Tyr Ala Asp Val Val Xaa Xaa His Lys Xaa Gly Ala Asp Xaa
            100                 105                 110

Thr Glu Xaa Val Xaa Ala Val Xaa Val Asn Pro Ser Xaa Arg Xaa Gln
            115                 120                 125

Asp Ile Ser Gly Xaa Tyr Xaa Ile Xaa Ala Trp Thr Xaa Phe Asp Phe
130                 135                 140

Pro Gly Arg Xaa Asn Xaa Tyr Ser Xaa Phe Lys Trp Arg Trp Phe His
145                 150                 155                 160

Phe Xaa Gly Val Asp Trp Asp Xaa Xaa Xaa Xaa Xaa Xaa Xaa Ile Phe
            165                 170                 175

Lys Phe Xaa Xaa Xaa Xaa Xaa Xaa Trp Xaa Trp Xaa Val Asp Xaa Glu
            180                 185                 190

Asn Gly Asn Tyr Asp Tyr Leu Leu Xaa Ala Xaa Ile Asp Xaa Xaa His
            195                 200                 205

Pro Glu Val Xaa Xaa Glu Leu Lys Xaa Trp Gly Xaa Trp Phe Xaa Xaa
210                 215                 220

Xaa Xaa Xaa Ile Asp Gly Phe Arg Leu Asp Ala Ile Lys His Ile Xaa
225                 230                 235                 240

Phe Xaa Phe Xaa Xaa Asp Trp Leu Xaa His Xaa Arg Ser Xaa Xaa Xaa
            245                 250                 255

Xaa Xaa Leu Phe Xaa Val Gly Glu Tyr Trp Xaa Xaa Asp Ile Xaa Xaa
            260                 265                 270

Leu Xaa Xaa Tyr Ile Xaa Xaa Xaa Asn Xaa Xaa Met Ser Leu Phe Asp
        275                 280                 285

Xaa Pro Leu Xaa Xaa Xaa Phe Tyr Xaa Ala Ser Lys Xaa Gly Gly Ala
        290                 295                 300

Phe Asp Met Arg Xaa Ile Leu Xaa Xaa Ser Leu Met Xaa Xaa Xaa Pro
305                 310                 315                 320

Xaa Xaa Ala Val Thr Phe Val Asp Asn His Asp Thr Xaa Pro Gly Xaa
```

```
                    325                 330                 335
Ala Leu Xaa Ser Trp Val Xaa Xaa Trp Phe Lys Pro Leu Ala Tyr Ala
            340                 345                 350

Xaa Ile Leu Thr Arg Xaa Xaa Gly Tyr Pro Xaa Val Phe Tyr Gly Asp
            355                 360                 365

Tyr Tyr Gly Ile Pro Asn Xaa Asn Ile Xaa Ala Xaa Lys Xaa Xaa Ile
            370                 375                 380

Asp Xaa Leu Leu Xaa Ala Arg Xaa Xaa Tyr Ala Tyr Gly Thr Gln His
385                 390                 395                 400

Asp Tyr Xaa Asp His Xaa Asp Ile Ile Gly Trp Thr Arg Glu Gly Xaa
            405                 410                 415

Ser Xaa Lys Pro Xaa Ser Gly Leu Ala Xaa Ile Ile Ser Xaa Gly Pro
            420                 425                 430

Gly Gly Ser Lys Trp Met Tyr Val Gly Xaa Gln His Ala Gly Xaa Xaa
            435                 440                 445

Phe Xaa Asp Leu Thr Gly Asn Xaa Ala Xaa Ser Val Thr Ile Asn Xaa
            450                 455                 460

Asp Gly Trp Gly Glu Phe Xaa Xaa Asn Gly Gly Ser Val Ser Val Trp
465                 470                 475                 480

Val Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa
        515

<210> SEQ ID NO 31
<211> LENGTH: 515
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (180)..(180)
<223> OTHER INFORMATION: Gly or not present
<220> FEATURE:
<221> NAME/KEY: MOD_RES
<222> LOCATION: (181)..(181)
<223> OTHER INFORMATION: Ile or not present
<220> FEATURE:
<221> NAME/KEY: MOD_RES
<222> LOCATION: (193)..(193)
<223> OTHER INFORMATION: Asn or Phe
<220> FEATURE:
<221> NAME/KEY: MOD_RES
<222> LOCATION: (416)..(416)
<223> OTHER INFORMATION: Val or Gly
<220> FEATURE:
<221> NAME/KEY: MOD_RES
<222> LOCATION: (489)..(489)
<223> OTHER INFORMATION: Thr or not present
<220> FEATURE:
<221> NAME/KEY: MOD_RES
<222> LOCATION: (490)..(490)
<223> OTHER INFORMATION: Ile or not present
<220> FEATURE:
<221> NAME/KEY: MOD_RES
<222> LOCATION: (491)..(491)
<223> OTHER INFORMATION: Ala or not present
<220> FEATURE:
<221> NAME/KEY: MOD_RES
<222> LOCATION: (492)..(492)
<223> OTHER INFORMATION: Arg or not present
<220> FEATURE:
```

```
<221> NAME/KEY: MOD_RES
<222> LOCATION: (493)..(493)
<223> OTHER INFORMATION: Pro or not present
<220> FEATURE:
<221> NAME/KEY: MOD_RES
<222> LOCATION: (494)..(494)
<223> OTHER INFORMATION: Ile or not present
<220> FEATURE:
<221> NAME/KEY: MOD_RES
<222> LOCATION: (495)..(496)
<223> OTHER INFORMATION: Thr or not present
<220> FEATURE:
<221> NAME/KEY: MOD_RES
<222> LOCATION: (497)..(497)
<223> OTHER INFORMATION: Arg or present
<220> FEATURE:
<221> NAME/KEY: MOD_RES
<222> LOCATION: (498)..(498)
<223> OTHER INFORMATION: Pro or not present
<220> FEATURE:
<221> NAME/KEY: MOD_RES
<222> LOCATION: (499)..(499)
<223> OTHER INFORMATION: Trp or not present
<220> FEATURE:
<221> NAME/KEY: MOD_RES
<222> LOCATION: (500)..(500)
<223> OTHER INFORMATION: Thr or not present
<220> FEATURE:
<221> NAME/KEY: MOD_RES
<222> LOCATION: (501)..(501)
<223> OTHER INFORMATION: Gly or not present
<220> FEATURE:
<221> NAME/KEY: MOD_RES
<222> LOCATION: (502)..(502)
<223> OTHER INFORMATION: Glu or not present
<220> FEATURE:
<221> NAME/KEY: MOD_RES
<222> LOCATION: (503)..(503)
<223> OTHER INFORMATION: Phe or not present
<220> FEATURE:
<221> NAME/KEY: MOD_RES
<222> LOCATION: (504)..(504)
<223> OTHER INFORMATION: Val or not present
<220> FEATURE:
<221> NAME/KEY: MOD_RES
<222> LOCATION: (505)..(505)
<223> OTHER INFORMATION: Arg or not present
<220> FEATURE:
<221> NAME/KEY: MOD_RES
<222> LOCATION: (506)..(506)
<223> OTHER INFORMATION: Trp or not present
<220> FEATURE:
<221> NAME/KEY: MOD_RES
<222> LOCATION: (507)..(507)
<223> OTHER INFORMATION: Thr or not present
<220> FEATURE:
<221> NAME/KEY: MOD_RES
<222> LOCATION: (508)..(508)
<223> OTHER INFORMATION: Glu or not present
<220> FEATURE:
<221> NAME/KEY: MOD_RES
<222> LOCATION: (509)..(509)
<223> OTHER INFORMATION: Pro or not present
<220> FEATURE:
<221> NAME/KEY: MOD_RES
<222> LOCATION: (510)..(510)
<223> OTHER INFORMATION: Arg or not present
<220> FEATURE:
<221> NAME/KEY: MOD_RES
<222> LOCATION: (511)..(511)
<223> OTHER INFORMATION: Leu or not present
<220> FEATURE:
<221> NAME/KEY: MOD_RES
<222> LOCATION: (512)..(512)
<223> OTHER INFORMATION: Val or not present
<220> FEATURE:
<221> NAME/KEY: MOD_RES
<222> LOCATION: (513)..(513)
<223> OTHER INFORMATION: Ala or not present
```

```
<220> FEATURE:
<221> NAME/KEY: MOD_RES
<222> LOCATION: (514)..(514)
<223> OTHER INFORMATION: Trp or not present
<220> FEATURE:
<221> NAME/KEY: MOD_RES
<222> LOCATION: (515)..(515)
<223> OTHER INFORMATION: Pro or not present

<400> SEQUENCE: 31

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Xaa Xaa Gly Lys Ala Trp Asp Trp Glu Val Asp Thr Glu
            180                 185                 190

Xaa Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365
```

```
Tyr Tyr Gly Ile Pro Gln Tyr Asn Ile Pro Ser Leu Lys Ser Lys Ile
        370             375             380

Asp Pro Leu Leu Ile Ala Arg Arg Asp Tyr Ala Tyr Gly Thr Gln His
385                 390             395                     400

Asp Tyr Leu Asp His Ser Asp Ile Ile Gly Trp Thr Arg Glu Gly Xaa
            405             410                 415

Thr Glu Lys Pro Gly Ser Gly Leu Ala Ala Leu Ile Thr Asp Gly Pro
            420             425             430

Gly Gly Ser Lys Trp Met Tyr Val Gly Lys Gln His Ala Gly Lys Val
            435             440             445

Phe Tyr Asp Leu Thr Gly Asn Arg Ser Asp Thr Val Thr Ile Asn Ser
    450             455             460

Asp Gly Trp Gly Glu Phe Lys Val Asn Gly Gly Ser Val Ser Val Trp
465             470             475             480

Val Pro Arg Lys Thr Thr Val Ser Xaa Xaa Xaa Xaa Xaa Xaa Xaa Xaa
            485             490             495

Xaa Xaa Xaa Xaa Xaa Xaa Xaa Xaa Xaa Xaa Xaa Xaa Xaa Xaa Xaa Xaa
            500             505             510

Xaa Xaa Xaa
        515
```

ALPHA-AMYLASE VARIANTS WITH ALTERED PROPERTIES

CROSS-REFERENCE TO RELATED APPLICATIONS

This claims benefit of U.S. Provisional Applications 60/985,619, filed Nov. 5, 2007, 61/026,579, filed Feb. 6, 2008, 61/041,075, filed Mar. 31, 2008, and 61/059,411, filed Jun. 6, 2008, the disclosures of each of which are incorporated herein by reference in their entireties, for all purposes.

SEQUENCE LISTING

Attached hereto is a sequence listing comprising SEQ ID NOS 1-31, each of which is herein incorporated by reference in its entirety.

FIELD OF THE DISCLOSURE

This disclosure relates to novel alpha-amylases. In particular, it relates to certain alpha-amylase variant activities, as well as blends thereof with one or more other enzymes, such as phytases.

BACKGROUND

Alpha-amylases (alpha-1,4-glucan-4-glucanohydrolases, E.C. 3.2.1.1) constitute a group of enzymes that catalyze hydrolysis of starch and related linear or branched 1,4-glucosidic oligo- and polysaccharides.

Alpha-amylases can be used for a variety of purposes. For examples, alpha-amylases are used commercially in the initial stages of starch processing (e.g., liquefaction); in wet milling processes; and in alcohol production from carbohydrate sources. They are also used as cleaning agents or adjuncts in detergent matrices; in the textile industry for starch desizing; in baking applications; in the beverage industry; in oilfields in drilling processes; in recycling processes, e.g. for de-inking paper, and in animal feed.

Attempts have been made to construct alpha-amylase variants with improved properties for specific uses, such as starch liquefaction and textile desizing.

There is a need for the creation and improvement of amylases that provide, e.g., manufacturing and/or performance advantages over the industry standard enzymes (e.g., from *Bacillus licheniformis*), for various uses, including commercial processing of grain, e.g., liquefaction processes. There is also a need for compositions comprising improved amylases and additional enzymes, such as phytases.

SUMMARY

In one aspect, the present disclosure relates, inter alia, to novel α-amylolytic enzymes variants of parent α-amylase such as a AmyS-like α-amylase, in particular variants exhibiting altered properties which are advantageous in connection with the industrial processing of starch (starch liquefaction, saccharification and the like).

For example, the variant is altered, as compared to a parent AmyS-like alpha-amylase or a reference alpha-amylase, in one or more of net charge, substrate specificity, substrate cleavage, substrate binding, thermal stability, activity at one or more pH's, stability at one or more pH's [such as increased stability at particular pHs (e.g. low (e.g. pH≦6, in particular, pH≦5) or high (e.g. pH≧9) pH values], stability in oxidizing conditions, metal ion requirements [for example, $Ca^{2+}$ dependency, or $Ca^{2+}$ requirements], specific activity, catalytic rate, catalytic efficiency, activity in the presence of phytic acid or another phytates (i.e, susceptibility to inhibition by phytates), thermal or pH stability in the presence of phytic acid or a phytate, ability to effect peak viscosity in a liquefaction test, or ability to effect final viscosity in a liquefaction test, and other properties of interest. For instance, one or more alterations may result in a variant that has reduced $Ca^{2+}$ dependency and/or an altered pH/activity profile and/or altered thermostability, as compared to a parent α-amylase, such as an AmyS-like alpha-amylase.

In one of its aspects, the disclosure relates to variant alpha-amylases comprising an amino acid sequence at least 95% identical to that of a parent AmyS-like alpha-amylase, and having a substitution at an amino acid position corresponding to position 242 of a reference alpha-amylase, and further comprising one or more of the following modifications to it amino acid sequence:

a) one or more of substitution at positions as follows: a cysteine at amino acid position 349, a cysteine at 428, a glutamic acid at 97, an arginine at 97, a glutamic acid at 319, an arginine at 319, a glutamic acid at 358, an arginine at 358, a glutamic acid at 443, or an arginine at 443;

b) other sequence modification at one or more amino acid positions corresponding to amino acid positions 97, 319, 349, 358, 428, or 443;

c) deletion of one or more amino acids at positions F178, R179, G180, I181, G182, or K183, or pairs thereof;

d) other sequence modifications at one or more amino acid positions 178, 179, 180, 181, 182, or 183;

e) substitution of N193F or V416G, or both;

f) other sequence modification at position 193, 416 or both;

g) substitution of one or more proline residues present in the part of the alpha-amylase variant that is modified, with an alanine, glycine, serine, threonine, valine or leucine residue.

h) substitution of one or more proline residues present in the part of the alpha-amylase variant that is modified, with another naturally-occurring amino acid residue;

i) substitution of one or more cysteine residues present in the parent alpha-amylase with a serine, alanine, threonine, glycine, valine or leucine residue;

j) substitution of one or more cysteine residues present in the parent alpha-amylase variant, with another naturally-occurring amino acid residue;

k) where SEQ ID NO: 7 is the reference amylase for numbering, any of the following mutations M15T, L, M15X, V128E, V128X, H133Y, H133X, N188S, T, P, N188X, M197T, L, M197X, A209V, A209X, M197T/W138F, M197T/138Y, M15T/H133Y/N188S, M15N128E/H133Y/N188S, E119C/S130C, D124C/R127C, H133Y/T149I, G475R, H133Y/S187D or H133Y/A209V.

l) other modification at one or more of positions M15, V128, A111, H133, W138, T149, M197, N188, A209, A210, H405, T412, where SEQ ID NO: 7 is the reference amylase;

m) where the parent alpha-amylase comprises SEQ ID NO: 7, deletion or substitution of one or more of a cysteine residue (C363) or one or more methionine residues located in any of positions M8, M9, M96, M200, M206, M284, M307, M311, M316 and M438 when SEQ ID NO: 2 is the reference amylase;

n) modification of one or more amino acid residues corresponding to P17, D19, T21, N28, S51, G72, V74, A82, Q86, Q89, A93, G95, Q97, W115, D117, P123, S124, D125, N127, I130, G132, Q135, P145, G146, G148, S153, Y159, W166, S169, K171, R179, G180, I181, G182, K183, W187, P209, N224, S242, P245, G256, D269, N271, T278, N281, G302, A304, R308, T321, Q358, P378, S382, K383, T398, H405, T417, E418, P420, G421, P432, W437, G446, G454, S457, T459, T461, S464, G474, or R483, where SEQ ID NO: 1 or 2 are the reference amylase; or o) a set of substitutions of a) Q97E, Q319E, Q358E, Q443E; b) Q97E, Q319R, Q358E, Q443R; c) Q97E, Q319R, Q358E; d) Q97E, Q319R, Q443E; e) Q97E, Q319R, Q443R; f) Q97E, Q358R; g) Q97E, Q443E; h) Q319R, Q358E, Q443E; or i) Q319R, Q358R, Q443E.

In presently preferred embodiments, the alpha-amylase variant is a S242A, S242D, S242E, S242F, S242G, S242H, S242L, S242M, S242N, S242Q, or S242T variant.

The alpha-amylase variant is preferably derived from a parent AmyS-like alpha-amylase comprising any of SEQ ID NOs: 1, 2, 6, 7, 8, 9, 10, 11, 12, 15, or 16. The reference alpha-amylase used for numbering the amino acid residues is preferably SEQ ID NO: 1 or 2 in certain embodiments.

In one embodiment, the amino acid sequence of the variant is at least 98% identical to that of a parent AmyS-like alpha-amylase.

Also provided are nucleic acids, i.e., polynucleotides, comprising an encoding sequence that encodes a) an amino acid sequence of the variants described herein; or b) any of SEQ ID NOs: 3, 4, 16, 22, 23, 24, 25, 26, 27, 28, 29, or 30. Provided as well are vectors and host cells comprising the polynucleotides or vectors.

In various embodiments, the host cell is a *Bacillus subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. thuringiensis*, *Streptomyces lividans*, *S. murinus*; *Escherichia coli*, or a *Pseudomonas* spp.

In another aspect, there is provided herein a variant of a parent *Geobacillus stearothermophilus* alpha-amylase, wherein the variant has an amino acid sequence which has at least 95% homology to a parent *Geobacillus stearothermophilus* alpha-amylase and comprises a substitution of amino acid 242, wherein the amino acid positions in the peptide sequence are numbered relative to SEQ ID NO:1 or 2, and wherein the variant has alpha-amylase activity.

In another aspect, provided are compositions comprising:
a) an alpha-amylase variant as provided herein, and
b) at least one additional enzyme.

In one embodiment, the composition is one comprising a) at least one variant amylase comprising an amino acid sequence at least 95% identical to that of a parent AmyS-like alpha-amylase, and having a substitution at an amino acid position corresponding to position 242 of a reference alpha-amylase, said variant having detectable alpha-amylase activity, and b) at least one additional enzyme.

The additional enzyme is preferably a phytase. The alpha-amylase variant in the composition is preferably a S242A, S242D, S242E, S242F, S242G, S242H, S242L, S242M, S242N, S242Q, or S242T variant.

In one embodiment, the alpha-amylase variant further comprises a sequence modification at one or more amino acid positions corresponding to amino acid positions 97, 179, 180, 193, 319, 349, 358, 416, 428, or 443 of the reference alpha-amylase. The alpha-amylase variant can also comprise one or more of substitution at positions as follows: a cysteine at 349, a cysteine at 428, a glutamic acid at 97, an arginine at 97, a glutamic acid at 319, an arginine at 319, a glutamic acid at 358, an arginine at 358, a glutamic acid at 443, or an arginine at 443.

In one embodiment, the alpha-amylase variant comprises a substitution of an N193 or a V416 or both, e.g., a substitution of N193F or V416G, or both.

The alpha-amylase variant comprises deletion of amino acids 179 and 180 in other embodiments. The composition in one embodiment comprises an alpha-amylase variant has at least 95% homology to SEQ ID NO: 2 and comprises a substitution of amino acid 242 relative to numbering in a reference alpha-amylase comprising the amino acid sequence SEQ ID NO: 1. As above, the parent AmyS-like alpha-amylase is preferably SEQ ID NO: 1, 2, 6, 7, 8, 9, 10, 11, 12, 15, or 16.

In one aspect, the disclosure relates to hydrolyzing a soluble starch substrate using alpha-amylase (AA) activity and a phytate-hydrolyzing enzyme (FTU). For example, wherein the ratio of AAU:FTU is from about 1:15 to about 15:1, preferably from 1:10 to about 10:1. In an embodiment the ratio of AAU:FTU is from 1:4 to 3:1. In a further embodiment the ratio of AAU:FTU is 1:1. In one presently preferred composition, the phytase has a sequence that is SEQ ID NO: 31.

More particularly, methods are provided for treating a starch slurry comprising the steps of a) adding to the starch slurry at least one phytase and at least one alpha-amylase; wherein the phytase and the alpha-amylase are added at or about the same time, or separately in any order, and wherein the alpha-amylase is a variant amylase comprising an amino acid sequence at least 95% identical to that of a parent AmyS-like alpha-amylase, and having a substitution at an amino acid position corresponding to position 242 of a reference alpha-amylase, said variant having detectable alpha-amylase activity; and b) incubating the starch slurry under conditions permissive of activity of the phytase and the alpha-amylase.

The alpha-amylase variant for use in the method is preferably a S242A, S242D, S242E, S242F, S242G, S242H, S242L, S242M, S242N, S242Q, or S242T variant. In one embodiment, the alpha-amylase variant further comprises a sequence modification at one or more amino acid positions corresponding to amino acid positions 97, 179, 180, 193, 319, 349, 358, 416, 428, or 443 of the reference alpha-amylase. The alpha-amylase variant can comprise one or more of substitution at positions as follows: a cysteine at −349, a cysteine at 428, a glutamic acid at 97, an arginine at 97, a glutamic acid at 319, an arginine at 319, a glutamic acid at 358, an arginine at 358, a glutamic acid at 443, or an arginine at 443. In one embodiment, the alpha-amylase variant comprises a substitution of an N193 or a V416 or both, e.g., a substitution of N193F or V416G, or both. The alpha-amylase variant features deletion of amino acids 179 and 180 in other embodiments.

In one embodiment of the method, the parent AmyS-like alpha-amylase is SEQ ID NO: 1, 2, 6, 7, 8, 9, 10, 11, 12, 15, or 16.

The phytase can be added before or after the alpha-amylase variant. The starch slurry may be preincubated after adding the phytase, and before adding the alpha-amylase variant. In one embodiment, the inclusion of the phytase results in an increase in thermostability of the alpha-amylase variant relative to a comparable method that does not include contacting the starch slurry with phytase. In one embodiment of the method, the phytase and the alpha-amylase variant are present in a single blend before adding to the starch slurry. In another, the phytase has the amino acid sequence of SEQ ID NO: 31.

In a further aspect, this relates to a method for liquefying starch in a slurry comprising a substrate which includes plant material such as granular starch from either a dry or wet milling process, the method comprising a primary and/or secondary liquefaction step, the method comprising adding to the slurry in the primary and/or secondary liquefaction step, in any order, a combination of at least one phytic acid hydrolyzing enzyme and at least one alpha-amylase simultaneously or separately. The method can further comprise saccharifying the liquefied starch to obtain fermentable sugars; and recovering the fermentable sugars. In some embodiments, the method further comprises fermenting the fermentable sugars under suitable fermentation conditions to obtain end-products such as alcohol. In some embodiments, the enzyme composition contains at least one alpha-amylase and a phytase. In some embodiments, the enzyme composition is in blended form. In a further aspect, this relates to a method for fermenting a starch substrate, the method comprising adding in any order a combination of an alpha-amylase and a phytase in a single or split dose. In another aspect, the treated starch substrate is fermented to ethanol.

In various embodiments of the method, the reference alpha-amylase is SEQ ID NO: 1 or 2, and the alpha-amylase variant is a S242A, S242D, S242E, S242F, S242G, S242H, S242L, S242M, S242N, S242Q, or S242T alpha-amylase variant.

In another aspect is a method of obtaining a fermentable substrate by contacting a slurry of milled grain containing granular starch, with a phytic acid-hydrolyzing enzyme at a temperature of about 0 to about 30° C. less than the starch gelatinization temperature, contacting the slurry with an alpha-amylase, raising the temperature above the gelatinization temperature for the granular starch to allow gelatinization of the starch, hydrolyzing the gelatinized starch by contacting the gelatinized starch with the alpha-amylase for a time sufficient to hydrolyze the starch, and obtaining a fermentable substrate. The phytic acid hydrolyzing enzyme can be a bacterial or fungal phytase. The fungal phytase can be an *Aspergillus* phytase or a *Buttiauxella* phytase. In some embodiments, the bacterial phytase is from *Escherichia coli*.

Provided, then, are methods of producing a fermentable substrate from a starch-containing slurry comprising milled grain, the method comprises the steps of
  a) contacting the starch-containing slurry with at least one phytase and at least one alpha-amylase in an amount sufficient to produce a fermentable substrate from the starch;
  wherein the contact with the phytase and the alpha-amylase is initiated at or about the same time, or separately in any order, and wherein the alpha-amylase is a variant amylase comprising an amino acid sequence at least 95% identical to that of a parent AmyS-like alpha-amylase, and having a substitution at an amino acid position corresponding to position 242 of a reference alpha-amylase, said variant having detectable alpha-amylase activity; and
  b) incubating the starch slurry under conditions permissive of activity of the phytase and the alpha-amylase for a time that allows production of the fermentable substrate; wherein when the contact with the phytase is initiated before the amylase, the slurry is incubated at a temperature that is 0-30° C. less than the gelatinization temperature prior to contacting the slurry with the amylase, after which the temperature is raised above the gelatinization for a time effective to hydrolyze the starch.

In one embodiment, the reference alpha-amylase is SEQ ID NO: 1 or 2, and the parent AmyS-like alpha-amylase comprises any of SEQ ID NOs: 1, 2, 6, 7, 8, 9, 10, 11, 12, 15, or 16. The alpha-amylase variant is preferably a S242A, S242D, S242E, S242F, S242G, S242H, S242L, S242M, S242N, S242Q, or S242T alpha-amylase variant.

In one embodiment, the method comprises use of at least one additional enzyme which is a phytase, cellulase, protease, aminopeptidase, amylase, carbohydrase, carboxypeptidase, catalase, chitinase, cutinase, cyclodextrin glucanotransferase, deoxyribonuclease, esterase, α-galactosidase, β-galactosidase, glucoamylase, α-glucosidase, β-glucosidase, haloperoxidase, invertase, isomerase, laccase, lipase, mannosidase, oxidase, pectinase, peptidoglutaminase, peroxidase, polyphenoloxidase, nuclease, ribonuclease, transglutaminase, xylanase, pullulanase, isoamylase, carrageenase, or a combination of two or more of the foregoing.

The method is preferably part of a process for starch degradation, liquefaction, fermentation, alcohol production, sweetener production, production of a fermentable substrate, cleaning, washing, stain removal, or baking process, or the like.

In another aspect, the disclosure relates to a process for producing a fermentable sugar comprising a) mixing milled starch-containing material with water and thin stillage, wherein the thin stillage is in the range of 10 to 70% v/v and obtaining a slurry comprising starch and having a dry solids (ds) content of 20 to 50% w/w, b) treating the slurry with a phytase prior to or simultaneously with liquefying the starch, c) liquefying the starch, d) adding an alpha-amylase to the starch either during step b) and/or simultaneously with the liquefying step and e) saccharifying the liquefied starch to obtain fermentable sugars, wherein the pH is not adjusted during any of the steps a), b), c), d) or e). In some embodiments, the fermentable sugar is recovered and purified or isomerized. In other embodiments, the phytase is added prior to the liquefaction step. In further embodiments, the alpha-amylase is added with the phytase. In yet further embodiments, a second alpha-amylase dose is added during the liquefaction step.

Also provided herein are methods of method of treating a starch-containing material or a starch with an amylase. The methods comprise the step of contacting the starch-containing material or the starch with a composition comprising at least one alpha-amylase variant disclosed herein under conditions sufficient to allow detectable activity of the alpha-amylase; wherein the variant amylase any variant disclosed herein; and wherein the starch is at least partially degraded by the variant amylase. In preferred embodiments, the alpha-amylase variant is a S242A, S242D, S242E, S242F, S242G, S242H, S242L, S242M, S242N, S242Q, or S242T variant alpha-amylase. The methods are conveniently used as part of a process for starch degradation, liquefaction, fermentation, alcohol production, sweetener production, production of a fermentable substrate, cleaning, washing, stain removal, or baking process, or the like.

BRIEF DESCRIPTION OF THE DRAWINGS

FIG. 1 shows alignment of amino acid sequences among several candidate parent alpha-amylases (AmyS-like amylases) for use herein. Positions corresponding to any amino acid position (e.g., 1 through 520) of the amylase from *Geobacillus stearothermophilus* (SEQ ID NO: 1) can be readily determined. SEQ ID NO: 1, alpha-amylase from *G. stearothermophilus* "BSG"; SEQ ID NO: 2, truncated amylase from *G. stearothermophilus* (AmyS, SPEZYME XTRA); SEQ ID NO: 3, *G. stearothermophilus* (S242A variant amylase); SEQ ID NO: 4, *G. stearothermophilus* (S242Q variant amylase); SEQ ID NO: 5, *G. stearothermophilus* (S242E variant amylase); SEQ ID NO: 6, Yamane 707 amylase; SEQ ID NO: 7, mature LAT amylase; SEQ ID NO: 8, *Bacillus licheniformis* wild-type amylase [TERMAMYL (NOVOZYMES)=SEQ ID NO: 8 in WO 02/10355A2]; SEQ ID NO: 9, *B. amyloliquefaciens* amylase, BAN; SEQ ID NO: 10, STAINZYME=AA560 which is SEQ ID NO: 2 in WO 0060060 or SEQ ID NO: 24 in U.S. Pat. No. 6,528,298; SEQ ID NO: 11, *B. halmapalus* amylase (NATALASE); SEQ ID NO: 12, KSM-1378 (KAO CORP., SEQ ID NO: 3 in EP1199356); SEQ ID NO: 13, *Bacillus* spp. KSM-K38 (KAO CORP., SEQ ID NO: 4 in U.S. Pat. No. 6,403,355 B1); SEQ ID NO: 14, *Bacillus* spp. KSM-K36 (KAO CORP., SEQ ID NO: 2 in U.S. Pat. No. 6,403,355 B1); SEQ ID NO: 15, LIQUOZYME SC(NOVOZYMES); SEQ ID NO: 16, Consensus Parent Alpha-Amylase Sequence #1;

FIG. 4: Panels A, B, C, D, E, F, G, H, and I show pair-wise alignments and consensus sequences for several sequences from FIG. 1, and feature, respectively, Consensus Sequences 2, 3, 4, 5, 6, 7, 8, 9, and 10, or SEQ ID NOs: 22, 23, 24, 25, 26, 27, 28, 29, and 30, respectively.

FIG. 25B is a graph depicting the relative microswatch-starch hydrolysis as a function of relative shake tube expression (i.e., relative microswatch-starch hydrolysis vs. relative shake tube expression). Reference is made to Example 19.

DETAILED DISCLOSURE

1. Definitions & Abbreviations

Figure 2:
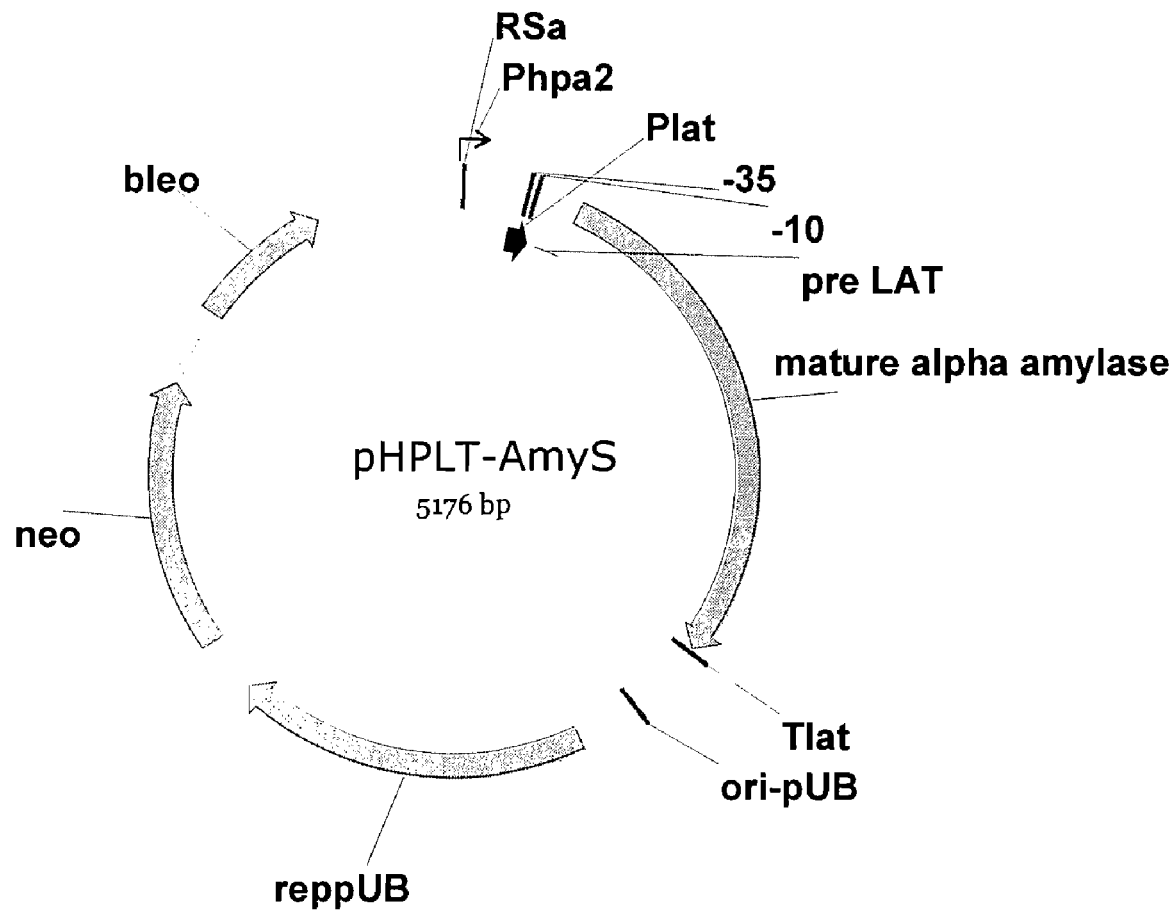
FIG. 2 shows the pHPLT-AmyS plasmid.

In accordance with this disclosure, the following abbreviations and definitions apply. It should be noted that as used herein, the singular forms "a," "an," and "the" include plural referents unless the context clearly dictates otherwise. Thus, for example, reference to "a polypeptide" includes a plurality of such polypeptides and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. Abbreviations

The following abbreviations apply unless indicated otherwise:

| | |
|---|---|
| AATCC | American Association of Textile Chemists and Colorists; |
| ADW | automatic dish washing; |
| AE | alcohol ethoxylate; |
| AEO | alcohol ethoxylate; |
| AEOS | alcohol ethoxysulfate; |
| AES | alcohol ethoxysulfate; |
| AFAU | acid fungal alpha-amylase units; |
| AGU | glucoamylase activity units; |
| AOS | α-olefinsulfonate; |
| AS | alcohol sulfate; |
| BAA | bacterial alpha-amylase; |
| ° C. | degrees Centigrade; |
| CCL | combinatorial charge library; |
| cDNA | complementary DNA; |
| CMC | carboxymethylcellulose; |
| dE | total color difference, as defined by the CIE-LAB color space; |
| dH$_2$O | deionized water; |
| dIH$_2$O | deionized water, Milli-Q filtration; |
| DE | Dextrose Equivalent; |
| DNA | deoxyribonucleic acid; |
| dNTP | deoxyribonucleotide triphosphates; |
| DO | dissolved oxygen; |
| DP3 | degree of polymerization with three subunits; |
| DPn | degree of polymerization with n subunits; |
| DS (or ds) | dry solids content; |
| DSC | differential scanning calorimetry; |
| DTMPA | diethyltriaminepentaacetic acid; |
| EC | enzyme commission for enzyme classification; |
| EDTA | ethylenediaminetetraacetic acid; |
| EDTMPA | ethylenediaminetetramethylene phosphonic acid; |
| EO | ethylene oxide; |
| eq | equivalents; |
| ETOH | ethanol; |
| F & HC | fabric and household care; |
| FTU | "fitase" units, phytate hydrolyzing unit; |
| g (or gm) | grams; |
| GAU | glucoamylase unit; |

-continued

| | |
|---|---|
| gpg | grains per gallon; |
| g/l | grams per liter; |
| Genencor | Danisco US Inc., Genencor Division, Palo Alto, CA; |
| H$_2$O | water; |
| HDG | heavy duty granular detergent; |
| HDL | heavy duty liquid detergent; |
| HFCS | high-fructose corn syrup; |
| HFSS | high-fructose starch-based syrup; |
| HPAEC-PAD | high performance anion exchange chromatography with pulsed amperometric detection; |
| hr(s) | hour/hours; |
| IKA | IKA Works Inc. 2635 North Chase Parkway SE, Wilmington, NC; |
| IPTG | isopropyl β-D-thiogalactoside; |
| JPN | Japan; |
| kg | kilograms; |
| LA | Luria Agar; |
| LAS | linear alkylbenezenesulfonate; |
| LB | Luria Broth; |
| LU | Lipase Units; |
| M | molar; |
| MBD medium | MOPS-based defined medium; |
| MES | 2-(N-morpholino)ethanesulfonic acid; |
| mg | milligrams; |
| min(s) | minute/minutes; |
| mL (or ml) | milliliters; |
| mm | millimeters; |
| mM | millimolar; |
| MOPS | 3-(N-Morpholino)-propanesulfonic acid; |
| MW | molecular weight; |
| NA | North America; |
| Ncm | Newton centimeter; |
| NEO | neomycin; |
| ng | nanogram; |
| nm | nanometer; |
| NOBS | nonanoyloxybenzenesulfonate; |
| N | Normal; |
| NTA | nitrilotriacetic acid; |
| PAHBAH | p-hydroxybenzoic acid hydrazide; |
| PCR | polymerase chain reaction; |
| PEG | polyethyleneglycol; |
| pI | isoelectric point; |
| ppm | parts per million; |
| PVA | poly(vinyl alcohol); |
| PVP | poly(vinylpyrrolidone); |
| RAU | Reference Amylase Units; |
| RMS | root mean square; |
| RNA | ribonucleic acid; |
| rpm | revolutions per minute; |
| SAPU | spectrophotometric acid protease unit; |
| SAS | secondary alkane sulfonates; |
| 1X SSC | 0.15 M NaCl, 0.015 M sodium citrate, pH 7.0; |
| sec | seconds; |
| % SRI | percent stain removal index; |
| SSF | simultaneous saccharification and fermentation; |
| TAED | tetraacetylethylenediamine; |
| T$_m$ | thermal midpoint for a DSC curve, or melting temperature of a protein; |
| TNBS | trinitrobenzenesulfonic acid; |
| µg | micrograms; |
| µl, (µL) | microliters; |
| µNm | microNewton meters; |
| µm | micrometer; |
| µM | micromolar; |
| U | units; |
| V/V | volume to volume; |
| WE | Western Europe; |
| wt % | weight percent; |
| w/v (or W/V) | weight/volume; |
| w/w (or W/w) | weight/weight; |
| wt | wild-type. |

1.2. Definitions

In some aspects, the present disclosure relies on routine techniques and methods used in the field of genetic engineering and molecular biology. The following resources include descriptions of general methodology useful in accordance with what is disclosed herein: Sambrook et al., MOLECULAR CLONING: A LABORATORY MANUAL ($2^{nd}$ Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994).

These general references provide definitions and methods known to those in the art. Unless defined otherwise herein, all technical and scientific terms used herein have the same meaning as commonly understood by one of ordinary skill in the art to which the disclosure pertains. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, N.Y. (1991) provide one of skill with general dictionaries of many of the terms used in this disclosure.

"Isolated" means that the isolated substance, e.g. a compound or a sequence, is modified by the hand of man relative to that compound or sequence as found in nature. For example, an isolated sequence is at least partially free, or even substantially free, from at least one other component with which the sequence is naturally associated as found in nature.

"Purified" when used to describe a material or substance means that the material or substance is in a relatively pure state, e.g., at least about 90% pure, at least about 95% pure, at least about 98% pure, or at least about 99% pure.

As used herein, "starch" refers to any carbohydrate composition comprising complex polysaccharides, comprising amylose and/or amylopectin with the formula $(C_6H_{10}O_5)_x$, wherein "X" can be any number. Preferably, starch refers to any such carbohydrate that is naturally present in plants, including but not limited to grains, grasses, tubers, and roots, and more specifically from wheat, barley, corn, rye, rice, sorghum, cassava, millet, potato, sweet potato, and tapioca. Starch can also refer to synthetic starches or modified starches, such as chemically-modified starch for use as a detectable substrate for enzyme assays, or starches chemically- or enzymatically-modified to improve one or more properties for use.

As used herein, "phytic acid" (or inositol hexakisphosphate (IP6)), is the principle storage form of phosphorus in many plant tissues, such as bran, seeds, and the like. Phytic acid is also referred to as "phytate" herein, especially when in salt form. Various other inositol phosphates such as inositol penta- (IP5), tetra- (IP4), and triphosphate (IP3) are also referred to herein as phytates. Phytates are generally indigestible by man and most monogastric animals.

Enzymes that degrade phytates are referred to herein as "phytases" or "fytases" are generally myo-inositol-hexaphosphate phosphohydrolases. Phytase activity is defined as fytase units (FTU or U), where one FTU is defined as the quantity of enzyme that liberates 1 micromol of inorganic-P per minute from 0.0015 mol/l sodium phytate at pH 5.5, and 37° C. This definition provides a useful measure of quantity of phytase activity and represents a simple bench mark measurement. Phytate-degrading enzymes of yeasts (e.g., *Schwanniomyces occidentalis, Pichia anomala, Arxula adeninivorans*), gram-negative bacteria (e.g., *Escherichia coli, Pseudomonas* spp., *Klebsiella* spp.), and gram-positive (e.g., *Bacillus* spp.) have been identified and characterized. Phytases from many plants, and from filamentous fungi such as *Penicillium* spp., *Aspergillus* spp., *Trichoderma* spp. *Mucor piriformis*, and *Cladosporium* spp., are also known. 3-phytases (EC 3.1.3.8) and 6-phytases (EC 3.1.3.26), depending on the site of initiation of hydrolysis, have been characterized. Also, phytase have been characterized, based on their pH "optima," as either acid (pH optima around 5) or alkaline (pH optima around 9). A variety of commercial phytases are available, including ROVABIO (Genencor International).

"Amylase" refers to an enzyme that is capable of catalyzing the cleavage of a starch substrate, leading to a degradation or partial degradation of the starch. Amylases are generally hydrolases that cleave glycosidic linkages in starch. As used herein amylase includes any glucoamylase, alpha-amylase, β-amylase, for example, the wild-type alpha-amylases of *Bacillus* spp., especially *B. licheniformis*. Generally, alpha-amylases (EC 3.2.1.1; α-D-(1→4)-glucan glucanohydrolase) are endo-acting enzymes defined as cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic alpha-amylase (EC 3.2.1.133) cleave the substrate starch molecule from the non-reducing end. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of specific length from starch. Wild-type alpha-amylase from *Bacillus stearothermophilus* or "AmyS" amylase is sometimes referred to herein as XTRA or SPEZYME XTRA, which are commercial AmyS products from Genencor International.

As used herein, "AmyS-like alpha-amylases" are useful as parent amylases herein. AmyS-like alpha-amylases constitute a class of alpha-amylases herein, based on the substantial homology found between them. "AmyS-like alpha-amylase" is intended to indicate the class of alpha-amylases, in particular *Bacillus* alpha-amylases, especially *Geobacillus stearothermophilus*-alpha-amylases, which, at the amino acid level, exhibit a substantial identity to the alpha-amylase having the amino acid sequence shown in SEQ ID NO: 2, herein. Spezyme Xtra is commercially available from Danisco US Inc, Genencor Division. *Geobacillus stearothermophilus* has been referred to as *Bacillus stearothermophilus* in the literature and the two may be used interchangeably herein. All the alpha-amylases having the amino acid sequences provided herein as SEQ ID NOS: 1, 6, 7, 8, 9, 10, 11, 12, 15 and 16, respectively, are considered to be AmyS-like alpha-amylases and thus are suitable as parent alpha-amylases. AmyS-like alpha-amylases also include alpha-amylases i) having amino acid sequences with at least 60% homology (identity), such as at least 70%, at least 75%, or at least 80%, at least 85%, at least 90%, at least 95%, at least 96%, at least 97%, at least 98%, or at least 99% identity, with at least one of the amino acid sequences shown in SEQ ID NOS: 1, 6, 7, 8, 9, 10, 11, 12, 15 and 16, and/or ii) that are encoded by a DNA sequence that hybridizes with a DNA sequence encoding any of the above-specified alpha-amylases, or those apparent from SEQ ID NOS: 9 (BAN), 5 (BSG), 3 (SP722), 1 (SP690), 7 (LAT), 11 (AA560) of WO 06/002643 or of the present specification, which encode any of the amino acid sequences shown in SEQ ID NOS: 1, 6, 7, 8, 9, 10, 11, 12, 15 and 16 herein, respectively. Still further homologous alpha-amylases useful as AmyS-like alpha-amylases and thus, as parent enzymes for producing variants herein, include the alpha-amylase produced by the *B. licheniformis* strain described in EP 0252666. (ATCC 27811) and the alpha-amylases identified in WO 91/00353 and WO 94/18314. Commercial AmyS-like alpha-amylases are comprised in the products sold under the following trade names: Spezyme® AA and ULTRAPHLOW (available from Danisco US Inc, Genencor Division), and Keistase™ (available from Daiwa) and LIQUEZYME SC (available from Novozymes, Denmark). Section 1.5 herein below provides further information regarding AmyS-like alpha-amylases. Table A therein provides a list of several useful AmyS-like alpha-amylases, as well as a convenient method of comparing amino acid sequence identities there between. The skilled artisan will appreciate the similar tables can be constructed for other alpha-amylases to determine their suitability for use herein as apparent enzyme.

As used herein, "spectrophotometric acid protease unit" ("SAPU") is a unit of protease enzyme activity, wherein in 1 SAPU is the amount of protease enzyme activity that liberates one micromole of tyrosine per minute from a casein substrate under conditions of the assay.

"Glucoamylase unit" ("GAU"), is a measure of amylolytic activity defined as the amount of enzyme activity that will produce 1 g of reducing sugar, calculated as glucose, per hour from a soluble starch substrate at pH 4.2 and 60° C.).

As used herein, the term "variant" may be used interchangeably with the term "mutant." "Variants" can refer to either polypeptides or nucleic acids. Variants include one or more sequence "modifications," which as used herein include substitutions, insertions, deletions, truncations, transversions, and/or inversions, at one or more locations relative to a reference sequence. Each modifications can include changes that result in a change of one or more amino acid residues or nucleotides in a sequence, relative to the reference sequence. Variant nucleic acids include sequences that are complementary to sequences that are capable of hybridizing to the nucleotide sequences presented herein. For example, a variant nucleic acid sequence herein can be at least partially complementary to a sequence capable of hybridizing under stringent conditions (e.g., 50° C. and 0.2×SSC {1×SSC=0.15 M NaCl, 0.015 M sodium citrate, pH 7.0}) to a nucleotide sequences presented herein. More preferably, the term variant encompasses sequences that are complementary to sequences that are capable of hybridizing under highly stringent conditions (e.g., 65° C. and 0.1×SSC) to the nucleotide sequences presented herein.

"Thermostable" when used to describe an enzyme means the enzyme is more thermostable than a reference enzyme. In the present application, an alpha-amylase variant is more thermostable than a wild-type B. licheniformis alpha-amylase if the variant has a relatively higher enzymatic activity after a specific interval of time under the same experimental conditions, e.g., the same temperature, substrate concentration, etc. Alternatively, a more thermostable enzyme has a higher heat capacity determined by differential scanning calorimetry, compared to a reference enzyme.

"Melting temperature" ($T_m$) of a polypeptide is a temperature at which the conformation of the polypeptide undergoes a measurable temperature-dependent change. Protein conformation and $T_m$ can be analyzed, for example, by circular dichroism, one of the most general and basic tools to study protein folding. Circular dichroism spectroscopy measures the absorption of circularly polarized light. In proteins, structures such as alpha helices and beta sheets are generally chiral, and thus absorb circularly polarized light. The light absorption provides a measure of the degree of foldedness of the protein. Changes in this absorption as a function of temperature or concentration of a denaturant can be used to study equilibrium unfolding of the protein. This type of spectroscopy can also be combined with devices, such as stopped flow mixers, to measure kinetics of protein folding/unfolding.

"Calcium dependent" means that, a particular enzyme requires calcium to substantially exhibit catalytic activity. Generally as used herein, "calcium dependent" encompasses a property of any enzyme that has a strict requirement for a divalent metal ion to exhibit catalytic activity, and also includes enzymes whose catalytic activity is substantially (e.g. more than 20%) increased in the presence of calcium or another divalent cation.

As used herein, "pH stable" with respect to an enzyme can refer to the enzyme activity or the protein conformation of the enzyme. In the first sense, "pH stable" means the enzyme remains catalytically-active at a specified pH or across a specified pH range. In the second sense, an enzyme may be deemed "stable" at a pH wherein the protein is not irreversibly denatured. In such a case, the enzyme would become catalytically active when returned to a pH capable of supporting catalytic activity. pH stability may also be used in a relative or comparative manner, for example, with a reference enzyme. In the present application, an alpha-amylase variant can be more pH stable than a wild-type B. licheniformis alpha-amylase when the variant has a relatively higher activity than the wild-type, e.g., when held at a given pH or assayed under the same conditions, including pH. pH's of most interest are typically either the conditions of actual use, or pH's that are at or near the boundaries or extremes of the enzyme's natural ability to remain catalytically active.

"pH range" means a range of pH values e.g., from more acid to more basic, or vice versa. With respect to an enzyme activity, a pH range indicates the upper and lower pH values at which the enzyme exhibits a specified level of activity—e.g. a minimum activity, a specified percentage of maximal activity, or a specified level of substrate conversion or product formation.

"Recombinant" when used in reference to a cell, nucleic acid, protein, or vector, indicates that the cell, nucleic acid, protein or vector, is the result of, or has been modified by, the introduction of a heterologous sequence or the alteration of a native sequence, or that the cell is derived from a cell so modified or altered. Thus, for example, recombinant cells may express genes that are not found within the native (non-recombinant) form of the cell or may express native genes that are otherwise differently expressed (e.g. under-expressed, or over-expressed), abnormally expressed, or not expressed at all.

As used herein, "nucleotide sequence" or "nucleic acid sequence" refers to any sequence of two or more nucleotides, ribonucleotides, or the like, or derivatives thereof. Nucleotide sequences include oligonucleotide and polynucleotide sequences, as well as variants, homologues, fragments and derivatives thereof. A nucleotide sequence may be single-, double-, or multi-stranded. The nucleotide sequence may be from any source or origin, e.g., genomic, synthetic, or recombinant, and includes genomic DNA, cDNA, synthetic DNA, and RNA, and the like as well as hybrids thereof. Nucleotide sequences may comprise one or more codons and may encode one or more polypeptides. Nucleotide sequences may preferentially assume one or more energetically preferred three-dimensional structures.

A "vector" refers to a nucleotide sequence frequently useful for experimental use in vitro, or for introduction of nucleic acids into one or more cell types. Vectors include cloning vectors, in vivo or in vitro expression vectors, shuttle vectors, plasmids, phagemids, cosmids, phage particles, cassettes and the like.

An "expression vector" as used herein means a DNA construct comprising a DNA sequence which is operably-linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A polynucleotide or a polypeptide having a certain percent (e.g., at least about 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Such programs may include the GCG Pileup program, FASTA (Pearson et al. (1988) *Proc. Natl, Acad. Sci USA* 85: 2444-2448), and BLAST (BLAST Manual, Altschul et al., Natl Cent. Biotechnol. Inf., Natl Lib. Med. (NCIB NLM NIH), Bethesda, Md., and Altschul et al., (1997) *NAR* 25:3389-3402). Another alignment program is ALIGN Plus (Scientific and Educational Software, PA), using default parameters. Another sequence software program that finds use is the TFASTA Data Searching Program available in the Sequence Software Package Version 6.0 (Genetics Computer Group, University of Wisconsin, Madison, Wis.).

One skilled in the art will recognize that sequences encompassed by the disclosure are also defined by the ability to hybridize under stringent hybridization conditions with the exemplified amyS sequence (e.g., SEQ ID NO:5 of WO 06/002643). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (see, e.g., Sambrook (1989) supra, particularly chapters 9 and 11). In some embodiments, stringent conditions correspond to a $T_m$ of 65° C. and 0.1×SSC, 0.1% SDS.

A "gene" refers to a DNA segment that is involved in producing a polypeptide and includes regions preceding and following the coding regions as well as intervening sequences (introns) between individual coding segments (exons).

"Heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes and nucleic acids encoding heterolorougs proteins such as fusion proteins, and/or synthetic genes.

"Endogenous" with reference to a polynucleotide or protein refers to a polynucleotide or protein that occurs naturally in the host cell.

As used herein, "transformed", "stably transformed", and "transgenic" used in reference to a cell means the cell comprises at least one non-native (e.g., heterologous) nucleic acid sequence. A stably-transformed cell comprises at least one such nucleic acid sequence integrated into its genome, or in an episomal plasmid that is maintained through multiple generations.

As used herein, "expression" refers to the process by which a polypeptide is produced based on the nucleic acid sequence of a gene. The process includes both transcription and translation.

A "signal sequence" means a sequence of amino acids covalently-bound to the N-terminal portion of a protein, which facilitates the transport of the protein, e.g., secretion of the mature form of the protein outside the cell. The definition of a signal sequence is functional. The mature form of the extracellular protein lacks the signal sequence which is cleaved off, e.g., during the secretion process.

As used herein, the term "derived" encompasses the terms "originated from", "obtained from" or "obtainable from", and "isolated from".

The terms "protein" and "polypeptide" are used interchangeably herein. The conventional one-letter or three-letter code for amino acid residues is used herein.

A "promoter" is a regulatory sequence that is involved in binding RNA polymerase to initiate transcription of a gene. The promoter may be an inducible promoter or a constitutive promoter. For example, cbh1 from *Trichoderma reesei*, an inducible promoter, can be used herein.

"Operably-linked" refers to juxtaposition wherein elements are in an arrangement allowing them to be functionally related, even where not in close physical proximity. For example, a promoter is operably-linked to a coding sequence if it is capable of controlling the coding sequence and does control the transcription of the sequence under conditions permissive thereof, or conducive thereto.

"Selective marker" refers to a gene capable of expression in a host, and which allows selecting those hosts expressing the marker gene. Examples of selectable markers include but are not limited to gene that provide altered resistance to an antimicrobial agent (e.g., hygromycin, bleomycin, or chloramphenicol) and/or genes that confer metabolic selectivity, for example, a nutritional advantage on the host cell, such as growth on a particular substrate as a sole source of carbohydrate.

"Introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

"Host," "host strain," or "host cell" means a suitable cell in which to place an expression vector or DNA construct comprising a polynucleotide, e.g., encoding a variant alpha-amylase. Host strains are preferably bacterial cells. In a preferred embodiment, "host cell" means cells and/or protoplasts created from the cells of a microbial strain, e.g., a *Bacillus* spp.

The term "culturing" refers to growing a population of microbial cells under suitable conditions in a medium capable of supporting such growth. In one embodiment, culturing refers to fermentative bioconversion of a starch substrate containing granular starch to an end-product (typically in a vessel or reactor).

"Fermentation" is the breakdown of organic substances by microorganisms to produce simpler organic compounds. While fermentation generally occurs under predominantly anaerobic conditions, it is not intended that the term be limited to strict anaerobic conditions, as fermentation also occurs in the presence of oxygen.

The term "enzymatic conversion" in general refers to the modification of a substrate by enzyme action. The term as used herein also refers to the modification of a starch substrate by the action of an enzyme.

As used herein the term "saccharification" refers to enzymatic conversion of starch to glucose.

The term "gelatinization" means at least partial solubilization of a starch granule or molecule, e.g., by cooking to form a viscous suspension.

The term "liquefaction" generally refers to a stage during starch conversion in which starch is at least partially hydrolyzed to give a lower molecular weight product, e.g., soluble dextrins.

The term "degree of polymerization (DP)" refers to the number (n) of anhydroglucopyranose units in a given saccharide. Examples of DP1 are monosaccharides, such as glucose and fructose. Examples of DP2 are disaccharides, such as maltose and sucrose. A DP>3 denotes polymers with a degree of polymerization of greater than 3. The skilled artisan will understand that compounds with greater DE are more polymeric.

"End-product" or "desired end-product" refer to any intended product of an enzymatic reaction, e.g. a starch-derived molecule that is enzymatically converted from the starch substrate.

As used herein "dry solids content (ds)" refers to the total solids of a slurry in % on a dry weight basis. The term "slurry" refers to an aqueous mixture containing insoluble solids.

The term "residual starch" refers to any remaining starch (soluble or insoluble) left in a composition after fermentation of a starch-containing substrate.

"A recycling step" refers to the recycling of mash components, which may include residual starch, enzymes and/or microorganisms to ferment substrates comprising starch.

The term "mash" refers to a mixture of a fermentable carbon source (carbohydrate) in water used to produce a fermented product, such as an alcohol. In some embodiments, the term "beer" and "mash" are used interchangeability.

"Stillage" means a mixture of non-fermented solids and water, such as the residue after removal of alcohol from a fermented mash.

The terms "distillers dried grain (DDG)" and "distillers dried grain with solubles (DDGS)" refer to a useful by-product of grain fermentation.

As used herein "ethanologenic microorganism" refers to a microorganism with the ability to convert a carbohydrate (e.g., mono-, di-, oligo-, or polysaccharides) to ethanol. The ethanologenic microorganisms are ethanologenic by virtue of their ability to express one or more enzymes that individually or collectively convert the carbohydrate to ethanol.

As used herein, "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast.

As used herein, "specific activity" means an enzyme unit defined as the number of moles of substrate converted to product by an enzyme preparation per unit time under specific conditions. Specific activity is expressed as units (U)/unit weight of protein, generally, U/mg protein.

"Yield" refers to the amount of end-product or desired end-products produced using the methods of the present disclosure. In some embodiments, the yield is greater than that produced using methods known in the art. In some embodiments, the term refers to the volume of the end product and in other embodiment the term refers to the concentration of the end product.

As used herein, "biologically-active" refers to a compound or sequence that has a measurable effect on a biological system, e.g., a cell, an organ, or an organism.

"ATCC" refers to American Type Culture Collection located at Manassas, Va. 20108 (ATCC).

"NRRL" refers to the Agricultural Research Service Culture Collection, National Center for Agricultural Utilization Research (and previously known as USDA Northern Regional Research Laboratory), Peoria, Ill.

As used herein, "food" means any ingredient, component or composition that provides a nutritive value for an animal, including a human.

As used herein, by convention, when describing proteins and genes that encode them, the term for the gene is generally italicized, (e.g., the gene that encodes amyL (*B. licheniformis* AA) may be denoted as amyL). The term for the protein is generally not italicized and the first letter is generally capitalized, (e.g., the protein encoded by the amyL gene may be denoted as AmyL or amyL). Unless otherwise indicated, nucleic acid sequences are presented left to right in 5' to 3' orientation, and amino acid sequences are written left to right in amino to carboxy orientation, respectively.

As used herein the term "comprising" and its cognates are used in their inclusive sense; that is, equivalent to the term "including" and its corresponding cognates. Numeric ranges are inclusive of the numbers defining the range.

The headings provided herein are not limitations of the various aspects or embodiments of what is disclosed.

Although any methods and materials similar or equivalent to those described herein can be used in the practice or testing of that which is disclosed, certain presently preferred methods and materials are described with no intention to limit the practitioner to any particular methods, protocols, and reagents described, as these may be varied. All patents and publications, including all sequences disclosed within such patents and publications, referred to herein are expressly incorporated by reference.

2. Nomenclature

In the present description and claims, the conventional one-letter and three-letter codes for amino acid residues are used. For ease of reference, alpha-amylase variants are generally described by use of the following nomenclature:
Original amino acid(s): position(s): substituted amino acid(s)

According to this nomenclature, for instance the substitution of serine by an alanine in position 242 is shown as:
Ser242Ala or S242A a deletion of alanine in position 30 is shown as:
Ala30* or A30* or AA30 and insertion of an additional amino acid residue, such as lysine, is shown as:
Ala30AlaLys or A30AK A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:
*36Asp or *36D for insertion of an aspartic acid in position 36.
Multiple mutations are separated by plus signs, i.e.:
Ala30Asp+Glu34Ser or A30N+E34S representing mutations in positions 30 and 34 substituting alanine and glutamic acid for asparagine and serine, respectively.

When one or more alternative amino-acid residues may be inserted in a given position it is indicated as:
A30N,E or alternatively, A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:

R, N, D, A, C, Q, E, G, H, I, L, K, M, F, P, S, T, W, Y, V.

Further, "A30X" means any one of the following substitutions: A30R, A30N, A30D, A30C, A30Q, A30E, A30G, A30H, A30I, A30L, A30K, A30M, A30F, A30P, A30S, A30T, A30W, A30Y, or A30 V; or in short:

A30R, N, D, C, Q, E, G, H, I, L, K, M, F, P, S, T, W, Y, V.

If the parent enzyme—used for the numbering—already has the amino acid residue in question suggested for substitution in that position the following nomenclature is used:

"X30N" or "X30N, V" in the case where, for instance, one or N or V is present in the wild-type. This indicates that other corresponding parent enzymes are substituted to an "Asn" or "Val" in position 30.

3. Characteristics of Amino Acid Residues

Charged amino acids:
Asp, Glu, Arg, Lys, His
Negatively charged amino acids (with the most negative residue first):
Asp, Glu
Positively charged amino acids (with the most positive residue first):
Arg, Lys, His
Neutral amino acids:
Gly, Ala, Val, Leu, Ile, Phe, Tyr, Trp, Met, Cys, Asn, Gln, Ser, Thr, Pro
Hydrophobic amino acid residues (with the most hydrophobic residue listed last):
Gly, Ala, Val, Pro, Met, Leu, Ile, Tyr, Phe, Trp,
Hydrophilic amino acids (with the most hydrophilic residue listed last):
Thr, Ser, Cys, His, Glu, Gln, Asn, Asp, Lys, Arg 4. Alpha-Amylases and AmyS-like Amylases 4.1 Amino Acid Identities of Various Alpha-amylase A number of alpha-amylases produced by *Bacillus* spp. are highly homologous (identical) on the amino acid level and may be useful as parent enzymes herein. The percent identity (based on amino acid sequence) of a number of known *Bacillus* alpha-amylases, relative to each other can be found in the below Table A:

TABLE A

Amino acid sequence identity of several known *Bacillus* alpha-amylases

|  | 707 | AP-1378 | BAN | BSG | SP690 | SP722 | AA560 | LAT |
|---|---|---|---|---|---|---|---|---|
| 707 | 100.0 | 86.4 | 66.9 | 66.5 | 87.6 | 86.2 | 95.5 | 68.1 |
| AP1378 | 86.4 | 100.0 | 67.1 | 68.1 | 95.1 | 86.6 | 86.0 | 69.4 |
| BAN | 66.9 | 67.1 | 100.0 | 65.6 | 67.1 | 68.8 | 66.9 | 80.7 |
| BSG | 66.5 | 68.1 | 65.6 | 100.0 | 67.9 | 67.1 | 66.3 | 65.4 |
| SP690 | 87.6 | 95.1 | 67.1 | 67.9 | 100.0 | 87.2 | 87.0 | 69.2 |
| SP722 | 86.2 | 86.6 | 68.8 | 67.1 | 87.2 | 100.0 | 86.8 | 70.8 |
| AA560 | 95.5 | 86.0 | 66.9 | 66.3 | 87.0 | 86.8 | 100.0 | 68.3 |
| LAT | 68.1 | 69.4 | 80.7 | 65.4 | 69.2 | 70.8 | 68.3 | 100.0 |

The skilled artisan will appreciate that percent identities can be determined from the literature, or by any means disclosed herein or known in the art. For instance, the *B. licheniformis* alpha-amylase (LAT) (SEQ ID NO: 7) has been found to be about 81% homologous with the *B. amyloliquefaciens* alpha-amylase (SEQ ID NO: 9) and about 65% homologous with the *G. stearothermophilus* alpha-amylase (BSG) (SEQ ID NO: 1). Further homologous alpha-amylases include SP690 and SP722 disclosed in WO 95/26397, as well as the #707 alpha-amylase derived from *Bacillus* spp. (SEQ ID NO: 6), described by Tsukamoto et al., *Biochemical and Biophysical Research Communications*, 151 (1988), pp. 25-31. The KSM AP1378 alpha-amylase is disclosed in WO 97/00324 (from KAO Corporation).

4.2 Parent Alpha-Amylases

AmyS-like alpha-amylases, as defined above, may be used as a parent alpha-amylase. In a preferred embodiment, the parent alpha-amylase is derived from *G. stearothermophilus*, e.g., one of those referred to above, such as the *G. stearothermophilus* alpha-amylase having the amino acid sequence shown in SEQ ID NO: 1 or 2.

4.3 Parent Hybrid Alpha-Amylases

The parent alpha-amylase (i.e., backbone alpha-amylase) may also be a hybrid alpha-amylase, i.e., an alpha-amylase that comprises a combination of partial amino acid sequences derived from at least two alpha-amylases.

The parent hybrid alpha-amylase may be one, which on the basis of amino acid homology (identity) and/or DNA hybridization (as defined above) can be determined to belong to the AmyS-like alpha-amylase family described above. In such a case, the hybrid alpha-amylase is typically composed of at least one part of a AmyS-like alpha-amylase and part(s) of one or more other alpha-amylases selected from AmyS-like alpha-amylases or non-AmyS-like alpha-amylases of microbial (bacterial or fungal) and/or mammalian origin.

Thus, the parent hybrid alpha-amylase may comprise a combination of partial amino acid sequences deriving from at least two AmyS-like alpha-amylases, or from at least one AmyS-like and at least one non-AmyS-like bacterial alpha-amylase, or from at least one AmyS-like and at least one fungal alpha-amylase. The AmyS-like alpha-amylase from which a partial amino acid sequence derives, may be any of the specific AmyS-like alpha-amylase referred to herein.

For instance, the parent alpha-amylase may comprise a C-terminal part of an alpha-amylase derived from a strain of *B. licheniformis*, and a N-terminal part of an alpha-amylase derived from a strain of *G. stearothermophilus* or from a strain of *G. stearothermophilus* (BSG).

5. Homology

Identity

Homology may be determined as the degree of identity between two sequences indicating a relationship there between, e.g. a derivation of the first sequence from the second or vice versa. The homology may be determined by visual inspection or manual calculations, but more conveniently by means of computer programs known in the art, such as GAP, a program provided in the GCG program package (described above). Thus, Gap GCG v8 may be used, for example with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, (1970), *J. Mol. Biol.* 48: 443-453, to make alignments and to calculate the identity.

A structural alignment between Spezyme Xtra (SEQ ID NO: 2) and, e.g., another alpha-amylase may be used to identify equivalent/corresponding positions in other AmyS-like alpha-amylases. One method of obtaining said structural alignment is to use the Pile Up program from the GCG package using default values of gap penalties, i.e., a gap creation penalty of 3.0 and gap extension penalty of 0.1. Other structural alignment methods include the hydrophobic cluster analysis (Gaboriaud et al., *FEBS Lett.* 224: 149-155, 1987) and reverse threading (Huber, T; Torda, A E, *Protein Sci.* 7(1): 142-149, 1998).

6. Hybridization

The oligonucleotide probe used in the characterization of the AmyS-like alpha-amylase above may suitably be prepared on the basis of the full or partial nucleotide or amino acid sequence of the alpha-amylase in question.

Suitable conditions for assessing hybridization involve pre-soaking in 5×SSC and pre-hybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridization method can be found in Sambrook et al., MOLECULAR CLONING: A LABORATORY MANUAL, $2^{nd}$ Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

7. General Mutations in Variant Alpha-Amylases

A variant described herein may, in one embodiment, comprise one or more modifications in addition to those outlined above. Thus, it may be advantageous that one or more proline residues (Pro) present in the part of the alpha-amylase variant that is modified is/are replaced with a non-proline residue which may be any of the possible, naturally occurring non-proline residues, and which preferably is an alanine, glycine, serine, threonine, valine or leucine.

Analogously, in one embodiment, one or more cysteine residues present in the parent alpha-amylase may be replaced with a non-cysteine residue such as serine, alanine, threonine, glycine, valine or leucine.

It is to be understood that the variants may incorporate two or more of the above outlined modifications.

Furthermore, it may be advantageous to introduce mutations in one or more of the following positions (using SEQ ID NO: 7 for the numbering):

M15, V128, A111, H133, W138, T149, M197, N188, A209, A210, H405, T412, in particular the following single, double, triple, or multi mutations:

M15X, in particular M15T,L;
V128X, in particular V128E;
H133X, in particular H133Y;
N188X, in particular N188S,T,P;
M197X, in particular M197T,L;
A209X, in particular A209V;
M197T/W138F; M197T/138Y; M15T/H133Y/N188S;
M15N128E1H133Y/N188S; E119C/S130C; D124C/R127c; H133Y/T149I;
G475R, H133Y/S187D; H133Y/A209V.

In the case of the parent alpha-amylase having the amino acid sequence shown in SEQ ID No. 7, relevant amino acid residues which may be deleted or substituted with a view to improving the oxidation stability include the single cysteine residue (C363) and the methionine residues located in positions M8, M9, M96, M200, M206, M284, M307, M311, M316 and M438 in SEQ ID NO: 2.

With respect to increasing the thermal stability of an alpha-amylase variant relative to its parent alpha-amylase, it appears to be particularly desirable to delete at least one, and preferably two, or even three, of the following amino acid residues in the amino acid sequence shown in SEQ ID NO: 2: F178, R179, G180, I181, G182 and K183.

Particularly interesting pair-wise deletions of this type are R179*+G180*; and I181*+G182*(SEQ ID No. 16 or 15, respectively) (or equivalents of these pair-wise deletions in another alpha-amylase meeting the requirements of a parent alpha-amylase in the context of the present disclosure).

Other residues of interest include N193F and V416G in the amino acid sequence shown in SEQ ID No. 2.

8. Altered Properties of Variants

8.1 General

The following section describes the relationship between mutations, which are present in a variant described herein, and desirable alterations in properties (relative to those of a parent AmyS-like alpha-amylase), which may result therefrom.

Described herein are AmyS-like alpha-amylases with altered properties. Parent alpha-amylases specifically contemplated herein are AmyS-like alpha-amylases and parent hybrid AmyS-like alpha-amylases.

In one embodiment, the *Geobacillus stearothermophilus* alpha-amylase (SEQ ID NO: 2) is used as the starting point, but in other embodiments, the SP722, BLA, BAN, AA560, SP690, KSM AP1378, #707 and other *Bacillus* alpha-amylases may be used. Amino acid positions corresponding to positions in SEQ ID NO: 2 are readily determined in accordance herewith.

The skilled artisan will appreciate that while any parent alpha-amylase could be used as a reference amylase for the purpose of numbering/identifying the amino acid residues modified or to be modified in a particular variant, SEQ ID NO: 1 is presently a preferred sequence for such purpose, because it is the longest *B. stearothermophilus* sequence presently available herein.

In one aspect, this disclosure relates to variant with altered properties, e.g., as described above.

In one of its several aspects, this disclosure provides a variant of a parent *G. stearothermophilus* alpha-amylase, comprising an alteration at one or more positions (using e.g., SEQ ID NO: 1 for the amino acid numbering) selected from the group of:

P17, D19, T21, N28, S51, G72, V74, A82, Q86, Q89, A93, G95, Q97, W115, D117, P123, S124, D125, N127, I130, G132, Q135, P145, G146, G148, S153, Y159, W166, S169, K171, W187, P209, N224, S242, G256, D269, N271, T278, N281, G302, A304, R308, T321, Q358, P378, S382, K383, T398, H405, T417, E418, P420, G421, P432, W437, G446, G454, S457, T459, T461, S464, G474, R483, wherein (a) the alteration(s) are independently (i) an insertion of an amino acid downstream of the amino acid that occupies the position; (ii) a deletion of the amino acid that occupies the position; or (iii) a substitution of the amino acid that occupies the position with a different amino acid, (b) the variant has alpha-amylase activity, and (c) each position corresponds to a position of the amino acid sequence of the parent amylase, e.g., a *G. stearothermophilus* alpha-amylase, e.g., having the amino acid sequence shown in SEQ ID NO: 2, e.g., a truncated alpha-amylase that is available commercially as SPEZYME XTRA from Genencor.

Specifically contemplated herein are S242A, S242Q, S242N and S242E variants.

Additionally, residues R179, G180, I181, G182, and K183 were chosen to explore the effect of mutations in the calcium-sodium binding region, and P245 was chosen because a proline in the middle of an alpha-helix is unusual.

Corresponding positions in other parent AmyS-like alpha-amylases can be found by alignment as described above, for example, as with those sequences shown in the alignment in FIG. 4. Thus, variants of a parent AmyS-like alpha-amylase, comprising an alteration at one or more of the above enumerated positions (using, e.g., SEQ ID NO: 1 for comparative amino acid numbering) is contemplated herein.

8.2 Altered Properties: Stability

In the context of the variants described herein, mutations (including amino acid substitutions and deletion) of importance with respect to achieving altered stability, in particular improved stability (i.e., higher or lower), at especially high temperatures (i.e., 70-120° C.) and/or extreme pH (i.e. low or high pH, i.e, pH 4-6 or pH 8-11, respectively), in particular at free (i.e., unbound, therefore in solution) calcium concentrations below 60 ppm, include any of the mutations listed in the "Altered Properties" section. The stability may be determined as described in the "Methods" section below.

8.3 Altered Properties: $Ca^{2+}$ Stability

Altered $Ca^{2+}$ stability means the stability of the enzyme under $Ca^{2+}$ depletion has been improved, i.e., higher or lower stability, relative to the parent enzyme. In the context of the presently described variants, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the "Altered Properties" section.

8.4 Altered Properties: Specific Activity

In a further aspect, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section. The specific activity may be determined as described in the "Methods" section below.

8.5 Altered Properties: Oxidation Stability

The described variants may have altered oxidation stability, in particular higher oxidation stability, in comparison to the parent alpha-amylase. Increased oxidation stability is advantageous in, e.g., detergent compositions and decreased oxidation stability may be advantageous in compositions intended for starch liquefaction. Oxidation stability may be determined as described in the "Methods" section below.

8.6 Altered Properties: Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues.

Preferred specific mutations/substitutions include those listed above in the section "Altered Properties" for the positions in question. Suitable assays are described in the "Methods" section below.

8.7 Altered Properties: Wash Performance

Important positions and mutations with respect to obtaining variants with improved wash performance at especially high pH (i.e., pH 8.5-11) include the specific mutations/substitutions listed above in the section "Altered Properties" for the positions in question. The wash performance may be tested as described below in the "Methods" section.

9. Methods of Preparing α-Amylase Variants

Methods for introducing mutations into genes are known in the art, as are cloning methods for α-amylase-encoding DNA sequences. Such methods including methods for generating mutations at specific sites within the α-amylase-encoding sequence will be discussed below.

9.1 Cloning a DNA Sequence Encoding an α-Amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. If the amino acid sequence of the α-amylase is known, homologous, labeled oligonucleotide probes may be synthesized and used to identify α-amylase-encoding clones from a genomic library prepared from the organism in question. Alternatively, a labeled oligonucleotide probe containing sequences homologous to a known α-amylase gene can be used as a probe to identify α-amylase-encoding clones, e.g., using hybridization and washing conditions of lower stringency.

Another method for identifying α-amylase-encoding clones is based on inserting fragments of genomic DNA into an expression vector, such as a plasmid, transforming a-amylase-negative bacteria with the resulting genomic DNA library, and plating the transformed bacteria onto agar containing a substrate for α-amylase, thereby allowing clones expressing the α-amylase to be readily identified.

Alternatively, the DNA sequence encoding the enzyme may be prepared synthetically by established, standard methods, e.g. the phosphoamidite method described by S. L. Beaucage and M. H. Caruthers, *Tetrahedron Letters* 22: 1859-1869 (1981) or the method described by Matthes et al., *EMBO J.* 3:801-895 (1984). In the phosphoamidite method, oligonucleotides are synthesized, e.g., in an automatic DNA synthesizer, purified, annealed, ligated, and cloned in appropriate vectors.

Finally, the DNA sequence may be of mixed origin comprising e.g., genomic and synthetic sequences, synthetic and cDNA sequences, or genomic and cDNA sequences, prepared by ligating fragments of synthetic, genomic, or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. *EMBO J.* 3:801-895 (1988).

9.2 Site-Directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. Biotechnology 2:636-639 (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long, *Analytical Biochem.*, 180:147-151 (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

The skilled artisan will appreciate that many alternative methods are available for providing or obtaining variants herein. For example, gene shuffling, e.g., as described in WO 95/22625 (from Affymax Technologies N.V.) or in WO 96/00343 (from Novo Nordisk A/S), or other corresponding techniques resulting in hybrid enzymes comprising the mutation(s), e.g., substitution(s) and/or deletion(s), in question.

9.3 Expression of Alpha-Amylase Variants

A DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant for use herein may be any vector, which may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage, an extrachromosomal element, a minichromosome, or an artificial chromosome. Alternatively, the vector may be integrated into the host cell genome and replicated together with the chromosome(s) into which it has been integrated.

In the vector, the DNA sequence should be operably-connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant for use herein, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Geobacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

Expression vectors for use herein may also comprise a suitable transcription terminator and, in eukaryotes, polyadenylation sequences operably-connected to the DNA sequence encoding the alpha-amylase variant. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pU702.

The vector may also comprise a selectable marker, e.g. a gene the product of which complements a defect in the host cell, such as the dal genes from *B. subtilis* or *B. licheniformis*, or one that confers antibiotic resistance such as ampicillin, kanamycin, chloramphenicol or tetracyclin resistance. Furthermore, the vector may comprise *Aspergillus* selection markers such as amdS, argB, niaD, and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a pre-region permitting secretion of the expressed protease into the culture medium. If desirable, this pre-region may be replaced by a different pre-region or signal sequence, conveniently accomplished by substitution of the DNA sequences encoding the respective pre-regions.

The procedures used to ligate a DNA construct encoding an alpha-amylase variant, the promoter, terminator and other elements, respectively, and to insert them into suitable vectors containing the information necessary for replication, are well known to persons skilled in the art (cf., for instance, Sambrook et al., MOLECULAR CLONING: A LABORATORY MANUAL, $2^{nd}$ Ed., Cold Spring Harbor, 1989).

Cells for use herein, e.g. comprising a DNA construct or an expression vector as defined above, can be used as host cells in the recombinant production of an alpha-amylase variant. The cell may be transformed with a DNA construct encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Cells for use herein may be cells of a higher organism such as a mammal or an insect, but are preferably microbial cells, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulars, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

Where used for expression, a yeast may favorably be selected from a species of *Saccharomyces* or *Schizosaccharomyces*, e.g. *Saccharomyces cerevisiae*. A filamentous fungus may advantageously be selected from a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the disclosure relates to a method of producing an alpha-amylase variant, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant. Suitable media are available from commercial suppliers or may be prepared according to published recipes (e.g., as described in catalogues of the ATCC).

The alpha-amylase variant secreted from the host cells may be recovered from the culture medium by known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

9.4 Methods for Characterizing and Screening Variants

9.4.1 Filter Screening Assays

The below assays may be used to screening of AmyS-like alpha-amylase variants having altered stability at high or low pH and/or under $Ca^{2+}$ depleted conditions compared to the parent enzyme and AmyS-like alpha-amylase.

9.4.2 High pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 micro g/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycine-NaOH buffer, pH 8.6-10.6 and incubated at room temperature (can be altered from 10-60° C.) for 15 min. The cellulose acetate filters with colonies are stored on the TY-plates at room temperature until use. After incubation, residual activity is detected on plates containing 1% agarose, 0.2% starch in glycine-NaOH buffer, pH 8.6-10.6. The assay plates with nitrocellulose filters are marked the same way as the filter sandwich and incubated for 2 hours at room temperature. After removal of the filters, the assay plates are stained with 10% Lugol solution. Starch degrading variants are detected as white spots on dark blue background and then identified on the storage plates. Positive variants are rescreened twice under the same conditions as the first screen.

9.4.3 Low Calcium Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with a relevant antibiotic, e.g., kanamycin or chloramphenicol, at 37° C. for at least 21 hours. The cellulose-acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

9.4.4 Low pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dasseli Germany) on TY agar plates with 10 micro g/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild-type backbone) or at 85° C. for 60 minutes (when screening for variants of the parent alpha-amylase). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters, the assay plates are stained with 10% Lugol solution. Starch degrading variants are detected as white spots on dark blue background and then identified on the storage plates. Positive variants are re-screened twice under the same conditions as the first screen.

9.4.5 Secondary Screening

Positive transformants after rescreening are picked from the storage plate and tested in a secondary plate assay. Positive transformants are grown for 22 hours at 37° C. in 5 mL LB+chloramphenicol. The *Bacillus* culture of each positive transformant and as a control a clone expressing the corresponding backbone are incubated in citrate buffer, pH 4.5 at 90° C. and samples are taken at 0, 10, 20, 30, 40, 60 and 80 minutes. A 3 µL sample is spotted on an assay plate. The assay plate is stained with 10% Lugol solution. Improved variants are seen as variants with higher residual activity (detected as halos on the assay plate) than the backbone. The improved variants are determined by nucleotide sequencing.

9.4.6 Stability Assay of Unpurified Variants

The stability of the variants may be assayed as follows: *Bacillus* cultures expressing the variants to be analyzed are grown for 21 hours at 37° C. in 10 mL LB with chloramphenicol. 800 microliter culture is mixed with 200 microliter citrate buffer, pH 4.5. A number of 70 µL aliquots corresponding to the number of sample time points are made in PCR tubes and incubated at 70° C. or 90° C. for various time points (typically 5, 10, 15, 20, 25 and 30 minutes) in a PCR machine. The 0 min sample is not incubated at high temperature. Activity in the sample is measured by transferring 20 microliter to 200 microliter of the alpha-amylase PNP-$G_7$ substrate MPR3 ((Boehringer Mannheim Cat. No. 1660730) as described below under "Assays for Alpha-Amylase Activity". Results are plotted as percentage activity (relative to the 0 time point) versus time, or stated as percentage residual activity after incubation for a certain period of time.

9.4.7 Fermentation and Purification of Alpha-Amylase Variants

A *B. subtilis* strain harboring the relevant expression plasmid may be fermented and purified as follows: The strain is streaked on a LB-agar plate with 10 µg/ml kanamycin from −80° C. stock, and grown overnight at 37° C. The colonies are transferred to 100 mL PS-1 media supplemented with 10 µg/ml chloramphenicol in a 500 mL shaking flask.

| Composition of PS-1 medium | |
|---|---|
| Pearl sugar | 100 g/l |
| Soy Bean Meal | 40 g/l |
| $Na_2HPO_4$, 12 $H_2O$ | 10 g/l |
| Pluronic ™ PE 6100 | 0.1 g/l |
| $CaCO_3$ | 5 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM acetate pH 5.5. The UF-filtrate is applied on an S-SEPHAROSE F.F. and elution is carried out by step elution with 0.2M NaCl in the same buffer. The eluate is dialyzed against 10 mM Tris, pH 9.0 and applied on a Q-SEPHAROSE F.F. and eluted with a linear gradient from 0-0.3M NaCl over 6 column volumes. The fractions that contain the activity (measured by the PHADEBAS assay) are pooled, pH was adjusted to pH 7.5 and remaining color was removed by treatment with 0.5% w/v active charcoal in 5 minutes.

9.4.8 Specific Activity Determination

The specific activity is determined using the PHADEBASO assay (Magle Life Sciences) as activity/mg enzyme. The manufactures instructions are followed (see also below under "Assay for Alpha-Amylase Activity).

9.4.9 Determination of Isoelectric Point

The pI is determined by isoelectric focusing (ex: Pharmacia, Ampholine, pH 3.5-9.3).

9.4.10 Stability Determination

The amylase stability may be measured using the method as follows:

The enzyme is incubated under the relevant conditions. Samples are taken at various time points, e.g., after 0, 5, 10, 15 and 30 minutes and diluted 25 times (same dilution for all taken samples) in assay buffer (50 mM Britton buffer pH 7.3) and the activity is measured using the PHADEBAS assay (Magle Life Sciences) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

9.4.11 Assays for Alpha-Amylase Activity

1. PHADEBAS Assay

Alpha-amylase activity is determined by a method employing PHADEBAS® tablets as substrate. PHADEBAS tablets (PHADEBAS® Amylase Test, supplied by Magle Life Sciences) contain a cross-linked insoluble blue-colored starch polymer, which has been mixed with bovine serum albumin and a buffer substance and tablet.

For every single measurement one tablet is suspended in a tube containing 5 m L50 mM Britton-Robinson buffer (50 mM acetic acid, 50 mM phosphoric add, 50 mM boric acid, 0.1 mM $CaCl_2$, pH adjusted to the value of interest with NaOH). The test is performed in a water bath at the temperature of interest. The alpha-amylase to be tested is diluted in 50 mM Britton-Robinson buffer. One milliliter of this alpha-amylase solution is added to the 5 mL 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 mm. In this absorbance range, there is linearity between activity and absorbance (Lambert-Beer law). The dilution of the enzyme must therefore be adjusted to fit this criterion. Under a specified set of conditions (temp., pH, reaction time, buffer conditions), 1 mg of a given alpha-amylase will hydrolyze a certain amount of substrate and a blue color will be produced. The color intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-$G_7$ substrate. PNP-$G_7$ which is a abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow color and thus can be measured by visible spectrophotometry at $\lambda$=405 nm (400-420 nm). Kits containing PNP-$G_7$ substrate and alpha-Glucosidase is manufactured by Boehringer-Mannheim (cat. No. 1054635).

To prepare the reagent solution 10 mL of substrate/buffer solution is added to 50 mL enzyme/buffer solution as recommended by the manufacturer. The assay is performed by transferring 20 micro l sample to a 96 well microtitre plate and incubating at 25° C. 200 μL reagent solution pre-equilibrated to 25° C. is added. The solution is mixed, and pre-incubated 1 minute, and absorption is measured every 30 seconds over 4 minutes at OD 405 nm in an ELISA reader.

The slope of the time dependent absorption-curve is directly proportional to the activity of the alpha-amylase in question under the given set of conditions.

9.4.12 Determination of LAS Sensitivity

The variant is incubated with different concentrations of LAS (linear alkyl benzene sulphonate; Nansa 1169/P) for 10 minutes at 40° C.

The residual activity is determined using the PHADEBAS® assay method or the alternative method employing the PNP-$G_7$ substrate.

LAS is diluted in 0.1 M phosphate buffer pH 7.5.

The following concentrations are used:

500 ppm, 250 ppm, 100 ppm, 50 ppm, 25 ppm, and 10 ppm on no LAS.

The variant is diluted in the different LAS buffers to concentration of 0.01-5 mg/l in a total volume of 10 mL and incubated for 10 minutes in a temperature controlled water bath. The incubation is stopped by transferring a small aliquot into cold assay buffer. It is important that during activity measurement the LAS concentration is below 1 ppm, in order not to affect the activity measurement. The residual activity is determined in duplicate using the above mentioned PHADEBAS® assay or alternative method. The activity is measured after subtraction of the blank. The activity with no LAS is 100%.

10. Methods of Using the Amylase Variants: Industrial Applications

The alpha-amylase variants presented herein possess valuable properties allowing for a variety of industrial applications. One or more of the variant enzymes or compositions described herein may also be used in detergents, in particular laundry detergent compositions and dishwashing detergent compositions, hard surface cleaning compositions, and in composition for desizing of textiles, fabrics or garments, for production of pulp and paper, beer making, ethanol production, and starch conversion processes as described above.

One or more of the variants with altered properties may be used for starch processes, in particular starch conversion, especially liquefaction of starch (see, e.g., U.S. Pat. No. 3,912,590, EP Patent Application Nos. 252,730 and 63,909, WO 99/19467, and WO 96/28567 all references hereby incorporated by reference). Also contemplated are compositions for starch conversion purposes, which may also comprise a glucoamylase, pullulanase, and/or other alpha-amylase(s).

Further, one or more of the variants are also particularly useful in the production of sweeteners and ethanol (see, e.g., U.S. Pat. No. 5,231,017 hereby incorporated by reference), such as fuel, drinking and industrial ethanol, from starch or whole grains.

The variants herein may also be useful for desizing of textiles, fabrics, and garments (see, e.g., WO 95/21247, U.S. Pat. No. 4,643,736, EP 119,920 hereby incorporated by reference), beer making or brewing, and in pulp and paper production or related processes.

10.1 Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice.

10.2 Starch Conversion

Conventional starch-conversion processes, such as liquefaction and saccharification processes are described, e.g., in U.S. Pat. No. 3,912,590 and EP Patent Publications Nos. 252,730 and 63,909, each of which are hereby incorporated by reference herein.

In an embodiment, the conversion process degrading starch to lower molecular weight carbohydrate components such as sugars or fat replacers includes a debranching step.

10.3 Starch to Sugar Conversion

In the case of converting starch into a sugar, the starch is depolymerized. Such a depolymerization process consists of, e.g., a pre-treatment step and two or three consecutive process steps, viz a liquefaction process, a saccharification process, and depending on the desired end-product, an optional isomerization process.

10.4 Isomerization

When the desired final sugar product is, e.g., high fructose syrup the dextrose syrup may be converted into fructose. After the saccharification process, the pH is increased to a value in the range of 6-8, preferably pH 7.5, and the calcium is removed by ion exchange. The dextrose syrup is then converted into high fructose syrup using, e.g., an immobilized glucose isomerase (such as Gensweet® IGI-HF).

10.5 Ethanol Production, Other Fermentation

In general, alcohol production (ethanol) from whole grain can be separated into 4 main steps:

Milling
Liquefaction
Saccharification
Fermentation

10.6 Milling

The grain is milled in order to open up the structure and allow for further processing. Two processes used are wet or dry milling. In dry milling, the whole kernel is milled and used in the remaining part of the process. Wet milling gives a very good separation of germ and meal (starch granules and protein) and is with a few exceptions applied at locations where there is a parallel production of syrups.

10.7 Liquefaction

In the liquefaction process the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

During a typical enzymatic liquefaction, the long-chained starch is degraded into branched and linear shorter units (maltodextrins) by an alpha-amylase. Enzymatic liquefaction is generally carried out as a three-step hot slurry process. The slurry is heated to between 60-95° C. (preferably 77-86° C., 80-85° C., and 83-85° C.) and the enzyme(s) is (are) added. The liquefaction process is carried out at 105-110° C. for 5 to 10 minutes followed by 1-2 hours at 95° C. The pH is generally between 5.5 and 6.2. In order to ensure optimal enzyme stability under these conditions, 1 mM of calcium is added (to provide about 40 ppm free calcium ions). After such treatment, the liquefied starch will have a "dextrose equivalent" (DE) of 10-15.

The slurry is subsequently jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

10.8 Saccharification and Fermentation

Liquefied starch-containing material is saccharified in the presence of saccharifying enzymes such as glucoamylases. The saccharification process may last for 12 hours to 120 hours (e.g. 12 to 90 hours, 12 to 60 hours and 12 to 48 hours). However, it is common to perform a pre-saccharification step for about 30 minutes to 2 hours (e.g., 30 to 90 minutes) in a temperature range of 30 to 65° C. and typically around 60° C. which is followed by a complete saccharification during fermentation referred to as simultaneous saccharification and fermentation (SSF). The pH is usually between 4.2-4.8, preferably pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by addition of a glucoamylase (e.g., OPTIDEX® L-400) and a debranching enzyme, such as an isoamylase (U.S. Pat. No. 4,335,208) or a pullulanase. The temperature is lowered to 60° C., prior to addition of the glucoamylase and debranching enzyme are added. The saccharification process proceeds for 24-72 hours.

Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc p$\alpha$1-6Glc p$\alpha$1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Fermentable sugars, (e.g. dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In a preferred embodiment, the fermentable sugars obtained during the liquefaction process steps are used to produce alcohol and particularly ethanol. In ethanol production, a SSF process is commonly used wherein the saccharifying enzymes and fermenting organisms (e.g., yeast) are added together and then carried out at a temperature of 30° C. to 40° C.

The organism used in fermentations will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g. to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, preferably around pH 4-5.

The fermentation may include, in addition to a fermenting microorganisms (e.g. yeast), nutrients, and additional enzymes, including phytases. The use of yeast in fermentation is well known and reference is made to THE ALCOHOL TEXTBOOK, K. JACQUES ET AL, EDS. 1999, NOTTINGHAM UNIVERSRRY PRESS, UK.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

10.9 Beer Making

The variant alpha-amylases provided for herein may also be very useful in a beer-making process and similar fermentations; the alpha-amylases will typically be added during the mashing process. The process is substantially similar to the milling, liquefaction, saccharification, and fermentation processes described above.

10.10 Using Amylase Variants for Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of phytase and optionally alpha-amylase to the slurry. In a preferred embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5. As a further example, Table B below illustrates the pH change that occurs with addition of increasing amounts of thin stillage to a whole ground corn slurry (32% ds) after stirring for 2 hours at 155° F.

TABLE B

| Thin stillage w/w % | Final pH |
|---|---|
| 0 | 5.52 |
| 20 | 5.29 |
| 40 | 5.16 |
| 50 | 5.09 |
| 60 | 5.05 |
| 80 | 4.98 |
| 100 | 4.94 |

During ethanol production, acids can be added to lower the pH in the beer well, to reduce the risk of microbial contamination prior to distillation.

In some embodiments, phytase is added to the slurry. In other embodiments, in addition to phytase, alpha-amylase is added to the slurry. In some embodiments, phytase and alpha-amylase are added to the slurry sequentially. In other embodiments, phytase and alpha-amylase are added simultaneously. In some embodiments, the slurry comprising phytase and optionally, alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C., (e.g. 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g. 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% ds, the pH is in the range of 4.8 to 5.2, and the slurry is incubated with a phytase and optionally an alpha-amylase for 5 minutes to 2 hours, at a temperature range of 60 to 75° C.

Currently, it is believed that commercially-available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at a pH of less than about 4.0.

In a further liquefaction step, the incubated or pretreated starch-containing material is exposed to an increase in temperature such as about 0 to about 45° C. above the starch gelatinization temperature of the starch-containing material (e.g. 70° C. to 120° C., 70° C. to 110° C., and 70° C. to 90° C.) for a period of time of about 2 minutes to about 6 hours (e.g. 2 minutes to 4 hrs, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch maybe further hydrolyzed at a temperature ranging from about 75° C. to 95° C., (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

10.11 Distillation

Optionally, following fermentation, alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

10.12 By-Products

Left over from the fermentation is the grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

10.13 Pulp and Paper Production

The variant alkaline alpha-amylase may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase variants are especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The alpha-amylases may also be very useful in modifying starch where enzymatically modified starch is used in papermaking together with alkaline fillers such as calcium carbonate, kaolin and clays. With the alkaline alpha-amylase variants it is possible to modify the starch in the presence of the filler thus allowing for a simpler integrated process.

10.14 Desizing of Textiles, Fabrics and Garments

An alpha-amylase variant may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylase variants as they have an improved performance in alkaline solutions. The alpha-amylases may be used alone or in combination with a cellulase when desizing cellulose-containing fabric or textile.

Desizing and bleaching processes are well known in the art. For instance, such processes are described in e.g., WO 95/21247, U.S. Pat. No. 4,643,736, EP 119,920 hereby incorporated by reference.

Commercially available products for desizing include OPTISIZE® FLEX from Genencor.

10.15 Cleaning Processes and Detergent Compositions

The variant alpha-amylases described herein may be added to and thus become a component of a detergent composition for various cleaning or washing processes, including laundry and dishwashing.

The detergent composition provided for herein may for example be formulated as a hand or machine laundry detergent composition, including a laundry additive composition suitable for pretreatment of stained fabrics and a rinse added fabric softener composition or be formulated as a detergent composition for use in general household hard surface cleaning operations, or be formulated for hand or machine dishwashing operations.

In a specific aspect, there is provided for herein a detergent additive comprising a variant enzyme described herein. The detergent additive as well as the detergent composition may comprise one or more other enzymes such as a protease, a lipase, a peroxidase, another amylolytic enzyme, e.g., another alpha-amylase, glucoamylase, maltogenic amylase, CGTase and/or a cellulase mannanase (such as MANNASTAR™ from Danisco US Inc., Genencor Division)), pectinase, pectin lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the *Fusarium* protease described in WO 89/06270 and WO 94/25583.

Preferred commercially available protease enzymes include ALCALASE®, SAVINASE®, PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3®, FN4® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas lipase*, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* spp. strain SD 705 (WO 95/06720 and WO 96/27002), *P. wisconsinensis* (WO 96/12012), a *Bacillus lipase*, e.g., from *B. subtilis* (Dartois et al. (1993), *Biochemica et Biophysica Acta*, 1131, 253-360), *B. stearothermophilus* (JP 64/744992) or *B. pumilus* (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASET™ and LIPOLASE ULTRA™ (Novozymes A/S).

Amylases: One or more additional amylases may also be included. Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful alpha-amylases are the variants described in WO 94/18314, WO 96/39528, WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available alpha-amylases are DURAMYL™, LIQUEZYME™ TERMAMY™, NATALASE™, FUNGAMYL™ and BAN™ (Novozymes A/S), RAPIDASE™ and PURASTAR™ (from Genencor).

Cellulases: Suitable cellulases include those of bacterial or fungal origin. Chemically modified or protein engineered mutants are included. Suitable cellulases include cellulases from the genera *Bacillus, Pseudomonas, Trichoderma, Humicola, Fusarium, Thielavia, Acremonium*, e.g., the fungal cellulases produced from *Humicola, insolens, Myceliophthora thermophila* and *Fusarium oxysporum* disclosed in U.S. Pat. No. 4,435,307, U.S. Pat. No. 5,648,263, U.S. Pat. No. 5,691, 178, U.S. Pat. No. 5,776,757 and WO 89/09259. The *Trichoderma reesei* cellulases are disclosed in U.S. Pat. No. 4,689, 297, U.S. Pat. No. 5,814,501, U.S. Pat. No. 5,324,649, WO 92/06221 and WO 92/06165. *Bacillus* cellulases are disclosed in U.S. Pat. No. 6,562,612.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME® (Novozymes A/S).

The detergent enzyme(s) may be included in a detergent composition by adding separate additives containing one or more enzymes, or by adding a combined additive comprising all of these enzymes. A detergent additive, e.g., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols, fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste or a liquid. A liquid detergent may be aqueous, typically containing up to about 70% water and 0 to about 30% organic solvent, or non-aqueous.

The detergent composition comprises one or more surfactants, which may be non-ionic including semi-polar and/or anionic and/or cationic and/or zwitterionic. The surfactants are typically present at a level of from about 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0 to about 65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleiclacrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxy acids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions any enzyme, in particular one or more of the variant enzymes described herein, may be added in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor.

One or more of the variant enzymes described herein may additionally be incorporated in the detergent formulations disclosed in WO 97/07202, which is hereby incorporated as reference.

10.16 Dishwashing Detergent Compositions

The enzymes may also be used in dish wash detergent compositions, including the following:

| 1) POWDER AUTOMATIC DISHWASHING COMPOSITION | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |
| 2) POWDER AUTOMATIC DISHWASHING COMPOSITION | |
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 % |
| 3) POWDER AUTOMATIC DISHWASHING COMPOSITION | |
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |
| 4) POWDER AUTOMATIC DISHWASHING COMPOSITION | |
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) Polymer | 0-3% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |
| 5) POWDER AUTOMATIC DISHWASHING COMPOSITION | |
| Nonionic surfactant | 1-7% |
| Sodium disilicate | 18-30% |
| Trisodium citrate | 10-24% |
| Sodium carbonate | 12-20% |
| Monopersulphate (2KHSO$_5$.KHSO$_4$.K$_2$SO$_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |
| 6) POWDER AND LIQUID DISHWASHING COMPOSITION WITH CLEANING SURFACTANT SYSTEM | |
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |
| 7) NON-AQUEOUS LIQUID AUTOMATIC DISHWASHING COMPOSITION | |
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |
| 8) NON-AQUEOUS LIQUID DISHWASHING COMPOSITION | |
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |
| 9) THIXOTROPIC LIQUID AUTOMATIC DISHWASHING COMPOSITION | |
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminum tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |
| 10) LIQUID AUTOMATIC DISHWASHING COMPOSITION | |
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

-continued

| 11) LIQUID AUTOMATIC DISHWASHING COMPOSITION CONTAINING PROTECTED BLEACH PARTICLES | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |
| 12) Automatic dishwashing compositions as described in 1), 2), 3), 4), 6) and 10), wherein perborate is replaced by percarbonate. | |
| 13) Automatic dishwashing compositions as described in 1)-6) which additionally contain a manganese catalyst. The manganese catalyst may, e.g., be one of the compounds described in "Efficient manganese catalysts for low-temperature bleaching", Nature 369: 637-39 (1994). | |
| 14) PREMIUM HDL LIQUID DETERGENT FORMULATIONS | |
| Bio-Soft S-101 | Linear alkylbenzene sulfonic acid |
| Steol CS-330 | Sodium Laureth sulfate |
| Bio-soft N25-7 | Linear alkylethoxylate with 7 moles of EO |
| Stepanate SXS | Sodium xylene sulfonate |
| 15) ULTRA LIQUID DETERGENT FORMULATION | |
| Tionopal CBS-X | Fluorescent whitening agent |
| Alpha-step MC-48 | Sodium alpha-sulfomethylester |
| Makon TD-6 | Tridecylalcoholethoxylate |

10.17 Use of Variants in Conjunction with Other Enzymes: Phytases

10.17.1 Use of Phytases

Phytases useful herein include enzymes capable of hydrolyzing phytates and/or phytic acid under the conditions of use, e.g., the incubation and/or liquefaction steps. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated, (e.g., as 3-phytases (EC 3.1.3.8) or as 6-phytases (EC 3.1.3.26)). A typical example of phytase is myo-inositol-hexakiphosphate-3-phosphohydrolase.

Phytases can be obtained from microorganisms such as fungal and bacterial organisms. Some of these microorganisms include e.g. Aspergillus (e.g., A. niger, A. terreus, A. ficum and A. fumigatus), Myceliophthora (M. thermophila), Talaromyces (T. thermophilus), Trichoderma spp (T. reesei), and Thermomyces (WO 99/49740). Also phytases are available from Penicillium species, e.g., P. hordei (ATCC No. 22053), P. piceum (ATCC No. 10519), or P. brevi-compactum (ATCC No. 48944). See, for example U.S. Pat. No. 6,475,762. In addition, phytases are available from Bacillus (e.g. B. subtilis, Pseudomonas, Peniophora, E. coli, Citrobacter, Enterbacter, and Buttiauxella (see e.g. WO2006/043178).

Commercial phytases are available such as NATUPHOS (BASF), RONOZYME P (Novozymes A/S), PHZYME (Danisco A/S, Diversa) and FINASE (AB Enzymes). The method for determining microbial phytase activity and the definition of a phytase unit has been published by Engelen et al. (1994) J. of AOAC International, 77: 760-764. The phytase may be a wild-type phytase, an active variant or active fragment thereof.

In one embodiment, the phytase is derived from the bacterium Buttiauxiella spp. The Buttiauxiella spp. includes B. agrestis, B. brennerae, B. ferragutiase, B. gaviniae, B. izardii, B. noackiae, and B. warmboldiae. Strains of Buttiauxella species are available from DSMZ, the German National Resource Center for Biological Material (Inhoffenstrabe 7B, 38124 Braunschweig, Germany). Buttiauxella sp. strain P1-29 deposited under accession number NCIMB 41248 is an example of a particularly useful strain from which a useful phytase may be obtained. In some embodiments, the phytase is BP-wild-type, a variant thereof (such as BP-11) disclosed in WO 06/043178, or a variant as disclosed in U.S. patent application Ser. No. 11/714,487, filed Mar. 6, 2007. For example, a BP-wild-type and variants thereof are disclosed in Table 1 of WO 06/043178, wherein the numbering is in reference to SEQ ID NO: 3 of the published PCT application.

In one preferred embodiment, a useful phytase is one having at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO: 31 shown below or an active variant thereof. More preferably, the phytase will have at least 95% to 99% sequence identity with the amino acid sequence set forth in SEQ ID NO: 31 or an active variant thereof. In some embodiments, the phytase comprises the amino acid sequence of SEQ ID NO: 31. In yet others, the phytase is SEQ ID NO: 31.

Mature Protein Sequence of Buttiauxella BP-17 Phytase (SEQ ID NO: 31)

```
NDTPASGYQV EKVVILSRHG VRAPTKMTQT MRDVTPNTWP EWPVKLGYIT

PRGEHLISLM GGFYRQKFQQ QGILSQGSCP TPNSIYVWAD VDQRTLKTGE

AFLAGLAPQC GLTIHHQQNL EKADPLFHPV KAGTCSMDKT QVQQAVEKEA

QTPIDNLNQH YIPFLALMNT TLNFSTSAWC QKHSADKSCD LGLSMPSKLS

IKDNGNKVAL DGAIGLSSTL AEIFLLEYAQ GMPQAAWGNI HSEQEWASLL

KLHNVQFDLM ARTPYIARHN GTPLLQAISN ALNPNATESK LPDISPDNKI

LFIAGHDTNI ANIAGMLNMR WTLPGQPDNT PPGGALVFER LADKSGKQYV

SVSMVYQTLE QLRSQTPLSL NQPAGSVQLK IPGCNDQTAE GYCPLSTFTR

VVSQSVEPGC QLQ
```
60

In some embodiments, the amount (dosage) of phytase used in the incubation and/or liquefaction processes is in the range of about 0.001 to 50 FTU/g ds, (e.g., in the range of about 0.01 to 25 FTU/g ds, about 0.01 to 15 FTU/g ds, about 0.01 to 10 FTU/g ds, about 0.05 to 15 FTU/g ds, or about 0.05 to 5.0 FTU/g).

10.17.2 Determination of Phytase Activity (FTU)

"Phytase Activity" ("FTU") is measured by the release of inorganic phosphate. The inorganic phosphate forms a yellow complex with acidic molybdate/vanadate reagent; and the yellow complex is measured at a wavelength of 415 nm in a spectrophotometer and the released inorganic phosphate is quantified with a phosphate standard curve. One unit of phytase (FTU) is the amount of enzyme that releases 1 micromole of inorganic phosphate from phytate per minute under the reaction conditions given in the European Standard (CEN/TC 327,2005-TC327WI 003270XX).

10.17.3 Determination of Phytic Acid Content

Phytic acid content: Phytic acid was extracted from the sample by adjusting the pH of the 5% slurry (if it is dry sample) to pH 10 and then determined by an HPLC method using an ion exchange column. Phytic acid was eluted from the column using a NaOH gradient system. Phytic acid content in the liquid was then calculated by comparing to a phytic acid standard.

11. Compositions (Blends) Comprising the Variant Alpha-Amylases

In one of its several aspects, this disclosure provides compositions comprising:

a) at least one alpha-amylase variant comprising an amino acid sequence at least 95% identical to that of a parent AmyS-like alpha-amylase, and having a substitution at an amino acid position corresponding to position 242 of a reference alpha-amylase, said variant having detectable alpha-amylase activity, and b) at least one additional enzyme.

The variant is altered, as compared to a parent AmyS-like alpha-amylase or a reference alpha-amylase, in one or more of any useful or measurable attributes including net charge, substrate specificity, substrate cleavage, substrate binding, thermal stability, activity at one or more pH's, stability at one or more pH's, stability in oxidizing conditions, $Ca^{2+}$ requirements, specific activity, catalytic rate, catalytic efficiency, activity in the presence of a phytate, thermal or pH stability in the presence of a phytate, ability to effect peak viscosity in a liquefaction test, or ability to effect final viscosity in a liquefaction test. In preferred embodiments, the variant will have more than one altered attribute, for example, improved thermostability, and the ability to reduce peak viscosity in a liquefaction, or the ability to reduce both peak viscosity and final viscosity in a liquefaction, as compared to a parent alpha-amylase, e.g. an AmyS-like amylase.

In various embodiments, the reference amylase is SEQ ID NO: 1 or 2. Other alpha-amylases can be used as the reference alpha-amylase. It is preferred that the reference alpha-amylase for use herein have a serine residue at amino acid position 242.

In various embodiments, the additional enzyme is a phytase, protease, lipase, pullulanase, glucoamylases, isomerase, or other enzymes useful in a commercial process in conjunction with an alpha-amylase. Such enzymes are known in the art in starch processing, sugar conversion, fermentations for alcohol and other useful end-products, commercial detergents and cleaning aids, stain removal, fabric treatment or desizing, and the like. Presently preferred additional enzymes are phytases. One embodiment uses a phytase that comprises SEQ ID NO: 17.

In certain embodiments, the variant is a S242A, S242D, S242E, S242F, S242G, S242H, S242L, S242M, S242N, S242Q, or S242T variant. Such variants are exemplified and characterized in the working examples provided herein.

The variant in some embodiments further comprises a sequence modification at one or more amino acid positions corresponding to amino acid positions 97, 179, 180, 193, 319, 349, 358, 416, 428, or 443 of the reference amylase, e.g., SEQ ID NO: 1 or 2. More specifically, the variant comprises one or more of substitution at positions as follows: a cysteine at 349, a cysteine at 428, a glutamic acid at 97, an arginine at 97, a glutamic acid at 319, an arginine at 319, a glutamic acid at 358, an arginine at 358, a glutamic acid at 443, or an arginine at 443. Substitution of an N193 or a V416 or both, such as a substitution of N193F or V416G, or both are useful herein for variants. Deletion of amino acids corresponding to positions 179 and 180 may also be used herein with any variant amylase.

In one embodiment of the composition, the alpha-amylase variant has at least 95% homology to SEQ ID NO: 2 and comprises a substitution of amino acid 242 relative to numbering in a reference amylase comprising the amino acid sequence SEQ ID NO: 1. As above, the variant preferably has detectable alpha-amylase activity under conditions permissive of such activity.

Useful parent amylases are discussed above. In some embodiments, the parent alpha-amylase is SEQ ID NO: 1, 2, 15, or 16. In others, the parent alpha-amylase is SEQ ID NO:6, 7, 8, 9, 10, 11, or 12.

In various embodiments, the variant amylase and the phytase are present in amounts such that the ratio of AAU:FTU is about 1:15 to about 15:1. Preferably, in some embodiments, the variant amylase and the phytase are present in amounts such that the ratio of AAU:FTU is about 1:4 to about 3:1.

12. Methods for Using Variants with Other Enzymes

In another aspect, this disclosure provides methods of using the variant alpha-amylases in conjunction with other enzymes, particularly phytases. In one embodiment, methods are provided for treating a starch slurry. The treatment can be part of a liquefaction process, a saccharification, a fermentation process, and the like. The method generally comprises the steps of a) adding at least one phytase and at least one alpha-amylase to the starch slurry, and b) incubating the starch slurry under conditions permissive of activity of the phytase and the alpha-amylase. The method encompasses any one or more adding steps such that the phytase and the alpha-amylase are added at, or about, the same time, or separately, in any order (i.e. phytase first or amylase first), with any useful amount of temporal separation between such adding steps. As with the compositions, the alpha-amylase is a variant amylase comprising an amino acid sequence at least 95% identical to that of a parent AmyS-like alpha-amylase, and having a substitution at an amino acid position corresponding to position 242 of a reference alpha-amylase. The variant has detectable alpha-amylase activity.

In one embodiment, the variant is altered, as compared to a parent AmyS-like alpha-amylase or a reference amylase, in any one or more of net charge, substrate specificity, substrate cleavage, substrate binding, thermal stability, activity at one or more pH's, stability at one or more pH's, stability in oxidizing conditions, $Ca^{2+}$ requirements, specific activity, catalytic rate, catalytic efficiency, activity in the presence of a phytate, thermal or pH stability in the presence of a phytate, ability to effect peak viscosity in a liquefaction test, and/or ability to effect final viscosity in a liquefaction test.

As discussed above, the use of phytases may impact the stability or other properties of alpha-amylases by relieving some inhibition on alpha-amylase activity due to the presence of one or more phytates in the plant material, e.g. milled grain. Without being limited to any particular theory, at least partial removal of the phytates appears to improve one or more properties of the amylase such that yield or results are improved.

Reference amylases are discussed above, and in one embodiment of the method, the reference amylase is SEQ ID NO: 1 or 2.

In various embodiments, the variant is a S242A, S242D, S242E, S242F, S242G, S242H, S242L, S242M, S242N, S242Q, or S242T variant. In others, the variant further comprises a sequence modification at one or more amino acid positions corresponding to amino acid positions 97, 179, 180, 193, 319, 349, 358, 416, 428, or 443 of the reference amylase. More particularly, the variant comprises one or more of substitution at positions as follows: a cysteine at 349, a cysteine at 428, a glutamic acid at 97, an arginine at 97, a glutamic acid at 319, an arginine at 319, a glutamic acid at 358, an arginine at 358, a glutamic acid at 443, or an arginine at 443 in various embodiments. Substitution of an N193 or a V416 or both, such as a substitution of N193F or V416G, or both are also useful in certain variants. As with the other modifications, the deletion of amino acids 179 and 180 can also be used—alone or in combination with any of the foregoing alterations.

In certain embodiments, the parent alpha-amylase is conveniently SEQ ID NO: 1, 2, 15, or 16, while in others, the parent alpha-amylase is SEQ ID NO: 6, 7, 8, 9, 10, 11, or 12.

In one embodiment, the adding step comprises addition of the phytase before the amylase. Preferably, when phytase is added first the slurry is pre-incubated after adding the phytase and before adding the alpha-amylase, e.g., for sufficient time to measurably reduce the phytate content.

In various embodiments, the inclusion of the phytase results in an increase in the thermostability of the alpha-amylase relative to a comparable method that does not include contacting the slurry with phytase.

In other applications, the phytase and the amylase are present in a single blend, such as a commercial blend, before adding to the slurry. In one presently preferred embodiment, the phytase has the amino acid sequence of SEQ ID NO: 17.

In another of its several aspects, this disclosure provides methods of producing a fermentable substrate from a starch-containing slurry comprising milled grain. The method comprises the steps of:
a) contacting the starch-containing slurry with at least one phytase and at least one alpha-amylase in an amount sufficient to produce a fermentable substrate from the starch; and
b) incubating the starch slurry under conditions permissive of activity of the phytase and the alpha-amylase for a time that allows production of the fermentable substrate; wherein when the contact with the phytase is initiated before the amylase, the slurry is incubated at a temperature that is about 0-30° C. less than the gelatinization temperature prior to contacting the slurry with the amylase, after which the temperature is raised above the gelatinization for a time effective to hydrolyze the starch.

In various embodiments, the contact with the phytase and the alpha-amylase is initiated at, or about, the same time, or separately in any order. The alpha-amylase used in such methods is a variant amylase comprising an amino acid sequence at least 95% identical to that of a parent AmyS-like alpha-amylase, and having a substitution at an amino acid position corresponding to position 242 of a reference alpha-amylase, said variant having detectable alpha-amylase activity.

The reference amylase is SEQ ID NO: 1 or 2, and the variant is a S242A, S242D, S242E, S242F, S242G, S242H, S242L, S242M, S242N, S242Q, or S242T variant in certain embodiments.

Also provided herein are kits comprising, in one or more packages provided as a unit:
i) at least one variant amylase comprising an amino acid sequence at least 95% identical to that of a parent AmyS-like alpha-amylase, and having a substitution at an amino acid position corresponding to position 242 of a reference alpha-amylase, said variant having detectable alpha-amylase activity, and
ii) at least one additional enzyme.

The kits further comprising instructions for using the enzymes in a useful process involving enzymatic cleavage of starch molecules. The kits can also further comprise one or more additional enzymes, acidulants or other compounds for adjusting the pH of a starch slurry, nutrients, cofactors, and the like.

This disclosure includes further detail in the following examples, which are not in any way intended to limit the scope of what is claimed. The figures are integral parts of the specification and description provided. All references cited are herein specifically incorporated by reference for all that is described therein. The following examples are thus offered to illustrate, but not to limit what is claimed.

EXAMPLES

Example 1

Construction of Variants

The variants at position S242 of the mature sequence of AmyS were constructed using site directed mutagenesis. The template for mutagenesis was methylated pHPLT-AmyS (see FIG. 2) using dam-Methylase from New England Biolabs (Massachusetts). Degenerate primers (S242F(forward) and S242R(reverse) SEQ ID NOS: 17 and 18 respectively, given below) were synthesized and diluted to 10 µM at Operon (Huntsville, Ala.) with complementary forward and reverse sequences both containing a 5' phosphate group for ligation in the reaction. The sequence of the parent alpha-amylase is SEQ ID NO: 2. Libraries were created with the Stratagene Quik-Change™ Multi-site kit (Stratagene, La Jolla Calif.) using oligonucleotide primers randomized with NN(G/C) at the target position. The selected amino acid (i.e., S242) was randomly replaced with all 19 possible alternatives.

S242 primers for mutagenesis:

S242 F:

5'[Phos]GTCAAGCATATTAAGTTCNNSTTTTTTC-CTGATTGGTTG 3' SEQ ID NO: 17

S242 R:

5'[Phos]CAACCAATCAGGAAAAAASNNGAACT-TAATATGCTTGAC 3' SEQ ID NO: 18

The reaction was performed as follows:
Quik-Change Reaction:
The reaction consisted of 18 µL of sterile distilled $H_2O$, 2.5 µL of 10× buffer from the kit, 1 µL dNTPs from the kit, 1.25 µL of the forward primers (of 10 µM stock), 1.25 µL of the reverse primers (of 10 µM stock), 1 µL of pHPLT-AmyS plasmid DNA as template (~70 ng), and 1 µL of the enzyme blend from the kit for a total of 26.5 µL.

Cycling Conditions:

The cycling conditions were 95° C. for 1 min once, then 95° C. for 1 min, 55° C. for 1 min, 65° C. for 10 min for 25 cycles.

One microliter Dpn I (10 U/μL) was added to the Multi-site Quik-Change™ reaction mixture and incubated at 37° C. for 18 hours and then another 0.5 μL was added for an additional 3 hours.

One microliter of DpnI digested reaction was used as template for rolling circle amplification with the TEMPLIPHI amplification kit (Amersham Biosciences, Piscataway, N.J.) and the reaction was performed according to the Amersham protocol. One microliter of rolling circle DNA was transformed into 100 μL of *Bacillus subtilis* competent cells (2 protease deleted *B. subtilis* strain (ΔaprE, ΔnprE, amyE:: xylRPxylAcomK-phleo)) and shaken at 37° C. for 1 hour. The entire transformation was next plated on LA+10 ppm Neo+ 1% insoluble starch plates (25 μL one plate, 75 μL on another plate) and incubated overnight at 37° C. Ninety-six transformants were picked into 150 μL of LB+10 ppm Neo in a micro-titer plate and grown overnight at 37° C. The overnight plate was stamped onto a large LA+10 ppm Neo+1% insoluble starch plate with a 96 pin replicating tool and submitted to Quintara Biosciences (Berkeley, Calif.) for colony PCR and sequencing.

After variant sequences were determined, the variants were picked into a 96 well micro-titer plates containing 125 μL of LB+10 ppm Neo, arraying the variants into a quad format with controls. The arrayed micro-titer plate was grown for 6 hours at 37° C. and 250 rpm. Using a replicating tool (Enzyscreen, Leiden, The Netherlands) the micro-titer culture plate was used to inoculate a new micro-titer plate (micro-titer plate and plate lids from Enzyscreen, Leiden, The Netherlands) containing 150 ul of MBD medium for protein expression (G. Vogtentanz et al., A *Bacillus subtilis* fusion protein system to produce soybean Bowman-Birk protease inhibitor, *Prot. Expr. & Purif.* 55 (2007) 40-52) and supplemented with 5 mM $CaCl_2$ for protein expression. Expression plates were grown for 64 hours at 37° C., 250 rpm, and 70% humidity. Expression cultures were next filtered through a micro-filter plate (0.22 μm, Millipore, Billerica, Mass.) and screened for improved thermostability (see Example 3).

Example 2

Expression, Purification & Characterization of Variants

Colonies were streaked from the microtiter plates from Example 1 onto starch plates with 10 ppm Neomycin. The plates were incubated overnight at 37° C. and singles colonies were picked and used to inoculate shake flasks (250 mL with 25 mL media) containing media (see below) and 20 ppm Neomycin. The cultures were grown up at 37° C., 275 rpm, for about 8 hrs (till an OD (600 nm) of 2.0 was reached). The culture broths were mixed with 50% glycerol at 2:1 ratio, put into individually-labeled culture vials and frozen at −80° C. Subsequent production of the selected alpha-amylases were made from these glycerol stocks.

Fermentations for amylases were carried out in 500 mL shake flasks grown at 37° C. for 60 hours in minimal MOPS culture medium (Neidhardt et al., *J. Bacteriol.* 119(3): 736-747, 1974) with 1% (w/v) Soytone. Enzymes were purified from the fermentation broth using hydrophobic interaction chromatography as follows: the broth was concentrated 10-fold then diluted back to its original volume with 50 mM MES, 2 mM $CaCl_2$, pH 6.8 with 1M ammonium sulfate, then sterile-filtered using glass fiber filter. Samples were then loaded onto PHENYL SEPHAROSE FF high density column (20×95 mm; Amersham, GE Healthcare Bio-Sciences, Sweden) pre-equilibrated with the same buffer. Non-amylase proteins were removed with 10 column volumes of the same buffer without ammonium sulfate followed by 5 column volumes of water. Enzymes of interest were eluted with 50 mM MES, 2 mM $CaCl_2$, pH 6.8 containing 40% propylene glycol.

Protein concentrations were determined either with a standard quantitative SDS page gel densitometry method or using an activity assay using a standard amylase assay kit from Megazyme (Wicklow, Ireland). A standard curve generated using purified amylase (Bacillus 707 amylase; SEQ ID NO: 6) was used for comparing assay data.

Example 3

Determination of Altered Properties: Thermal stress

This example shows that the variants described herein may have an altered property relative to the parent alpha-amylase. A high-throughput thermal stability screen of *G. stearothermophilus* alpha-amylase (AmyS) variants was carried out.

After an initial investigation, heat-stress conditions were chosen such that the wild-type enzyme showed approximately 40% of its initial (pre-stress) activity after the heat stress (i.e., (activity after heat stress)/(activity before heat stress) was approximately 0.4). Libraries of mutants were screened in quadruplicate, and potential winners were identified as those that showed residual activity after heat stress that was at least two standard deviations more than the average residual activity of the wild-type enzyme.

Amylase expression was approximately 100 ppm in the culture supernatants of the expression plates. After 60-65 hours of growth at 37° C. in a humidified shaker (250 rpm and 70% relative humidity), the culture supernatants were clarified to remove cellular material using filter plates. The clarified supernatants were diluted 10-fold into buffer containing 50 mM NaOAc/2.6 mM $CaCl_2$/0.002% Tween-20, pH 5.8, to a final concentration of approximately 10 ppm. One aliquot of each supernatant was further diluted to 0.02 ppm, for determination of activity of the enzyme variants as described below using a fluorescently-labeled corn starch substrate. A second aliquot of each supernatant was subjected to a 30 minute heat stress at 95° C. in a thermocycler then diluted to 0.02 ppm in 50 mM NaOAc/2.6 mM $CaCl_2$/0.002% Tween-20, pH 5.8 and assayed for residual activity using the fluorescent substrate and assay described below.

Amylase activity was determined using the amylase ENZCHECK ULTRA AMYLASE assay kit essentially as described by the manufacturer (Invitrogen, San Diego Calif.). Final concentration of the amylase in the assay was approximately 0.02 ppm. Assay buffer was 50 mM NaOAc/2.6 mM $CaCl_2$/0.002% Tween-20, pH 5.8. The substrate was BODIPY fluorescence dye conjugated 100 pg/mL DQ™ starch from corn (Invitrogen, Eugene, Oreg.). Increased fluorescence, indicating amylase activity, was measured using a SpectraMAX M2 (Molecular Devices, Sunnyvale, Calif.). The reaction was monitored at room temperature for 5 minutes with the instrument recording in kinetic mode. Excitation wavelength was 485 nm; emission was monitored at 520 nm with a cutoff filter at 515 nm.

Figure 3:
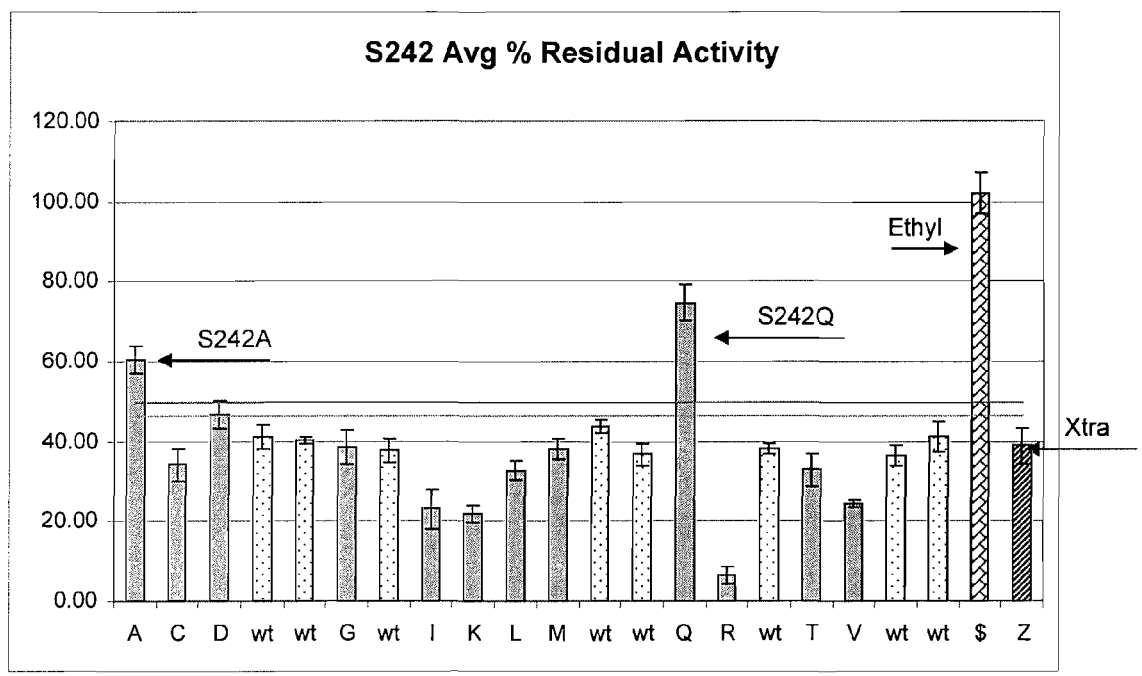
FIG. 3 shows percent residual activity of S242 variants after heat stress at 95° C. for 30 minutes. A positive control, *G. stearothermophilus* with the C-terminus truncated by 29 amino acids (i.e., SEQ ID NO: 2) with A179-180 is also shown. Lines indicate 2× and 3× above the standard deviation of the percent residual activity of the wild-type enzyme. S242A and S242Q clearly show higher residual activities than the wild-type.

The wild-type AmyS (Xtra) showed 33-43% residual activity after being subject to thermal stress for 30 minutes at 95° C. AmyS variants, S242A and S242Q, retained 55-65% and 70-80% residual activities, respectively, following the same thermal stress conditions. See FIG. 3 and Table 3-1. These residual activity measurements indicate the two variants are more thermostable than the wild-type alpha-amylase.

TABLE 3-1

Percent residual activities of each variant. Wild-type (SPEZYME XTRA). Each plate includes SPEZYME ETHYL and SPEZYME XTRA as controls as indicated.

| Variant | % Residual Activity | | | | Avg | Std. Dev |
|---|---|---|---|---|---|---|
| A | 65.0 | 53.4 | 48.5 | 71.1 | 59.5 | 10.4 |
| C | 35.9 | 24.5 | 27.3 | 29.6 | 29.3 | 4.9 |
| D | 52.2 | 32.6 | 38.5 | 43.3 | 41.6 | 8.3 |
| E | 40.2 | 53.3 | 33.2 | 51.8 | 44.6 | 9.6 |
| F | 41.7 | 31.8 | 30.1 | 31.7 | 33.8 | 5.3 |
| G | 34.3 | 27.1 | 27.4 | 37.5 | 31.6 | 5.2 |
| H | 22.6 | 20.5 | 16.2 | 17.8 | 19.3 | 2.8 |
| I | 36.2 | 26.9 | 19.7 | 25.5 | 27.0 | 6.8 |
| K | 22.3 | 22.6 | 23.3 | 23.0 | 22.8 | 0.5 |
| L | 26.1 | 29.6 | 30.6 | 27.8 | 28.5 | 2.0 |
| M | 48.8 | 46.6 | 40.5 | 35.9 | 42.9 | 5.9 |
| N | 32.0 | 29.0 | 24.6 | 35.1 | 30.2 | 4.5 |
| P | 7.2 | 7.7 | 6.4 | 5.7 | 6.7 | 0.9 |
| Q | 61.0 | 65.7 | 49.1 | 69.3 | 61.3 | 8.8 |
| R | 14.5 | 14.3 | 11.7 | 11.7 | 13.0 | 1.5 |
| wildtype | 44.3 | 27.1 | 29.2 | 35.5 | 34.0 | 7.7 |
| T | 24.6 | 25.4 | 27.7 | 21.5 | 24.8 | 2.5 |
| V | 17.5 | 25.9 | 22.1 | 23.9 | 22.3 | 3.6 |
| W | 5.0 | 6.3 | 3.9 | 7.0 | 5.6 | 1.4 |
| Y | 18.5 | 13.5 | 14.2 | 16.5 | 15.7 | 2.3 |
| Ethyl | 111.8 | 77.3 | 84.3 | 66.7 | 85.0 | 19.2 |
| Xtra | 27.1 | 36.1 | 40.7 | 25.2 | 32.3 | 7.4 |

Example 4

Determination of Altered Properties: DSC

Spezyme Xtra, S242A, S242E, and S242Q were purified from shake flask fermentation broth (see Example 2) using hydrophobic interaction chromatography. The protein was eluted from the column in purified form using 50 mM MES, pH 6.8, containing 40% propylene glycol and 2 mM $CaCl_2$.

Figure 5:
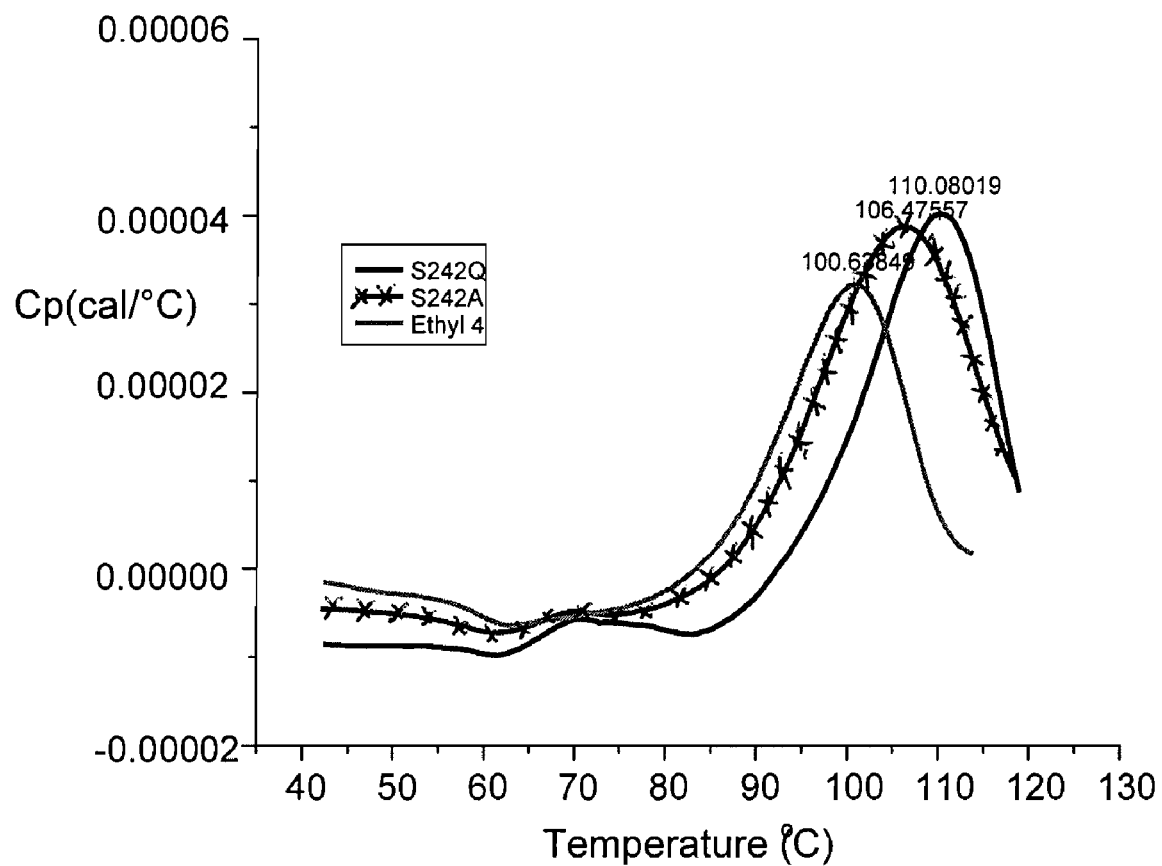
FIG. 5 shows the thermal melting curves and the melting points for the wild-type and amylase variants without added calcium.

Excessive heat capacity curves were measured using an ultrasensitive scanning high-throughput microcalorimeter, VP-CAP DSC (MicroCal, Inc., Northampton, Mass.). The standard procedure for DSC measurements and the theory of the technique has been published (Freire, E., "Differential Scanning Calorimetry," Methods. Mol. Biol. 41, 191-218, 1995). Approximately 500 µL of 0.5 mg/ml wild-type Bacillus stearothermophilus α-amylase or variant S242A, S242E, and S242Q (both in the absence and in the presence of 2 mM calcium chloride) were scanned over a 30-120° C. temperature range. The same sample was then re-scanned to check the reversibility of the process. For α-amylase the thermal unfolding process was irreversible. The buffer used was 10 mM sodium acetate, pH 5.5. A 200° C./hr scan rate was used to minimize any artifacts that may have resulted from aggregation. The thermal midpoint ($T_m$) of the DSC curves was used as an indicator of the thermal stability of the tested protein. Table 4-1 shows the thermal melting points for the amylase proteins tested. The thermal melting curves and the melting points for the wild-type and variant amylases are shown in FIG. 5.

The thermal unfolding for the amylase variants S242A, S242E, and S242Q in the absence and presence of 2 mM calcium chloride show considerable increase in the melting points for the variants when compared to that for the wild-type. In the absence of added calcium chloride, the wild-type amylase has a thermal melting point of 100.8° C. whilst the $T_m$'s for S242A, S242E, and S242Q are 106.5° C., 107.8° C., and 110.1° C., respectively. Thus, the substitution of S242 with A results in an increase in the $T_m$ of 5.7° C., the substitution of S242 with E results in an increase in the $T_m$ of 7.0° C., and the substitution of S242 with Q results in an increase in the $T_m$ of 9.3° C.

In the presence of 2 mM calcium chloride, the wild-type amylase displayed a thermal melting point of 106.8° C. whilst the $T_m$'s for S242A, S242E, and S242Q were 111.8° C., 112.2° C. and 113.8° C., respectively. Thus, relative to measurements in the absence of calcium, in the presence of 2 mM calcium chloride, all four proteins had increased $T_m$ values. The increase in $T_m$ for wild-type and the S242A variants in the presence of calcium was 6° C. and 5.3° C., respectively. The increase in $T_m$ for the S242E variant was 4.4° C. The increase in $T_m$ for the S242Q variant was 3.7° C. This suggests that the S242Q variants is stabilized less by calcium, or the variant is less dependent on calcium for stability. The increase in the $T_m$ of the S242A. S242E, and S242Q relative to wild-type in the presence of calcium chloride was 5° C., 5.4° C., and 3° C., respectively. This suggests that the thermodynamic properties of the variants differ from those of the wild-type, or Spezyme Xtra. This observation was consistent with its enhanced performance in application studies (see Example 5).

TABLE 4-1

Tm (° C.) for various amylases by DSC

| | Tm (No $Ca^{2+}$) | ΔT (° C.) | Tm (w/2 mM $Ca^{2+}$) | ΔT (° C.) |
|---|---|---|---|---|
| Spezyme Xtra | 100.8 | | 106.8 | |
| S242A | 106.5 | 5.7 | 111.8 | 5.7 |
| S242E | 107.8 | 7.0 | 112.2 | 5.4 |
| S242 | 110.1 | 9.3 | 113.8 | 7.0 |

Example 5

Activity Profiles

This example shows that the tested variants have altered activity profiles relative not only to the parent alpha-amylase but also to an industry standard enzyme. Protein determinations were made on purified or plate samples. The variants and standard alpha-amylases were each assayed on the basis of equal protein concentration.

Either plate or purified variants were diluted to approximately 20 ppm using pH 5.6 malic acid buffer. The substrate consisted of 15% cornstarch in the same 50 mM malic acid buffer, pH 5.6. Four hundred microliters of the starch suspension was equilibrated to 70° C. for 2.5 minutes. Then 7 µL of the diluted enzyme was quickly added to the equilibrated starch at a final protein concentration of about 0.36 ppm. The reaction mix was then put into a pre-heated 85° C. shaking heating block and mixed at 300 rpm. The reactions were quenched with 50 µL of 125 mM NaOH at predetermined time intervals. The reaction tubes were spun and the supernatant was diluted 10 fold into 10 mM NaOH, for analysis of DP profile by HPAEC-PAD, Reactions were set up for 4, 10 and 20 minutes. The 4 min reaction provides an indication of the enzyme initial conversion of product to substrate; the 10 minute reaction provides an indication of the enzyme's thermal activity, and the 20 minute reaction provides an indication of the enzyme's thermal stability.

Figure 6:
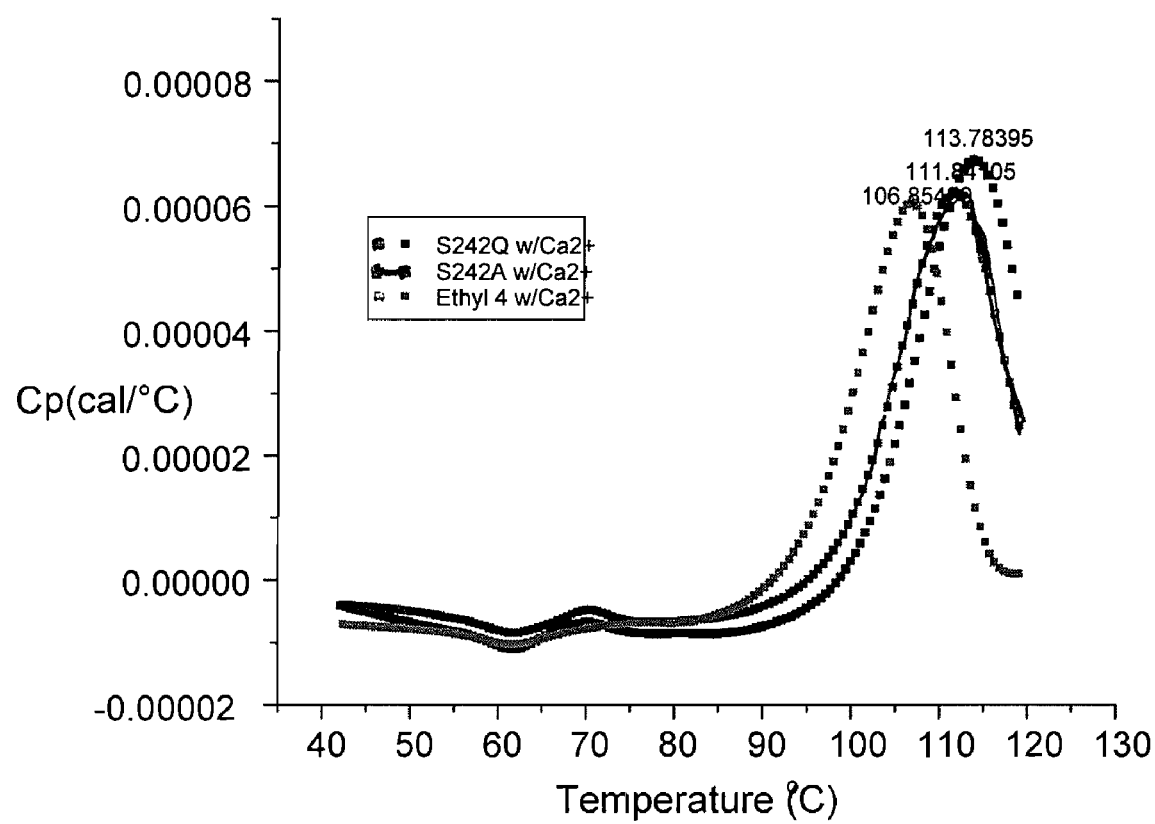
FIG. 6 shows the thermal melting curves and the melting points in the presence of 2 mM added calcium for both the wild-type and the amylase variants.
Figure 7:
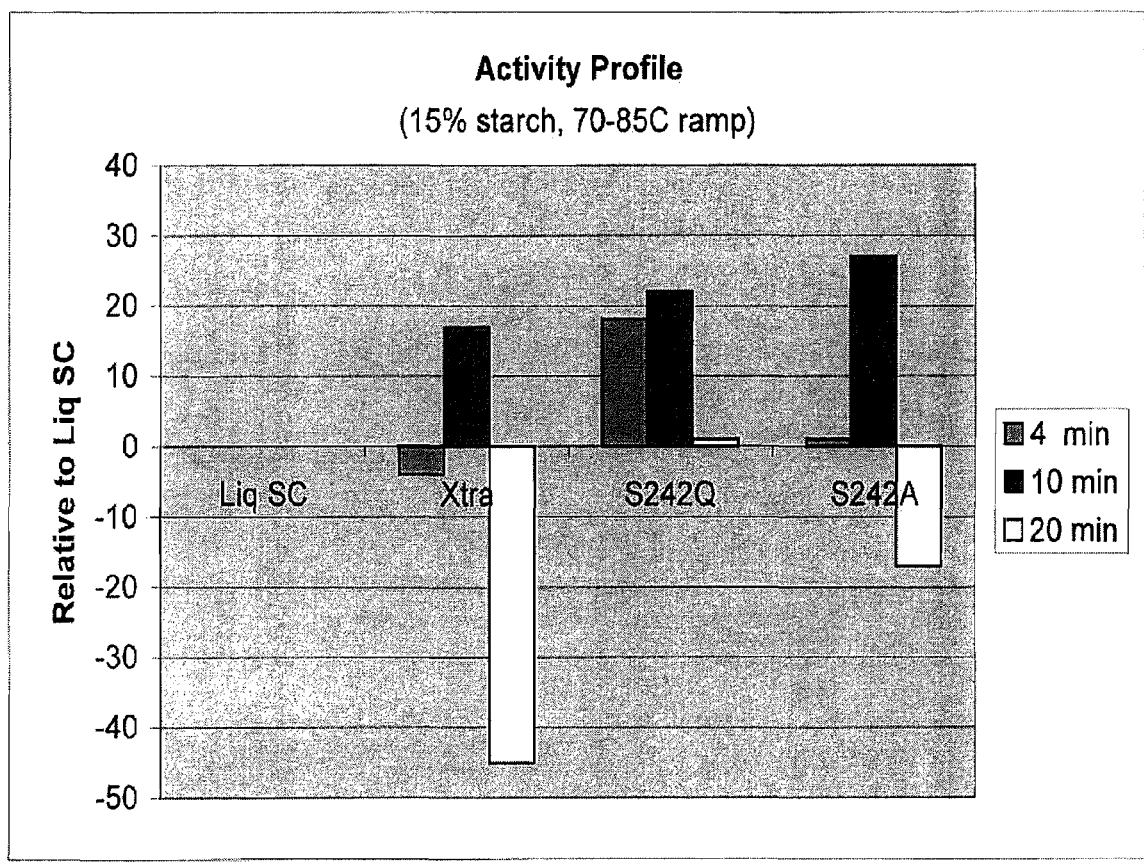
FIG. 7 shows the activity profile at 4, 10, and 20 minutes for Spezyme Xtra and two variants, relative to Liquozyme SC.
Figure 8:
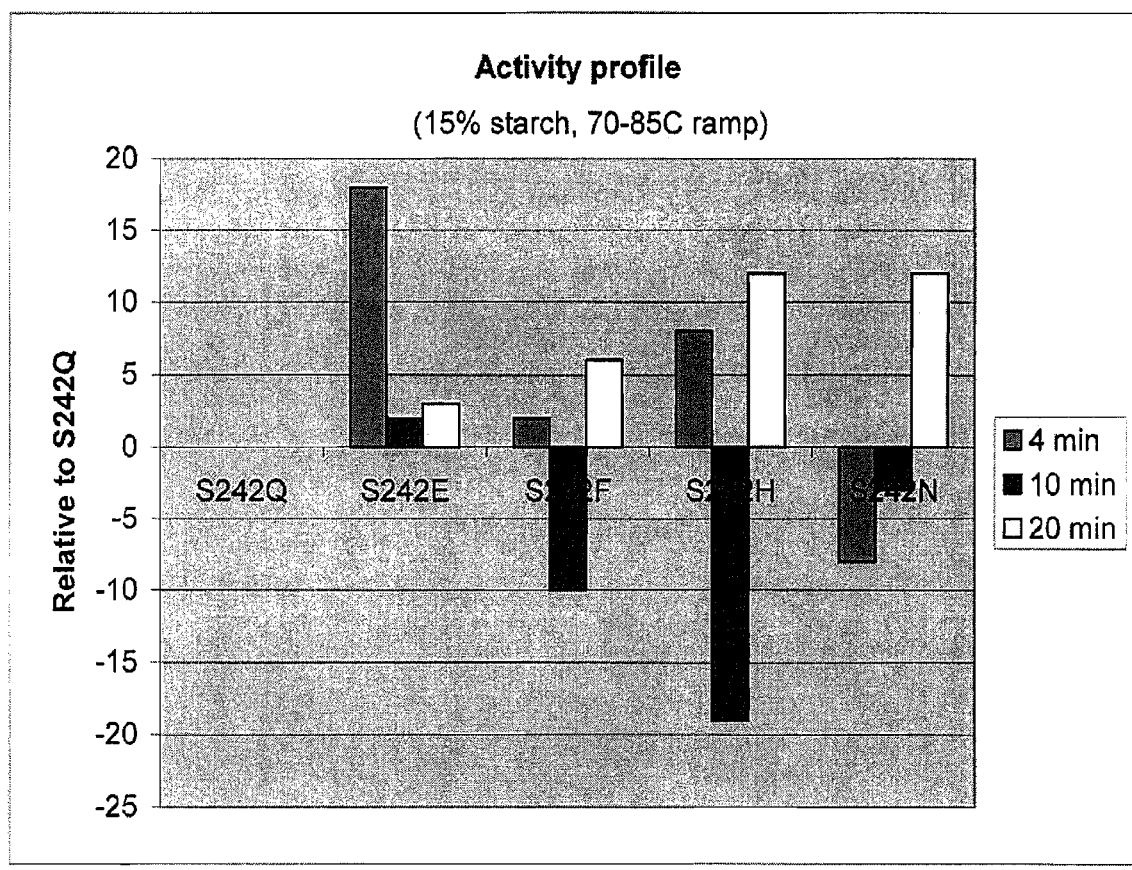
FIG. 8 shows the activity profile of four variants relative to the S242Q variant for three time points.

Total area from DP2 to the end of the HPLC run was integrated, and divided by the total protein and reaction time. The results are provided in FIGS. 6 and 7.

Example 6

Liquefaction in the Viscometer

This example shows that the S242A and S242Q variants, which showed altered residual activity relative to the wild-type parent, also have altered performance relative to the parent alpha-amylase. The variant alpha-amylases of Example 2 were purified and characterized for total protein and specific activity before testing in the viscometer.

Viscosity reduction of corn flour due to the action of the alpha-amylase was monitored using a HAAKE VISCOTESTER 550 instrument. The substrate slurry was made up fresh daily in batch mode with 30% corn flour dry solids. The pH was adjusted to 5.8 using sulfuric acid. Fifty (50) g of the slurry (15 g dry solids) was weighed out and pre-incubated, with stirring, for 10 minutes to warm up to 70° C. Upon alpha-amylase addition, the temperature was immediately ramped up from 70° C. to 85° C. with a rotation speed of 75 rpm. Once the temperature of the slurry and enzyme mixture reached 85° C., the temperature was held constant. Viscosity was monitored for an additional 30 minutes. The viscosity was measured throughout the run and reported in μNm. Wild-type AmyS, S242A, and S242Q were each assayed on an equal protein basis at two protein concentrations (20 and 30 μg/50 g of corn flour slurry).

Figure 9:
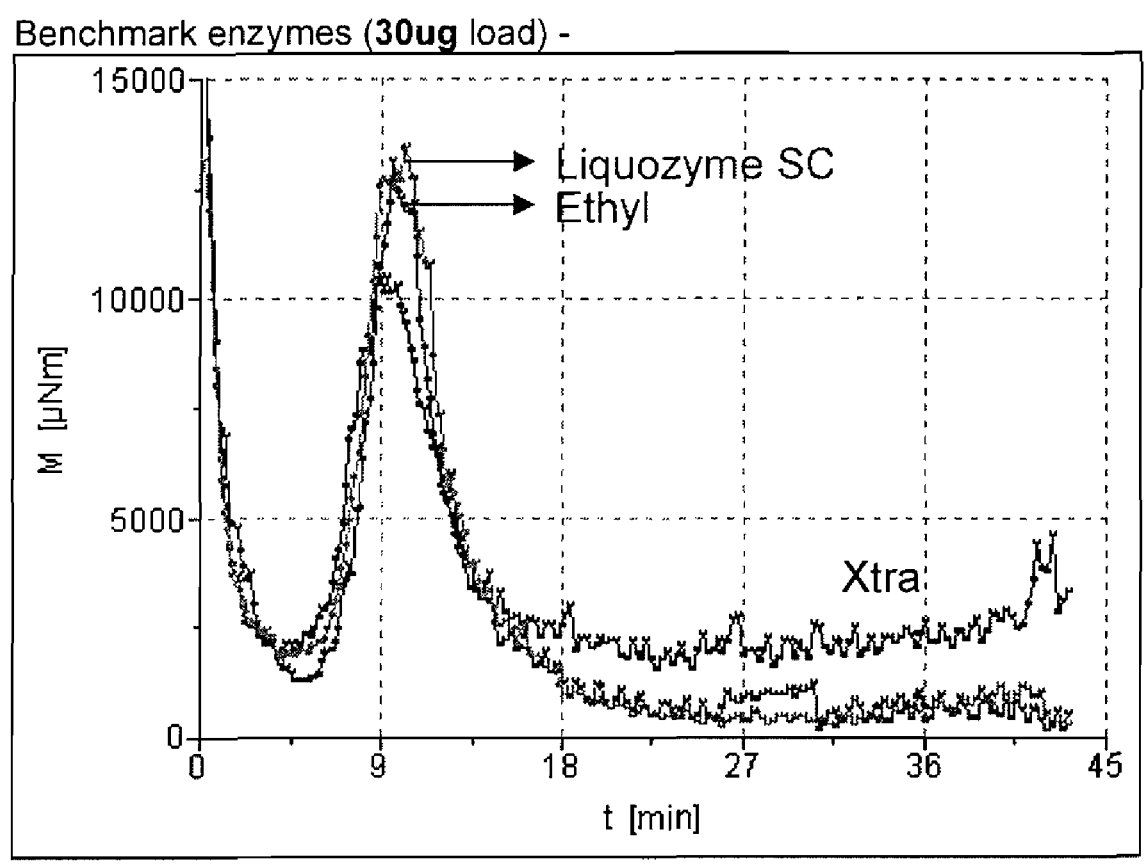
FIG. 9 shows the viscosity reduction of corn flour due to the action of the alpha-amylases Liquozyme SC, Spezyme Ethyl or Spezyme Xtra at a 30 µg dose.
Figure 10:
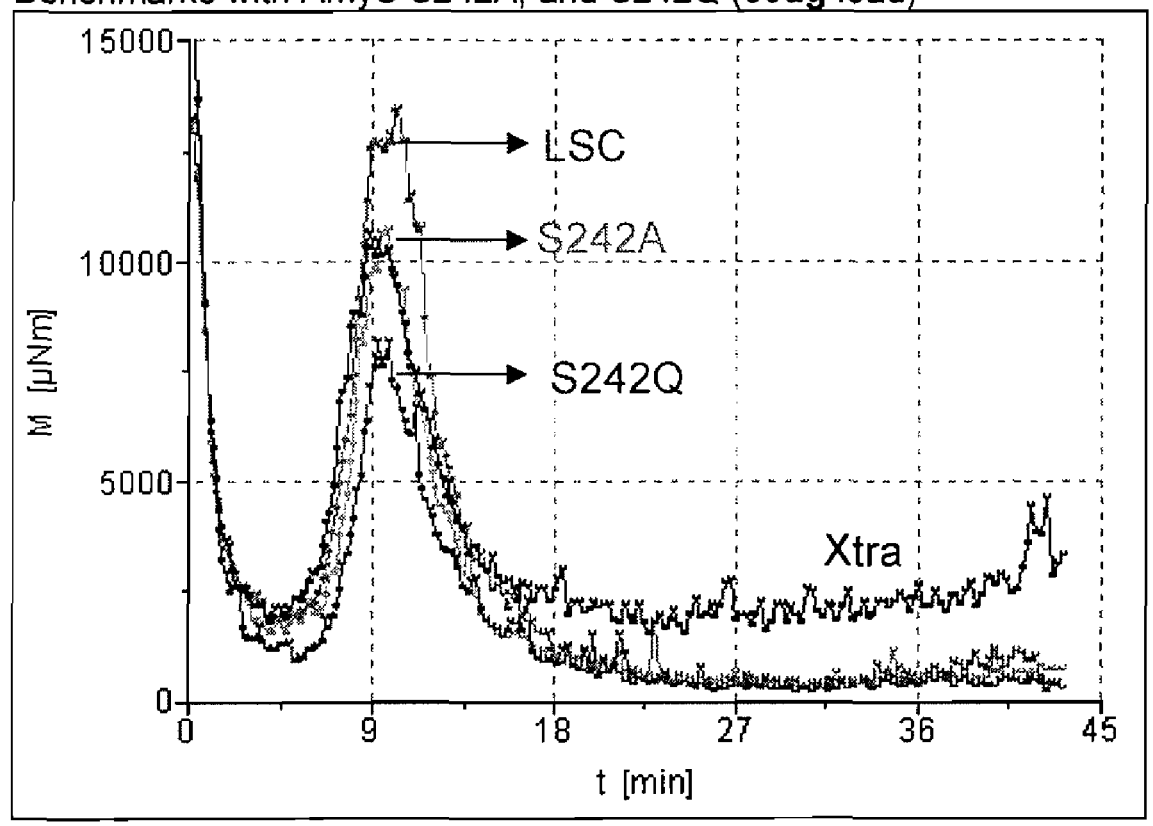
FIG. 10 shows the viscosity reduction of corn flour due to the action of the alpha-amylases Liquozyme SC or Spezyme Xtra, or one of two variants (S242A and S242Q) at a 30 µg dose.
Figure 11:
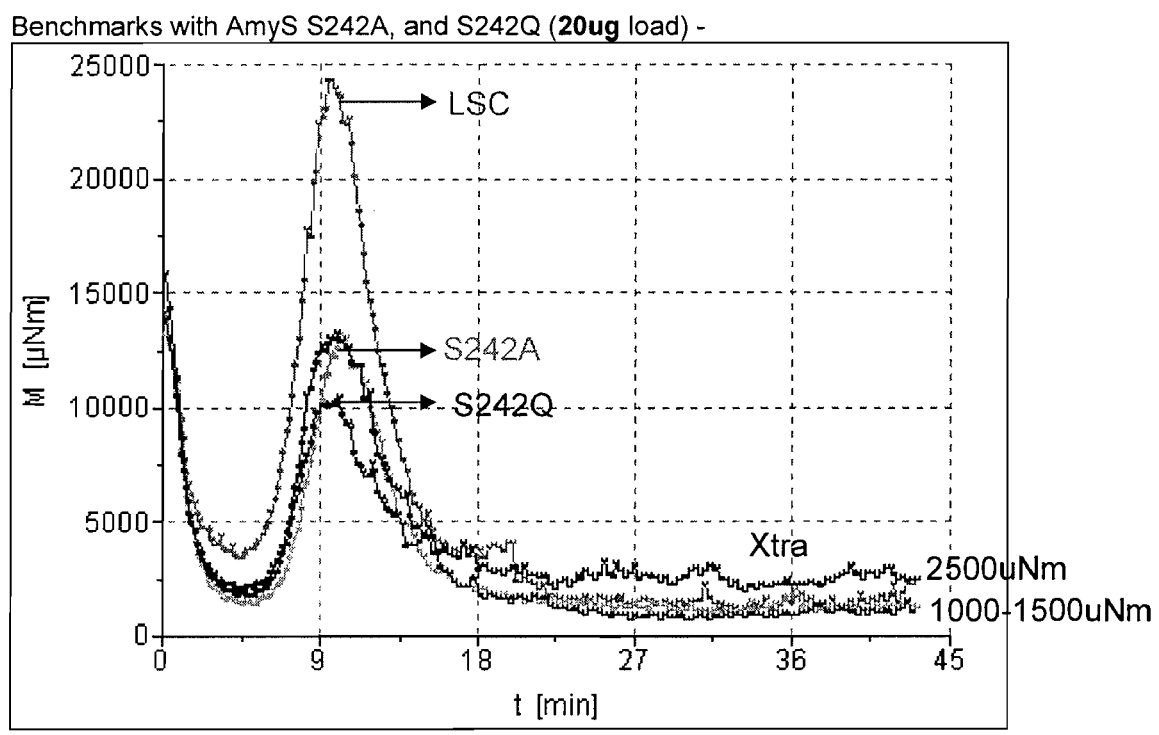
FIG. 11 shows the viscosity reduction of corn flour due to the action of the alpha-amylase Liquozyme SC or Spezyme Xtra, or one of two variants (S242A and S242Q) at a 20 µg dose.

The viscometer application showed that both AmyS variants, S242A and S242Q, had better performance than the benchmark alpha-amylases—Liquozyme SC, Ethyl, and Xtra. The variants exhibited both a low peak viscosity, characteristic of Xtra, as well as a low final viscosity, characteristic of Liquozyme SC and Ethyl. When loaded at the lower protein concentration (20 μg total protein), the difference between the lower peak viscosity of the variants compared to that of Liquozyme SC was even more evident. See FIGS. 9, 10 and 11.

Example 7

Liquefaction in a Jet Cooker

Figure 12:
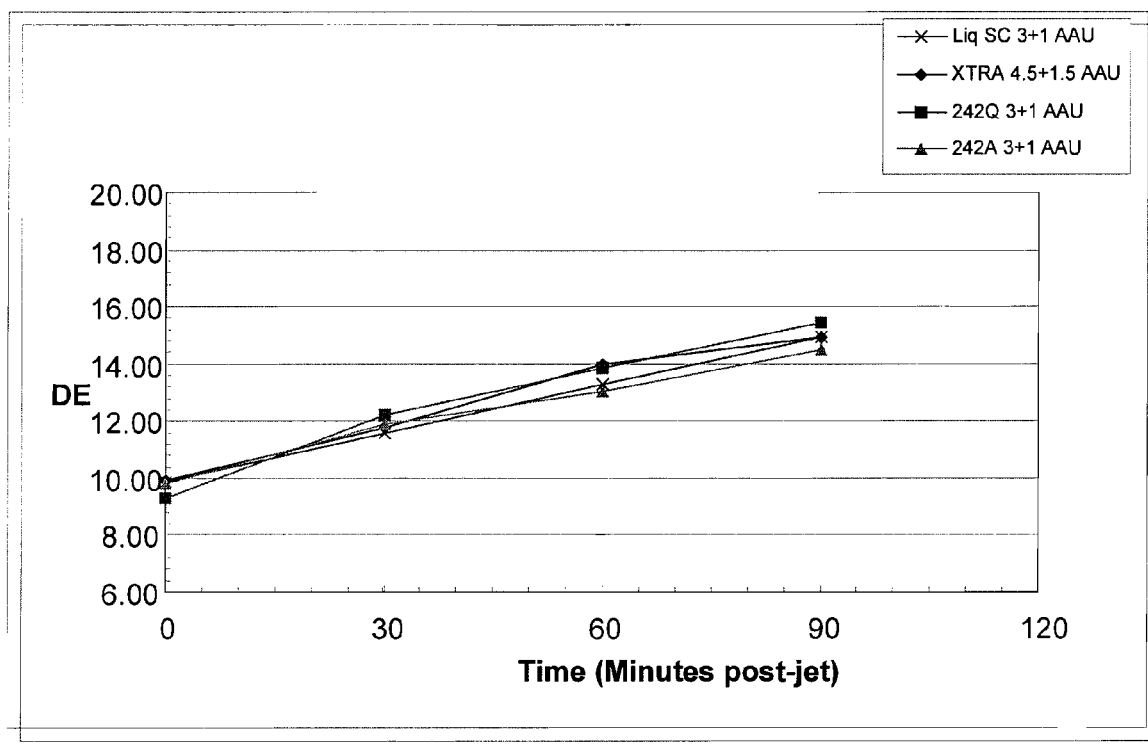
FIG. 12 shows the DE progression of whole ground corn treated with Liquozyme SC, Spezyme Xtra, or one of two variants (S242A and S242Q) over time (0, 30, 60 and 90 minutes). Dosing of liquefaction enzymes pre- and post-jet are indicated as "X+Y" where: X and Y represent the number of units of enzyme added before and after the jet, respectively.
Figure 13:
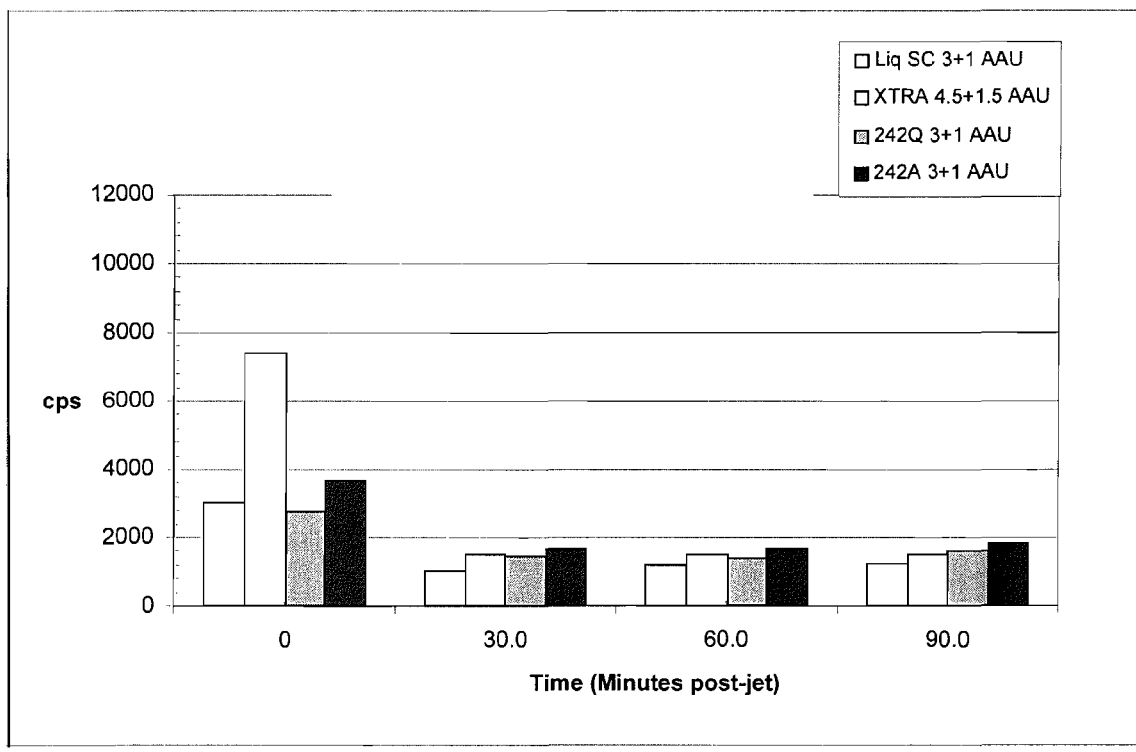
FIG. 13 shows the viscosity post-jet of whole ground corn treated with Liquozyme SC, Spezyme Xtra, or one of two variants (S242A and S242Q) over time (0, 30, 60 and 90 minutes). X and Y are as in FIG. 12.

Whole ground corn was slurried to a 32% (dry solids corn) slurry by using a 70:30 ratio of water to thin stillage. The slurry pH was adjusted to pH 5.8 with 10 N NaOH. The slurry was heated to 70° C. (158° F.) using water and steam in a jacketed kettle. The liquefaction enzymes (SPEZYME Xtra, LiquozymeSC, or S242Q) were added and the slurry was heated to 85° C. (185° F.) over approximately 10 minutes. After the slurry reached 85° C., it was incubated 10 additional minutes at that temperature. The slurry was passed through a jet-cooker maintained at 107° C. (225° F.) with a 3 minute hold time using a pilot plant jet cooker (equipped with an M103 hydro-heater from Hydro-Thermal Corp., Waukesha, Wis.). The liquefact was collected from the jet and placed in an 85° C. water bath. A second dose of liquefaction enzyme was added post-jet. The liquefact was continuously stirred and held at 85° C. for 90 minutes. Samples were collected at 0, 30, 60 and 90 minutes. All post-jet samples were tested for DE (using the Schoorls method), and viscosity (Brookfield-type viscometer (Lab-Line Instruments Inc., Melrose Park, Ill.), spindle 3 at 20 rpm). Dosing of liquefaction enzymes pre- and post-jet are indicated in the following figures as "X+Y" where X represents the number of units of enzyme added before the jet, and Y represents the number of units added to the liquefact after it passes through the jet cooker. Results are shown in FIGS. 12 and 13.

Example 8

Effect of Removal of Phytic Acid Inhibition on Alpha-Amylase Thermostability

The effect of the removal of phytic acid inhibition on the thermostability of liquefying thermostable alpha-amylases was studied.

A. No Jet Cooking (Single Enzyme Dose)

A slurry of whole ground corn (obtained from Badger State Ethanol, Monroe, Wis.) was made with water containing 30% v/v thin stillage to a final concentration of about 32% ds. Corn solids were prepared in a jacketed kettle. The slurry was mixed well and the pH was measured (pH 5.2). No pH adjustment was made. The slurry was mixed in a jacketed kettle and brought to the pretreatment temperature of 70° C. Just prior to reaching 70° C., the liquefying enzyme, i.e., an alpha-amylase (4 AAU per gram ds corn), was added. Identical slurries were treated, one with and one without added phytase (4 FTU per gram ds corn), to begin the incubation or primary liquefaction step. The slurry was incubated for 30 minutes in the presence of the amylase with or without added phytase. The phytase used in this experiment was BP-17. Although the phytase was added at the same time as the alpha-amylase in this example, it may be added at other times, such as prior to the amylase.

Figure 15:
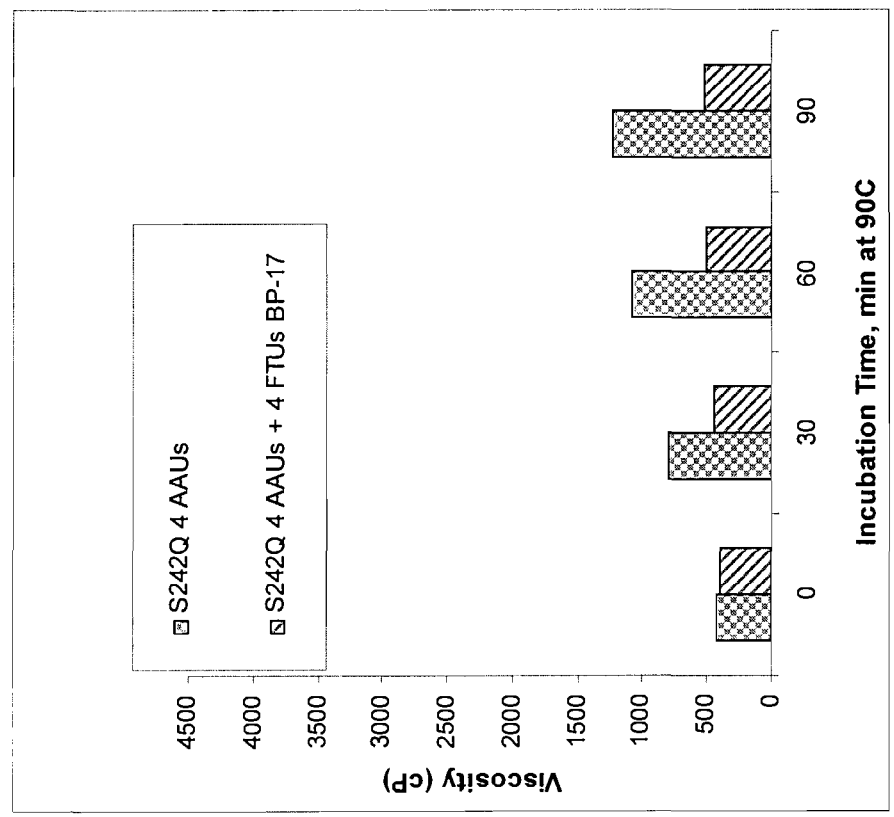
FIG. 15 shows the viscosity post-jet of whole ground corn treated with phytase and amylase (e.g., Spezyme Xtra or S242Q variant) over time (0, 30, 60 and 90 minutes). Conditions were as in FIG. 14. Reference is made to Example 8.
Figure 14:
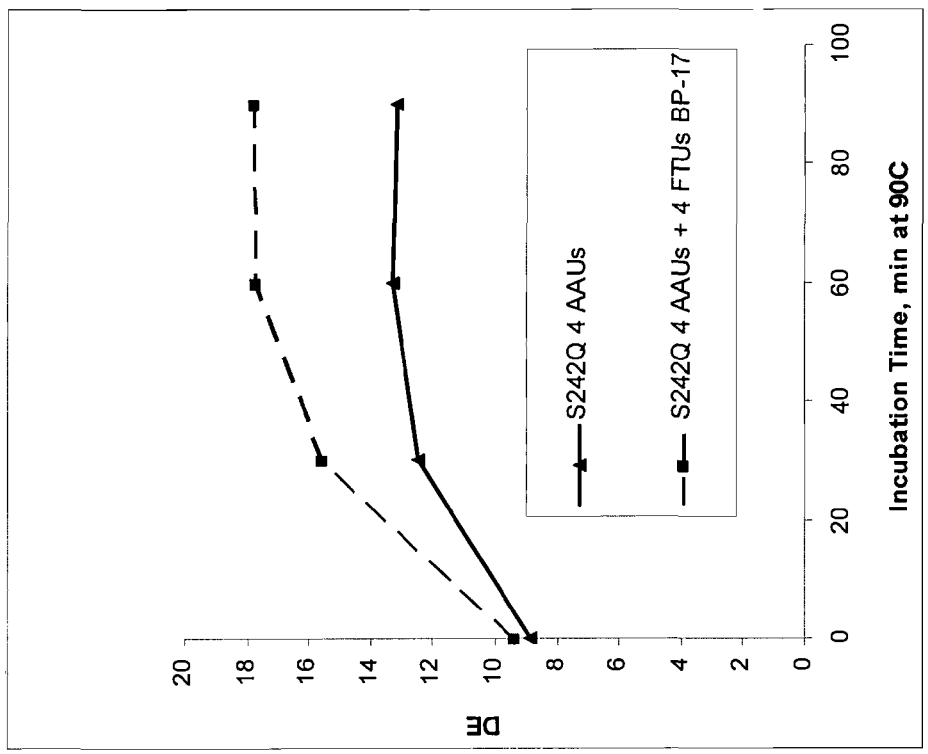
FIG. 14 shows the DE progression of whole ground corn treated with phytase and an amylase (Spezyme Xtra or S242Q variant) over time (0, 30, 60 and 90 minutes). MAXALIQ is a phytase/amylase blend available from Genencor, a Danisco Division. Phytase effect was observed during primary liquefaction using 242Q AA in low pH (5.2) liquefaction process of whole ground corn, 32% ds. corn containing 30% thin stillage, no jet cooking. Reference is made to Example 8.

The treated slurry was then placed in a water bath maintained at 90° C. to begin the secondary liquefaction (2° liquefaction) step. Samples of each of the treated slurries (amylase with or without phytases) were taken at 0, 30, 60 and 90 minutes for viscosity (by Brookfield) and DE (by Schoorls) testing. The results are shown in FIGS. 14 and 15.

B. With Jet Cooking (Split Enzyme Dose)

A slurry of whole ground corn (obtained from Badger State Ethanol, Monroe, Wis.) was made with water containing 30% v/v thin stillage to a final concentration of about 32% ds. Corn solids were prepared in a jacketed kettle. The slurry was mixed well and the pH of the slurry was measured (pH 5.2). This slurry was mixed in a jacketed kettle and brought to 70° C. Just prior to reaching 70° C., the liquefying enzyme, i.e., an S242Q alpha-amylase variant (3 AAU per gram ds corn), was added to begin the incubation, or primary liquefaction step. Identical slurries were incubated for 30 minutes in the presence of the alpha-amylase, with or without added phytase (4 FTU per gram ds corn).

Although the phytase was added at the same time as the alpha-amylase in this example, it may be added at other times, such as prior to the amylase.

Each incubated slurry was passed through a jet cooker (225° F.; 107.2° C.) that was preheated to the desired temperature using steam and water. The slurry was sent through the jet at the maximum speed (1.5 setting) of about 4 liters/minute. Use of the hold coil resulted in a hold time of just over 3 minutes. After all of the water was displaced and the desired temperature held steady, an aliquot of solubilized corn mash was collected and placed in a secondary bath (w/overhead stirring) at 85° C. to begin the secondary liquefaction step (2° liquefaction). A second dose of the S242Q (1 AAU/gm ds) was added and the liquefaction continued for an additional 90 minutes. Samples of each slurry (amylase with or without phytases) were taken to test for viscosity (by Brookfield) and DE (by Schoorls) at 0, 30, 60, and 90 minutes.

The resultant liquefact was used in Example 10B.

C. Jet Cooking, Conventional

A slurry of whole ground corn (obtained from Badger State Ethanol, Monroe, Wis.) was made with water containing 30% v/v thin stillage to a final concentration of about 32% ds. Corn solids were prepared in a jacketed kettle. The slurry was mixed well and the pH of the slurry was measured (pH 5.2). The pH was adjusted to pH 5.8 with dilute NaOH. The slurry was mixed in a jacketed kettle and brought up to the pretreatment temperature of 70° C. Just prior to reaching 70° C., the liquefying enzyme, i.e., an S242Q alpha-amylase variant (3 AAU per gram ds corn), was added to begin the incubation or primary liquefaction step. The slurry was incubated for 30 minutes in the presence of the alpha-amylase without added phytase.

Figure 21:
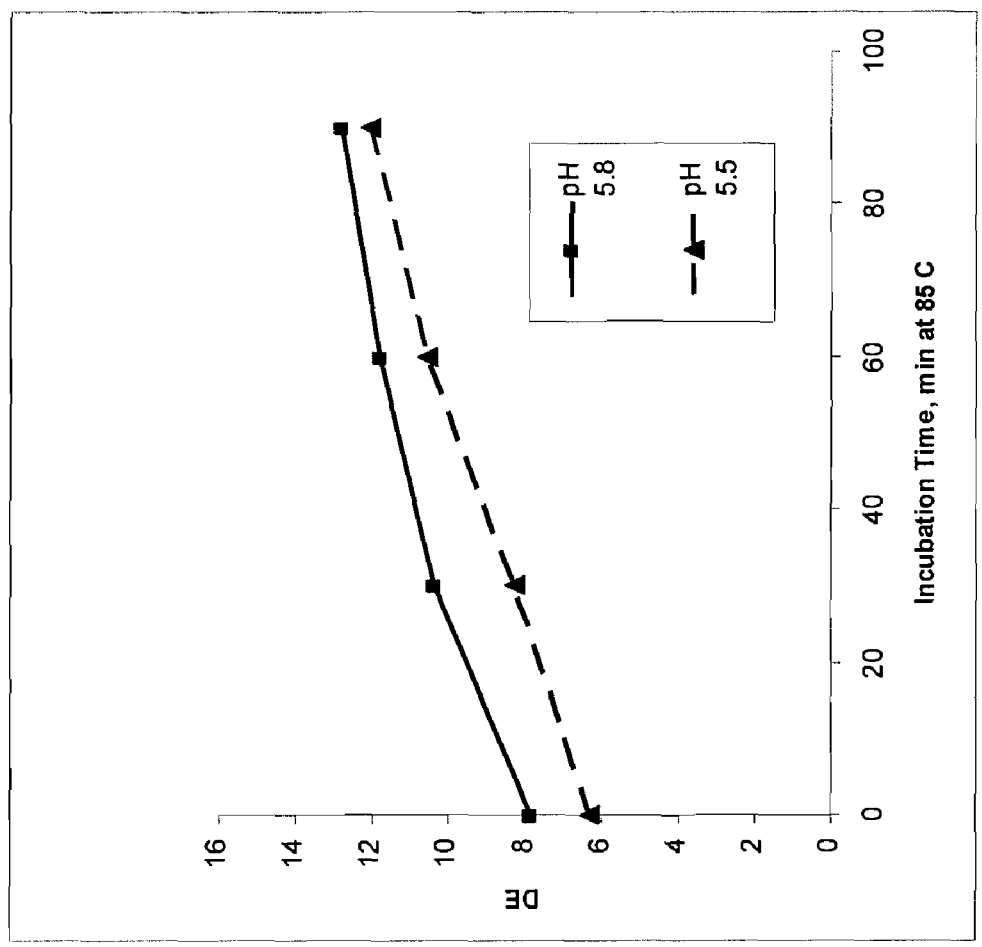
FIG. 21 is a graph showing the effect of the S242Q alpha-amylase variant on DE progression under conventional processing conditions. Observing effects of pH on S242Q performance in liquefaction with jet cooking (32% DS, 30% thin stillage, 10 min slurry at 85° C.+107° C. jet+3 min residence time+90 min secondary batch liquefaction at 85° C.). Squares, pH 5.8; diamonds, pH 5.5. Reference is made to Example 8.

The incubated slurry was passed through a jet cooker (225° F.; 107.2° C.) that was preheated to the desired temperature using steam and water. The slurry was sent through the jet at the maximum speed (1.5 setting) of about 4 liters/minute. The hold coil resulted in a hold time of just over 3 minutes. After all of the water was displaced and the desired temperature held steady, an aliquot of solubilized corn mash was collected and placed in a secondary bath (overhead stirring) at 85° C. to begin the secondary liquefaction step (2° liquefaction). A second dose of the S242Q alpha-amylase variant (1 AAU/gm ds) was added and the liquefaction continued for an additional 90 minutes. Samples were taken at 0, 30, 60, and 90 minutes to test for viscosity (by Brookfield) and DE (by Schoorls). The above experiment was conducted at a slurry pH of 5.5. See FIG. 21.

The resultant liquefact was used in Example 10A.

D. Results with and without Jet Cooking

Figure 20:
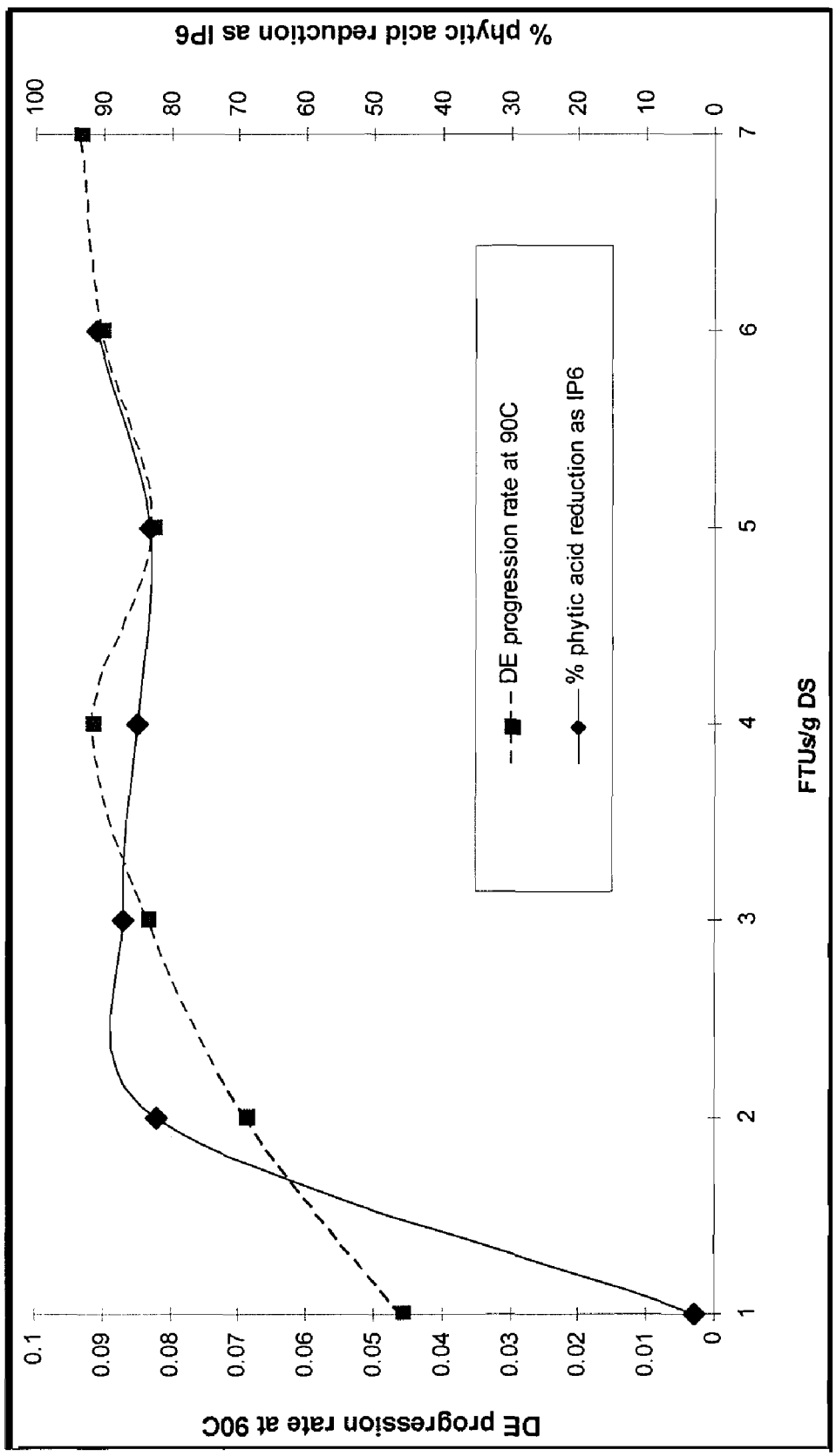
FIG. 20 is a graph showing the effects of BP-17 concentration during primary liquefaction of whole ground corn, pH 5.2 by S242Q variant AA (4AAU/gds corn) on the rate of DE progression at 90° C. were observed. The rates of DE progression (squares) and the percent phytic acid reduction as IP6 (diamonds) were measured.

Addition of BP-17 phytase during incubation (primary liquefaction) reduced the phytic acid content of the whole ground corn from 0.60% ds corn to 0.09% ds corn (>85% reduction) (FIG. 20). It is also evident from FIGS. 14 and 15 that the alpha-amylases were inactivated at a jet cooking temperature of 225° F. (107° C.) based on DE development or viscosity reduction. However, the inclusion of phytase prior to jet cooking resulted in a significant increase in the thermostability of the alpha-amylases, as shown by DE progression and viscosity reduction at 90° C. during the secondary liquefaction step. Similar results were seen with jet cooking (data not shown) as shown in FIGS. 14 and 15. Without being limited to any particular theory of operation, it is believed that addition of the phytase helps to minimize, reduce, or eliminate phytic acid inhibition of the amylase activity.

Example 9

Effect of BP-17 Phytase Concentration on Alpha-Amylase Stability at Low pH

The increase in the thermostability of alpha-amylase due to the removal of the phytic acid inhibition of alpha-amylase was studied. The phytic acid was hydrolyzed using phytase prior to the secondary liquefaction of whole ground corn and the improvement in the pH stability at low pH was determined.

In a typical experiment, whole ground corn was slurried to a 32% (ds corn) by using a 70:30 ratio of water and thin stillage. The slurry pH was pH 5.2. The slurry was heated to 70° C. using water and steam in a jacketed kettle. The liquefaction enzyme, i.e., the S242Q alpha-amylase variant (4 AAU/gm ds corn), and varied concentrations of BP-17 (0-12 FTU/gm ds corn) were added. The slurry was pretreated by holding the temperature at 70° C. for 45 minutes. The slurry was then placed in a 90° C. water bath. The liquefact was continuously stirred and held at 90° C. for 90 minutes. Samples were collected at 0, 30, 60 and 90 minutes. All samples were tested for DE (using the Schoorls method), and for viscosity (Brookfield viscometer, spindle 2 at 20 rpm). The DE progression and viscosity data are summarized in FIGS. 16-17.

Figure 16:
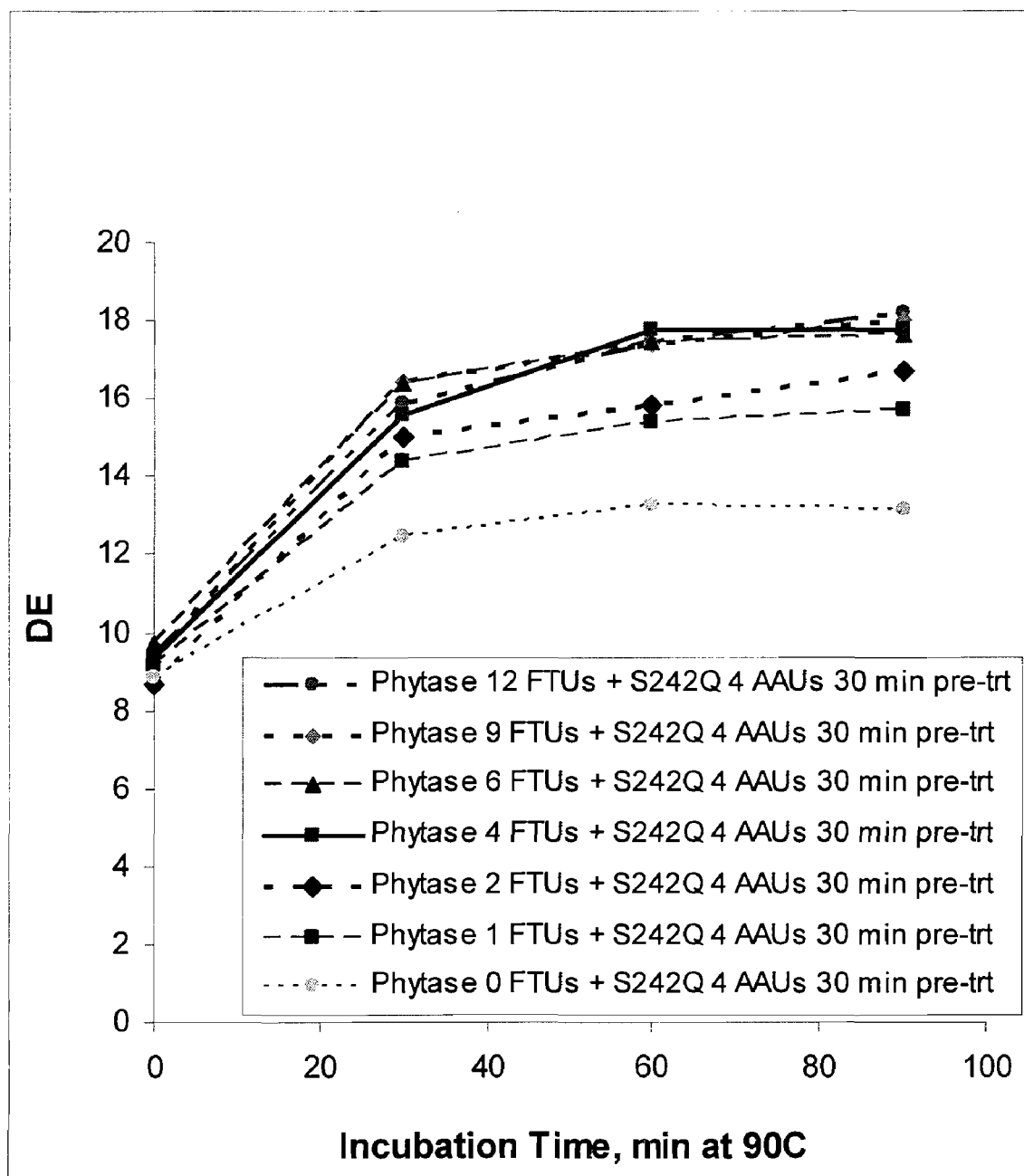
FIG. 16 shows the DE progression of whole ground corn treated with the S242Q variant and phytase. Conditions included: 32% whole ground corn containing 30% thin stillage, pH 5.2. During 30 min preincubation, BP-17 phytase was added at 0 (control), 1, 2, 4, 6, 9, and 12 FTU, primary liquefaction followed. Enzymes used during primary liquefaction: 242Q 4 AAU/gm ds corn, incubation time was 45 min at 70° C. Secondary liquefaction was at 90° C. for 90 min. Reference is made to Example 9.
Figure 17:
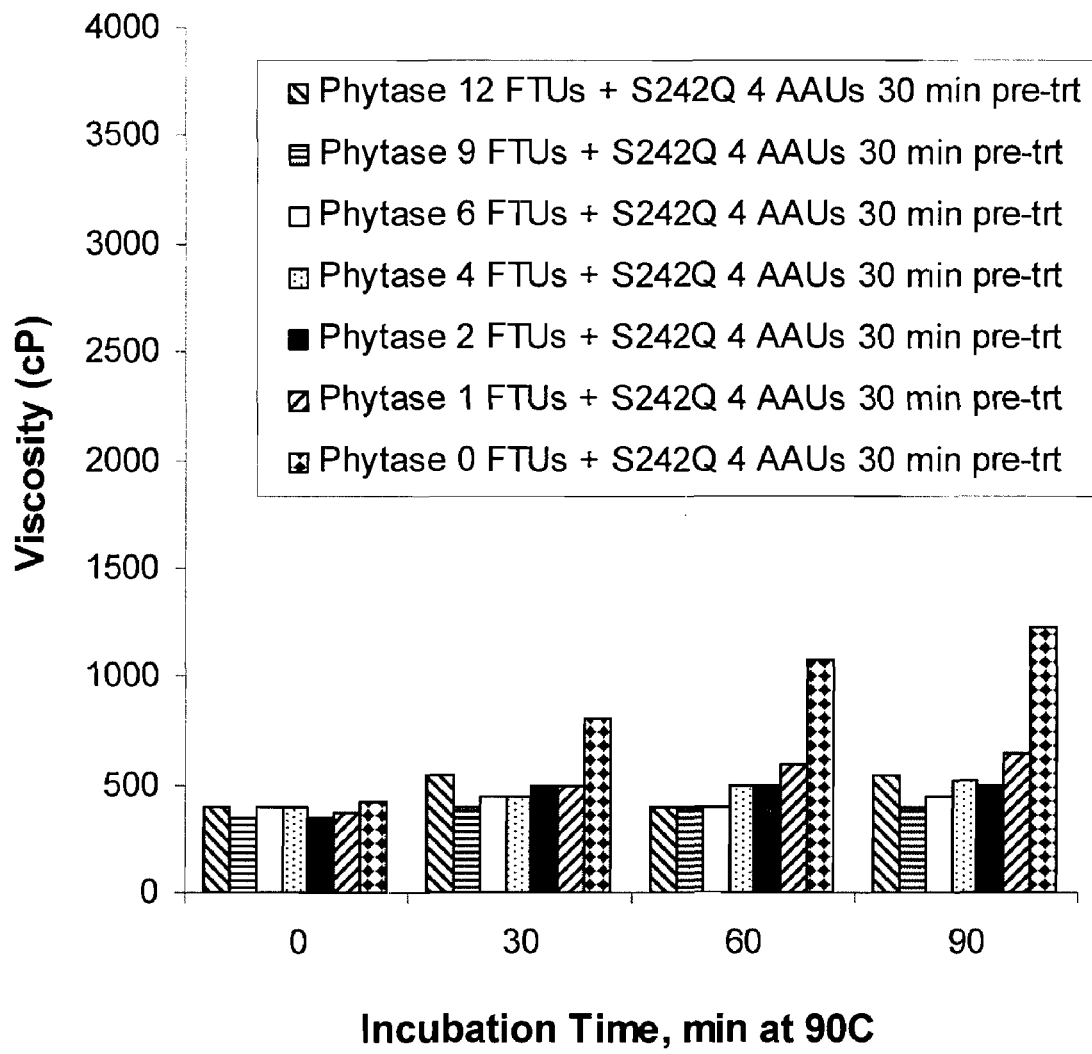
FIG. 17 shows the viscosity post-jet of whole ground corn treated with the S242Q variant and phytase. Effects of phytate removal on the viscosity reduction of during batch liquefaction of whole ground corn at 90° C., pH 5.2 were observed. Pre-incubation with phytase was as in FIG. 16. Reference is made to Example 9.

The results showed that the addition of phytase resulted in a significant increase in the pH stability (at low pH) for amylase activity, as evidenced by a steady increase in the DE progression at 90° C., with a concomitant decrease in the viscosity of the liquefact (see FIGS. 16-17). This may be due to reduction of phytic acid inhibition of the alpha-amylase. The data show that the S242Q alpha-amylase variant can be successfully used in the liquefaction process for whole ground corn at a pH 5.2 in the presence of an added phytase. In FIG. 20, it can be seen that the rate of DE progression increases with the increased addition of phytase, and reaches a maximum at 4 FTU/gm ds. These results may indicate that phytase increases the thermostability of the S242Q alpha-amylase variant by removing phytic acid from the slurry.

Example 10

Effect of pH

The effect of pH on the S242Q alpha-amylase variant was studied in this example.

Figure 19:
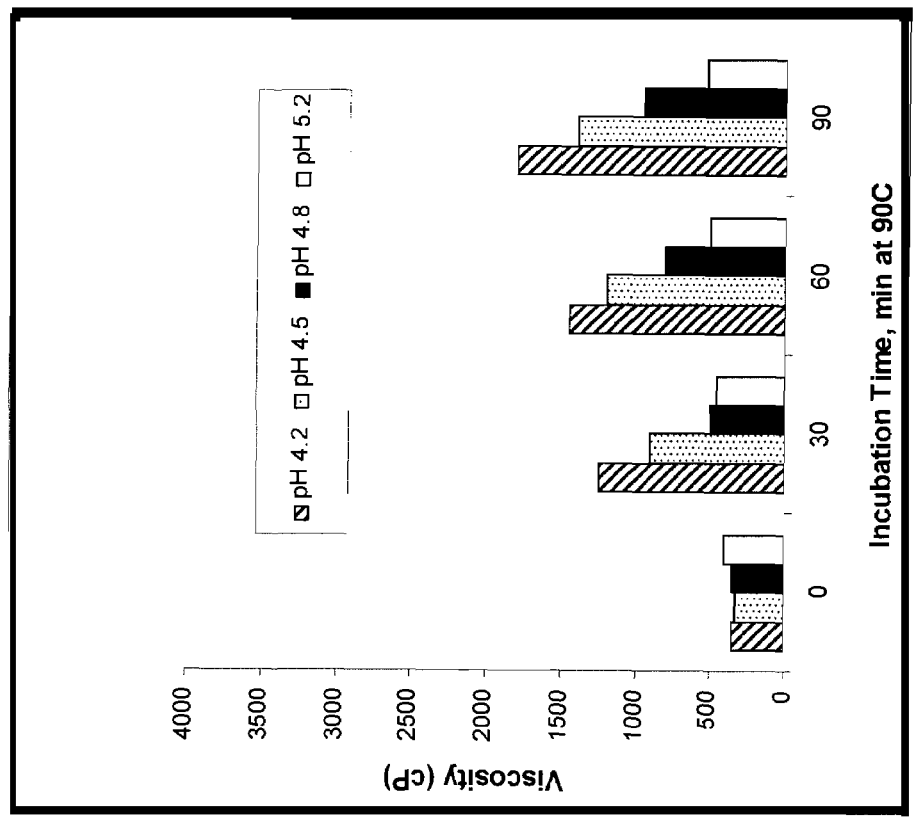
FIG. 19 shows the effect of phytase addition during primary liquefaction of whole ground corn on the viscosity reduction after jet cooking. Conditions were as in FIG. 18. White, pH 5.2; black, pH 4.8; stippled, pH 4.5; and hashed, pH 4.2. Reference is made to Example 9.
Figure 18:
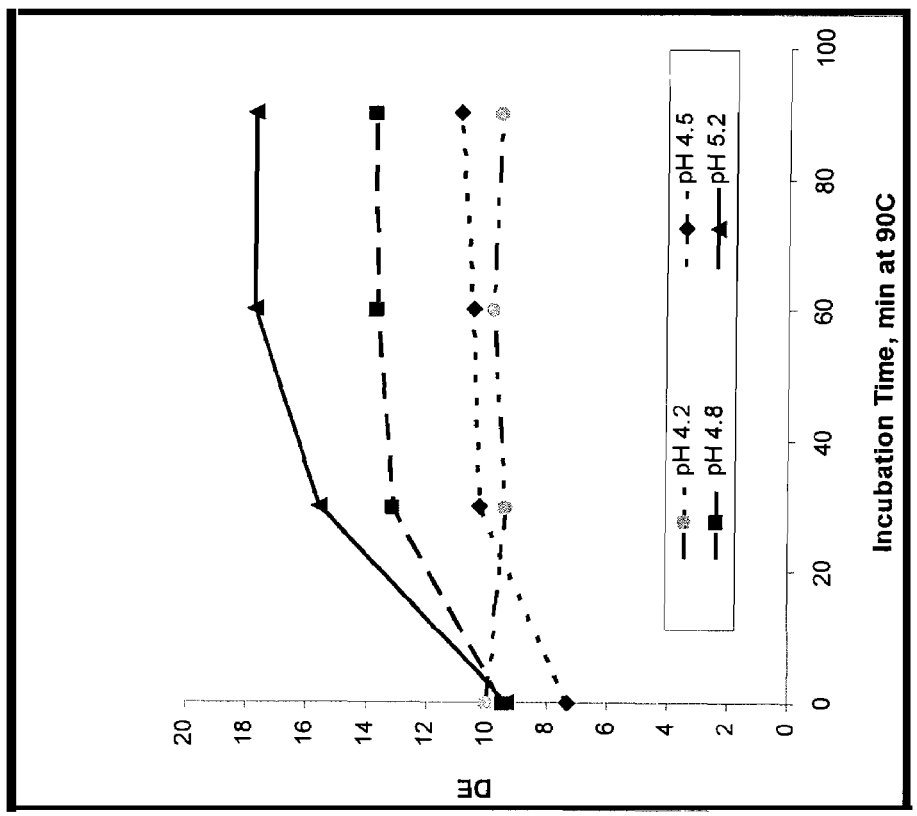
FIG. 18 shows the effect of phytase treatment of whole ground corn on the increase in the thermostability and low pH stability of the S242Q variant. The effects of low pH on the liquefaction process of whole ground corn, 32% ds. corn containing 30% thin stillage were observed. Triangles, pH 5.2; squares, pH 4.8; diamonds, pH 4.5; and circles, pH 4.2. Reference is made to Example 9.

In a typical experiment, whole ground corn was slurried to a 32% (ds corn) by using a 70:30 ratio of water and thin stillage. The slurry pH was pH 5.2. The pH was lowered to between 4.2 and 4.8 using $H_2SO_4$. The slurry was heated to 70° C. using water and steam in a jacketed kettle. The liquefaction enzyme, i.e., the S242Q variant (4 AAU/gm ds), and BP-17(4 FTU/gm ds) were added and the slurry was pretreated by holding the temperature at 70° C. for 45 minutes. The slurry was then placed in a 90° C. water bath. The liquefact was continuously stirred and held at 90° C. for 90 minutes. Samples were collected at 0, 30, 60 and 90 minutes. All samples were tested for DE (using the Schoorls method), and for viscosity (Brookfield viscometer, spindle 2 at 20 rpm). The DE progression and viscosity data are summarized in FIGS. 18-19.

The DE decreased with decreasing pH from 5.2 to 4.5. The amylase enzyme was completely inactivated at pH 4.2.

Example 11

Effect on Ethanol Production

Liquefacts were used as fermentation feedstocks in ethanol fermentation for alcohol production. A slurry of whole ground corn (obtained from Badger State Ethanol, Monroe, Wis.) was mixed with water containing 30% v/v thin stillage to a final concentration of about 32% ds.

A. Conventional Process

The liquefact from Example 8, Part C was used (Liquefact A).

The pH of the secondary liquefact was adjusted to 4.2 using $H_2SO_4$ prior to the simultaneous saccharification and fermentation (SSF) stage.

B. Low pH, Jet Cooking (Split Dose)

The liquefact from Example 8B was used (Liquefact B). No pH adjustment was done prior to SSF.

C. Simultaneous Saccharification and Fermentation

In each experiment, tare weights of the vessels were obtained prior to preparation of media. A 32% DS corn liquefact (2 liters) was placed in a 2 L flask. Red Star Ethanol Red yeast (RED STAR (Lesaffre)) inoculums were prepared by adding 10 grams of yeast and 1 gram of glucose to 40 grams of water under mild agitation for one hour. Five mls of each inoculum was added to equilibrated fermentors, followed by the addition of G Zyme™ 480 Ethanol (Danisco US Inc, Genencor Division) at 0.4 GAU/g ds corn, to initiate the simultaneous saccharification and fermentation. The initial gross weight was noted and the flask was placed in a water bath maintained at 32° C. Samples were taken at different intervals of time and analyzed for carbohydrate and ethanol content using HPLC. Fermentations were also carried out using one kilogram of each liquefact. Weight loss during fermentation was measured at different intervals of time. The alcohol was determined based on the weight loss due to loss of carbon dioxide. At the conclusion of the fermentation, a final gross weight was obtained. The broth was quantitatively transferred into a 5 L round bottom vessel. Distillation was performed under vacuum until approximately 800 mls of ethanol were collected in a receptacle containing 200 mls water. The ethanol was diluted to 2 L and was analyzed by HPLC. The weight and DS of the still bottoms was obtained prior to drying. Residual starch analysis was performed on the DDGS. Stoichiometric calculations were performed based on weight loss, distillation, and residual starch analysis.

Ethanol calculation using $CO_2$ weight loss:

EtOH production (mmol)=$CO_2$ loss (g)/88

EtOH production (g)=($CO_2$ loss (g)/88)*92=>$CO_2$ loss (g)*1.045

EtOH production (ml)=(($CO_2$ loss (g)/88)*92)/0.789=>$CO_2$ loss (g)×1.325

Table 11 summarizes a comparison of sulfate and phytic acid content in DDGS from a conventional process with that from the process with no pH adjustment. The data show a major difference in free sulphate and phytic acid content between the two processes. Addition of phytase with the thermostable alpha-amylase in the incubation resulted in the DDGS with reduced phytic acid content, higher available (free) phosphate and reduced sulfate. Thus, the process with no pH adjustment confers pH stability at low pH for liquefying thermostable alpha-amylases in the starch liquefaction.

A. Protein Content Determination

BCA (Bicinchoninic Acid) Assay

BCA (Pierce) assay was used to determine the protein concentration in samples on microtiter plate (MTP) scale. The chemical and reagent solutions used were: BCA protein assay reagent, and Pierce dilution buffer (50 mM MES, pH 6.5, 2 mM $CaCl_2$, 0.005% TWEEN®-80). The equipment included a SpectraMAX (type 340; Molecular Devices) MTP reader. The MTPs were obtained from Costar (type 9017).

Two-hundred (200) µL BCA Reagent was pipetted into each well, followed by 20 µL diluted protein. After thorough mixing, the MTPs were incubated for 30 minutes at 37° C. Air bubbles were removed before the optical density (OD) of the solution in the wells was read at 562 nm. To determine the protein concentration, the background reading was subtracted from the sample readings. The $OD_{562}$ was plotted for protein standards (purified enzyme) to produce a standard curve. The protein concentration of the samples were interpolated from the standard curve.

Bradford Assay

The Bradford dye reagent (Quick Start) assay was used to determine the protein concentration in samples on MTP scale. The chemical and reagent solutions used were: Quick Start Bradford Dye Reagent (BIO-RAD Catalog No. 500-0205), Dilution buffer (1 mM NaCl, 0.1 mM CaCl2, 0.005% TWEEN®-80. The equipment used was a Biomek FX Robot (Beckman) and a SpectraMAX (type 340) MTP reader. The MTPs were from Costar (type 9017).

Two-hundred (200) µL Bradford dye reagent was pipetted into each well, followed by 15 µL dilution buffer. Ten (10) µL of filtered culture broth were added to the wells. After thorough mixing, the MTPs were incubated for at least 10 minutes at room temperature. Air bubbles were blown away and the OD of each well was read at 595 nm. To determine the protein concentration, the background reading (i.e., from un-inoculated wells) was subtracted form the sample readings. The $OD_{595}$ values obtained provide a relative measure of the protein content in the samples.

B. Microswatch Assay for Testing Enzyme Performance

The detergents used in this assay did not contain enzymes or the enzymes present in commercial detergents had been destroyed through heat deactivation as described elsewhere in

TABLE 11

| Liquefaction conditions | Alcohol yield Gallons/Bushel | DDGS,% ds | | | | |
|---|---|---|---|---|---|---|
| | | Starch | Phytic acid | % IP 6 | Free Phosphate | Sulphate* |
| Conventional Process-pH 5.8 (Liquefact A) | 2.70 | 7.25 | 0.6 | 100 | 1.20 | 1.92 |
| No pH adjustment-Process, pH 5.2 3 + 1 AAU (Split dose), 4 FTU BP-17, with jet cooking, 225° F. (Liquefact B) | 2.69 | 9.28 | 0.2 | 0 | 1.33 | 0.23 |

*mg/g ds

Example 12

Additional Methods

The following assays were used in the Examples. Deviations from the protocols provided below are generally indicated in the Examples. In these experiments, a spectrophotometer was used to measure the absorbance of the products formed during the reactions.

this document. The equipment used included an Eppendorf Thermomixer and a SpectraMAX (type 340) MTP reader. The MTPs were obtained from Costar (type 9017).

Detergent Preparation (AATCC HDL; US Conditions)

Milli-Q water was adjusted to 6 gpg water hardness (Ca/Mg=3/1), and 1.5 g/l AATCC 2003 standard reference liquid detergent without brightener was added. The detergent solution was vigorously stirred for at least 15 minutes. Then, 5 mM HEPES (free acid) was added and the pH adjusted to 8.0.

Rice Starch Microswatch Assay for Testing Amylase Performance

Test detergents were prepared as described elsewhere in this document. The equipment used included a New Brunswick Innova 4230 shaker/incubator and a SpectraMAX (type 340) MTP reader. The MTPs were obtained from Corning (type 3641). Aged rice starch with orange pigment swatches (CS-28) were obtained from Center for Test Materials (Vlaardingen, Netherlands). Before cutting 0.25-inch circular microswatches, the fabric was washed with water. Two microswatches were placed in each well of a 96-well microtiter plate. The test detergent was equilibrated at 20° C. (North America) or 40° C. (Western Europe). 190 µL of detergent solution were added to each well of the MTP, containing microswatches. To this mixture, 10 µL of the diluted enzyme solution was added. The MTP was sealed with adhesive foil and placed in the incubator for 1 hour with agitation at 750 rpm at the desired test temperature (typically 20° C. or 40° C.). Following incubation, 150 µL of the solution from each well were transferred into a fresh MTP and read at 488 nm using a SpectraMAX MTP reader to quantify cleaning. Blank controls, as well as controls containing microswatches and detergent, but no enzyme, were also included.

Calculation of Enzyme Performance

The obtained absorbance value was corrected for the blank value (i.e., obtained after incubation of microswatches in the absence of enzyme). The resulting absorbance was a measure of the hydrolytic activity.

C. Amylase Concentration Determination by Antibody Titration

Alpha-amylase concentration and specific activity was determined, in some cases, by titration with an inhibitory polyclonal antibody. Polyclonal antibodies raised to *Bacillus stearothermophilus* alpha-amylase (AmyS) were found to be strongly inhibitory of AmyS and the alpha-amylase from *Bacillus* sp. TS23 (e.g., the binding is tight enough to produce a linear titration of activity loss). Therefore, this antibody can be used to measure enzyme concentration, which, in turn, is used to calculate specific activity.

Briefly, the amount of enzyme inhibition produced by several known concentrations of antibody is measured. From this information, the concentration of antibody required for complete inhibition is extrapolated, which is equivalent to the enzyme concentration in the sample. Alpha-amylase activity and inhibition was measured using the fluorogenic BODIPY-starch assay. The buffer was 50 mM MOPS, pH 7.0, containing 0.005% Tween-80.

A polyclonal antibody directed against purified AmyS was raised in a rabbit and purified by standard methods. An empirical "apparent concentration" value of an antibody stock solution was determined by measuring the inhibition of a sample of AmyS of known specific activity. The antibody sample was used to determine the concentration and specific activity of AmyS and TS23t variants. These values were used to create normalized 96-well enzyme stock plates, in which all of the variants were diluted to a common concentration.

D. Native Protein Gel Electrophoresis

Electrophoretic mobility of variant protein samples was measured using the PHASTGEL system (GE Healthcare) on pre-cast native polyacrylamide gels (PHASTGEL Homogeneous) at either 7.5% or 12.5% concentration. Buffer strips (PHASTGEL Native) were used and consisted of pH 8.8 in 0.88 M L-Alanine, 0.25 M Tris buffer. Typical run conditions consisted of 400 V for 12.75 minutes with an anode-to-cathode distance of 3.7 cm.

Alternatively, electrophoretic mobility of variant protein samples was measured on 1 mm-thick 0.5-1.5% agarose gels at various pH values (i.e. 5.8, 8.0 and 10.0) through a choice of a suitable buffer system. The electrophoresis was carried out under non-denaturing conditions. The Cathode-Anode length was 13.9 cm. A sample of 1-2 µg protein was mixed with 5% glycerol+0.05% bromophenol blue and loaded on each lane. Gels were run typically for 1 hour at 100V.

Gels were stained with Louisville blue dye dissolved in 10% acetic acid and destained with 10% methanol and 10% acidic acid-in-water. Between 12 and 20 protein variants were loaded simultaneously, depending on native gel system used. As a consequence, the electrophoretic mobility of a protein variant can be immediately assessed, relative to charge ladder standards loaded on the same gel.

E. Detergent Heat Inactivation

Heat inactivation of commercial detergent formulas serves to destroy the enzymatic activity of any protein components while retaining the properties of non-enzymatic components. Thus, this method was suitable for preparing commercially-purchased detergents for use in testing the enzyme variants. For North American (NA) and Western European (WE) heavy duty liquid laundry (HDL) detergents, heat inactivation was performed by placing pre-weighed liquid detergent (in a glass bottle) in a water bath at 95° C. for 2 hours. The incubation time for heat inactivation of North American (NA) and Japanese (JPN) heavy duty granular laundry (HDG) detergent was 8 hours and that for Western European (WE) HDG detergent was 5 hours. The incubation time for heat inactivation of NA and WE auto dishwashing (ADW) detergents was 8 hours. The detergents were purchased from local supermarket stores. Both un-heated and heated detergents were assayed within 5 minutes of dissolving the detergent to accurately determine percentage deactivated. Enzyme activity was tested by the suc-AAPF-pNA assay.

For testing of enzyme activity in heat-inactivated detergents, working solutions of detergents were made from the heat inactivated stocks. Appropriate amounts of water hardness (6 gpg or 12 gpg) and buffer were added to the detergent solutions to match the desired conditions (Table 12-1). The solutions were mixed by vortexing or inverting the bottles.

TABLE 12-1

Laundry and Dish Washing Conditions

| Region | Form | Dose | Detergent* | Buffer | Gpg | pH | T (° C.) |
|---|---|---|---|---|---|---|---|
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel Persil | 5 mM HEPES | 12 | 8.2 | 40 |
| WE | HDG | 8.0 g/L | P&G Ariel | 2 mM $Na_2 CO_3$ | 12 | 10.5 | 40 |
| JPN | HDG | 0.7 g/L | P&G TIDE ® | 2 mM $Na_2 CO_3$ | 6 | 10.0 | 20 |
| NA | HDG | 1.0 g/L | P&G TIDE ® | 2 mM $Na_2 CO_3$ | 6 | 10.0 | 20 |

TABLE 12-1-continued

Laundry and Dish Washing Conditions

| Region | Form | Dose | Detergent* | Buffer | Gpg | pH | T (° C.) |
|---|---|---|---|---|---|---|---|
| Automatic Dish Washing | | | | | | | |
| WE | ADW | 3.0 g/L RB Calgonit | | 2 mM $Na_2CO_3$ | 21 | 10.0 | 40 |
| NA | ADW | 3.0 g/L P&G Cascade | | 2 mM $Na_2CO_3$ | 9 | 10.0 | 40 |

*Abbreviations: Procter & Gamble (P&G); and Reckitt Benckiser (RB).

F. TERG-O-TOMETER Assay for Cleaning Performance Determination

A standard protocol for assessing protein and carbohydrate soil cleaning was used whereby the soil level on a fabric swatch was measured before and after cleaning under standard conditions. The fabric swatches consisted of woven cotton fabric soiled with either maize starch, rice starch or a blood, milk, and carbon black mixture. Swatches were purchased from Testfabrics, Inc. (West Pittiston, Pa.). Maize Starch (EMPA 161) and Blood, Milk, Carbon Black (EMPA 116) technical soils were produced by EMPA Test materials AG (St. Gallen, Switzerland). Rice Starch (CFT CS-28) soils were produced by the Center for Testmaterials BV (Vlaardingen, Netherlands). Each stain was measured before and after treatment by optical reflectance using a Minolta Reflectometer CR410 set to a D65 (6500° K) standard illuminant. The difference in the L, a, b values was converted to total color difference (dE), as defined by the CIE-LAB color space. Cleaning of the stains are expressed as percent stain removal index (% SRI) by taking a ratio between the color difference before and after washing and comparing it to the difference of unwashed soils (before wash) to unsoiled fabric.

Cleaning experiments were conducted in a TERG-O-TOMETER (United States Testing Co., Hoboken, N.J.) equipped with 6 stainless steel 2 L pots fitted with overhead agitators. Each treatment was conducted in 1 L total volume consisting of either 6 grains per gallon 3:1 (calcium:magnesium) water hardness or 12 grains per gallon water hardness. Detergents used in the wash experiments were 1.5 g/L AATCC HDL WOB 2003 liquid detergent with 5 mM HEPES buffer at pH 8, 0.7 g/L AATCC HDD WOB 1993 granular detergent, 8 g/L EEC A*60456 granular detergent with perborate and TAED bleach, or 5 g/L Persil Power Gel liquid detergent. Enzyme was added directly into the wash solution and reactions were then initiated by addition of either 40 g/L or 200 g/L of soiled and ballast fabric. The washing reactions were agitated at 100 rpm for 10, 15, or 40 minutes at 20° C., 25° C., 30° C., 40° C., or 50° C. Following cleaning, swatches were rinsed for 3 minutes in tap water, spun in a front-loading washing machine at 1000 rpm to remove excess water, and dried in a dryer at low heat on a permanent press cycle for approximately 45 minutes. Comparison of the extent of soil removal was assessed by reflectometry and expressed as the % soil removal index (% SRI). The control condition did not contain enzyme and the positive control consisted of various doses of benchmark commercial enzymes.

G. BODIPY-Starch Assay for Determination of Amylase Activity

The BODIPY-starch assay was performed using the EnzChek® Ultra Amylase Assay Kit (E33651, Invitrogen). A 1 mg/mL stock solution of the DQ starch substrate was prepared by dissolving the contents of the vial containing the lyophilized substrate in 100 µL of 50 mM sodium acetate buffer at pH 4.0. The vial was vortexed for about 20 seconds and left at room temperature, in the dark, with occasional mixing until dissolved. 900 µL of assay buffer (50 mM sodium acetate with 2.6 mM $CaCl_2$ pH 5.8) was added and the vial was mixed by vortex for about 20 seconds. The substrate solution was stored at room temperature, in the dark, until ready to use or at 4° C. For the assay, a 100 µg/mL of working solution of the DQ substrate was prepared from the 1 mg/mL substrate solution in the assay buffer. 190 µL of 100 µg/mL substrate solution was added to each well in a flat-bottom 96-well microtiter plate. 10 µL of each enzyme sample was added to a well, mixed for 30 seconds using a thermomixer at 800 rpm. A blank sample containing buffer and substrate only (no-enzyme blank) was included in the assay. The rate of change of fluorescence intensity was measured (excitation: 485 nm, emission: 520 nm) in a fluorescence microtiter plate reader at 25° C. for 5 minutes.

H. Corn Flour Hydrolysis for Determination of Amylase Activity

Starch Hydrolysis of Corn Flour Substrate Assay for Enzymatic Activity. Organic corn flour (Azure Farms, lot no. 03227) was evenly spread into Greiner 96-well microplate, polypropylene, black, flat bottom chimney wells, (Cat. No. 655209), using a solids dispensing device (V&P Scientific). 85 µL of 20 mM sodium acetate pH 5.6 were added to each well and mixed. A foil seal was applied to the top of the plate and the plate pre-incubated at 70° C. in the Thermomixer for 20-30 minutes. Enzyme samples were diluted in Agilent polypropylene plate (5042-1385) in 20 mM sodium acetate buffer. 11 µL of diluted enzyme samples were added to the substrate plate and the plate sealed firmly with another foil. Plates were then transferred to Labnet VorTemp 56 Incubator/Shaker with metal blocks (Cat. No. S2056A), pre-heated to 95° C. and the shake speed set to 500 rpm. The incubation was continued for 30 minutes. At the end of the incubation, the plates were rapidly cooled in an ice bucket and the starch hydrolysis reaction was stopped by addition of 100 µL of 0.1N H2SO4 to each well. The plate was mixed briefly and the starch hydrolysis reaction products were either analyzed by the PAHBAH assay or HPLC.

Colorimetric detection of Soluble Sugar Concentrations from Enzymatic Hydrolysis of Corn Flour Substrate. Aliquots of 80 µL of 0.5 N NaOH were added to all wells of an empty PCR plate followed by 20 µL of PAHBAH reagent (5% w/v p-hydroxybenzoic acid hydrazide (PAHBAH, Sigma #H9882, dissolved in 0.5 N HCl) and mixed (PAHBAH reaction plate). 10 µL of the starch hydrolysis reaction supernatants were added to the PAHBAH reaction plate. All plates were sealed and placed in the thermocycler (MJ Research Tetrad), programmed for 2 minutes at 95° C., and then cooled to 20° C. Samples of 80 µL of the developed PAHBAH reaction mixtures were transferred to a read plate and absorbance was measured at 405 nm in a spectrophotometer.

HPLC Determination of Soluble Sugar Concentrations from Enzymatic Hydrolysis of Corn Flour Substrate. Soluble sugar standards (DP1-DP7) obtained from Sigma (St. Louis, Mo.) were all diluted in Milli-Q water to 100 mg/mL and used for converting peak area for the sugars to actual sugar concentrations. The quenched plate from the starch hydrolysis assay was spun in a Beckman Coulter Allegra 6R Centrifuge for 5 minutes at 3000 rpm 25° C. The supernatant was pipetted from the spun plate and transferred to a Multiscreen-HV filter plate (Catalog No. MAHVN4550). The filter plate was spun over an Agilent HPLC plate in the Hettich Rotanta centrifuge for 10 minutes at 6000 rpm 25° C. 50 µL of 0.01N sulfuric acid mobile phase (0.1N sulfuric acid diluted 10× with Milli-Q water) was transferred to each well of another clean Agilent HPLC plate. The filtered plate was briefly mixed and 50 µL of the filtrate was transferred the corresponding wells in the plate with 50 µL per well of mobile phase. Diluted sugar standards were added to empty wells in the plate to be included in the calibration. The contents were mixed briefly on a platform shaker and the plate covered with a Nalgene Pre-slit Well Cap. The HPLC column (Bio-Rad Aminex HPX-87H column Cat No. 125-0140) was prepared ahead of time with 2L of mobile phase running at a constant flow rate of 0.6 mL/minute. All samples in the plate were run with 20 µL injection volume and analyzed using AMIN-EXH.M and RID (refractive index) as the detector. After the run was completed, the flow rate in the HPLC was dropped down to 0.05 mL/min.

I. Determination of Starch Viscosity Reduction by Alpha-Amylase

In this assay, viscosity reduction of cornstarch substrate solution was measured in a viscometer. The cornstarch substrate slurry was made up fresh in batch mode with 30% corn flour dry solids in distilled water and adjusted to pH 5.8 using sulfuric acid. For each run, 50 grams of the slurry (15 grams dry solids) was weighed out and pre-incubated for 10 minutes to warm up to 70° C. Upon amylase addition, the temperature was immediately ramped up from 70° C. to 85° C. with a rotation speed of 75 rpm. Once the temperature of the slurry and amylase mixture reached 85° C., the temperature was held constant and viscosity was monitored for an additional 30 minutes.

J. Measurement of Enzyme Binding to Macromolecular Substrates

Binding assays were done to determine substrate binding of Amylase (AmyS) charge ladder variants (charge change=−12 to +12 relative to wild-type AmyS) to corn stover and bagasse. Substrates used included bagasse (sugarcane bagasse from Brazil, dilute-acid pre-treated by National Renewable Energy Laboratory, washed and buffered at pH 5), AFEX (ammonia fiber expansion corn stover), and PCS (dilute sulfuric acid pre-treated corn stover, washed and adjusted to pH 5). All substrates were brought to the desired percentage solids prior to use.

Amylase Binding: Amylase charge ladder variants were purified and diluted to 200 ppm for testing. A 1% cellulose bagasse solution was prepared in borate buffer (40 mM, pH 8.5, 0.016% Tween-80). 150 µL of the bagasse solution was added into each well in a microtiter filtration plate. 150 µL of borate buffer was added into a set of separate wells, which served as controls. 10 µL of amylase charge ladder variants was added into the filtration plate, each condition was in duplicates. The plate was incubated at room temperature for 2 hours. The filtrate was collected and amylase activity in the supernatant was measured by BODIPY-starch assay.

Measurement of Enzyme Binding to Microswatches: Amylase variants were incubated with or without CS-28 rice starch microswatches under standard wash conditions for 30 min. The amount of free enzyme was measured by the BODIPY-starch assay. The fraction of enzyme bound to the microswatches was calculated as follows: Fraction bound= (Activity of enzyme in absence of swatch—Activity of enzyme in presence of swatch)/(Activity of enzyme in absence of swatch).

Example 13

Amylase Production in *B. subtilis*

In this Example, production of a mutant truncated form *Bacillus stearothermophilus* amylase alpha-amylase (having a S242Q mutation and a 29 amino acid deletion from the C-terminus; also referred to herein as S242Q) and variants thereof in *B. subtilis* are described. Transformation was performed as known in the art (see e.g., WO 02/14490). Briefly, the gene encoding the parent amylases was cloned into the pHPLT expression vector, which contains the LAT promoter (PLAT), a sequence encoding the LAT signal peptide (preLAT), followed by PstI and HpaI restriction sites for cloning.

The coding region for the LAT signal peptide is shown below:

atgaaacaac aaaaacggct ttacgcccga ttgctgacgc tgttatttgc gct-catcttc ttgctgcctc attctgcagc ttcagca (SEQ ID NO: 19).

The amino acid sequence of the LAT signal peptide is shown below:

MKQQKRLYAR LLTLLFALIF LLPHSAASA (SEQ ID NO: 20)

The amino acid sequence of the mature truncated S242Q amylase with the substituted amino acid shown in italics was used as the basis for making the variant libraries described herein:

```
AAPFNGTMMQ YFEWYLPDDG TLWTKVANEA NNLSSLGITA LWLPPAYKGT

SRSDVGYGVY DLYDLGEFNQ KGTVRTKYGT KAQYLQAIQA AHAAGMQVYA DVVFDHKGGA

DGTEWVDAVE VNPSDRNQEI SGTYQIQAWT KFDFPGRGNT YSSFKWRWYH FDGVDWDESR

KLSRIYKFRG IGKAWDWEVD TENGNYDYLM YADLDMDHPE VVTELKNWGK WYVNTTNIDG

FRLDAVKHIK FQFFPDWLSY VRSQTGKPLF TVGEYWSYDI NKLHNYITKT NGTMSLFDAP

LHNKFYTASK SGGAFDMRTL MTNTLMKDQP TLAVTFVDNH DTEPGQALQS WVDPWFKPLA

YAFILTRQEG YPCVFYGDYY GIPQYNIPSL KSKIDPLLIA RRDYAYGTQH DYLDESDIIG

WTREGVTEKP GSGLAALITD GPGGSKWMYV GKQHAGKVFY DLTGNRSDTV TINSDGWGEF

KVNGGSVSVW VPRKTT (SEQ ID NO:21).
```

The PCR products were purified using QIAQUIK columns from Qiagen, and resuspended in 50 µL of deionized water. 50 µL of the purified DNA was digested with HpaI (Roche) and PstI (Roche), and the resultant DNA resuspended in 30 μL of deionized water. 10-20 ng/μL of the DNA was cloned into plasmid pHPLT using PstI and HpaI cloning sites. The ligation mixtures were directly transformed into competent *B. subtilis* cells (genotype: Δvpr, ΔwprA, Δmpr-ybfJ, ΔnprB). The *B. subtilis* cells have a competency gene (comK) which is placed under a xylose inducible promoter, so xylose was used to induce competency for DNA binding and uptake (see Hahn et al., *Mol. Microbiol.*, 21: 763-775, 1996).

The elements of plasmid pHPLT-AmyS include: pUB110=DNA fragment from plasmid pUB110 (McKenzie et al., *Plasmid* 15: 93-103, 1986). Plasmid features include: ori-pUB110=origin of replication from pUB110; neo=neomycin resistance gene from pUB110; Plat=transcriptional promoter from *B. licheniformis amylase*; Pre LAT=signal peptide from *B. licheniformis* amylase; SAMY 425ss=The coding region for truncated AmyE gene sequence (replaced by the coding regions for each truncated AmyE variant expressed in this study); and Terminator=transcriptional terminator from *B. licheniformis* amylase.

Example 14

Expression of Enzyme Variants

This Example describes the methods used to express various recombinant enzymes of the transformed *B. subtilis* of the preceding Examples.

Amylase Expression—2 mL Scale

*B. subtilis* clones containing S242Q (or a variant thereof) expression vectors were replicated with a steel 96-well replicator from glycerol stocks into 96-well culture plates (BD, 353075) containing 150 μL of LB media+10 μg/ml neomycin, grown overnight at 37° C., 220 rpm in a humidified enclosure. A 100 μL aliquot from the overnight culture was used to inoculate 2000 μL defined media+10 μg/ml neomycin in 5 mL plastic culture tubes. The cultivation media was an enriched semi-defined media based on MOPS buffer, with urea as major nitrogen source, glucose as the main carbon source, and supplemented with 1% SOYTONE and 5 mM calcium for robust cell growth. Culture tubes were incubated at 37° C., 250 rpm, for 72 hours. Following this incubation, the culture broths were centrifuged for 10 minutes at 3000×g. The supernatant solution was decanted into 15 mL polypropylene conical tubes and 80 μL of each sample were aliquoted into 96 well plates for protein quantitation.

Example 15

Production of Enzyme Variants

This Example describes the production of enzyme charge ladders and combinatorial charge libraries.

Enzyme Charge Ladders

Multiple protein variants spanning a range of physical properties of interest are selected from existing libraries or are generated by site-directed mutagenesis techniques as known in the art (See e.g., U.S. patent application Ser. Nos., 10/576,331, 11/581,102, and 11/583,334, assigned to Genencor International). This defined set of probe proteins is then assayed in a test of interest.

Exemplary amylase charge ladder variants are shown in the following tables and assayed as described herein. In these tables, the charge change is relative to the parent enzyme.

TABLE 15-1

| AmyS-S242Q Charge Ladder | |
|---|---|
| AmyS-S242Q Variant | Δ Charge |
| Q97E-Q319E-Q358E-Q443E | −4 |
| Q97E-Q319E-Q358E | −3 |
| Q97E-Q319E | −2 |
| Q97E | −1 |
| Q97R-Q319E | 0 |
| Parent AmyS-S242Q | 0 |
| Q97R | +1 |
| Q97R-Q319R | +2 |
| Q97R-Q319R-Q358R | +3 |
| Q97R-Q319R-Q358R | +4 |

Enzyme Combinatorial Charge Libraries (CCL)

Generation of *B. stearothermophilus* AmyS-S242Q CCL

The AmyS-S242Q plasmid DNA was isolated from a transformed *B. subtilis* strain (genotype: ΔaprE, ΔnprE, amyE::xylRPxylAcomK-phleo) and sent to DNA2.0 Inc. as the template for CCL construction. A request was made to DNA2.0 Inc. (Mountain View, Calif.) for the generation of positional libraries at each of the four sites in AmyS-S242Q (S242Q) amylase that are shown in Table 15-2. Variants were supplied as glycerol stocks in 96-well plates.

The AmyS S242Q combinatorial charge library was designed by identifying the following four residues: Gln-97, Gln 319, Gln 358, and Gln 443. A four site, 81-member CCL was created by making all combinations of three possibilities at each site: wild-type, arginine, or aspartic acid.

TABLE 15-2

| S242Q CCL Variants | | | | | |
|---|---|---|---|---|---|
| Variant # | Q97 | Q319 | Q358 | Q443 | Δ Charge |
| 1 | Q97E | Q319E | Q358E | Q443E | −4 |
| 2 | Q97E | Q319E | Q358E | Q443R | −2 |
| 3 | Q97E | Q319E | Q358E | — | −3 |
| 4 | Q97E | Q319E | Q358R | Q443E | −2 |
| 5 | Q97E | Q319E | Q358R | Q443R | 0 |
| 6 | Q97E | Q319E | Q358R | — | −1 |
| 7 | Q97E | Q319E | — | Q443E | −3 |
| 8 | Q97E | Q319E | — | Q443R | −1 |
| 9 | Q97E | Q319E | — | — | −2 |
| 10 | Q97E | Q319R | Q358E | Q443E | −2 |
| 11 | Q97E | Q319R | Q358E | Q443R | 0 |
| 12 | Q97E | Q319R | Q358E | — | −1 |
| 13 | Q97E | Q319R | Q358R | Q443E | 0 |
| 14 | Q97E | Q319R | Q358R | Q443R | +2 |
| 15 | Q97E | Q319R | Q358R | — | +1 |
| 16 | Q97E | Q319R | — | Q443E | −1 |
| 17 | Q97E | Q319R | — | Q443R | +1 |
| 18 | Q97E | Q319R | — | — | 0 |
| 19 | Q97E | — | Q358E | Q443E | −3 |
| 20 | Q97E | — | Q358E | Q443R | −1 |
| 21 | Q97E | — | Q358E | — | −2 |
| 22 | Q97E | — | Q358R | Q443E | −1 |
| 23 | Q97E | — | Q358R | Q443R | +1 |
| 24 | Q97E | — | Q358R | — | 0 |
| 25 | Q97E | — | — | Q443E | −2 |
| 26 | Q97E | — | — | Q443R | 0 |
| 27 | Q97E | — | — | — | −1 |
| 28 | Q97R | Q319E | Q358E | Q443E | −2 |
| 29 | Q97R | Q319E | Q358E | Q443R | 0 |
| 30 | Q97R | Q319E | Q358E | — | −1 |
| 31 | Q97R | Q319E | Q358R | Q443E | 0 |
| 32 | Q97R | Q319E | Q358R | Q443R | +2 |
| 33 | Q97R | Q319E | Q358R | — | +1 |
| 34 | Q97R | Q319E | — | Q443E | −1 |
| 35 | Q97R | Q319E | — | Q443R | +1 |
| 36 | Q97R | Q319E | — | — | 0 |
| 37 | Q97R | Q319R | Q358E | Q443E | 0 |

TABLE 15-2-continued

S242Q CCL Variants

| Variant # | Q97 | Q319 | Q358 | Q443 | Δ Charge |
|---|---|---|---|---|---|
| 38 | Q97R | Q319R | Q358E | Q443R | +2 |
| 39 | Q97R | Q319R | Q358E | — | +1 |
| 40 | Q97R | Q319R | Q358R | Q443E | +2 |
| 41 | Q97R | Q319R | Q358R | Q443R | +4 |
| 42 | Q97R | Q319R | Q358R | — | +3 |
| 43 | Q97R | Q319R | — | Q443E | +1 |
| 44 | Q97R | Q319R | — | Q443R | +3 |
| 45 | Q97R | Q319R | — | — | +2 |
| 46 | Q97R | — | Q358E | Q443E | −1 |
| 47 | Q97R | — | Q358E | Q443R | +1 |
| 48 | Q97R | — | Q358E | — | 0 |
| 49 | Q97R | — | Q358R | Q443E | +1 |
| 50 | Q97R | — | Q358R | Q443R | +3 |
| 51 | Q97R | — | Q358R | — | +2 |
| 52 | Q97R | — | — | Q443E | 0 |
| 53 | Q97R | — | — | Q443R | +2 |
| 54 | Q97R | — | — | — | +1 |
| 55 | — | Q319E | Q358E | Q443E | −3 |
| 56 | — | Q319E | Q358E | Q443R | −1 |
| 57 | — | Q319E | Q358E | — | −2 |
| 58 | — | Q319E | Q358R | Q443E | −1 |
| 59 | — | Q319E | Q358R | Q443R | +1 |
| 60 | — | Q319E | Q358R | — | 0 |
| 61 | — | Q319E | — | Q443E | −2 |
| 62 | — | Q319E | — | Q443R | 0 |
| 63 | — | Q319E | — | — | −1 |
| 64 | — | Q319R | Q358E | Q443E | −1 |
| 65 | — | Q319R | Q358E | Q443R | +1 |
| 66 | — | Q319R | Q358E | — | 0 |
| 67 | — | Q319R | Q358R | Q443E | +1 |
| 68 | — | Q319R | Q358R | Q443R | +3 |
| 69 | — | Q319R | Q358R | — | +2 |
| 70 | — | Q319R | — | Q443E | 0 |
| 71 | — | Q319R | — | Q443R | +2 |
| 72 | — | Q319R | — | — | +1 |
| 73 | — | — | Q358E | Q443E | −2 |
| 74 | — | — | Q358E | Q443R | 0 |
| 75 | — | — | Q358E | — | −1 |
| 76 | — | — | Q358R | Q443E | 0 |
| 77 | — | — | Q358R | Q443R | +2 |
| 78 | — | — | Q358R | — | +1 |
| 79 | — | — | — | Q443E | −1 |
| 80 | — | — | — | Q443R | +1 |
| 81 (parent) | Q97 | Q319 | Q358 | Q443 | 0 |

Example 16

Enzyme Wash Performance

This Example describes the testing of S242Q variant in a microswatch assay 1.0 μg/ml in AATCC HDL detergent or 5 mM HEPES buffer under varying ionic strength. The methods provided in Example 12 were used (See, "Rice Starch Microswatch Assay for testing Amylase Performance" and "Corn Four Hydrolysis").

There is an optimal net charge change for cleaning performance for enzyme in AATCC HDL detergent. Performance is measured in terms of relative cleaning performance observed in a rice starch microswatch activity assay. A value of around 1.0 indicates top cleaning performance in this assay. This is an example of optimizing a protein physical property (e.g., net charge) for improving a given outcome or benefit (e.g., cleaning performance in a liquid laundry detergent). The charge optimum identified with this limited set of probe proteins coincides with the optimum charge observed when measuring the entire charge combinatorial library. The use of probe proteins is therefore predictive of the behavior of the entire library.

According to the Debye-Hückel theory (Israelachivili Intermolecular and Surface Forces, $2^{nd}$ Edition: With Applications to Colloidal and Biological Systems, Academic Press $2^{nd}$ Ed. [1992]), electrostatic interactions are governed primarily by the strength of double-layer forces between interacting species at constant potential or constant charge (enzymes, substrates, fabric, and detergent), their size, and the dielectric constant of the surrounding medium. In order to characterize the electrostatic behavior of particles in a complex medium, such as a detergent formulation, their interaction in a reduced environment possessing the same Debye screening length is sufficient. This was accomplished by choosing a buffer of matching pH and conductivity to that of the detergent under wash conditions. An appropriate buffer for such testing is 5 mM HEPES buffer at pH 8.0 with varying amounts of indifferent electrolyte, such as NaCl. Addition of 2.5 mM NaCl to this buffer matches the pH and conductivity of typical North American wash conditions. Addition of a higher concentration of NaCl is representative of Japanese and European wash conditions, typically higher in ionic strength due to both increased water hardness and detergent concentrations.

Figure 22:
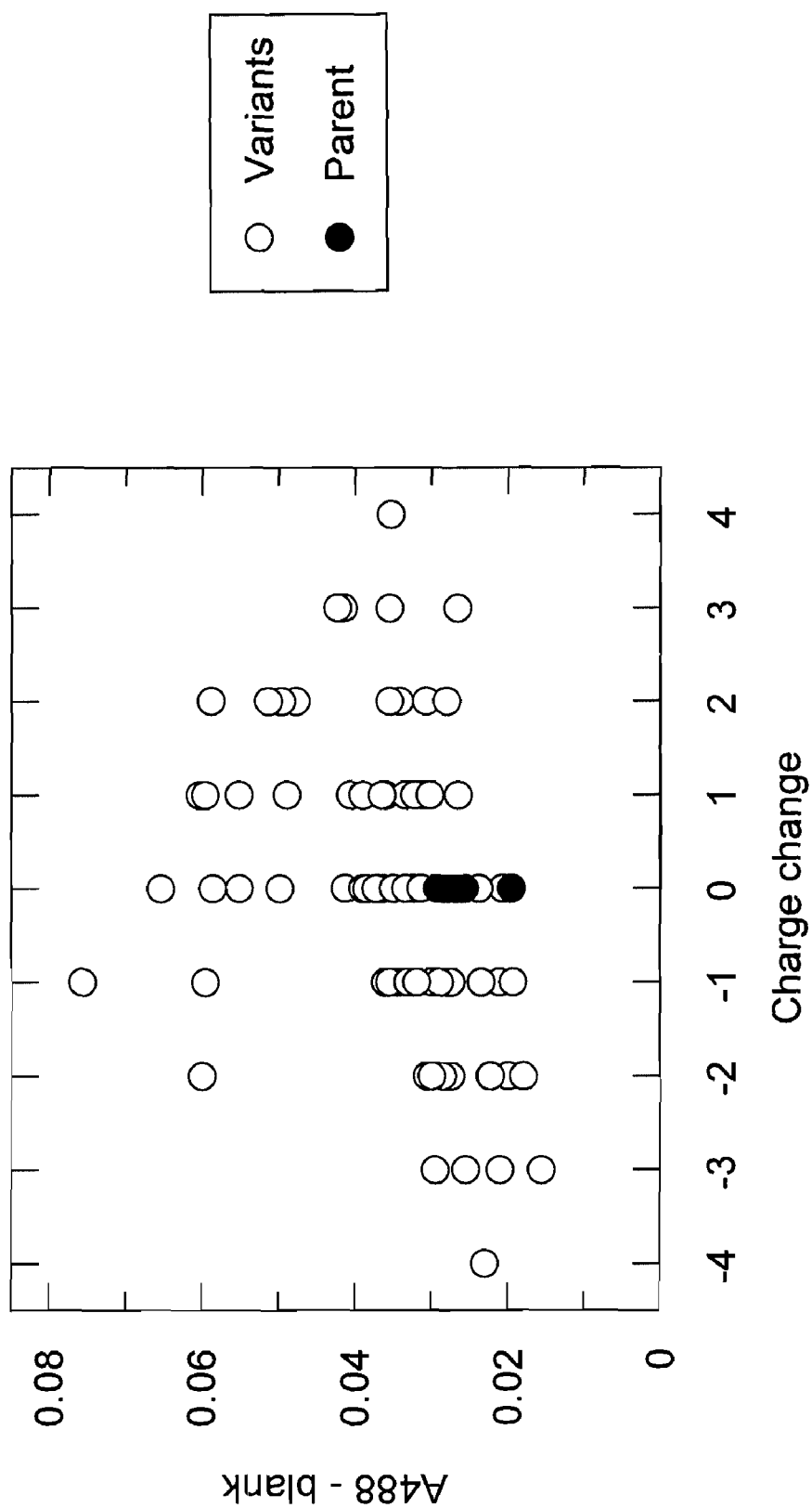
FIG. 22 is a graph depicting the performance of S242Q (filled circles) and its variants (open circles), as a function of charge, in the rice starch microswatch assay under North American laundry conditions using S242Q combinatorial charge library, rice starch microswatch cleaning in Tide 2×, at 20° C. Reference is made to Example 16.
Figure 23:
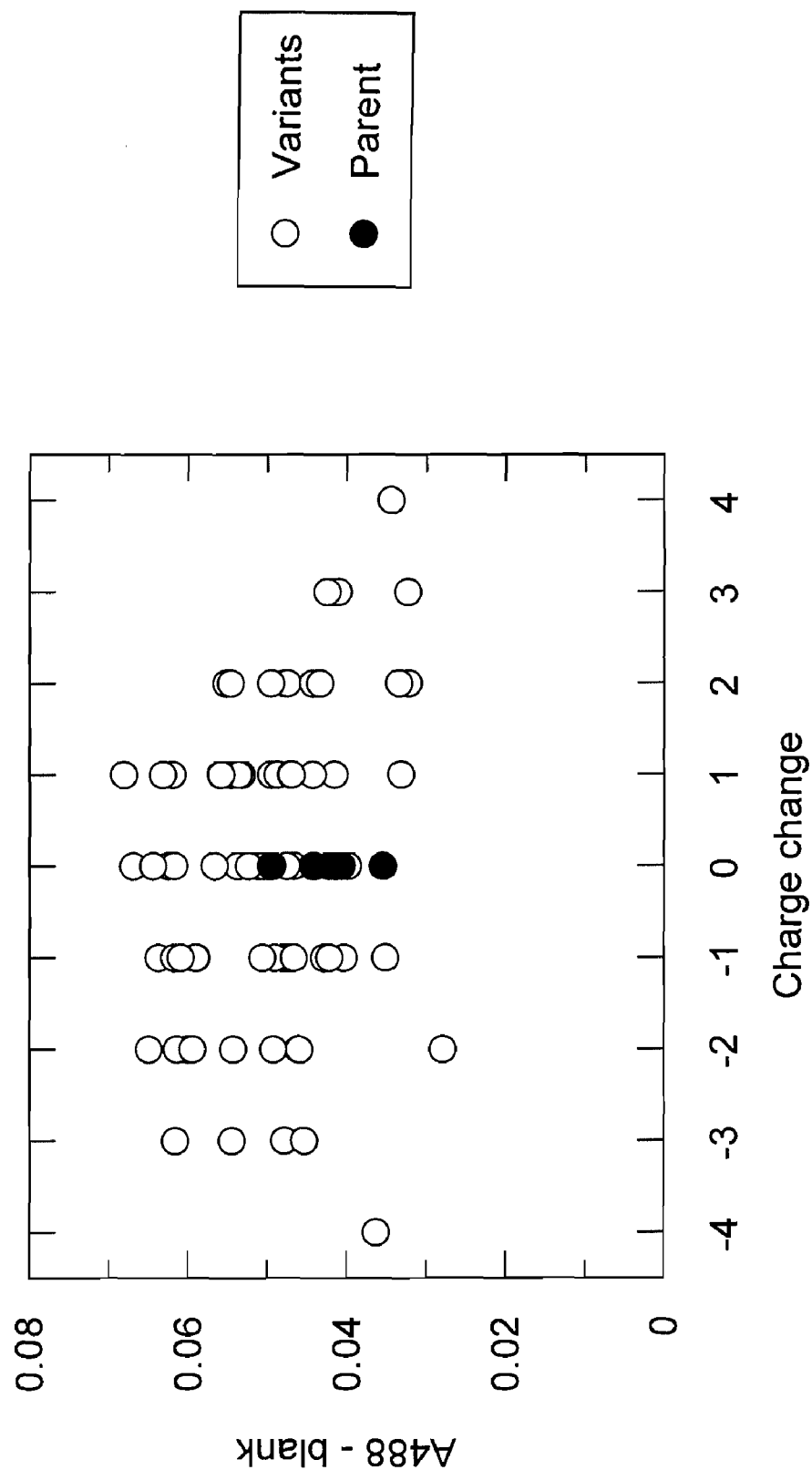
FIG. 23 is a graph depicting the performance of a truncated *Bacillus* sp. TS-23 amylase (closed circles) with the following mutations: Q98R, M201L, S243Q R309A, Q320R, Q359E, and K444E and its charge variants (open circles) (see co-pending U.S. Patent Application No. PCT/US2008/007103, filed 6 Jun. 2008) in the rice starch microswatch assay as a function of charge under Western European laundry conditions with TS23t combinatorial charge library, rice starch microswatch cleaning in Persil at 40° C. Reference is made to Example 16.

FIG. 22 shows that positive charge S242Q charge variants are superior for cleaning of rice starch microswatch under North American laundry conditions. Likewise negative charge TS23t variants are superior for cleaning of rice starch microswatches in Western European laundry conditions (FIG. 23).

Figure 24:
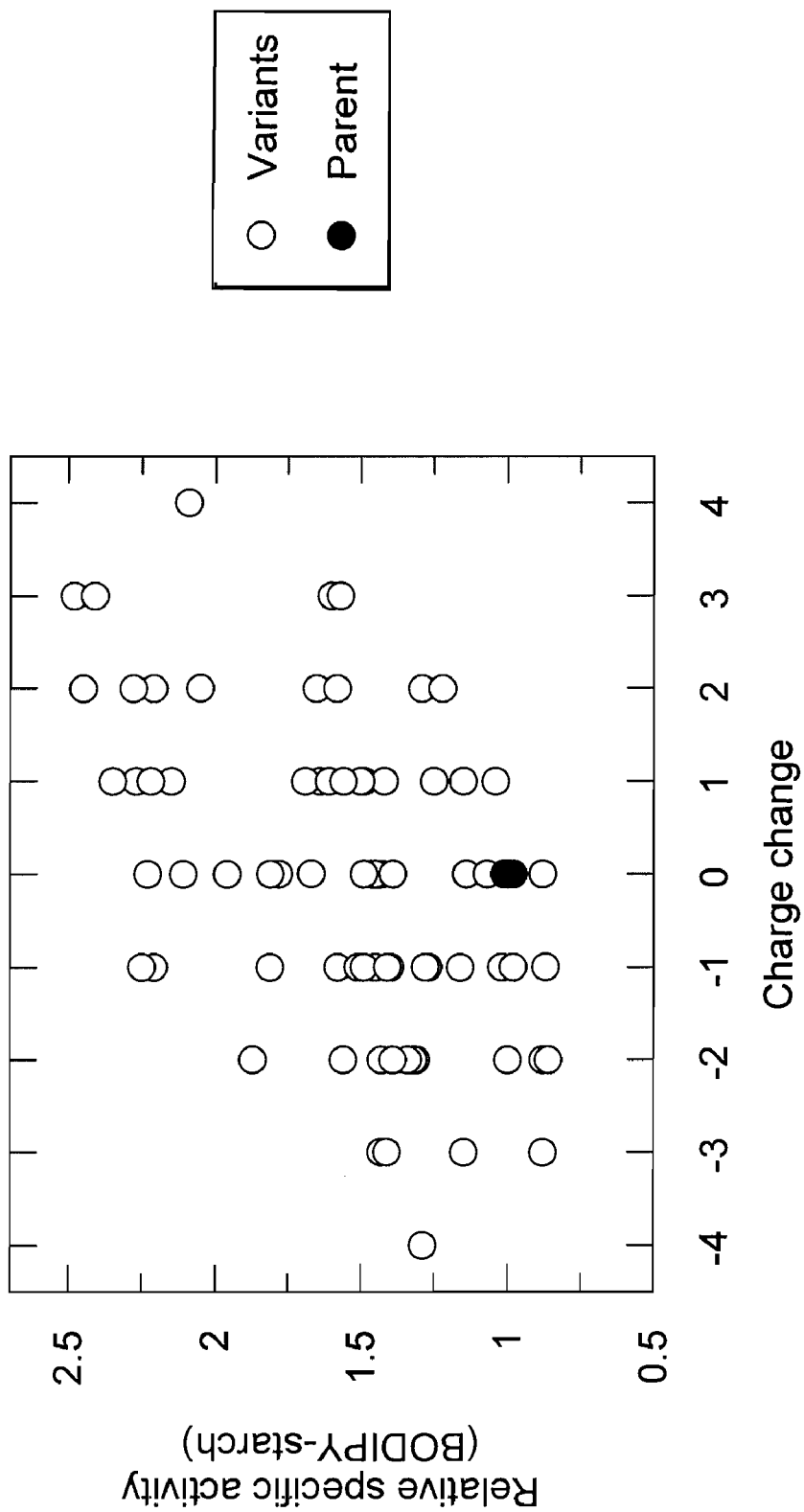
FIG. 24 is a graph depicting the performance of S242Q (closed circles) and its variants (open circles) in the BODIPY-starch assay as a function of charge. S242Q combinatorial charge library (CCL), specific activity on BODIPY-starch, standard assay conditions Reference is made to Example 16.

FIG. 24 demonstrates that positive S242Q variants exhibit higher specific activity for granular corn starch substrates hydrolysis.

Example 17

Thermostability

This Example describes determining the relationship between protein charge and thermal stability. Alpha-amylase assays were based on BODIPY starch hydrolysis before and after heating the culture supernatant. The same chemical and reagent solutions were used as described in Example 12.

Thermal Stability Assay for Alpha-Amylases

The filtered culture supernatants were serially diluted in 50 mM sodium acetate+2 mM $CaCl_2$ pH 5.8 with 002% Tween. 10 μL of each diluted culture supernatant was assayed to determine the initial amylase activity by the BODIPY starch assay. 50 μL of each diluted culture supernatant was placed in a VWR low profile PCR 96 well plate. 30 μL of mineral oil was added to each well as a sealant. The plate was incubated in a BioRad DNA engine Peltier Thermal Cycler at 95° C. for 30 or 60 minutes depending on the stability of the parent enzyme. Following incubation, the plate was cooled to 4° C. for 5 min and then kept at room temperature. 10 μL of each sample was added to a fresh plate and assayed to determine the final amylase activity by the BODIPY starch assay as described in Example 1.

Calculation of Thermostability

The residual activity of a sample was expressed as the ratio of the final absorbance and the initial absorbance, both corrected for blanks. A higher index indicates a more thermally stable variant. This is an example of optimizing a protein physical property, in this case net charge, for improving enzyme thermal stability for a liquid laundry application.

Thermostability Assay

Thermostability of the variants was assessed as described above. Thermostability winners are listed in Table 17-1. Winners were defined as those having a ratio of mutant residual activity to parent (i.e., S242Q) residual activity greater than 1.

TABLE 17-1

S242Q CCL - thermal stability winners

| Variant # | 97 | 319 | 358 | 443 | Mut residual act./WT residual act. |
|---|---|---|---|---|---|
| 2 | Q97E | Q319E | Q358E | Q443R | 1.12 |
| 10 | Q97E | Q319R | Q358E | Q443E | 1.12 |
| 13 | Q97E | Q319R | Q358R | Q443E | 1.36 |
| 14 | Q97E | Q319R | Q358R | Q443R | 1.16 |
| 15 | Q97E | Q319R | Q358R |  | 1.37 |
| 17 | Q97E | Q319R |  | Q443R | 1.29 |
| 18 | Q97E | Q319R |  |  | 1.11 |
| 27 | Q97E |  |  |  | 1.16 |
| 32 | Q97R | Q319E | Q358R | Q443R | 1.18 |
| 37 | Q97R | Q319R | Q358E | Q443E | 1.29 |
| 38 | Q97R | Q319R | Q358E | Q443R | 1.22 |
| 39 | Q97R | Q319R | Q358E |  | 1.21 |
| 40 | Q97R | Q319R | Q358R | Q443E | 1.20 |
| 41 | Q97R | Q319R | Q358R | Q443R | 1.26 |
| 42 | Q97R | Q319R | Q358R |  | 1.48 |
| 43 | Q97R | Q319R |  | Q443E | 1.21 |
| 44 | Q97R | Q319R |  | Q443R | 1.21 |
| 45 | Q97R | Q319R |  |  | 1.14 |
| 50 | Q97R |  | Q358R | Q443R | 1.14 |
| 62 |  | Q319E |  | Q443R | 1.26 |
| 63 |  | Q319E |  |  | 1.18 |
| 64 |  | Q319R | Q358E | Q443E | 1.19 |
| 65 |  | Q319R | Q358E | Q443R | 1.28 |
| 68 |  | Q319R | Q358R | Q443R | 1.14 |
| 70 |  | Q319R |  | Q443E | 1.22 |
| 73 |  |  | Q358E | Q443E | 1.15 |
| 74 |  |  | Q358E | Q443R | 1.15 |
| 75 |  |  | Q358E |  | 1.18 |

Example 18

Enzyme Performance

This Example demonstrates that enzyme performance may be affected by charge.

Enzyme performance was assessed using heat inactivated detergents as described above in Example 12. Winners were defined as those having Performance Index (PI) a greater than 1. PI is the ratio of mutant residual activity to parent (i.e., S242Q) residual activity. Results are shown in Tables 18-1 and 18-2.

TABLE 18-1

S242Q CCL - CS-28 rice starch microswatch winners, Tide 2x (North American conditions as described in Ex. 12)

| Variant # | 97 | 319 | 358 | 443 | rel charge | PI |
|---|---|---|---|---|---|---|
| 13 | Q97E | Q319R | Q358R | Q443E | 0 | 1.44 |
| 14 | Q97E | Q319R | Q358R | Q443R | 2 | 1.32 |
| 15 | Q97E | Q319R | Q358R |  | 1 | 1.40 |
| 16 | Q97E | Q319R |  | Q443E | -1 | 1.33 |
| 17 | Q97E | Q319R |  | Q443R | 1 | 1.40 |
| 18 | Q97E | Q319R |  |  | 0 | 1.41 |
| 20 | Q97E |  | Q358E | Q443R | -1 | 1.15 |
| 23 | Q97E |  | Q358R | Q443R | 1 | 1.21 |
| 25 | Q97E |  |  | Q443E | -2 | 1.18 |
| 26 | Q97E |  |  | Q443R | 0 | 1.25 |
| 27 | Q97E |  |  |  | -1 | 1.16 |
| 28 | Q97R | Q319E | Q358E | Q443E | -2 | 2.32 |
| 29 | Q97R | Q319E | Q358E | Q443R | 0 | 2.54 |
| 30 | Q97R | Q319E | Q358E |  | -1 | 2.93 |
| 31 | Q97R | Q319E | Q358R | Q443E | 0 | 2.27 |
| 32 | Q97R | Q319E | Q358R | Q443R | 2 | 2.28 |

TABLE 18-1-continued

S242Q CCL - CS-28 rice starch microswatch winners, Tide 2x (North American conditions as described in Ex. 12)

| Variant # | 97 | 319 | 358 | 443 | rel charge | PI |
|---|---|---|---|---|---|---|
| 33 | Q97R | Q319E | Q358R |  | 1 | 2.34 |
| 34 | Q97R | Q319E |  | Q443E | -1 | 2.31 |
| 35 | Q97R | Q319E |  | Q443R | 1 | 2.31 |
| 36 | Q97R | Q319E |  |  | 0 | 2.14 |
| 37 | Q97R | Q319R | Q358E | Q443E | 0 | 1.93 |
| 38 | Q97R | Q319R | Q358E | Q443R | 2 | 1.85 |
| 39 | Q97R | Q319R | Q358E |  | 1 | 2.14 |
| 40 | Q97R | Q319R | Q358R | Q443E | 2 | 1.92 |
| 41 | Q97R | Q319R | Q358R | Q443R | 4 | 1.37 |
| 42 | Q97R | Q319R | Q358R |  | 3 | 1.61 |
| 43 | Q97R | Q319R |  | Q443E | 1 | 1.90 |
| 44 | Q97R | Q319R |  | Q443R | 3 | 1.64 |
| 45 | Q97R | Q319R |  |  | 2 | 1.99 |
| 46 | Q97R |  | Q358E | Q443E | -1 | 1.40 |
| 47 | Q97R |  | Q358E | Q443R | 1 | 1.29 |
| 48 | Q97R |  | Q358E |  | 0 | 1.60 |
| 49 | Q97R |  | Q358R | Q443E | 1 | 1.57 |
| 50 | Q97R |  | Q358R | Q443R | 3 | 1.38 |
| 51 | Q97R |  | Q358R |  | 2 | 1.37 |
| 52 | Q97R |  |  | Q443E | 0 | 1.51 |
| 54 | Q97R |  |  |  | 1 | 1.51 |
| 55 |  | Q319E | Q358E | Q443E | -3 | 1.14 |
| 56 |  | Q319E | Q358E | Q443R | -1 | 1.38 |
| 57 |  | Q319E | Q358E |  | -2 | 1.10 |
| 58 |  | Q319E | Q358R | Q443E | -1 | 1.25 |
| 59 |  | Q319E | Q358R | Q443R | 1 | 1.41 |
| 60 |  | Q319E | Q358R |  | 0 | 1.49 |
| 61 |  | Q319E |  | Q443E | -2 | 1.16 |
| 62 |  | Q319E |  | Q443R | 0 | 1.45 |
| 63 |  | Q319E |  |  | -1 | 1.28 |
| 64 |  | Q319R | Q358E | Q443E | -1 | 1.12 |
| 65 |  | Q319R | Q358E | Q443R | 1 | 1.19 |
| 66 |  | Q319R | Q358E |  | 0 | 1.36 |
| 67 |  | Q319R | Q358R | Q443E | 1 | 1.24 |
| 69 |  | Q319R | Q358R |  | 2 | 1.19 |
| 70 |  | Q319R |  | Q443E | 0 | 1.29 |
| 76 |  |  | Q358R | Q443E | 0 | 1.22 |
| 78 |  |  | Q358R |  | 1 | 1.25 |
| 79 |  |  |  | Q443E | -1 | 1.24 |
| 80 |  |  |  | Q443R | 1 | 1.17 |

TABLE 18-2

S242Q CCL - CS-28 rice starch microswatch winners, Persil (Western European conditions)

| Variant # | 97 | 319 | 358 | 443 | rel charge | PI |
|---|---|---|---|---|---|---|
| 2 | Q97E | Q319E | Q358E | Q443R | -2 | 1.41 |
| 3 | Q97E | Q319E | Q358E |  | -3 | 1.94 |
| 4 | Q97E | Q319E | Q358R | Q443E | -2 | 1.61 |
| 5 | Q97E | Q319E | Q358R | Q443R | 0 | 1.39 |
| 6 | Q97E | Q319E | Q358R |  | -1 | 2.04 |
| 7 | Q97E | Q319E |  | Q443E | -3 | 2.05 |
| 8 | Q97E | Q319E |  | Q443R | -1 | 1.84 |
| 9 | Q97E | Q319E |  |  | -2 | 2.27 |
| 10 | Q97E | Q319R | Q358E | Q443E | -2 | 1.35 |
| 13 | Q97E | Q319R | Q358R | Q443E | 0 | 1.45 |
| 14 | Q97E | Q319R | Q358R | Q443R | 2 | 1.17 |
| 15 | Q97E | Q319R | Q358R |  | 1 | 1.22 |
| 16 | Q97E | Q319R |  | Q443E | -1 | 1.26 |
| 17 | Q97E | Q319R |  | Q443R | 1 | 1.29 |
| 18 | Q97E | Q319R |  |  | 0 | 1.76 |
| 26 | Q97E |  |  | Q443R | 0 | 1.36 |
| 27 | Q97E |  |  |  | -1 | 1.31 |
| 28 | Q97R | Q319E | Q358E | Q443E | -2 | 2.21 |
| 29 | Q97R | Q319E | Q358E | Q443R | 0 | 1.96 |
| 30 | Q97R | Q319E | Q358E |  | -1 | 1.94 |
| 31 | Q97R | Q319E | Q358R | Q443E | 0 | 2.11 |
| 32 | Q97R | Q319E | Q358R | Q443R | 2 | 1.87 |
| 33 | Q97R | Q319E | Q358R |  | 1 | 2.41 |

TABLE 18-2-continued

S242Q CCL - CS-28 rice starch microswatch winners, Persil (Western European conditions)

| Variant # | 97 | 319 | 358 | 443 | rel charge | P1 |
|---|---|---|---|---|---|---|
| 34 | Q97R | Q319E | | Q443E | −1 | 2.20 |
| 35 | Q97R | Q319E | | Q443R | 1 | 2.21 |
| 36 | Q97R | Q319E | | | 0 | 2.07 |
| 37 | Q97R | Q319R | Q358E | Q443E | 0 | 1.86 |
| 38 | Q97R | Q319R | Q358E | Q443R | 2 | 1.83 |
| 39 | Q97R | Q319R | Q358E | | 1 | 1.99 |
| 40 | Q97R | Q319R | Q358R | Q443E | 2 | 1.85 |
| 41 | Q97R | Q319R | Q358R | Q443R | 4 | 1.36 |
| 42 | Q97R | Q319R | Q358R | | 3 | 1.90 |
| 43 | Q97R | Q319R | | Q443E | 1 | 1.99 |
| 44 | Q97R | Q319R | | Q443R | 3 | 1.94 |
| 45 | Q97R | Q319R | | | 2 | 1.75 |
| 46 | Q97R | | Q358E | Q443E | −1 | 1.71 |
| 47 | Q97R | | Q358E | Q443R | 1 | 1.39 |
| 48 | Q97R | | Q358E | | 0 | 1.85 |
| 50 | Q97R | | Q358R | Q443R | 3 | 1.24 |
| 51 | Q97R | | Q358R | | 2 | 1.36 |
| 52 | Q97R | | | Q443E | 0 | 1.25 |
| 54 | Q97R | | | | 1 | 1.88 |
| 55 | | Q319E | Q358E | Q443E | −3 | 1.12 |
| 56 | | Q319E | Q358E | Q443R | −1 | 1.17 |
| 58 | | Q319E | Q358R | Q443E | −1 | 1.16 |
| 59 | | Q319E | Q358R | Q443R | 1 | 1.25 |
| 60 | | Q319E | Q358R | | 0 | 1.50 |
| 63 | | Q319E | | | −1 | 1.36 |
| 64 | | Q319R | Q358E | Q443E | −1 | 1.10 |
| 65 | | Q319R | Q358E | Q443R | 1 | 1.18 |
| 66 | | Q319R | Q358E | | 0 | 1.25 |
| 67 | | Q319R | Q358R | Q443E | 1 | 1.29 |
| 70 | | Q319R | | Q443E | 0 | 1.15 |

Activity was also measured using the BODIPY starch hydrolysis assay as provided herein. The results are shown in Table 18-3. The relative specific activity on this starch substrate (a corn starch) greater than 1 indicates the variant has higher specific activity than the S242Q parent. Relative ppm is expression titers, greater than 1 indicates higher titers (in shake tubes) than the S242Q parent.

Table 18-3

S242Q CCL - titer and/or BODIPY-starch winners

| Variant # | 97 | 319 | 358 | 443 | Charge | Rel ppm | Rel Sp act |
|---|---|---|---|---|---|---|---|
| 1 | Q97E | Q319E | Q358E | Q443E | −4 | 1.27 | 1.29 |
| 2 | Q97E | Q319E | Q358E | Q443R | −2 | 1.19 | 1.31 |
| 3 | Q97E | Q319E | Q358E | | −3 | 1.00 | 1.43 |
| 4 | Q97E | Q319E | Q358R | Q443E | −2 | 1.23 | 1.43 |
| 5 | Q97E | Q319E | Q358R | Q443R | 0 | 0.94 | 1.78 |
| 6 | Q97E | Q319E | Q358R | | −1 | 0.89 | 1.81 |
| 7 | Q97E | Q319E | | Q443E | −3 | 1.40 | 1.41 |
| 8 | Q97E | Q319E | | Q443R | −1 | 1.12 | 1.58 |
| 9 | Q97E | Q319E | | | −2 | 1.09 | 1.56 |
| 10 | Q97E | Q319R | Q358E | Q443E | −2 | 1.45 | 1.32 |
| 11 | Q97E | Q319R | Q358E | Q443R | 0 | 1.32 | 1.49 |
| 12 | Q97E | Q319R | Q358E | | −1 | 1.58 | 1.27 |
| 13 | Q97E | Q319R | Q358R | Q443E | 0 | 0.65 | 1.44 |
| 14 | Q97E | Q319R | Q358R | Q443R | 2 | 0.66 | 1.65 |
| 15 | Q97E | Q319R | Q358R | | 1 | 0.80 | 1.64 |
| 16 | Q97E | Q319R | | Q443E | −1 | 1.09 | 1.51 |
| 17 | Q97E | Q319R | | Q443R | 1 | 1.00 | 1.42 |
| 18 | Q97E | Q319R | | | 0 | 0.87 | 1.78 |
| 19 | Q97E | | Q358E | Q443E | −3 | 1.22 | 0.88 |
| 21 | Q97E | | Q358E | | −2 | 1.12 | 0.88 |
| 22 | Q97E | | Q358R | Q443E | −1 | 0.91 | 1.16 |
| 23 | Q97E | | Q358R | Q443R | 1 | 0.78 | 1.25 |
| 24 | Q97E | | Q358R | | 0 | 1.08 | 1.14 |
| 25 | Q97E | | | Q443E | −2 | 1.12 | 1.00 |
| 28 | Q97R | Q319E | Q358E | Q443E | −2 | 0.78 | 1.87 |
| 29 | Q97R | Q319E | Q358E | Q443R | 0 | 0.80 | 1.81 |
| 30 | Q97R | Q319E | Q358E | | −1 | 0.68 | 2.21 |
| 31 | Q97R | Q319E | Q358R | Q443E | 0 | 0.68 | 1.96 |
| 32 | Q97R | Q319E | Q358R | 0443R | 2 | 0.70 | 2.05 |
| 33 | Q97R | Q319E | Q358R | | 1 | 0.60 | 2.27 |
| 34 | Q97R | Q319E | | Q443E | −1 | 0.65 | 2.25 |
| 35 | Q97R | Q319E | | Q443R | 1 | 0.70 | 2.15 |
| 36 | Q97R | Q319E | | | 0 | 0.73 | 2.23 |
| 37 | Q97R | Q319R | Q358E | Q443E | 0 | 0.93 | 2.11 |
| 38 | Q97R | Q319R | Q358E | Q443R | 2 | 0.65 | 2.21 |
| 39 | Q97R | Q319R | Q358E | | 1 | 0.82 | 2.22 |
| 40 | Q97R | Q319R | Q358R | Q443E | 2 | 0.74 | 2.28 |
| 41 | Q97R | Q319R | Q358R | Q443R | 4 | 0.55 | 2.09 |
| 42 | Q97R | Q319R | Q358R | | 3 | 0.67 | 2.48 |
| 43 | Q97R | Q319R | | Q443E | 1 | 0.84 | 2.35 |
| 44 | Q97R | Q319R | | Q443R | 3 | 0.73 | 2.41 |
| 45 | Q97R | Q319R | | | 2 | 0.76 | 2.45 |
| 46 | Q97R | | Q358E | Q443E | −1 | 0.79 | 1.45 |
| 47 | Q97R | | Q358E | Q443R | 1 | 0.75 | 1.42 |
| 48 | Q97R | | Q358E | | 0 | 0.82 | 1.46 |
| 49 | Q97R | | Q358R | Q443E | 1 | 0.67 | 1.69 |
| 50 | Q97R | | Q358R | Q443R | 3 | 0.60 | 1.60 |
| 51 | Q97R | | Q358R | | 2 | 0.64 | 1.29 |
| 52 | Q97R | | | Q443E | 0 | 0.83 | 1.43 |
| 54 | Q97R | | | | 1 | 0.72 | 1.49 |
| 55 | | Q319E | Q358E | Q443E | −3 | 0.99 | 1.15 |
| 56 | | Q319E | Q358E | Q443R | −1 | 0.77 | 1.40 |
| 57 | | Q319E | Q358E | | −2 | 0.83 | 1.34 |
| 58 | | Q319E | Q358R | Q443E | −1 | 0.73 | 1.49 |
| 59 | | Q319E | Q358R | Q443R | 1 | 0.67 | 1.61 |
| 60 | | Q319E | Q358R | | 0 | 0.80 | 1.67 |
| 61 | | Q319E | | Q443E | −2 | 0.91 | 1.39 |
| 62 | | Q319E | | Q443R | 0 | 0.73 | 1.45 |
| 63 | | Q319E | | | −1 | 0.75 | 1.41 |
| 64 | | Q319R | Q358E | Q443E | −1 | 1.05 | 1.28 |
| 65 | | Q319R | Q358E | Q443R | 1 | 0.94 | 1.42 |
| 66 | | Q319R | Q358E | | 0 | 0.96 | 1.39 |
| 67 | | Q319R | Q358R | Q443E | 1 | 1.02 | 1.50 |
| 68 | | Q319R | Q358R | Q443R | 3 | 0.71 | 1.57 |
| 69 | | Q319R | Q358R | | 2 | 0.71 | 1.58 |
| 70 | | Q319R | | Q443E | 0 | 0.91 | 1.49 |
| 72 | | Q319R | | | 1 | 0.95 | 1.56 |
| 77 | | | Q358R | Q443R | 2 | 0.67 | 1.22 |
| 78 | | | Q358R | | 1 | 0.66 | 1.15 |

Example 19

Balancing Mutational Effects on Amylase Activity and Expression

This example illustrates that two separate enzyme properties can be simultaneously optimized by the introduction of multiple amino acid substitutions, even where the properties are negatively correlated due, for example, to oppositely linked to charge characteristics of the protein.

It was determined during experimentation that the median expression of AmyS-242Q decreased with increasing positive charge. However, specific BODIPY starch hydrolysis increased with increasing positive charge. Enhanced recombinant amylase expression and starch hydrolysis are desirable in an engineered variant of AmyS-242Q suitable for starch liquefaction in the fuel ethanol industry or cleaning in detergent applications for instance. These properties, however, are apparently conflicting properties. Using the methods provided herein, it is possible to produce a more highly expressed amylase variant without severely compromising starch hydrolysis by selectively combining single mutations. The strategy described herein was successfully used to produce and select multiply-substituted AmyS-242Q variants having improvements in a first property (e.g., expression as the primary property), while improving or not sacrificing a second property (e.g., starch hydrolysis as the secondary property).

In addition, in converse to median expression of AmyS-242Q variants, cornstarch microswatch cleaning increased with increasing positive charge. Enhanced recombinant amylase expression and cleaning performance are desirable in an engineered variant of AmyS-242Q. These properties, however, are also apparently conflicting properties. Using the methods disclosed herein, it is possible to produce a more highly expressed amylase variant without severely compromising cleaning performance by selectively combining single mutations. The strategy described herein was successfully used to produce and select multiply-substituted AmyS-242Q variants having improvements in a first property (e.g., expression as the primary property), while improving or not sacrificing a second property (e.g., rice starch microswatch cleaning as the secondary property).

In particular, an eighty member AmyS-S242Q charge combinatorial library (CCL) comprising variants having combinations of from one to four substitutions of charged residues was tested for shake tube expression, BODIPY-starch hydrolysis, and rice starch cleaning activity. AmyS-S242Q winners are shown in Tables 7-1 and 7-1. Importantly, the multiply-substituted variants of Table 19-1 have equal or improved expression and equal or improved BODIPY-starch hydrolysis as compared to the parent enzyme. Similarly, the multiply-substituted variants of Table 19-2 have equal or improved expression and equal or improved rice starch cleaning activity as compared to the parent enzyme.

TABLE 19-1

AmyS-S242Q Expression and BODIPY-Starch Hydrolysis Winners

| Variant | 97 | 319 | 358 | 443 | Charge | Expression (PI) | BODIPY (PI) |
|---|---|---|---|---|---|---|---|
| 1 | Q97E | Q319E | Q358E | Q443E | −4 | 1.27 | 1.29 |
| 2 | Q97E | Q319E | Q358E | Q443R | −2 | 1.19 | 1.31 |
| 3 | Q97E | Q319E | Q358E | | −3 | 1.00 | 1.43 |
| 4 | Q97E | Q319E | Q358R | Q443E | −2 | 1.23 | 1.43 |
| 7 | Q97E | Q319E | | Q443E | −3 | 1.40 | 1.41 |
| 8 | Q97E | Q319E | | Q443R | −1 | 1.12 | 1.58 |
| 9 | Q97E | Q319E | | | −2 | 1.09 | 1.56 |
| 10 | Q97E | Q319R | Q358E | Q443E | −2 | 1.45 | 1.32 |
| 11 | Q97E | Q319R | Q358E | Q443R | 0 | 1.32 | 1.49 |
| 12 | Q97E | Q319R | Q358E | | −1 | 1.58 | 1.27 |
| 16 | Q97E | Q319R | | Q443E | −1 | 1.09 | 1.51 |
| 17 | Q97E | Q319R | | Q443R | +1 | 1.00 | 1.42 |
| 24 | Q97E | | Q358R | | 0 | 1.08 | 1.14 |
| 25 | Q97E | | | Q443E | −2 | 1.12 | 1.00 |
| 64 | | Q319R | Q358E | Q443E | −1 | 1.05 | 1.28 |
| 67 | | Q319R | Q358E | Q443E | +1 | 1.02 | 1.50 |

TABLE 19-2

AmyS-S242Q Expression and Rice-Starch Hydrolysis Winners

| Variant | 97 | 319 | 358 | 443 | Charge | Expression | CS-28 |
|---|---|---|---|---|---|---|---|
| 1 | Q97E | Q319E | Q358E | Q443E | −4 | 1.27 | 1.01 |
| 11 | Q97E | Q319R | Q358E | Q443R | 0 | 1.32 | 1.18 |
| 12 | Q97E | Q319R | Q358E | | −1 | 1.58 | 1.13 |
| 16 | Q97E | Q319R | | Q443E | −1 | 1.09 | 1.43 |
| 17 | Q97E | Q319R | | Q443R | +1 | 1.00 | 1.55 |
| 24 | Q97E | | Q358R | | 0 | 1.08 | 1.15 |
| 25 | Q97E | | | Q443E | −2 | 1.12 | 1.09 |

TABLE 19-2-continued

AmyS-S242Q Expression and Rice-Starch Hydrolysis Winners

| Variant | 97 | 319 | 358 | 443 | Charge | Expression | CS-28 |
|---|---|---|---|---|---|---|---|
| 64 | | Q319R | Q358E | Q443E | −1 | 1.05 | 1.18 |
| 67 | | Q319R | Q358R | Q443E | +1 | 1.02 | 1.15 |

Figure 25:
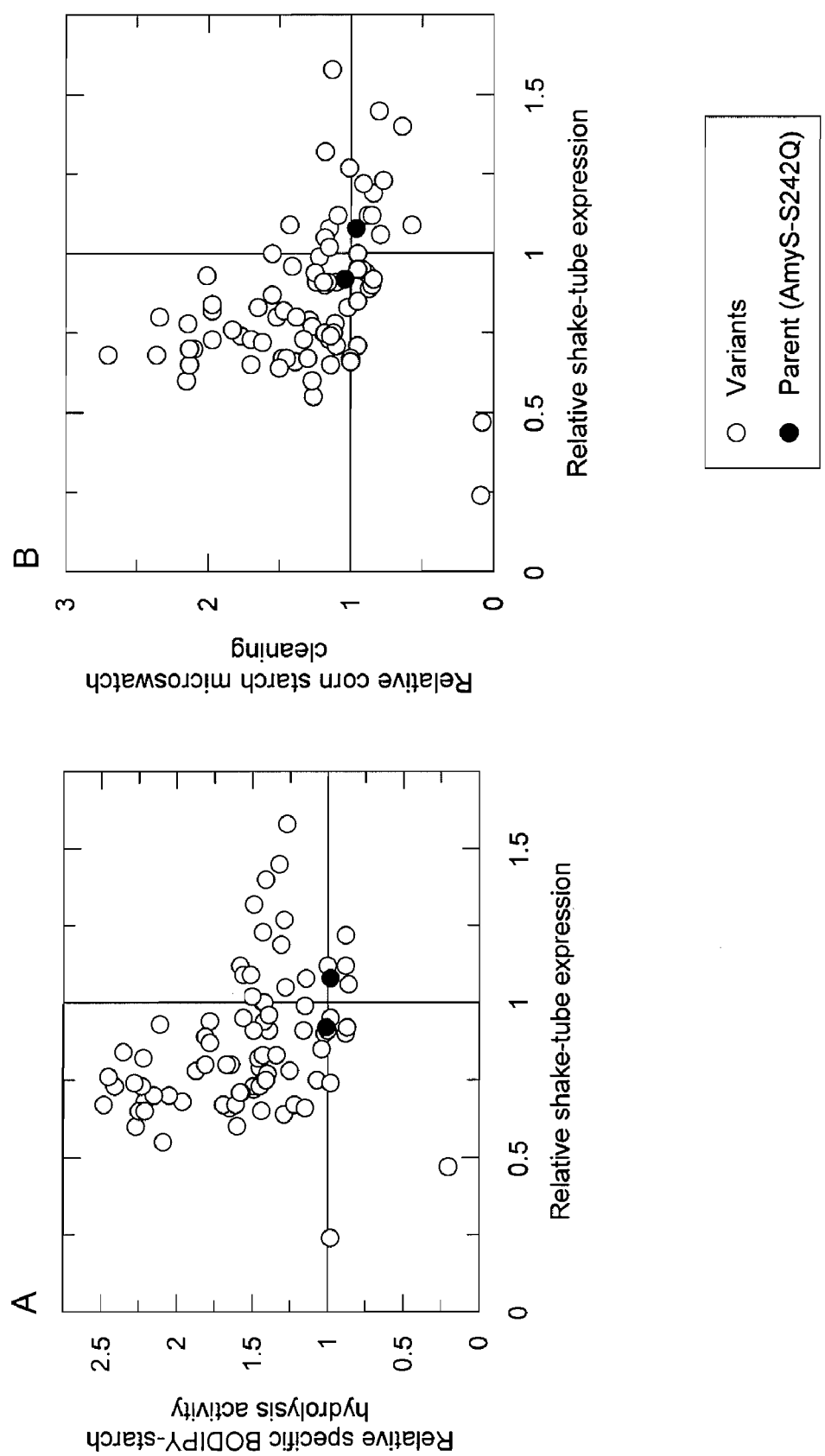
FIG. 25 A is a graph depicting the relative BODIPY-starch hydrolysis as a function of relative shake tube expression (i.e., relative BODIPY-starch hydrolysis vs. relative shake tube expression).
Figure 26:
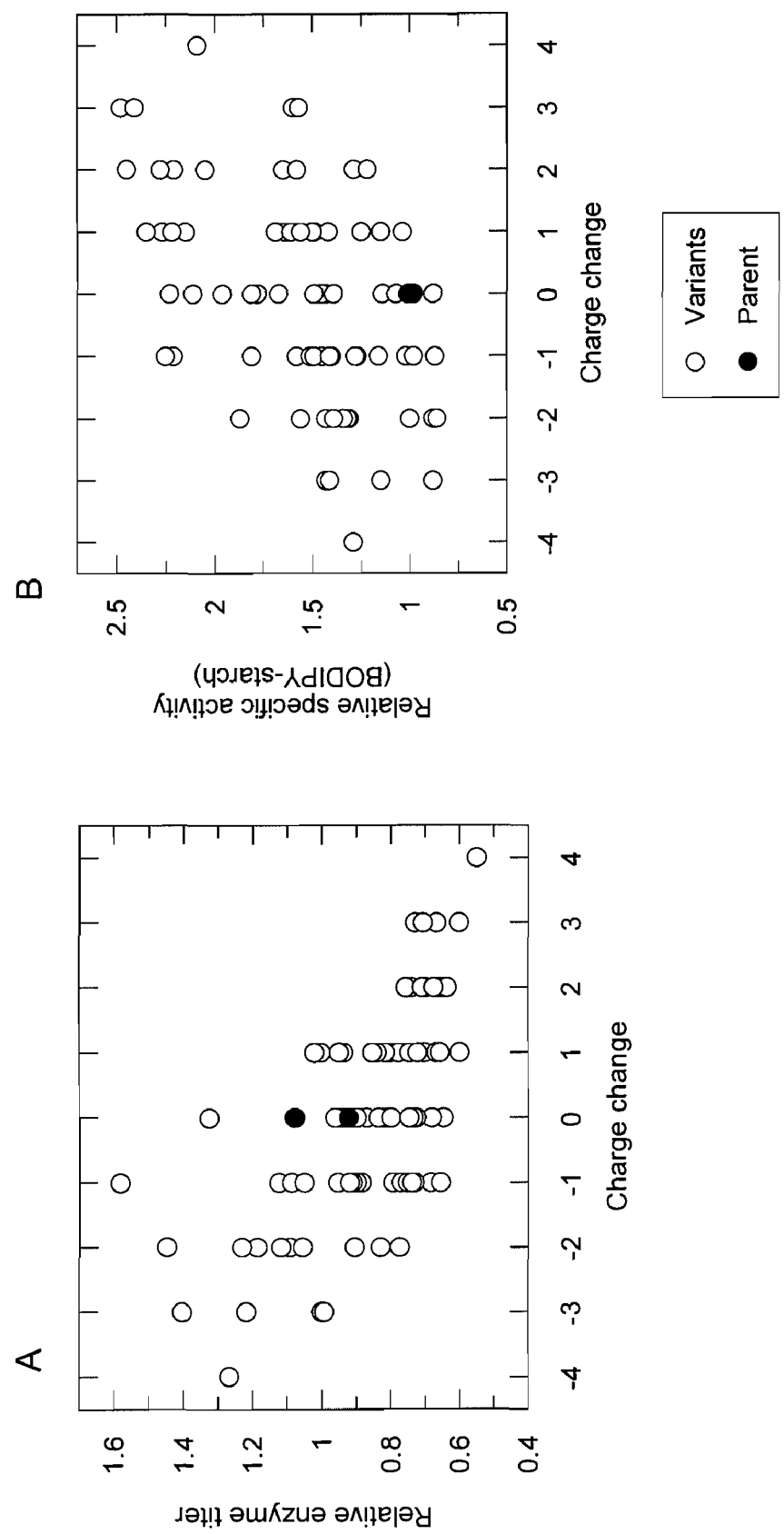
FIG. 26A is a graph depicting the relative shake tube expression as a function of charge.
FIG. 26B is a graph depicting the relative BODIPY-starch hydrolysis as a function of charge. Reference is made to Example 19.
Figure 27:
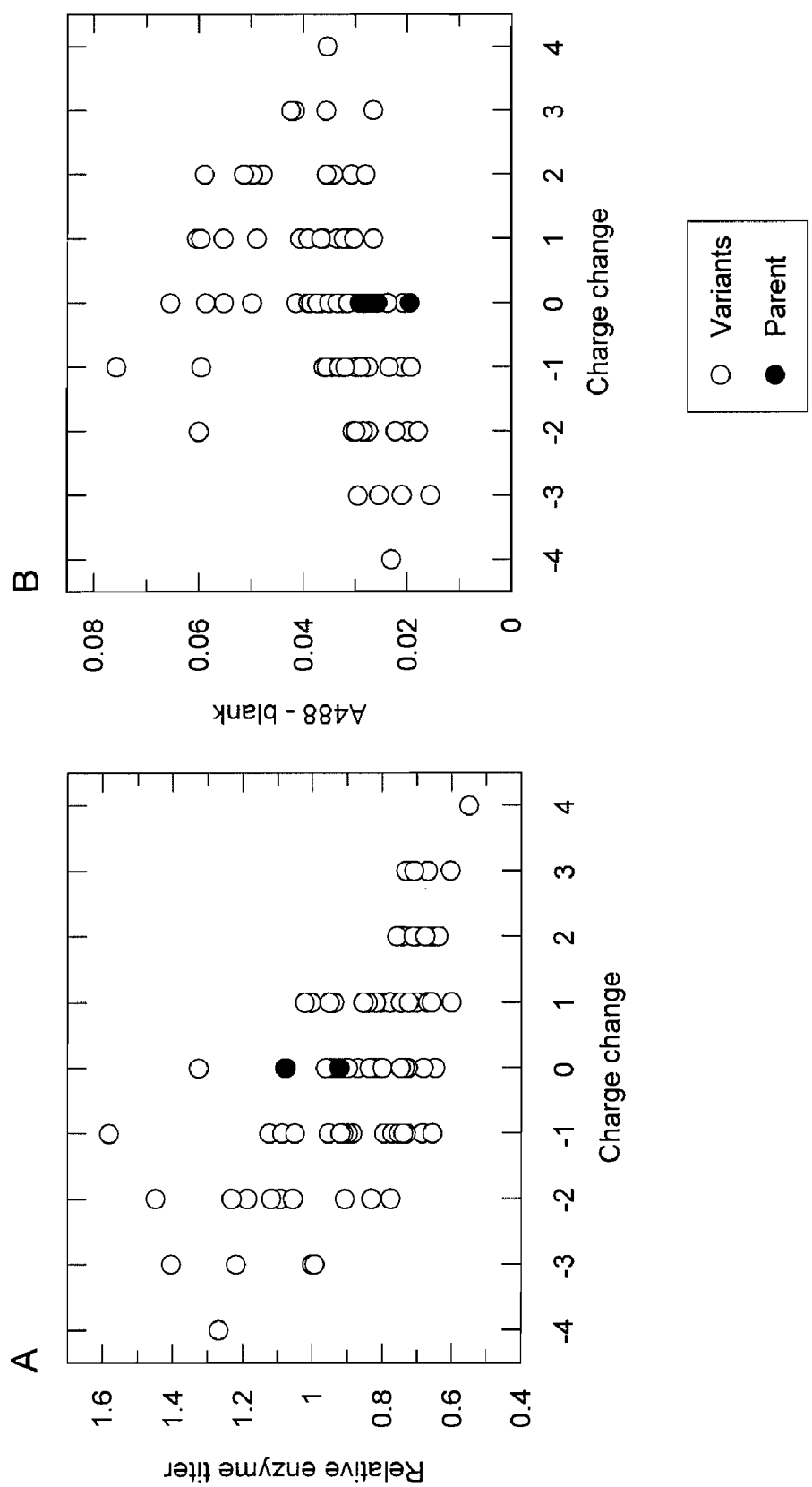
FIG. 27A is a graph depicting the relative shake tube expression as a function of charge.
FIG. 27B is a graph depicting the relative microswatch cleaning activity as a function of charge. Reference is made to Example 19.

In sum, because enzyme activity and enzyme production have different charge dependencies (see FIGS. 26A, 26B, 27A and 27B) they are negatively correlated (see FIGS. 25A and 25B). However, there are a number of variants that are improved in both expression and activity, and analyzing the library in this manner allows them to be identified.

Although demonstrated with amylases this method is applicable to other enzyme classes such as proteases, lipases, cellulases, transferases and pectinases. Moreover any combination of two or more properties can be analyzed simultaneously such as expression, activity, binding, thermal stability, detergent and chelant stability.

Example 20

Further Characterization of S242 Variants

A library of S242 variants (S242A, 242A, 242C, 242D, 242E, 242F, 242G, 242H, 242I, 242K, 242L, 242M, 242N, 242P, 242Q, 242R, 242T, 242V, 242W, and 242Y) were further characterized to determine the Protein Expression, Specific Activity at pH 5.8 and pH 4, Specific Activity on Corn Flour 85, and % Residual Activity at Temperature (see also Example 3). Results are shown with relative comparison to wild-type (or S242S parent amylase) and the control enzyme (SPEZYME ETHYL).

Data are shown in Table 20-1.

The specific activity at pH 5.8 and pH 4 was measured using the Alpha-Amylase Activity on Maltoheptaose Assay (pH Stability Determination) as follows:

The alpha-amylase activity of B. subtilis AmyS and AmyS variants on maltoheptaose at pH 5.8 and pH 4 was measured by monitoring production of glucose, using an enzyme-coupled colorimetric kinetic assay. Enzyme reactions were carried out in flat-bottom polystyrene 96-well microtiter plates at room temperature. For the assay conducted at pH 5.8, 10 μL of culture supernatant of AmyS and AmyS variants were mixed with 40 μL of buffer containing sodium acetate (pH 5.8), CaCl$_2$, Tween-20, horseradish peroxidase (Sigma-Aldrich, cat. No. 8375) and glucose oxidase (Genencor OxyGo™), at concentrations such that the final 50 μL volume contained 50 mM, 2.6 mM, 0.005% (w/v), 20 U/ml and 50 U/ml of each component, respectively. Reactions were initiated by the addition of 50 μl of buffer containing 50 mM sodium acetate (pH 5.8), 5.4 mg/mL 2,2'-Azino-bis(3-ethylbenzothiazoline-6-sulfonic acid) diammonium salt (Sigma-Aldrich, cat. no. A1888) and 10 mM maltoheptaose (Sigma-Aldrich, cat. No. M7753), and was followed by 5 seconds of mixing. Color formation in the reaction was monitored at 405 nm in 9 second intervals for 240 seconds using a SpectraMAX 250 spectrophotometer (Molecular Devices). Enzyme activity was reported as the rate of color formation during the 120-240 second interval of monitoring. For the assay conducted at pH 4.0, the method as described above was repeated exactly except using buffers at pH 4.0.

TABLE 20-1

Characterization of S242 Variants

| Variant | Protein Expression | Specific Activity pH 5.8 | Specific Activity pH 4 | Specific Activity Corn Flour 85 | Residual Activity (%) |
|---|---|---|---|---|---|
| 242A | 133 | 0.189 | 0.0540 | 0.0112 | 59.5 |
| 242C | 95 | 0.193 | 0.0502 | 0.0109 | 29.3 |
| 242D | 176 | 0.140 | 0.0344 | 0.0045 | 41.6 |
| 242E | 179 | 0.151 | 0.0400 | 0.0145 | 44.6 |
| 242F | 116 | 0.162 | 0.0441 | 0.0072 | 33.8 |
| 242G | 172 | 0.164 | 0.0444 | 0.0102 | 31.6 |
| 242H | 174 | 0.145 | 0.0414 | 0.0074 | 19.3 |
| 242I | 115 | 0.154 | 0.0445 | 0.0118 | 27.0 |
| 242K | 187 | 0.148 | 0.0444 | 0.0083 | 22.8 |
| 242L | 120 | 0.202 | 0.0729 | 0.0114 | 28.5 |
| 242M | 95 | 0.241 | 0.0735 | 0.0122 | 42.9 |
| 242N | 170 | 0.161 | 0.0419 | 0.0082 | 30.2 |
| 242P | 168 | 0.149 | 0.0322 | 0.0041 | 6.7 |
| 242Q | 142 | 0.152 | 0.0374 | 0.0177 | 61.3 |
| 242R | 176 | 0.154 | 0.0368 | 0.0062 | 13.0 |
| 242S | 135 | 0.164 | 0.0367 | 0.0122 | 34.0 |
| 242T | 165 | 0.145 | 0.0334 | 0.0081 | 24.8 |
| 242V | 106 | 0.168 | 0.0407 | 0.0089 | 22.3 |
| 242W | 112 | 0.199 | 0.0471 | 0.0083 | 5.6 |
| 242Y | 127 | 0.189 | 0.0541 | 0.0077 | 15.7 |
| pos | 75 | 0.189 | 0.0445 | 0.0311 | 85.0 |
| wildtype | 156 | 0.153 | 0.0416 | 0.0068 | 32.3 |

All publications and patents mentioned in the above specification are incorporated herein by reference. Although the disclosed methods and enzymes have in some instances been described in connection with specific or preferred embodiments, it should be understood what is covered by the appended claims is not limited to such specific or preferred embodiments. Indeed, various modifications and variations of the disclosed methods and enzymes will be apparent to those skilled in the art, and various modifications of the described modes for practicing what has been disclosed are included within the scope of the following claims.

---

The invention claimed is:

1. A variant of a parent *G. stearothermophilus* alpha-amylase having the amino acid sequence of SEQ ID NO. 1, 2 or 15, consisting of an alteration corresponding to position 242 of SEQ ID NO: 1, wherein (a) the alteration is a substitution of the amino acid which occupies the position with a different amino acid selected from the group consisting of A, E and Q, and (b) the variant has alpha-amylase activity.

2. The variant of claim 1, which variant has the amino acid sequence of SEQ ID NO. 1 and comprises the substitution S242A.

3. The variant of claim 1, which variant has the amino acid sequence of SEQ ID NO. 1 and comprises the substitution S242E.

4. The variant of claim 1, which variant has the amino acid sequence of SEQ ID NO. 1 and comprises the substitution S242Q.

5. The variant of claim 1, which variant has the amino acid sequence of SEQ ID NO. 2 and comprises the substitution S242A.

6. The variant of claim 1, which variant has the amino acid sequence of SEQ ID NO. 2 and comprises the substitution S242E.

7. The variant of claim 1, which variant has the amino acid sequence of SEQ ID NO. 2 and comprises the substitution S242Q.

8. The variant of claim 1, which variant has the amino acid sequence of SEQ ID NO. 15 and comprises the substitution S242A.

9. The variant of claim 1, which variant has the amino acid sequence of SEQ ID NO. 15 and comprises the substitution S242E.

10. The variant of claim 1, which variant has the amino acid sequence of SEQ ID NO. 15 and comprises the substitution S242Q.

11. A composition comprising an alpha-amylase variant of claim 1.

* * * * *